United States Patent
Park et al.

(10) Patent No.: US 11,502,256 B2
(45) Date of Patent: Nov. 15, 2022

(54) COMPOUND, COATING COMPOSITION COMPRISING SAME, AND ORGANIC LIGHT EMITTING DIODE

(71) Applicant: LG Chem, Ltd., Seoul (KR)

(72) Inventors: Youngju Park, Daejeon (KR); Sungkyoung Kang, Daejeon (KR); Kwanghyun Kim, Daejeon (KR); Jaesoon Bae, Daejeon (KR); Jaechol Lee, Daejeon (KR); Seokhee Yoon, Daejeon (KR); Jiyeon Shin, Daejeon (KR); Keunsoo Lee, Daejeon (KR)

(73) Assignee: LG Chem, Ltd.

( * ) Notice: Subject to any disclaimer, the term of this patent is extended or adjusted under 35 U.S.C. 154(b) by 377 days.

(21) Appl. No.: 16/761,929

(22) PCT Filed: May 23, 2019

(86) PCT No.: PCT/KR2019/006208
§ 371 (c)(1),
(2) Date: May 6, 2020

(87) PCT Pub. No.: WO2019/225989
PCT Pub. Date: Nov. 28, 2019

(65) Prior Publication Data
US 2021/0151685 A1    May 20, 2021

(30) Foreign Application Priority Data
May 23, 2018 (KR) .......... 10-2018-0058326

(51) Int. Cl.
*H01L 51/50* (2006.01)
*H01L 51/00* (2006.01)
*C09D 7/63* (2018.01)
*C08F 230/06* (2006.01)
*C07D 209/86* (2006.01)
(Continued)

(52) U.S. Cl.
CPC ........ *H01L 51/0039* (2013.01); *C07D 209/86* (2013.01); *C07F 7/0812* (2013.01); *C08F 230/065* (2020.02); *C09D 4/00* (2013.01); *C09D 5/24* (2013.01); *C09D 7/63* (2018.01); *H01L 51/0043* (2013.01); *H01L 51/001* (2013.01);
(Continued)

(58) Field of Classification Search
None
See application file for complete search history.

(56) References Cited

U.S. PATENT DOCUMENTS

2017/0213967 A1    7/2017    Chen et al.
2017/0213977 A1    7/2017    Shin et al.
(Continued)

FOREIGN PATENT DOCUMENTS

CN    102263205 A    11/2011
KR    20140132562 A    11/2014
(Continued)

OTHER PUBLICATIONS

Extended European Search Report for Application No. 19806412.3 dated Jan. 28, 2021, 3 pages.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a compound, a coating composition including the same, and an organic light emitting device.

18 Claims, 1 Drawing Sheet

(51) Int. Cl.
  *C07F 7/08*    (2006.01)
  *C09D 4/00*    (2006.01)
  *C09D 5/24*    (2006.01)

(52) U.S. Cl.
  CPC ...... *H01L 51/5056* (2013.01); *H01L 51/5088* (2013.01)

(56) References Cited

U.S. PATENT DOCUMENTS

| | | |
|---|---|---|
| 2019/0019956 A1 | 1/2019 | Gorohmaru et al. |
| 2020/0052220 A1 | 2/2020 | Lee et al. |
| 2020/0055803 A1 | 2/2020 | Yu et al. |

FOREIGN PATENT DOCUMENTS

| | | |
|---|---|---|
| KR | 20150024018 A | 3/2015 |
| KR | 20150093995 A | 8/2015 |
| KR | 20170089095 A | 8/2017 |
| KR | 20180044720 A | 5/2018 |
| WO | 2016026122 A1 | 2/2016 |
| WO | 2017107117 A1 | 6/2017 |
| WO | 2017164268 A1 | 9/2017 |
| WO | 2018230848 A1 | 12/2018 |
| WO | 2019066306 A1 | 4/2019 |

OTHER PUBLICATIONS

International Search Report for Application No. PCT/KR2019/006208 dated Aug. 30, 2019, 2 pages.

| 701 |
|---|
| 601 |
| 501 |
| 401 |
| 301 |
| 201 |
| 101 |

COMPOUND, COATING COMPOSITION COMPRISING SAME, AND ORGANIC LIGHT EMITTING DIODE

CROSS-REFERENCE TO RELATED APPLICATIONS

This application is a national phase entry under 35 U.S.C. § 371 of International Application No. PCT/KR2019/006208 filed May 23, 2019, which claims priority from Korean Patent Application No. 10-2018-0058326 filed May 23, 2018, all of which are incorporated herein by reference.

TECHNICAL FIELD

The present specification relates to a compound, a coating composition including the same, and an organic light emitting device.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic electroluminescent device using such a principle may be generally formed with a cathode, an anode, and an organic material layer placed therebetween, for example, an organic material layer including a hole injection layer, a hole transfer layer, a light emitting layer, an electron transfer layer and an electron injection layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heat produced by charge migration in the organic light emitting device. NPB (n-propyl bromide) normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. Poly(3,4-ethylenedioxythiophene) doped with poly(styrenesulfonic acid) (PEDOT:PSS) currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

DISCLOSURE

Technical Problem

The present specification is directed to providing a compound, a coating composition including the same, and an organic light emitting device.

Technical Solution

One embodiment of the present specification provides a compound represented by the following Chemical Formula 1.

[Chemical Formula 1]

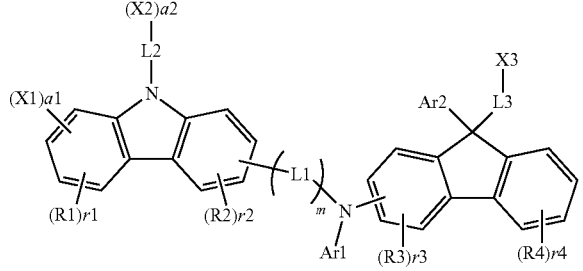

In Chemical Formula 1,

Ar1 and Ar2 are the same as or different from each other, and each independently a substituted or unsubstituted aryl group, R1 to R4 are the same as or different from each other, and each independently hydrogen; deuterium; a halogen group; a nitrile group; a substituted or unsubstituted alkyl group; a substituted or unsubstituted aryl group; or a substituted or unsubstituted heterocyclic group, r1 to r3 are each from 1 to 3, r4 is from 1 to 4, when r1 to r4 are each 2 or greater, the two or more R1 to R4 are each the same as or different from each other, X3 is

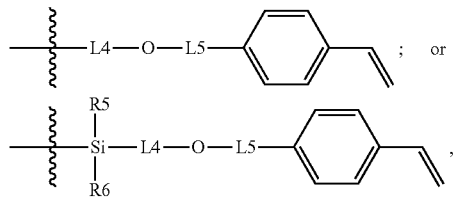

X1 and X2 are the same as or different from each other, and each independently

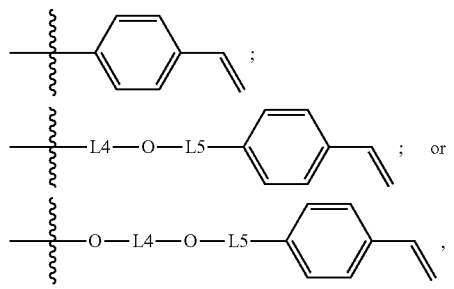

each

means a linking site,

L4 is a substituted or unsubstituted alkylene group,

L5 is a direct bond; or a substituted or unsubstituted arylene group,

R5 and R6 are the same as or different from each other, and each independently a substituted or unsubstituted alkyl group, a1 and a2 are each 0 or 1, when a2 is 0, L2 is a substituted or unsubstituted aryl group, when a2 is 1, L2 is a direct bond; or a substituted or unsubstituted arylene group, L1 is a substituted or unsubstituted arylene group; or a substituted or unsubstituted heteroarylene group, m is 1 or 2, and when m is 2, Lis are the same as or different from each other, L3 is a direct bond; or a substituted or unsubstituted alkylene group, and $0 \le a1+a2 \le 2$.

Another embodiment of the present specification provides a coating composition including the compound.

Another embodiment of the present specification provides an organic light emitting device including a first electrode; a second electrode provided opposite to the first electrode; and one or more organic material layers provided between the first electrode and the second electrode, wherein one or more layers of the organic material layers include the coating composition and a cured material thereof.

Advantageous Effects

An organic material layer formed using a compound according to one embodiment of the present specification has excellent thermal and photostability after being cured through heat and light, and does not have solubility for other solvents, and therefore, a lamination film-forming process can be performed on the formed film through another solution process.

In addition, a compound according to one embodiment of the present specification is used as a material of an organic material layer of an organic light emitting device, and is capable of lowering a driving voltage of the organic light emitting device.

In addition, a compound according to one embodiment of the present specification is used as a material of an organic material layer of an organic light emitting device, and is capable of enhancing light efficiency.

In addition, a compound according to one embodiment of the present specification is used as a material of an organic material layer of an organic light emitting device, and is capable of enhancing lifetime properties of the device.

In addition, a compound according to one embodiment of the present specification is curable at a low temperature, which is advantageous for mass production of an organic light emitting device, and a solution process can be used by the compound having high solubility, and as a result, large area organic light emitting devices can be manufactured.

DESCRIPTION OF DRAWINGS

The FIGURE is a diagram illustrating an example of an organic light emitting device according to one embodiment of the present specification.

REFERENCE NUMERAL

101: Substrate
201: Anode
301: Hole Injection Layer
401: Hole Transfer Layer
501: Light Emitting Layer
601: Electron Injection and Transfer Layer
701: Cathode

MODE FOR DISCLOSURE

Hereinafter, the present specification will be described in more detail.

One embodiment of the present specification provides a compound represented by Chemical Formula 1.

The compound of the present specification enables curing at a relatively low temperature by increasing mobility of a curing group, which is effective for mass production. In addition, by having an alkylene group between the curing group and the fluorene group, solubility increases expanding the choice of a solvent when preparing an ink of a solution process. A thin film prepared by heat or light treating a coating composition of the amine group-bonding compound of the present disclosure, a curing initiator and a p-doping material has excellent tolerance for a solvent, and an organic light emitting device having excellent current efficiency and device properties are provided.

Examples of substituents in the present specification are described below, however, the substituents are not limited thereto.

In the present specification,

means a linking site.

The term "substitution" means a hydrogen atom bonding to a carbon atom of a compound is changed to another substituent. The position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; an alkyl group; a cycloalkyl group; an amine group; a silyl group; a phosphine oxide group; an aryl group; and a heteroaryl group including one or more of N, O, S, Se and Si atoms, being substituted with a substituent linking two or more substituents among the substituents illustrated above, or having no substituents.

In the present specification, the alkyl group may be linear or branched, and although not particularly limited thereto, the number of carbon atoms is preferably from 1 to 50 and more preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 60 carbon atoms, and more preferably has 3 to 30 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkenyl group may be linear or branched, and although not particularly limited thereto, the number of carbon atoms is preferably from 2 to 40 and more preferably from 2 to 20. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, specific examples of the phosphine oxide group may include a diphenylphosphine oxide group, a dinaphthylphosphine oxide group and the like, but are not limited thereto.

When the aryl group is a monocyclic aryl group in the present specification, the number of carbon atoms is not particularly limited, but is preferably from 6 to 50 and more preferably from 6 to 30. Specific examples of the monocyclic aryl group may include a phenyl group, a biphenyl group, a terphenyl group, a quaterphenyl group and the like, but are not limited thereto.

When the aryl group is a polycyclic aryl group, the number of carbon atoms is not particularly limited, but is preferably from 10 to 50 and more preferably from 10 to 30. Specific examples of the polycyclic aryl group may include a naphthyl group, an anthracenyl group, a phenanthryl group, a pyrenyl group, a perylenyl group, a triphenyl group, a chrysenyl group, a fluorenyl group and the like, but are not limited thereto.

In the present specification, the number of carbon atoms of the amine group is not particularly limited, but is preferably from 1 to 50 and more preferably from 10 to 30. The amine group may be substituted with the above-described alkyl group, aryl group, heterocyclic group, alkenyl group, cycloalkyl group, a combination thereof and the like, and specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups. For example, the aryl group in the arylamine group may be selected from among the examples of the aryl group described above. Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, the heterocyclic group includes one or more of N, O, S, Si and Se as a heteroatom, and although not particularly limited thereto, the number of carbon atoms is preferably from 2 to 60 and more preferably from 2 to 30. Examples of the heterocyclic group may include a thiophene group, a furan group, a pyrrole group, an imidazole group, a triazole group, an oxazole group, an oxadiazole group, a triazole group, a pyridine group, a bipyridine group, a pyrimidine group, a triazine group, an acridine group, a pyridazine group, a pyrazine group, a quinoline group, a quinazoline group, a quinoxaline group, a phthalazine group, a pteridine group, a pyrido pyrimidine group, a pyrido pyrazine group, a pyrazino pyrazine group, an isoquinoline group, an indole group, a pyrido indole group, 5H-indeno pyrimidine group, a carbazole group, a benzoxazole group, a benzimidazole group, a benzothiazole group, a benzocarbazole group, a benzothiophene group, a dibenzothiophene group, a benzofuran group, a dibenzofuran group, a phenanthroline group, a thiazolyl group, an isoxazolyl group, an oxadiazolyl group, a thiadiazolyl group and the like, but are not limited thereto.

In the present specification, the heteroaryl group may be selected from among the examples of the heterocyclic group except for those that are aromatic, but is not limited thereto.

In the present specification, the alkylene group means an alkyl group having two bonding sites, that is, a divalent group. Descriptions on the alkyl group provided above may be applied thereto except for those that are each divalent.

In the present specification, the arylene group means an aryl group having two bonding sites, that is, a divalent group. Descriptions on the aryl group provided above may be applied thereto except for those that are each divalent.

In the present specification, the heteroarylene group means a heteroaryl group having two bonding sites, that is, a divalent group. Descriptions on the heteroaryl group provided above may be applied thereto except for those that are each divalent.

In one embodiment of the present specification, Ar1 and Ar2 are the same as or different from each other, and each independently a substituted or unsubstituted aryl group.

In one embodiment of the present specification, Ar1 is a substituted or unsubstituted phenyl group; a substituted or unsubstituted biphenyl group; or a substituted or unsubstituted naphthyl group.

In one embodiment of the present specification, Ar1 is a phenyl group unsubstituted or substituted with an alkyl group; a biphenyl group unsubstituted or substituted with an alkyl group; or a naphthyl group unsubstituted or substituted with an alkyl group.

In one embodiment of the present specification, Ar1 is a phenyl group unsubstituted or substituted with an alkyl group; or a biphenyl group unsubstituted or substituted with an alkyl group.

In one embodiment of the present specification, Ar1 is a phenyl group unsubstituted or substituted with a methyl group or a butyl group; or a biphenyl group unsubstituted or substituted with a methyl group or a butyl group.

In one embodiment of the present specification, Ar2 is a substituted or unsubstituted phenyl group.

In one embodiment of the present specification, Ar2 is a phenyl group.

In one embodiment of the present specification, R1 to R4 are the same as or different from each other, and each independently hydrogen; deuterium; a halogen group; a nitrile group; a substituted or unsubstituted alkyl group; a substituted or unsubstituted aryl group; or a substituted or unsubstituted heterocyclic group.

In one embodiment of the present specification, R1 to R4 are the same as or different from each other, and each independently hydrogen; or a substituted or unsubstituted aryl group.

In one embodiment of the present specification, R1 to R4 are the same as or different from each other, and each independently hydrogen; or a substituted or unsubstituted phenyl group.

In one embodiment of the present specification, R1 to R4 are the same as or different from each other, and each independently hydrogen; or a phenyl group unsubstituted or substituted with an alkyl group.

In one embodiment of the present specification, R1 to R4 are the same as or different from each other, and each independently hydrogen; or a phenyl group unsubstituted or substituted with a butyl group.

In one embodiment of the present specification, R1 to R4 are the same as or different from each other, and each independently hydrogen; or a phenyl group unsubstituted or substituted with a tert-butyl group.

In one embodiment of the present specification, R1 is hydrogen; or a substituted or unsubstituted aryl group.

In one embodiment of the present specification, R1 is hydrogen; or a substituted or unsubstituted phenyl group.

In one embodiment of the present specification, R1 is hydrogen; or a phenyl group unsubstituted or substituted with an alkyl group.

In one embodiment of the present specification, R1 is hydrogen; or a phenyl group unsubstituted or substituted with a butyl group.

In one embodiment of the present specification, R1 is hydrogen; or a phenyl group unsubstituted or substituted with a tert-butyl group.

In one embodiment of the present specification, R2 to R4 are hydrogen.

In one embodiment of the present specification, r1 to r3 are each from 1 to 3, r4 is from 1 to 4, and when r1 to r4 are each 2 or greater, the two or more R1 to R4 are each the same as or different from each other.

In one embodiment of the present specification, X3 is

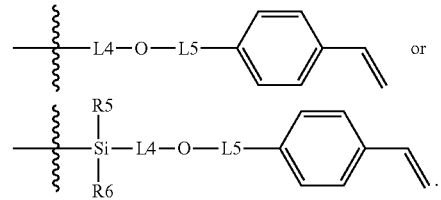

In one embodiment of the present specification, X1 and X2 are the same as or different from each other, and each independently

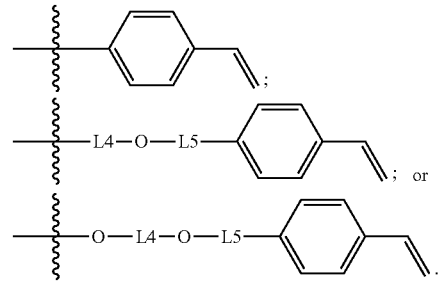

In one embodiment of the present specification, L4 is a substituted or unsubstituted alkylene group.

In one embodiment of the present specification, L4 is a substituted or unsubstituted alkylene group having 1 to 20 carbon atoms.

In one embodiment of the present specification, L4 is a substituted or unsubstituted alkylene group having 1 to 10 carbon atoms.

In one embodiment of the present specification, L4 is a substituted or unsubstituted alkylene group having 1 to 8 carbon atoms.

In one embodiment of the present specification, L4 is a substituted or unsubstituted linear or branched alkylene group having 1 to 20 carbon atoms.

In one embodiment of the present specification, L4 is a substituted or unsubstituted linear or branched alkylene group having 1 to 10 carbon atoms.

In one embodiment of the present specification, L4 is a substituted or unsubstituted linear or branched alkylene group having 1 to 8 carbon atoms.

In one embodiment of the present specification, L5 is a direct bond; or a substituted or unsubstituted arylene group.

In one embodiment of the present specification, L5 is a direct bond; a substituted or unsubstituted phenylene group; or a substituted or unsubstituted naphthylene group.

In one embodiment of the present specification, L5 is a direct bond; a phenylene group unsubstituted or substituted with an alkyl group; or a naphthylene group unsubstituted or substituted with an alkyl group.

In one embodiment of the present specification, L5 is a direct bond; a phenylene group unsubstituted or substituted with an alkyl group having 1 to 3 carbon atoms; or a naphthylene group unsubstituted or substituted with an alkyl group having 1 to 3 carbon atoms.

In one embodiment of the present specification, L5 is a direct bond; a phenylene group unsubstituted or substituted with a methyl group; or a naphthylene group unsubstituted or substituted with a methyl group.

In one embodiment of the present specification, L5 is a direct bond; a phenylene group unsubstituted or substituted with a methyl group; or a naphthylene group.

In one embodiment of the present specification, R5 and R6 are the same as or different from each other, and each independently an alkyl group having 1 to 20 carbon atoms.

In one embodiment of the present specification, R5 and R6 are the same as or different from each other, and each independently an alkyl group having 1 to 10 carbon atoms.

In one embodiment of the present specification, R5 and R6 are the same as or different from each other, and each independently a linear or main chain alkyl group having 1 to 20 carbon atoms.

In one embodiment of the present specification, R5 and R6 are the same as or different from each other, and each independently a linear or main chain alkyl group having 1 to 10 carbon atoms.

In one embodiment of the present specification, R5 and R6 are a methyl group.

In one embodiment of the present specification, a1 and a2 are each 0 or 1.

In one embodiment of the present specification, when a2 is 0, L2 is a substituted or unsubstituted aryl group.

In one embodiment of the present specification, when a2 is 0, L2 is a phenyl group.

In one embodiment of the present specification, when a2 is 1, L2 is a direct bond; or a substituted or unsubstituted arylene group.

In one embodiment of the present specification, when a2 is 1, L2 is a direct bond; or a substituted or unsubstituted phenylene group.

In one embodiment of the present specification, when a2 is 1, L2 is a direct bond; or a phenylene group.

In one embodiment of the present specification, m is 1 or 2, and when m is 2, Lis are the same as or different from each other, and L1 is a substituted or unsubstituted arylene group; or a substituted or unsubstituted heteroarylene group.

In one embodiment of the present specification, L1 is a substituted or unsubstituted phenylene group; a substituted or unsubstituted divalent fluorene group; or a substituted or unsubstituted divalent dibenzofuran group.

In one embodiment of the present specification, L1 is a phenylene group; a divalent fluorene group unsubstituted or substituted with an alkyl group; or a divalent dibenzofuran group.

In one embodiment of the present specification, L1 is a phenylene group; a divalent fluorene group substituted with a methyl group; or a divalent dibenzofuran group.

In one embodiment of the present specification, L3 is a direct bond; or an alkylene group.

In one embodiment of the present specification, L3 is a direct bond; or an alkylene group having 1 to 20 carbon atoms.

In one embodiment of the present specification, L3 is a direct bond; or an alkylene group having 1 to 10 carbon atoms.

In one embodiment of the present specification, L3 is a direct bond; or an alkylene group having 1 to 5 carbon atoms.

In one embodiment of the present specification, L3 is a direct bond; or a linear alkylene group having 1 to 5 carbon atoms.

In one embodiment of the present specification, L3 is a direct bond.

In one embodiment of the present specification, $0 \leq a1+a2 \leq 2$.

In one embodiment of the present specification, Chemical Formula 1 may be represented by the following Chemical Formula 2.

[Chemical Formula 2]

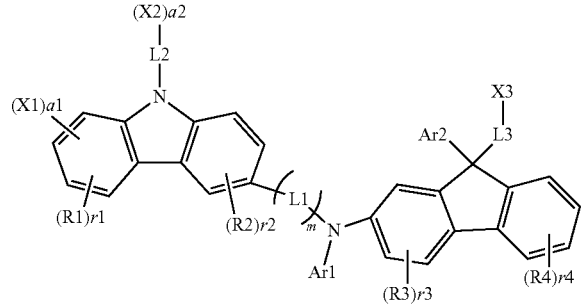

In Chemical Formula 2,

L1 to L3, Ar1, Ar2, R1 to R4, r1 to r4, X1 to X3, m, a1 and a2 have the same definitions as in Chemical Formula 1.

In one embodiment of the present specification, the compound represented by Chemical Formula 1 is any one selected from among the following compounds.

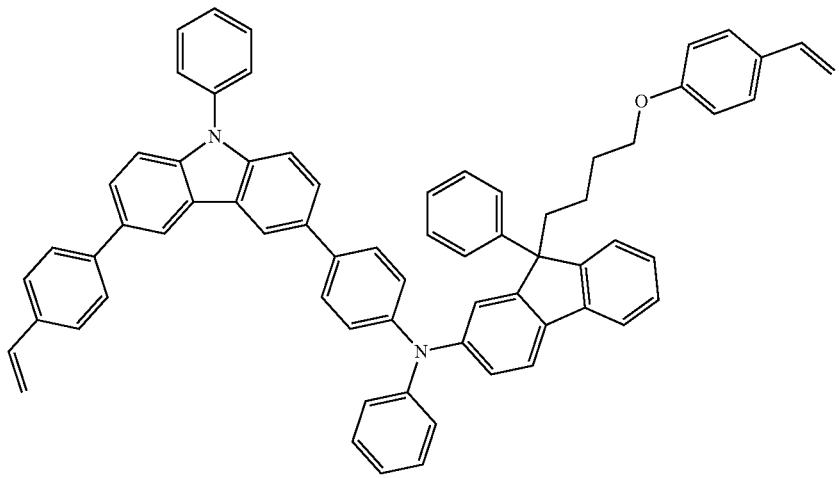
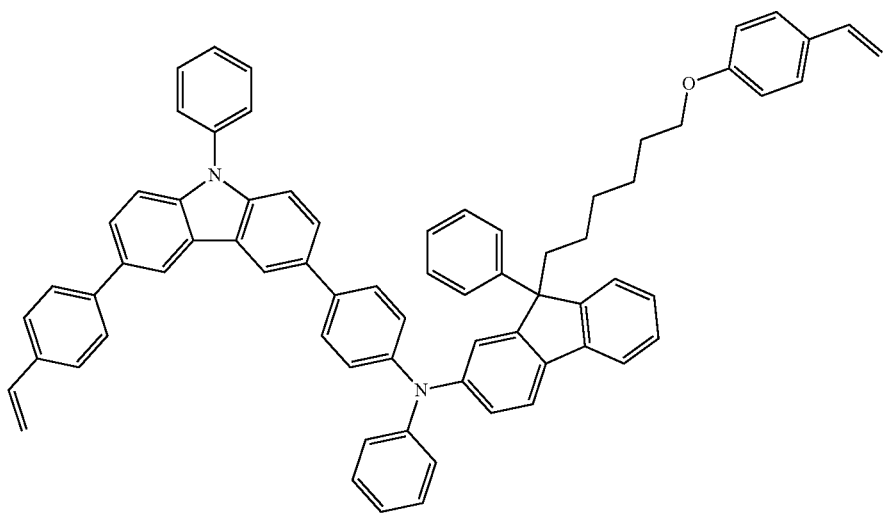
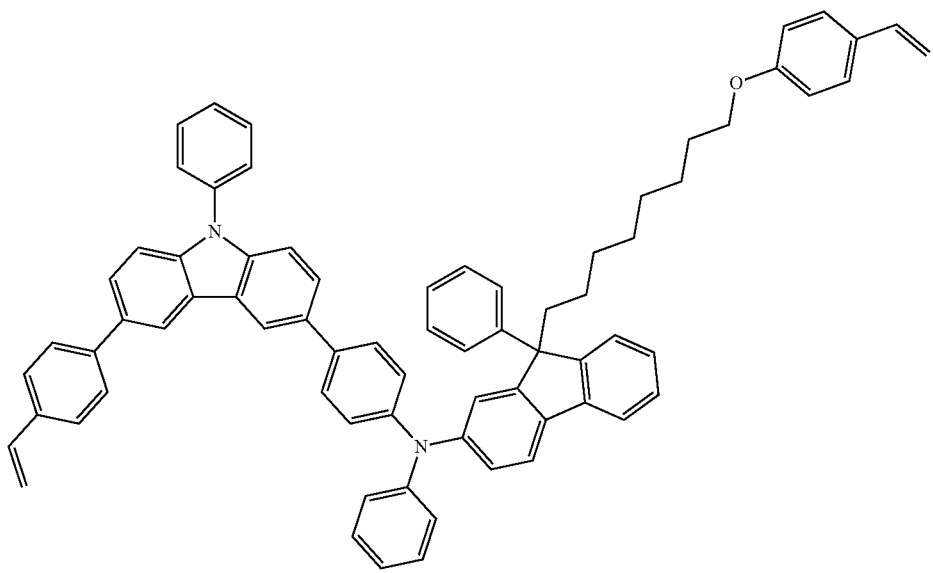

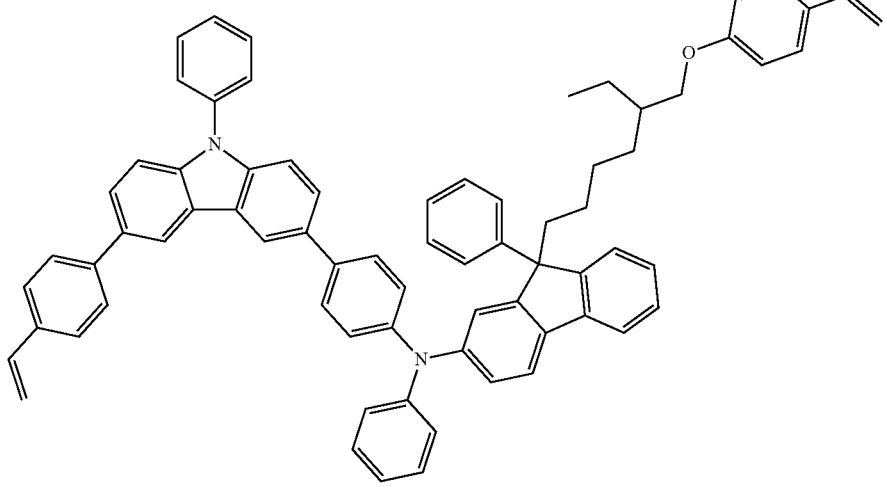
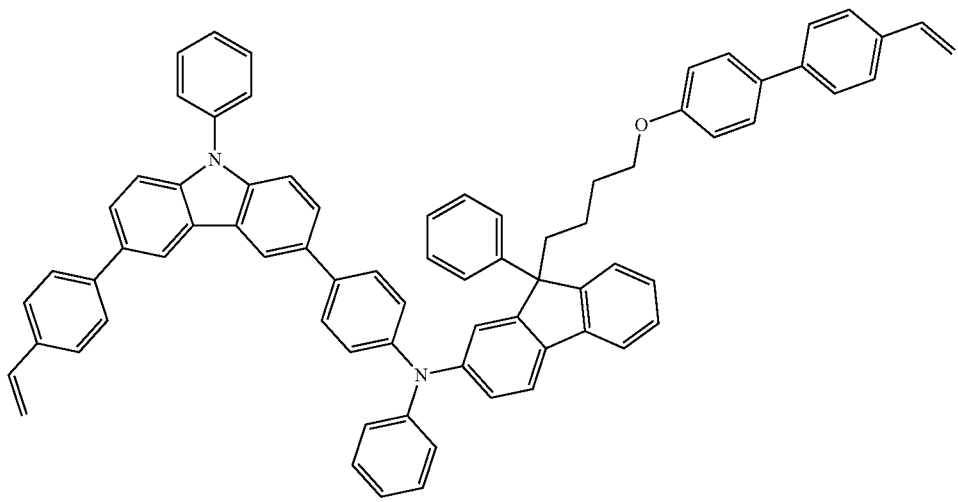
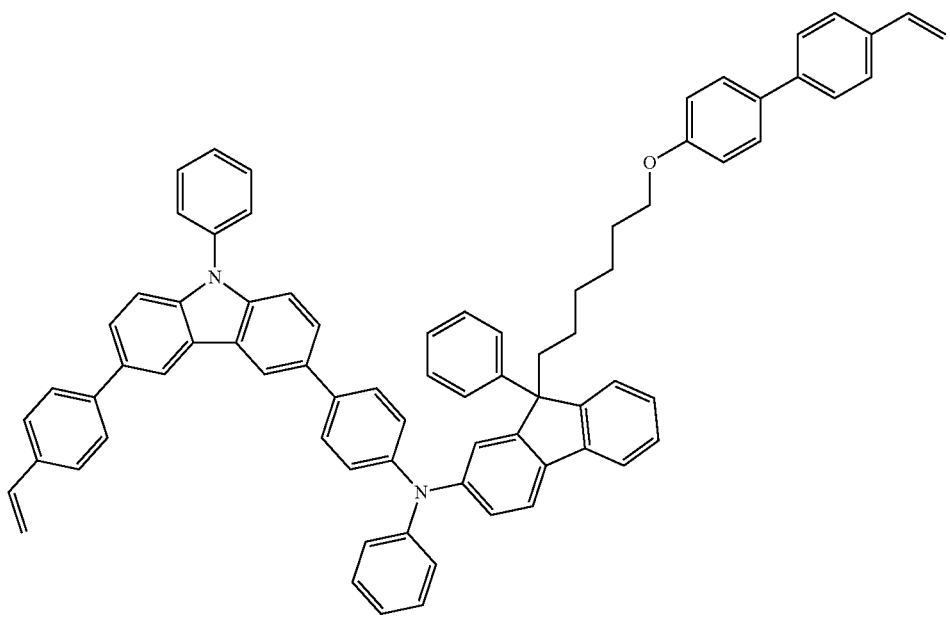

-continued
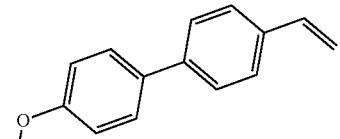
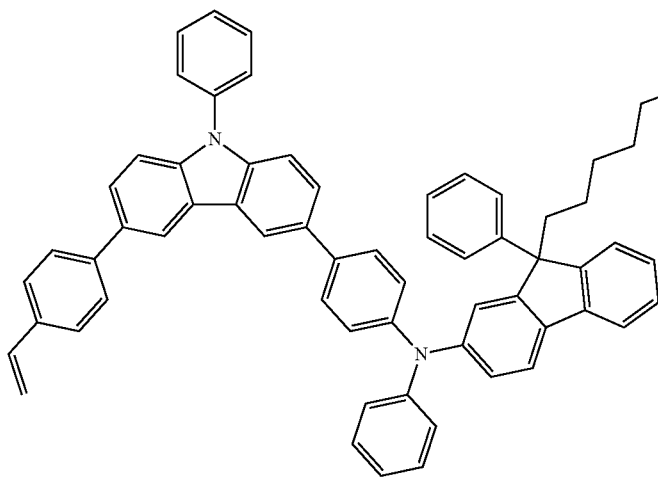
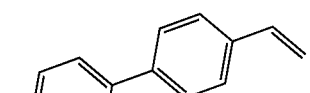
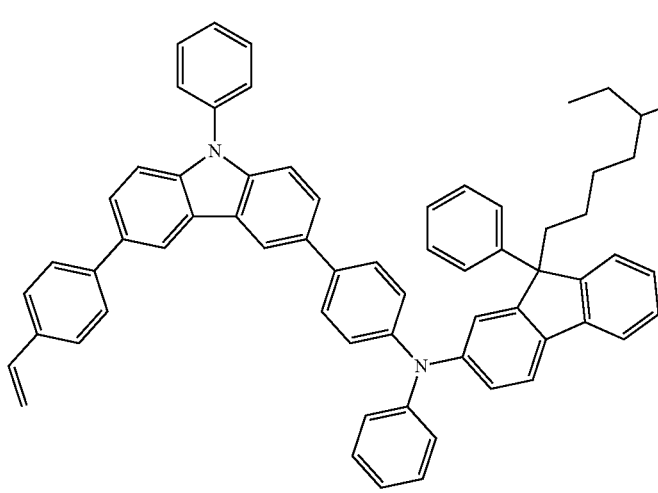
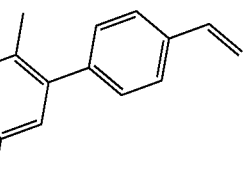
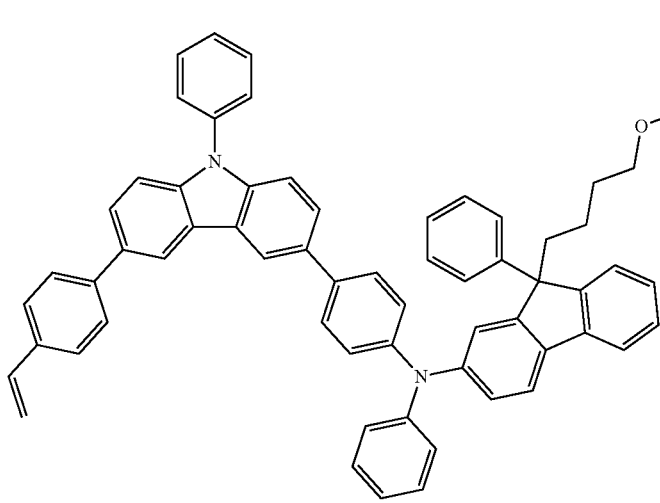

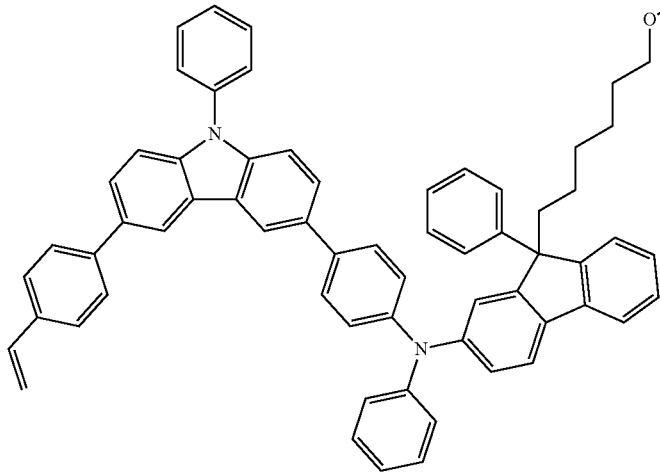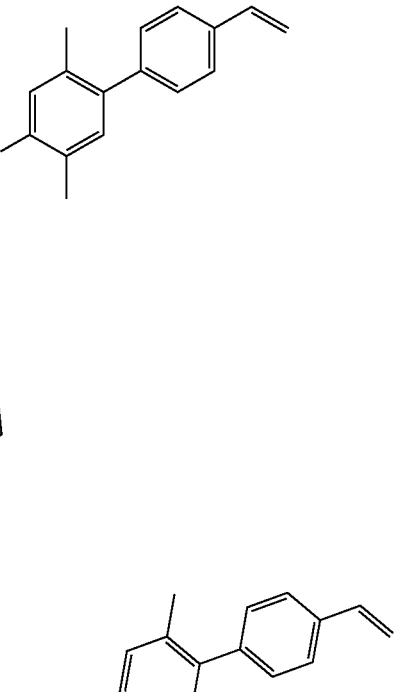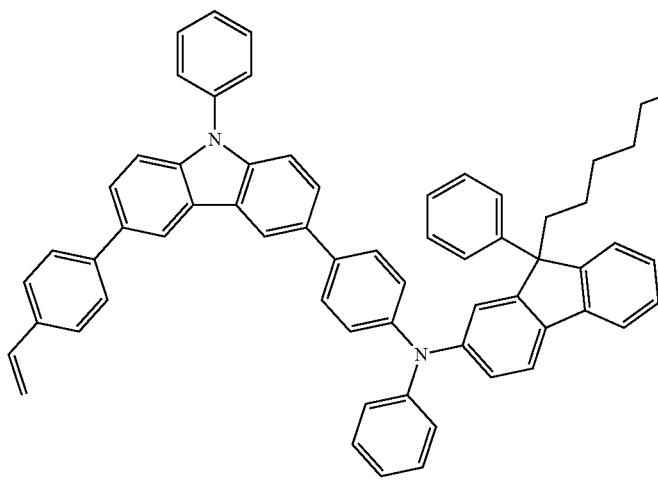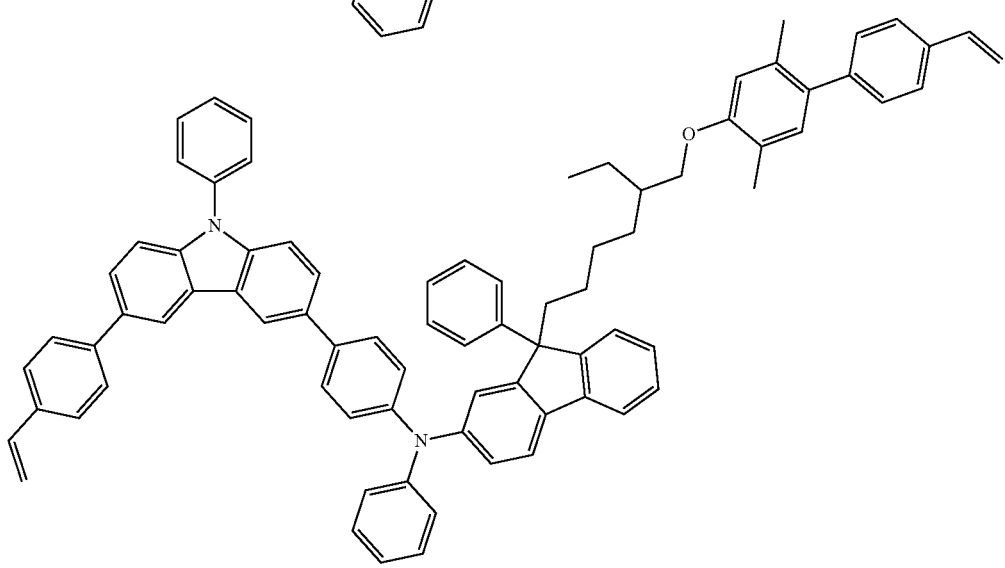

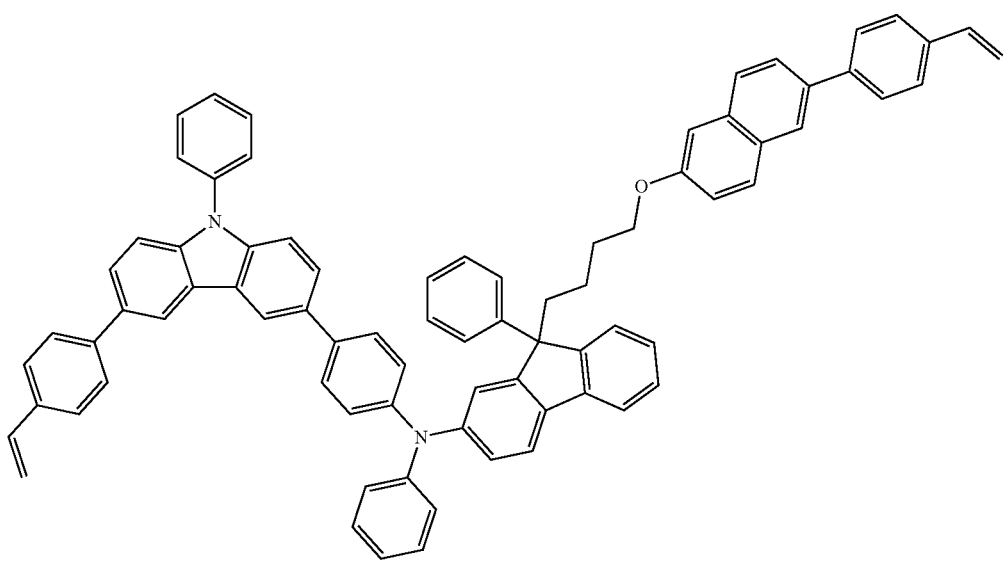
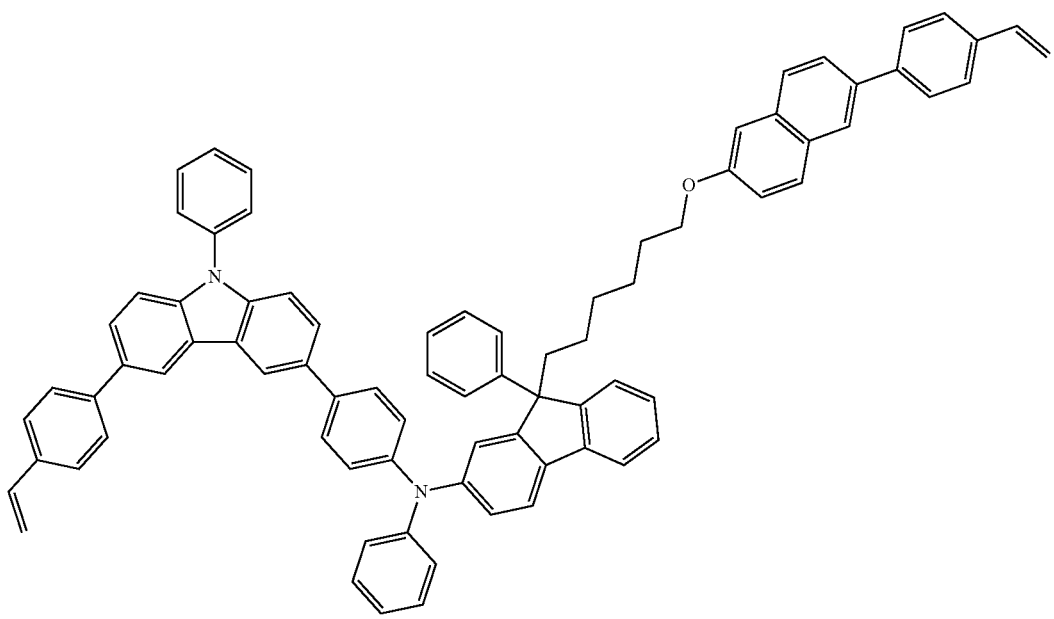

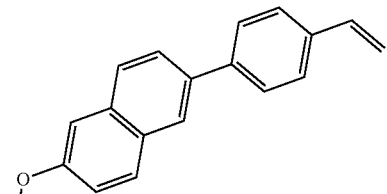
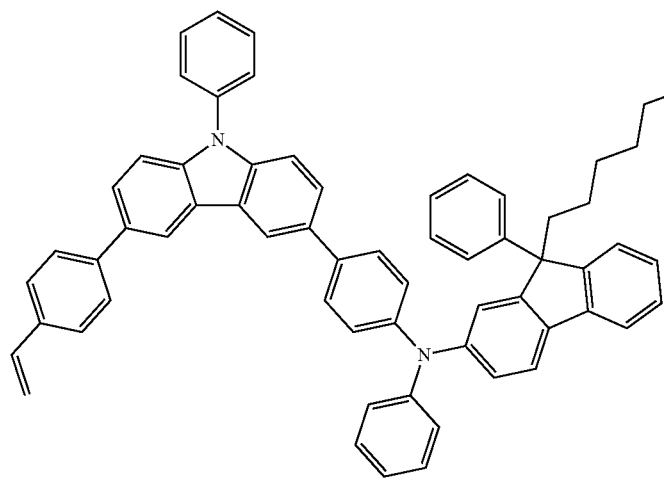
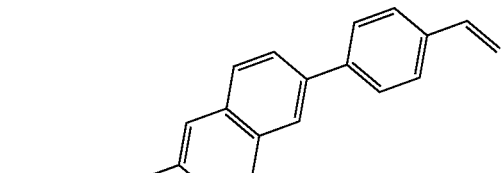
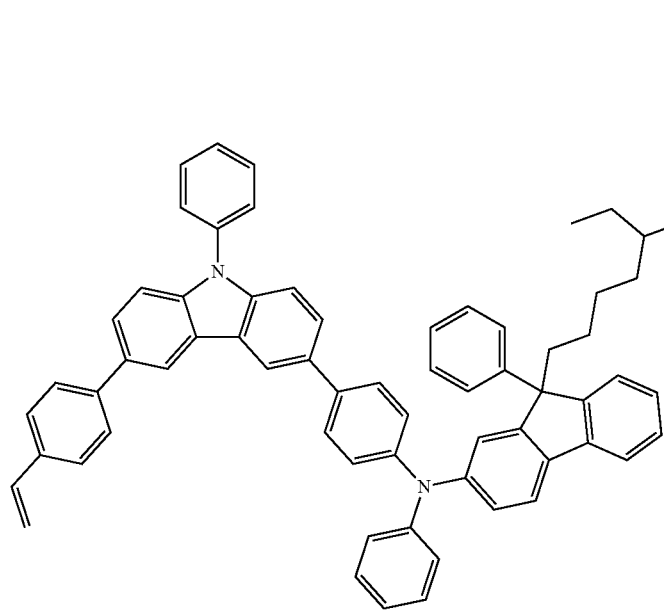

-continued
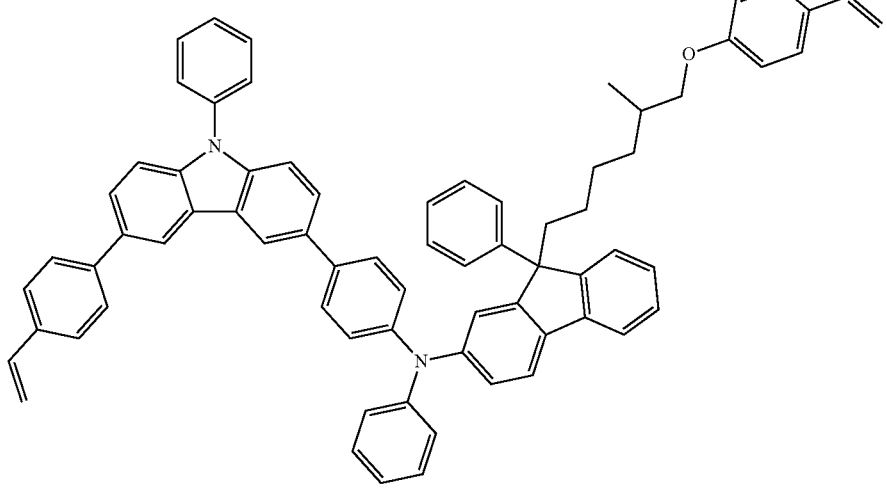
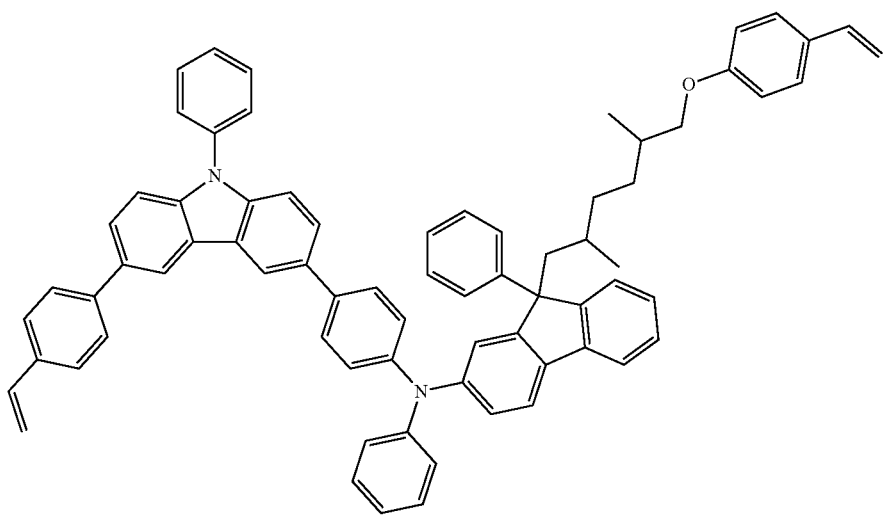
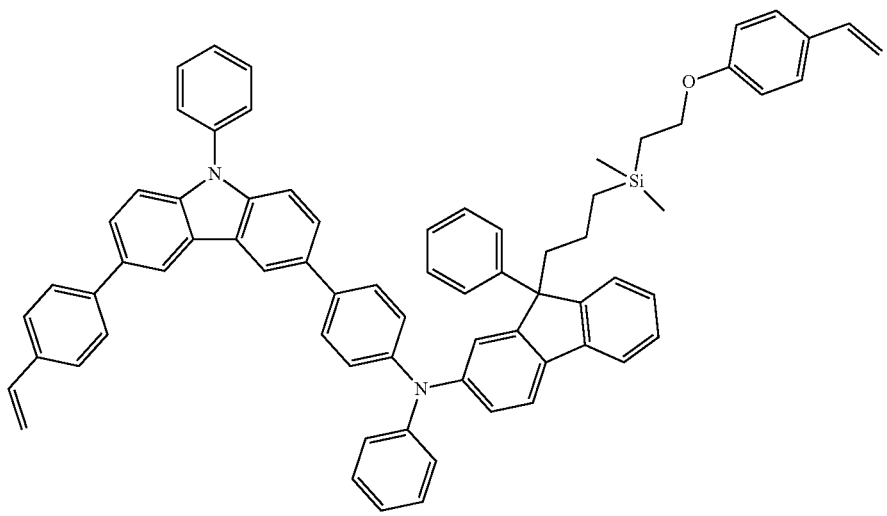

-continued
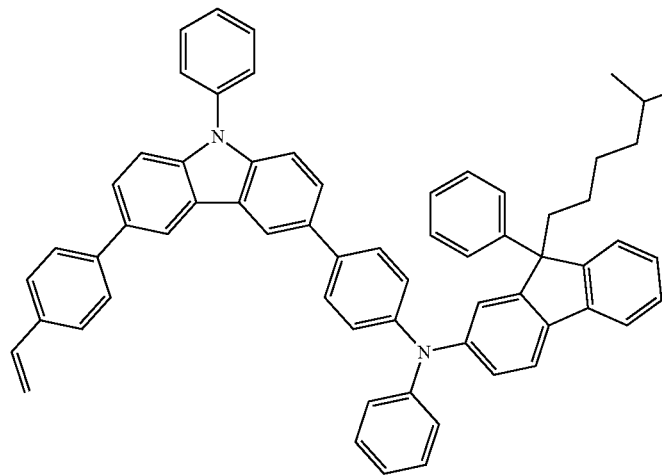
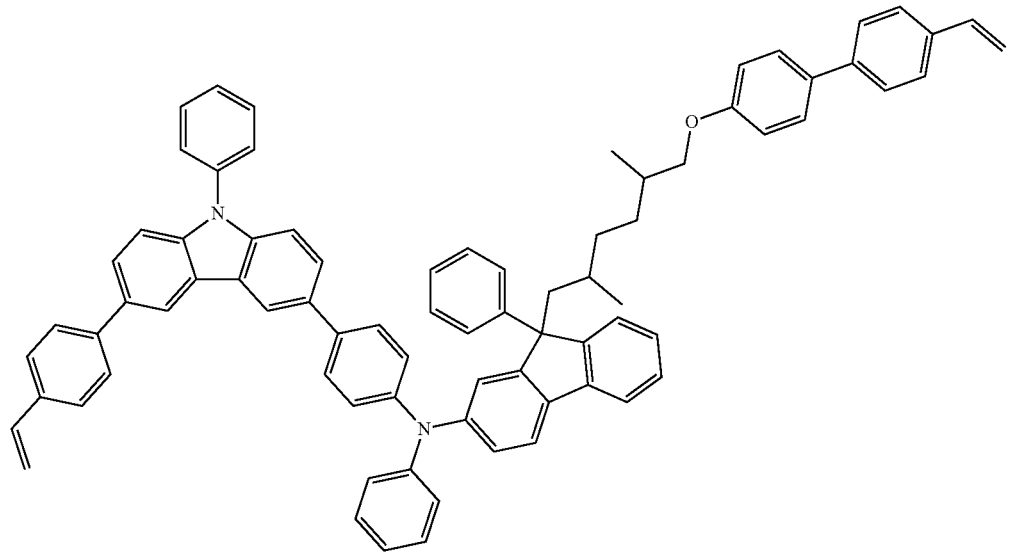
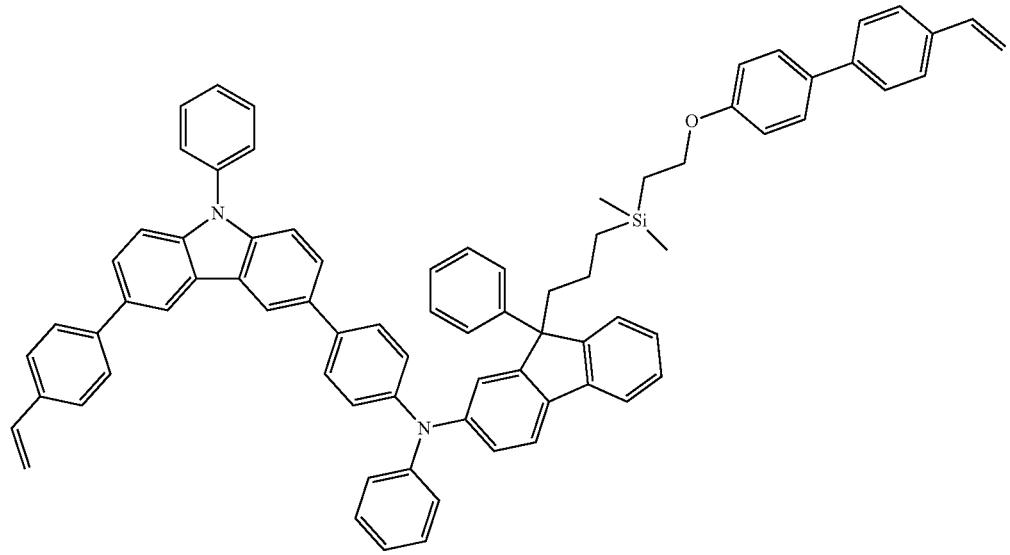

-continued
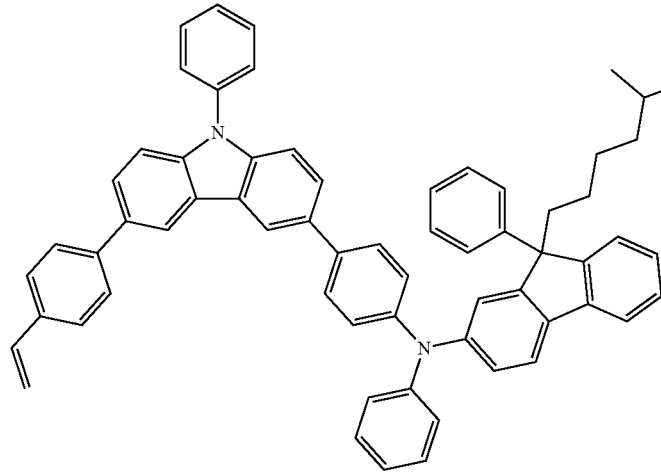
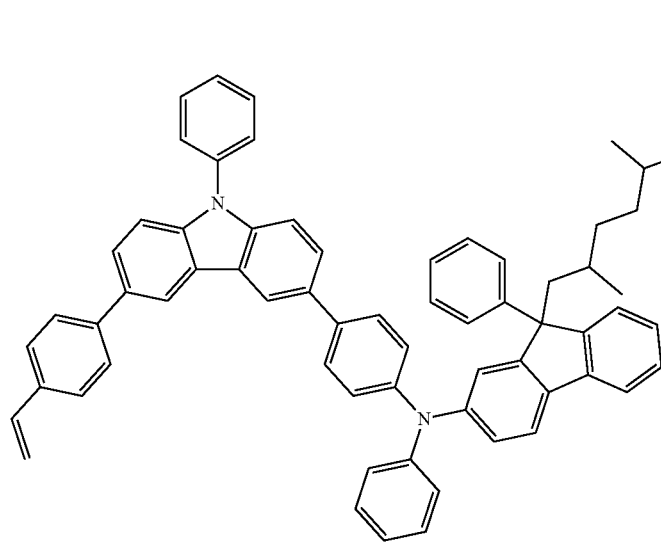
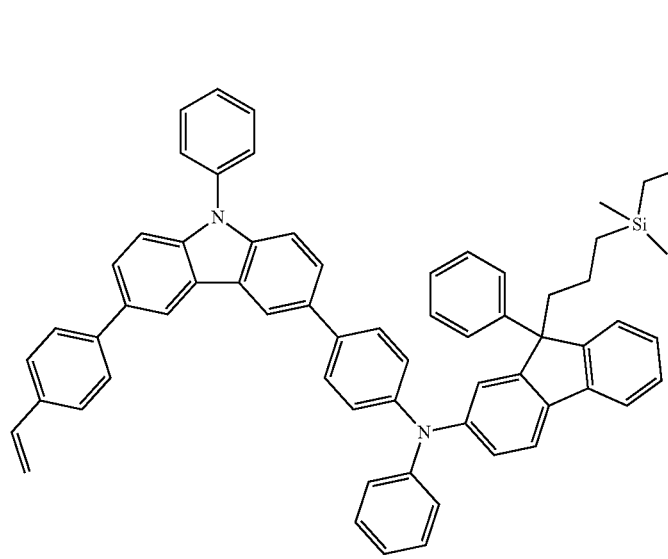

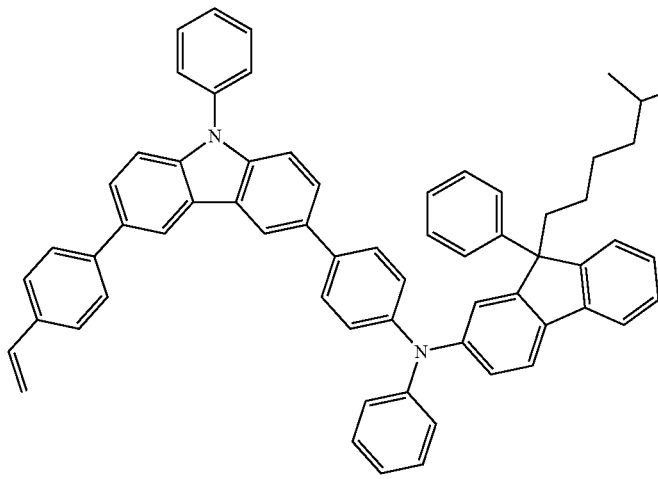
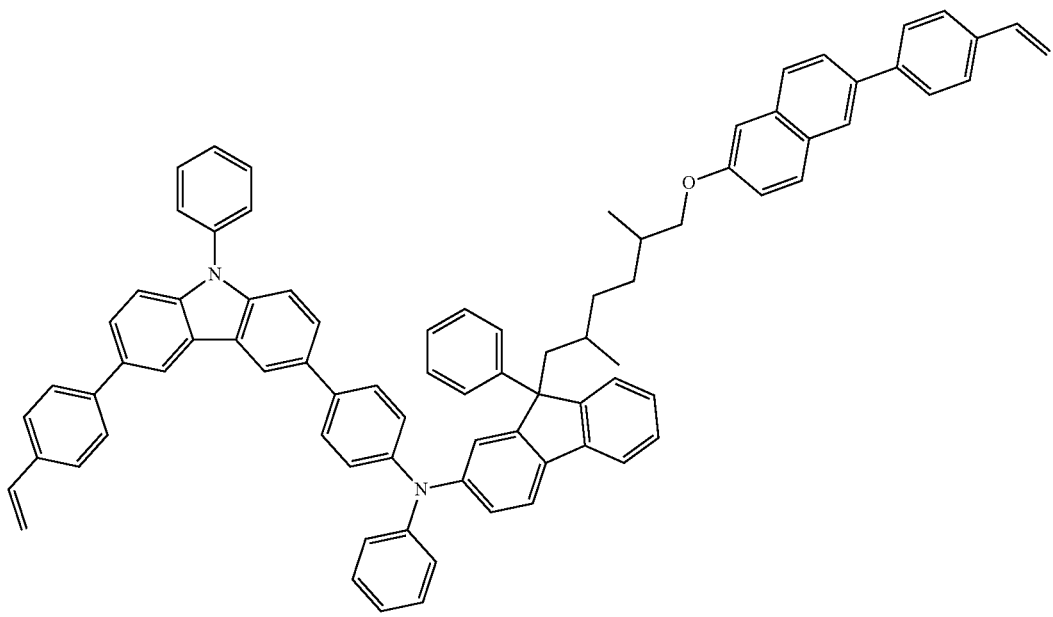

-continued
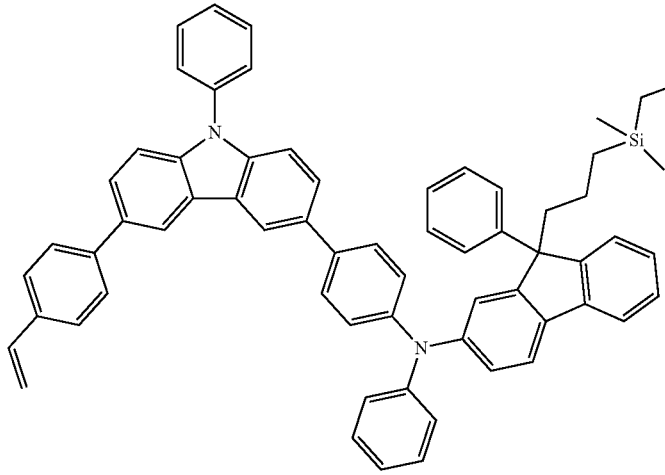
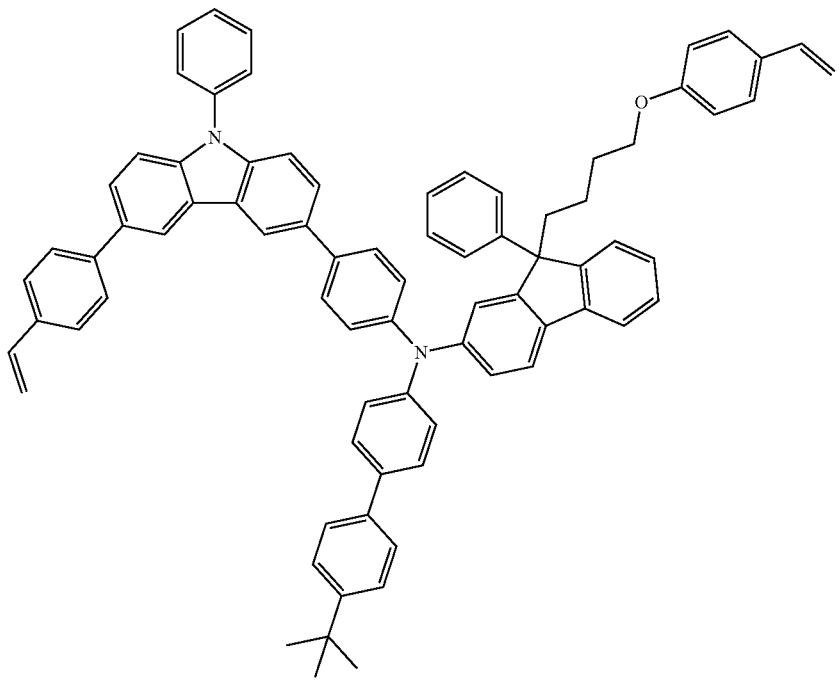

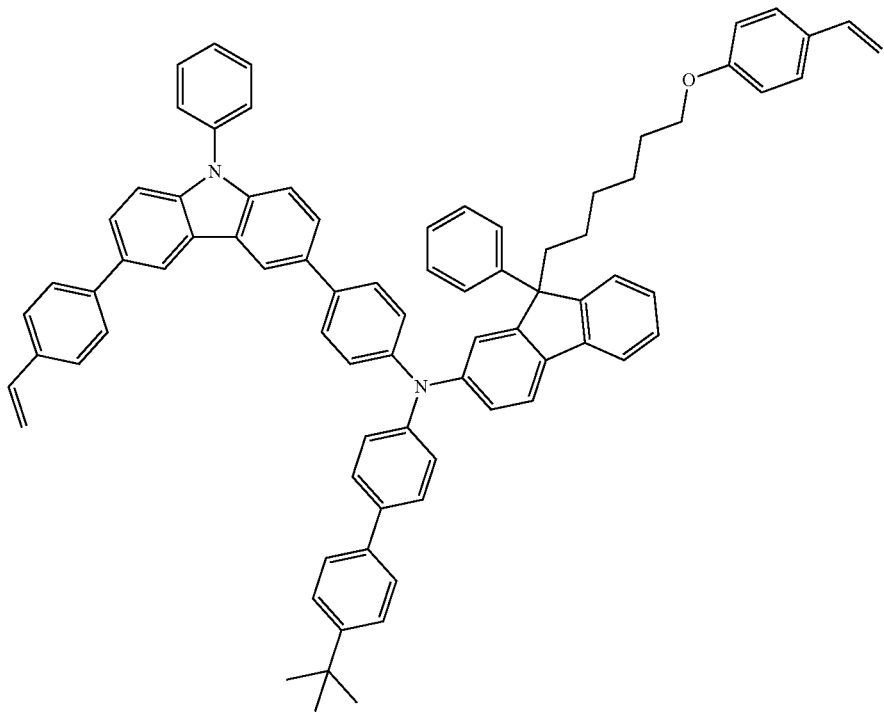 [SMILES: C=Cc1ccc(OCC[Si](C)(C)CCCC2(c3ccccc3)c3ccccc3-c3ccc(N(c4ccc(-c5ccc(C(C)(C)C)cc5)cc4)c4ccc(-c5ccc6c(c5)c5cc(-c7ccc(C=C)cc7)ccc5n6-c5ccccc5)cc4)cc32)cc1]
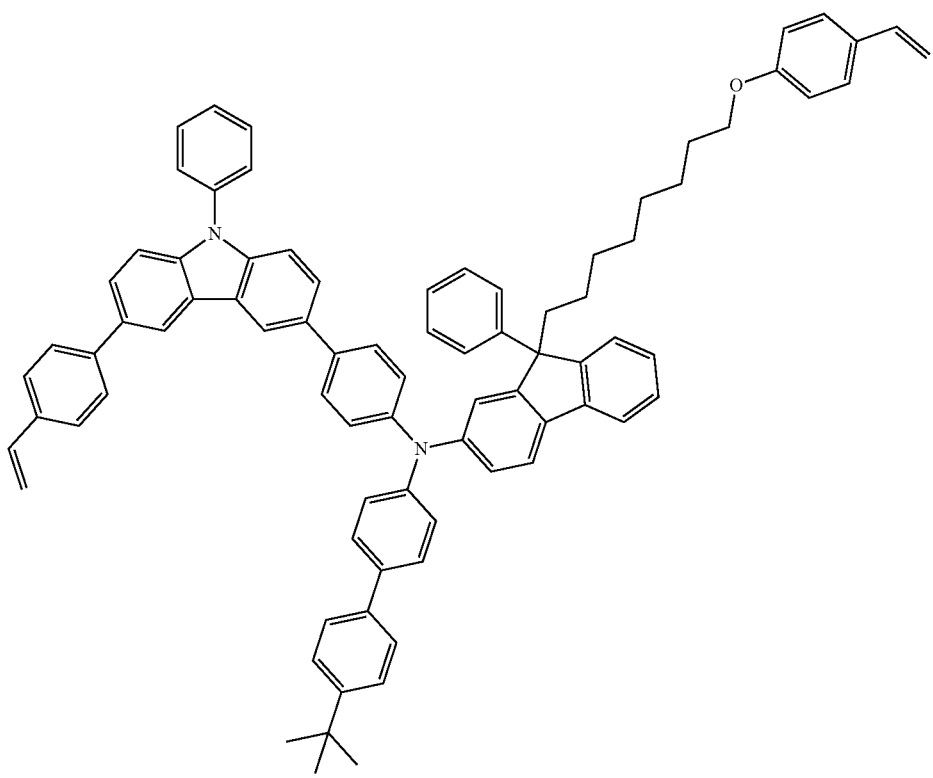

-continued
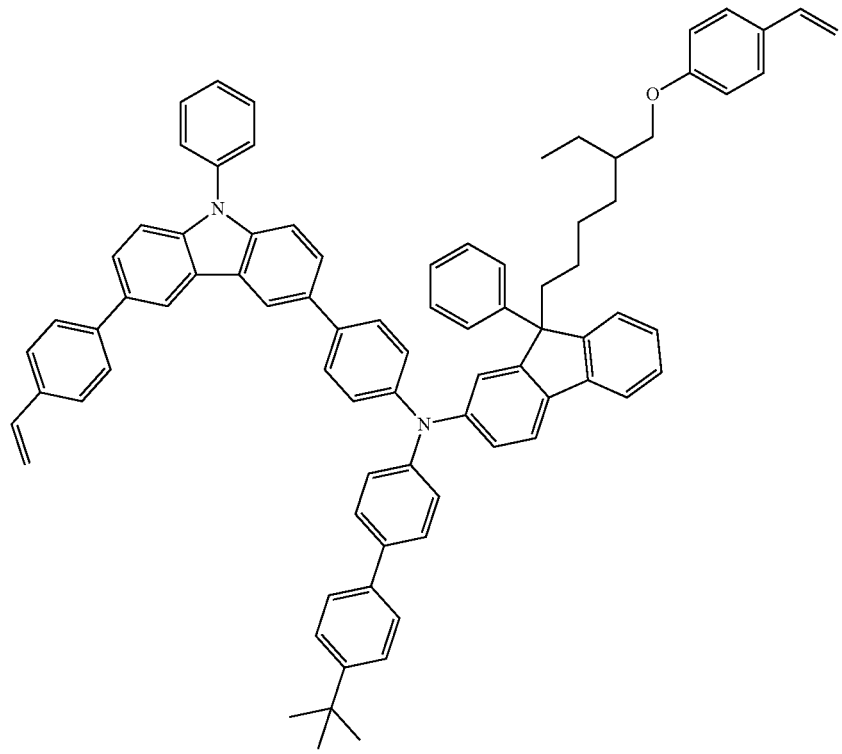
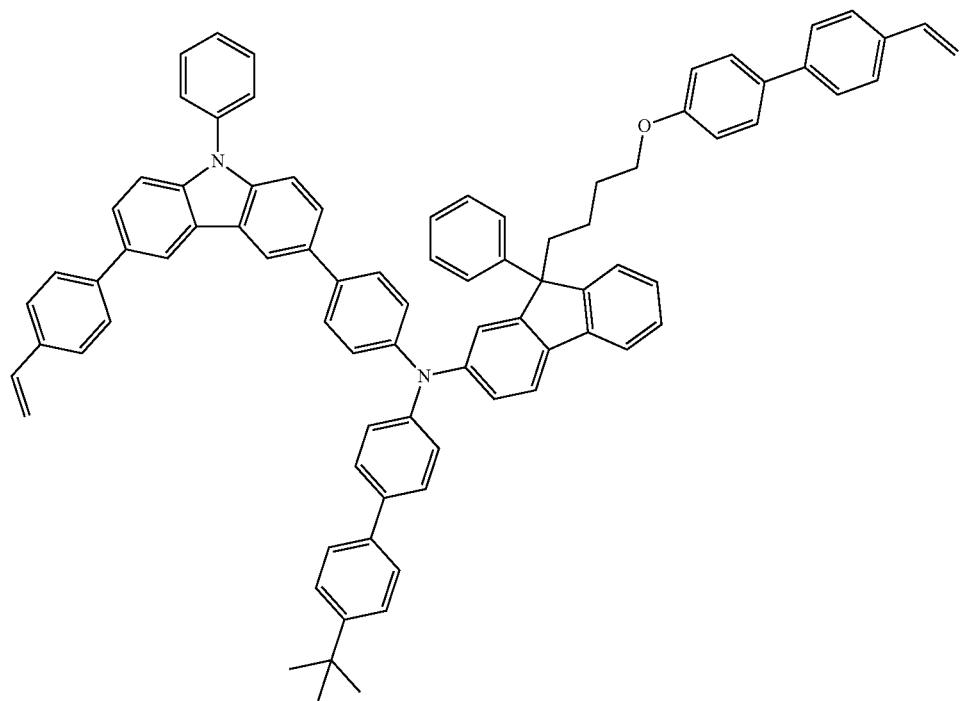

37 38
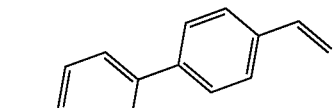
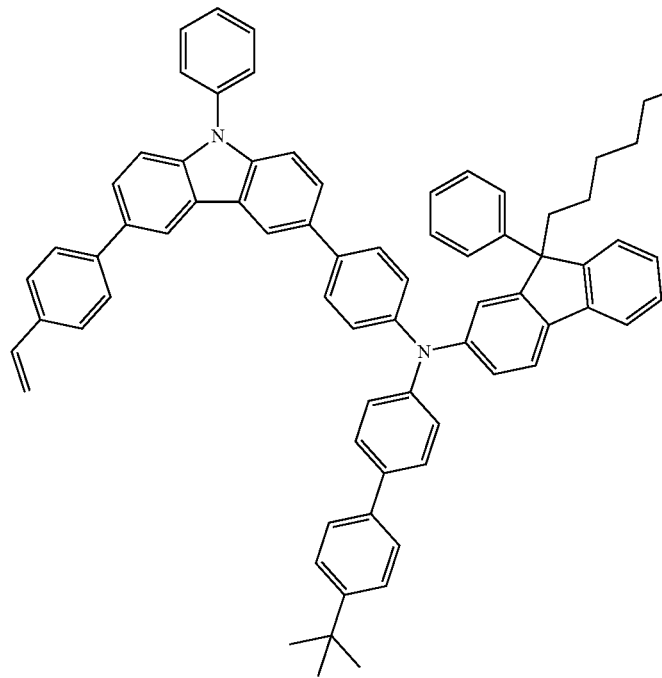
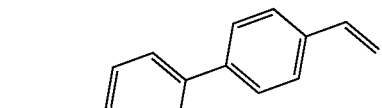
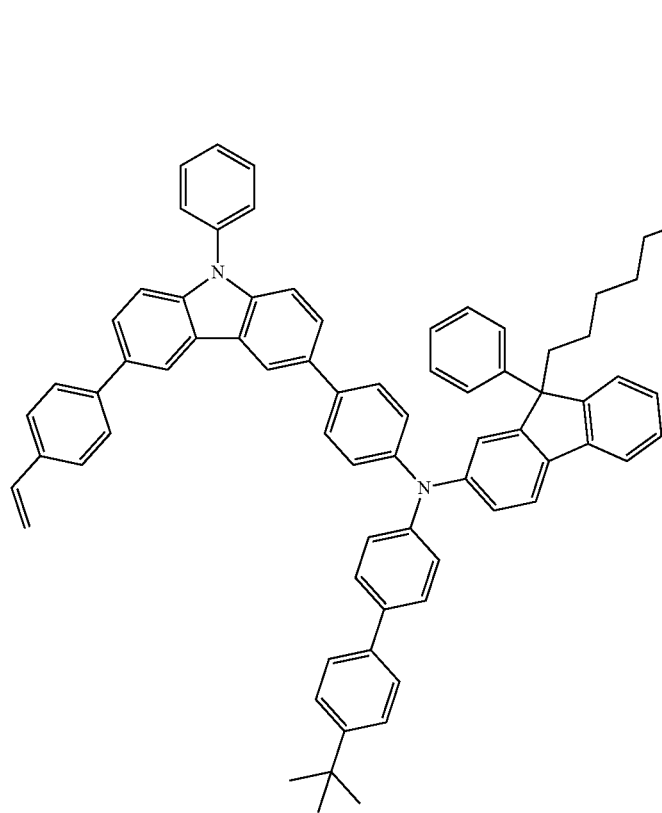

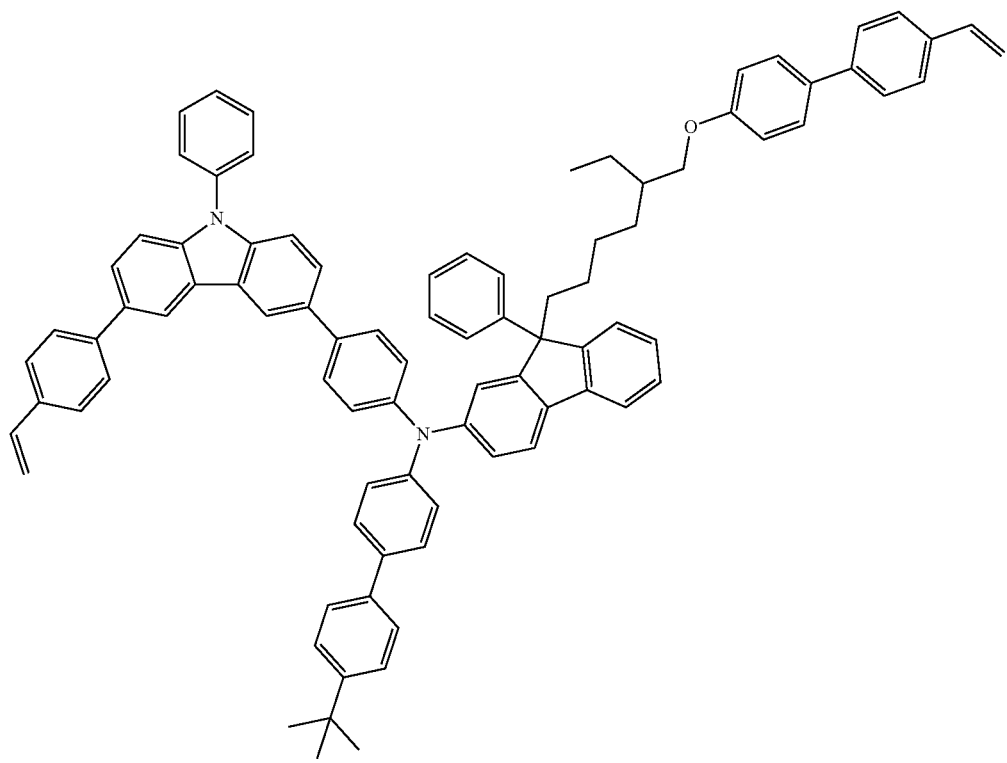 [SMILES: C=Cc1ccc(-c2ccc(OCC[Si](C)(C)CCCC3(c4ccccc4)c4ccccc4-c4ccc(N(c5ccc(-c6ccc(C(C)(C)C)cc6)cc5)c5ccc(-c6ccc7c(c6)c6cc(-c8ccc(C=C)cc8)ccc6n7-c6ccccc6)cc5)cc43)cc2)cc1]
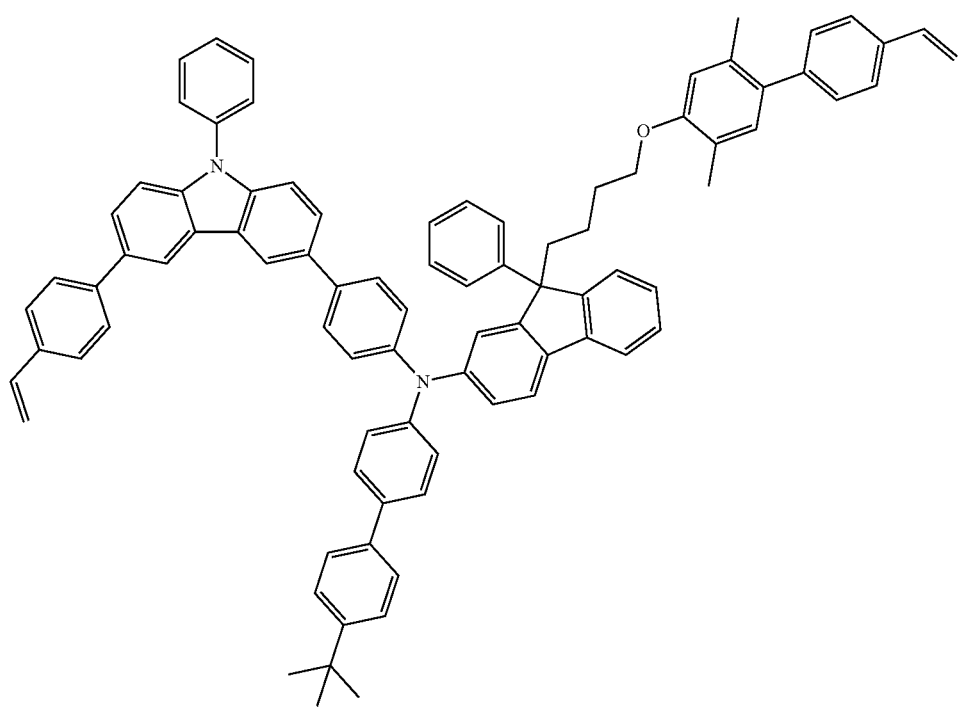

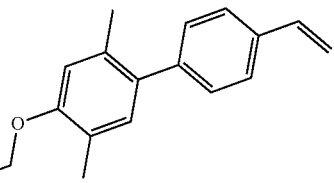
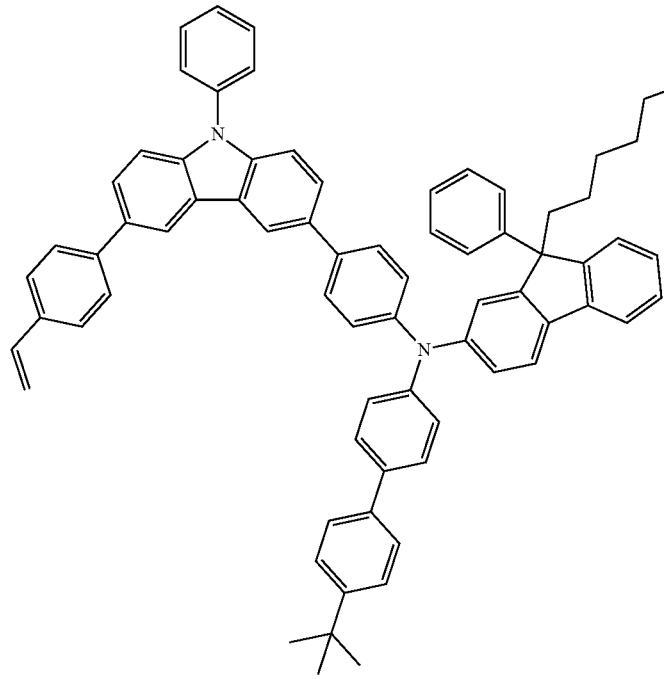
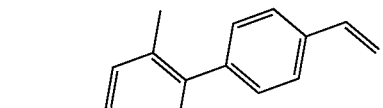
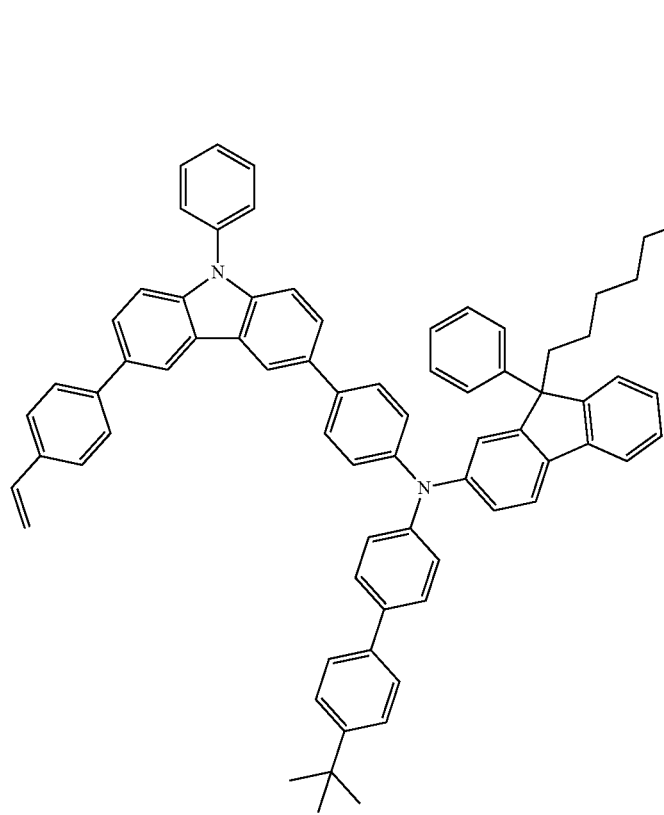

-continued
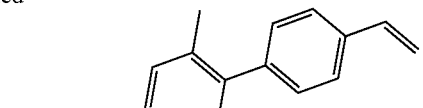
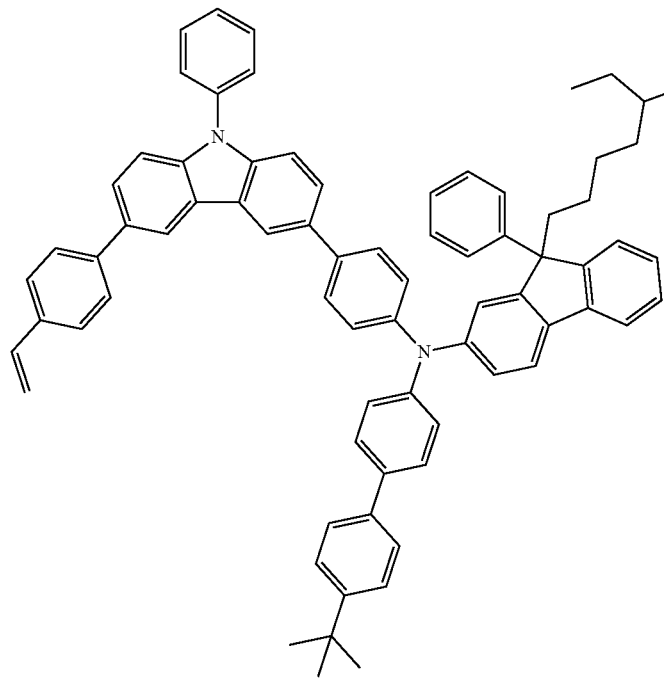
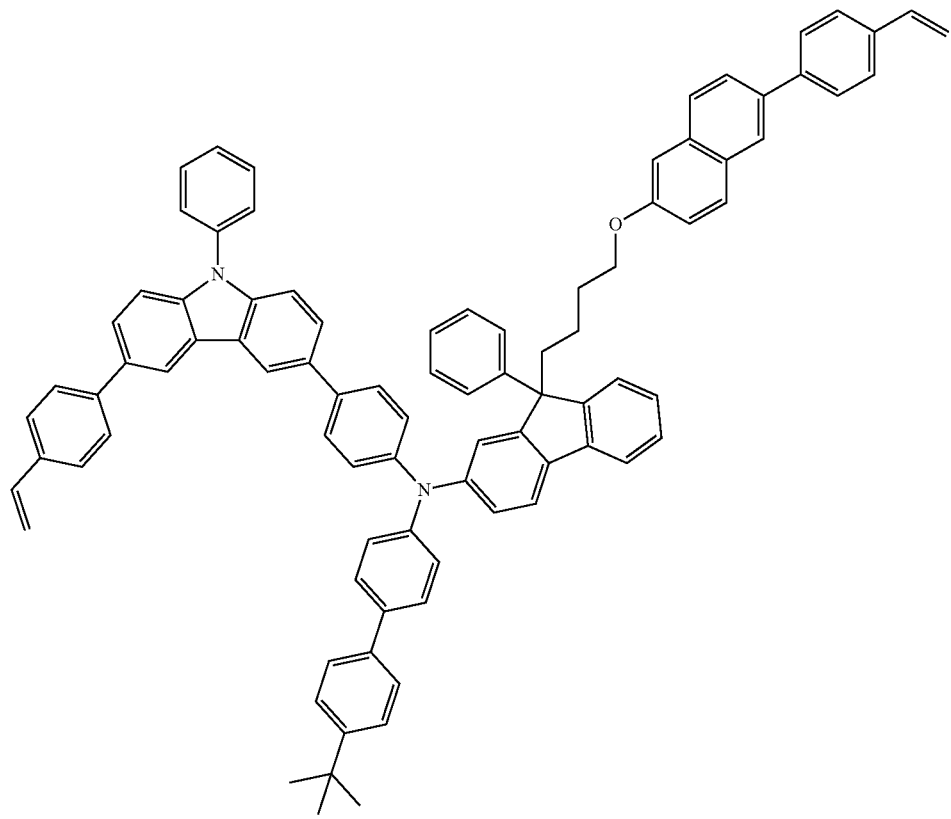

-continued
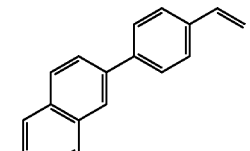
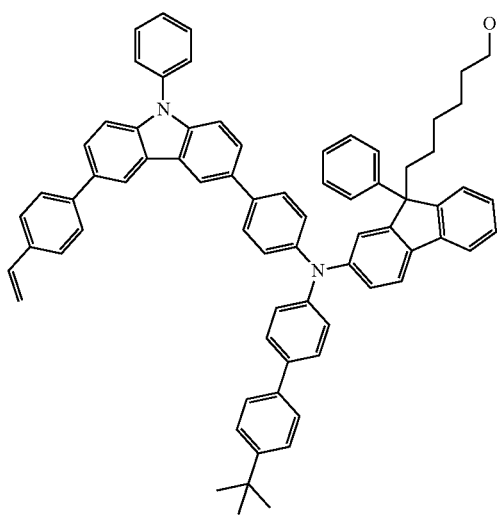
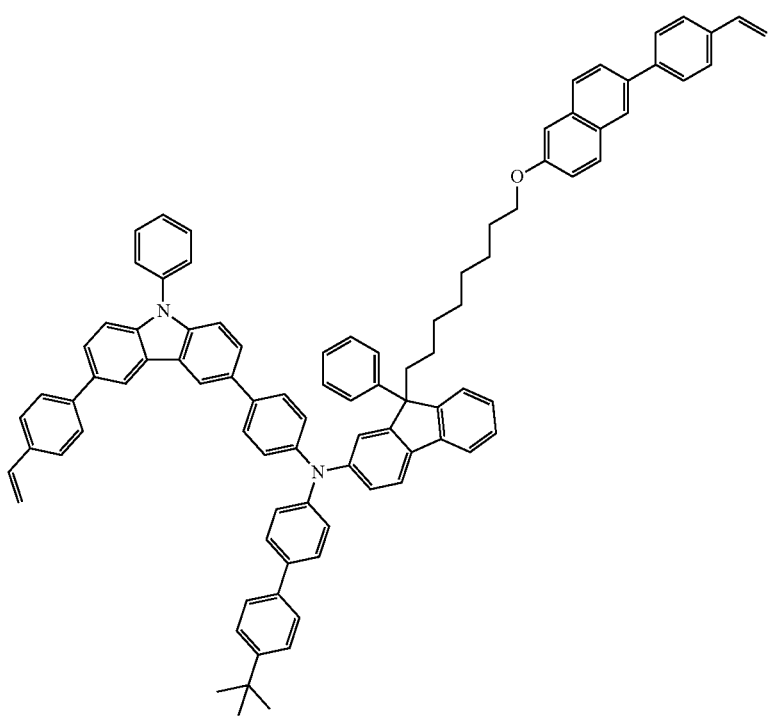

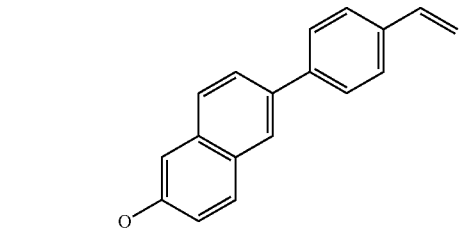
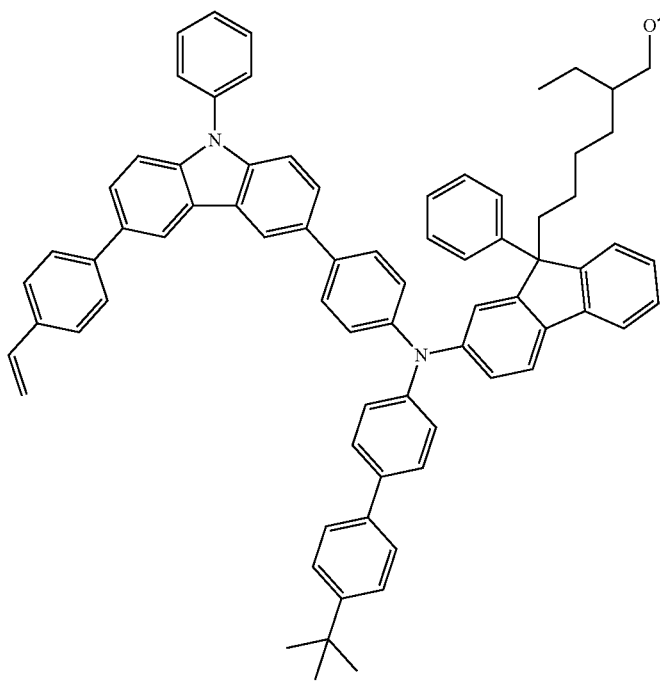
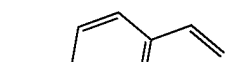
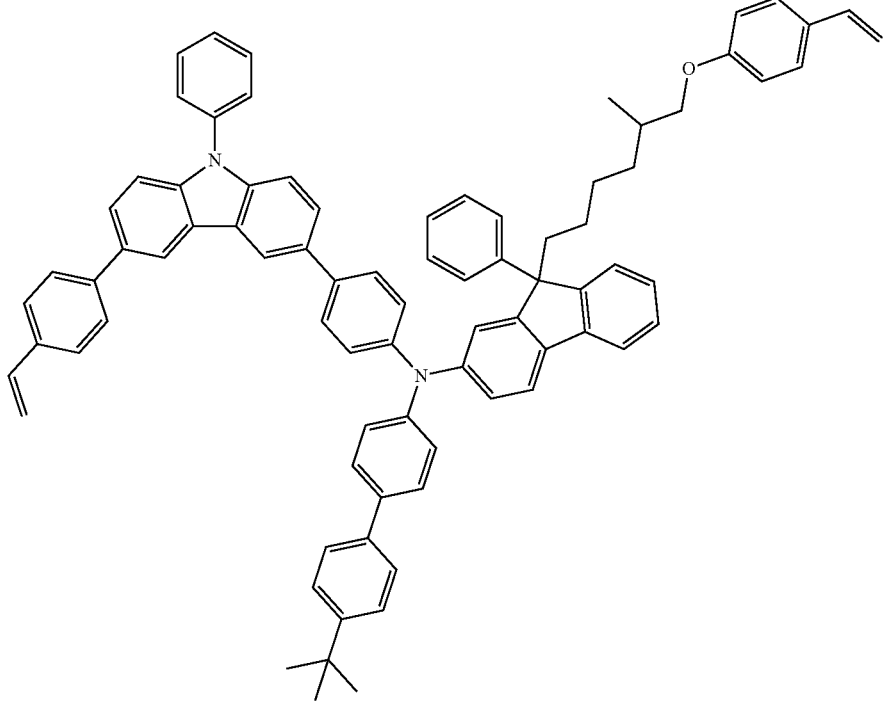

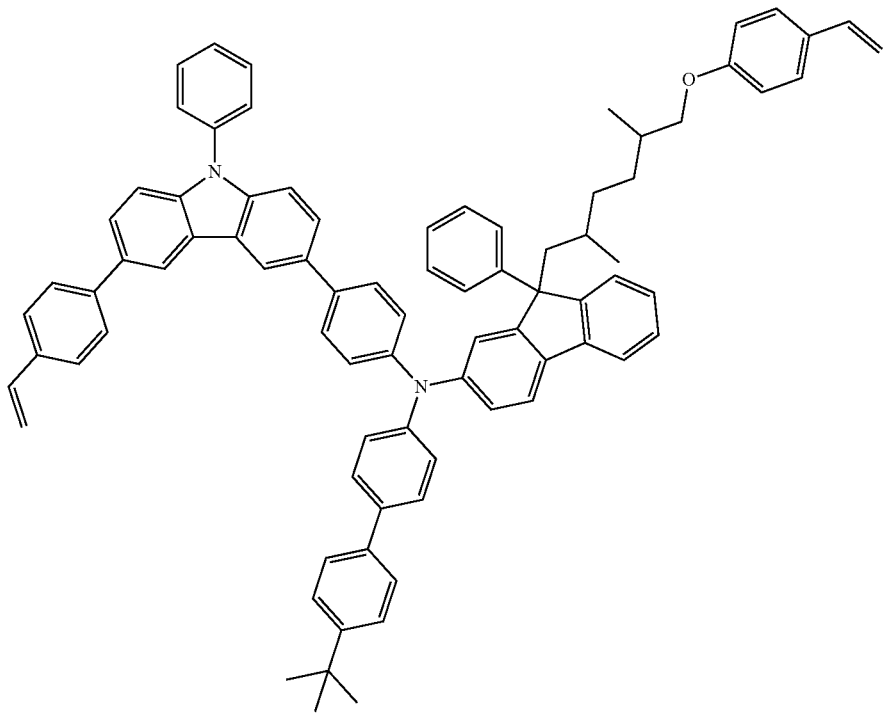
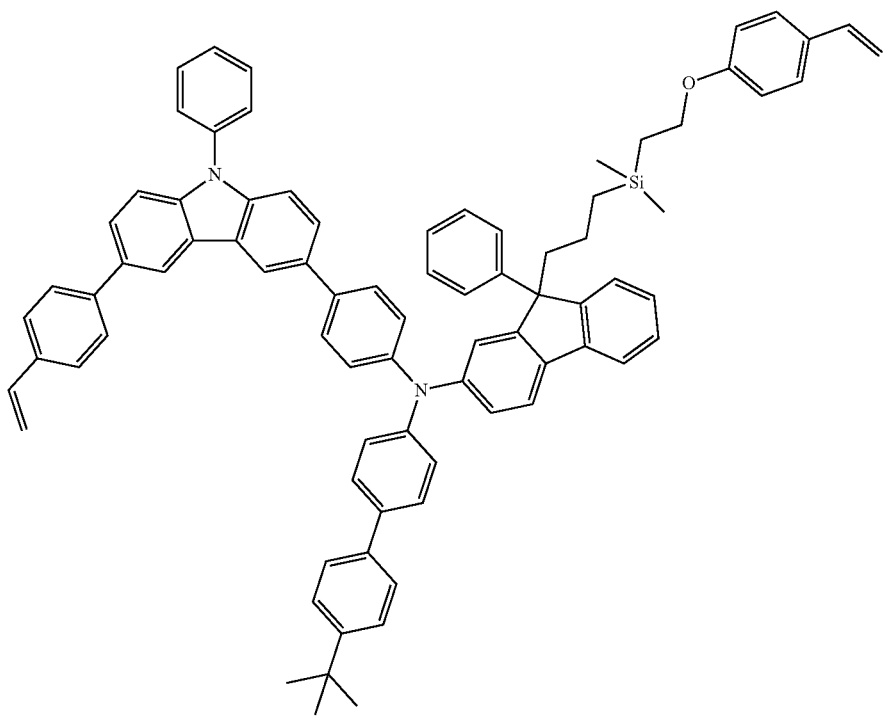

51
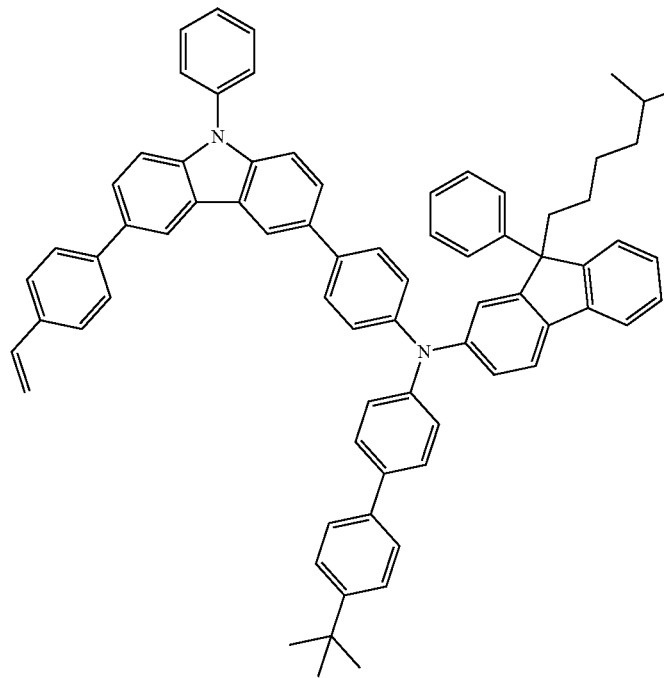
52
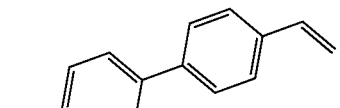
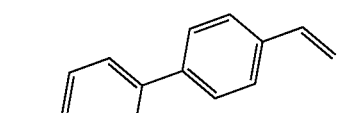
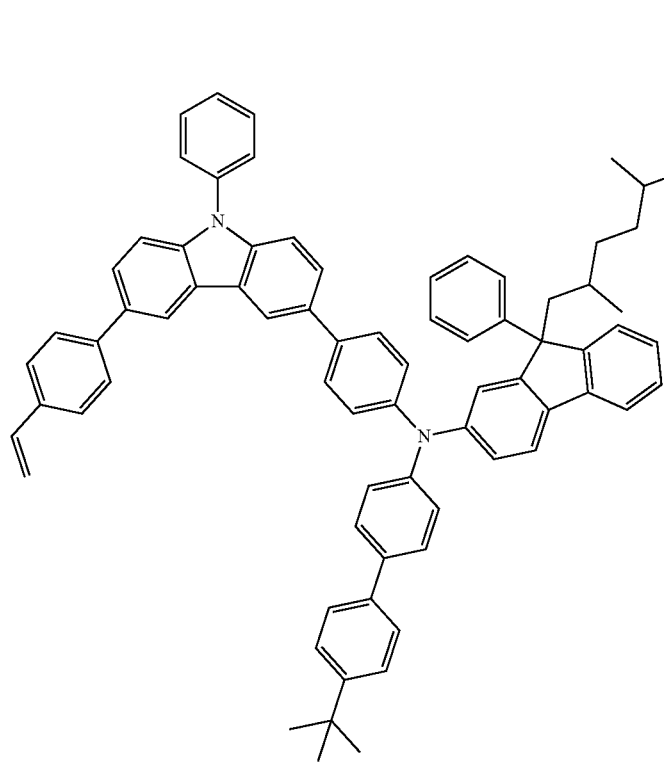

53 54
-continued
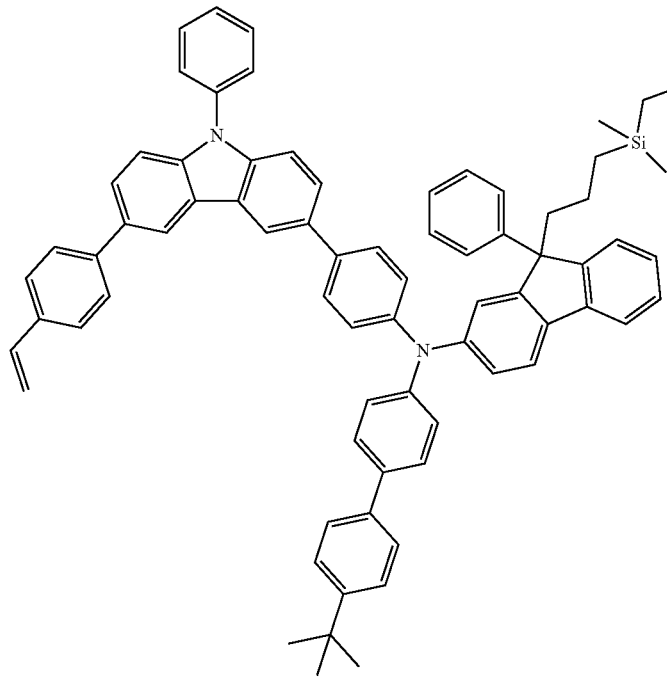
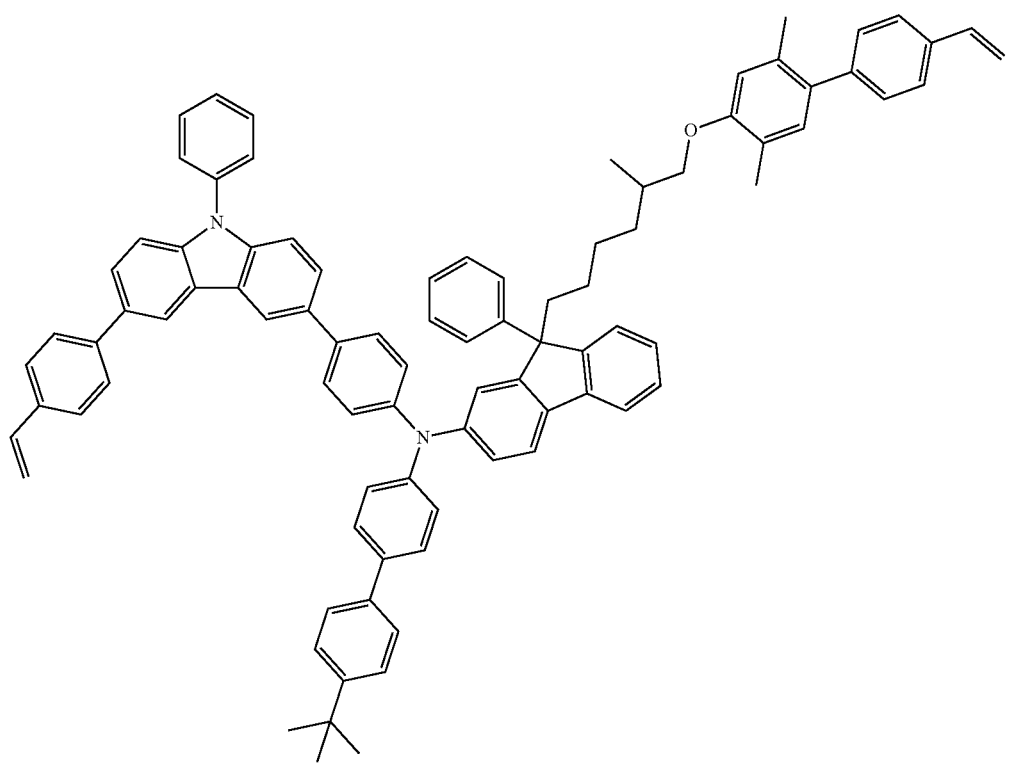

55
-continued
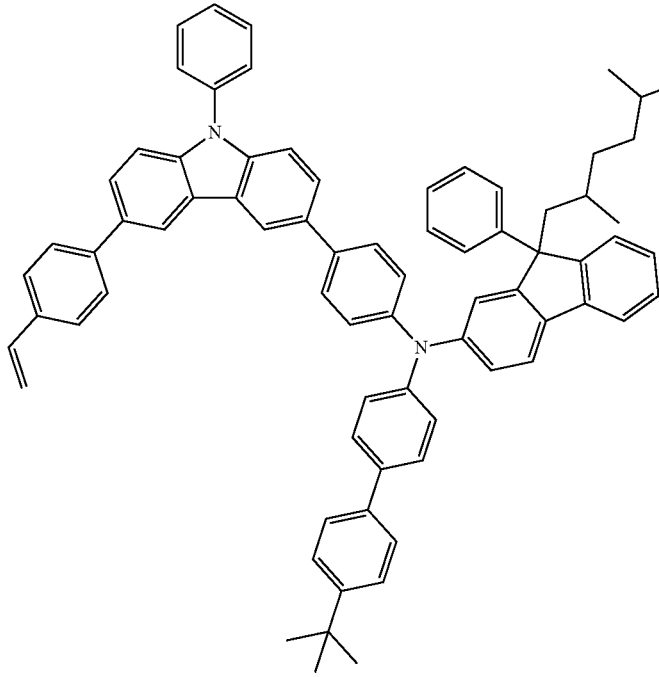
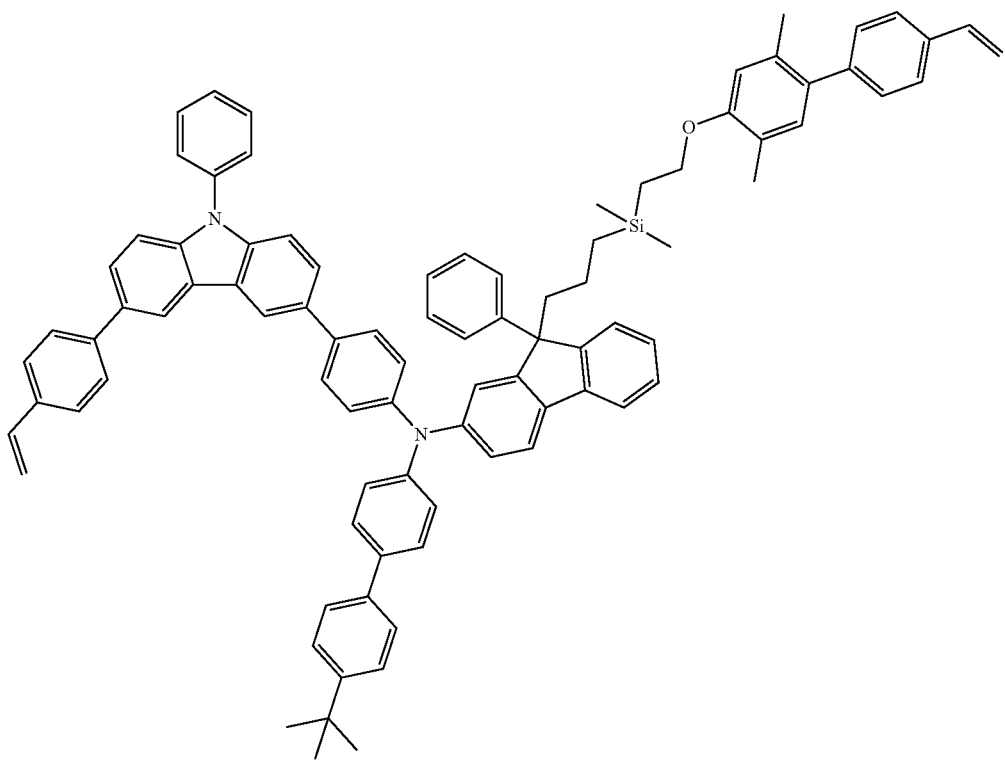 [SMILES: C=Cc1ccc(-c2ccc3c(c2)c2cc(-c4ccc(N(c5ccc(-c6ccc(C(C)(C)C)cc6)cc5)c5ccc6c(c5)C(CCC[Si](C)(C)CCOc5cc(C)c(-c7ccc(C=C)cc7)cc5C)(c5ccccc5)c5ccccc5-6)cc4)ccc2n3-c2ccccc2)cc1]

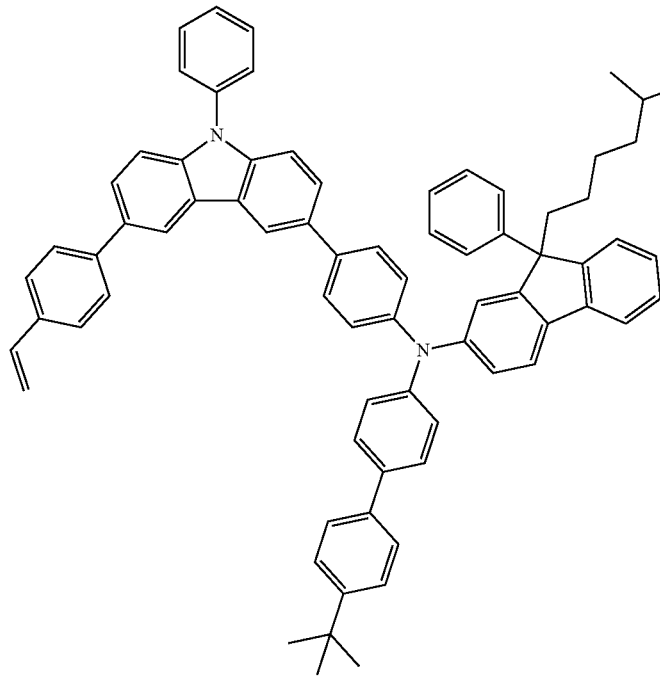
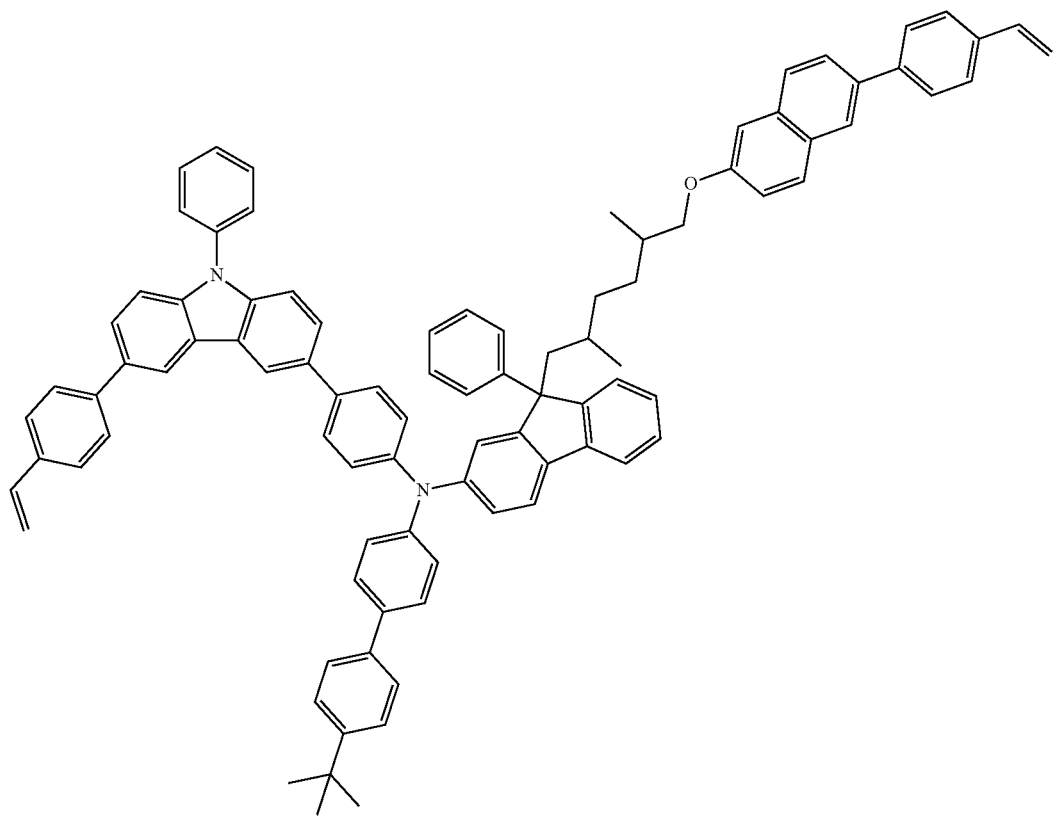 [SMILES: C=Cc1ccc(-c2ccc3cc(OCC[Si](C)(C)CCCC4(c5ccccc5)c5ccccc5-c5ccc(N(c6ccc(-c7ccc(C(C)(C)C)cc7)cc6)c6ccc(-c7ccc8c(c7)c7cc(-c9ccc(C=C)cc9)ccc7n8-c7ccccc7)cc6)cc54)ccc3c2)cc1]

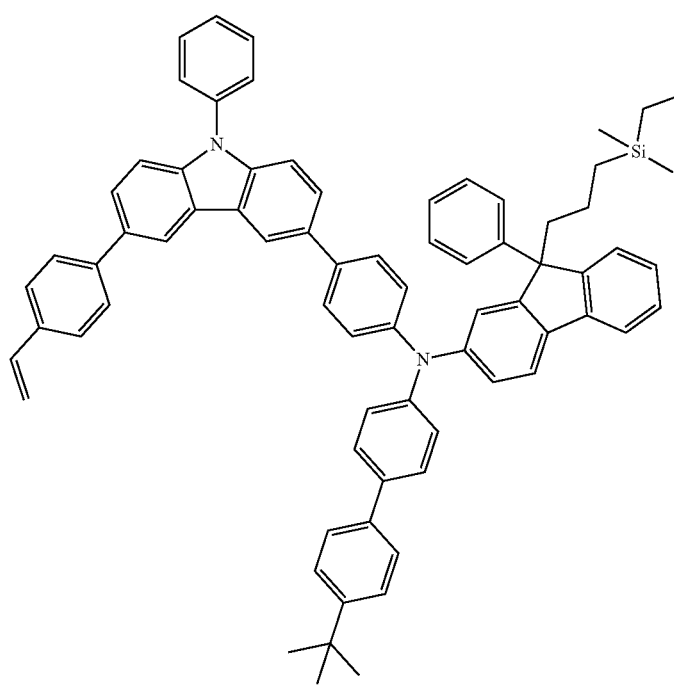
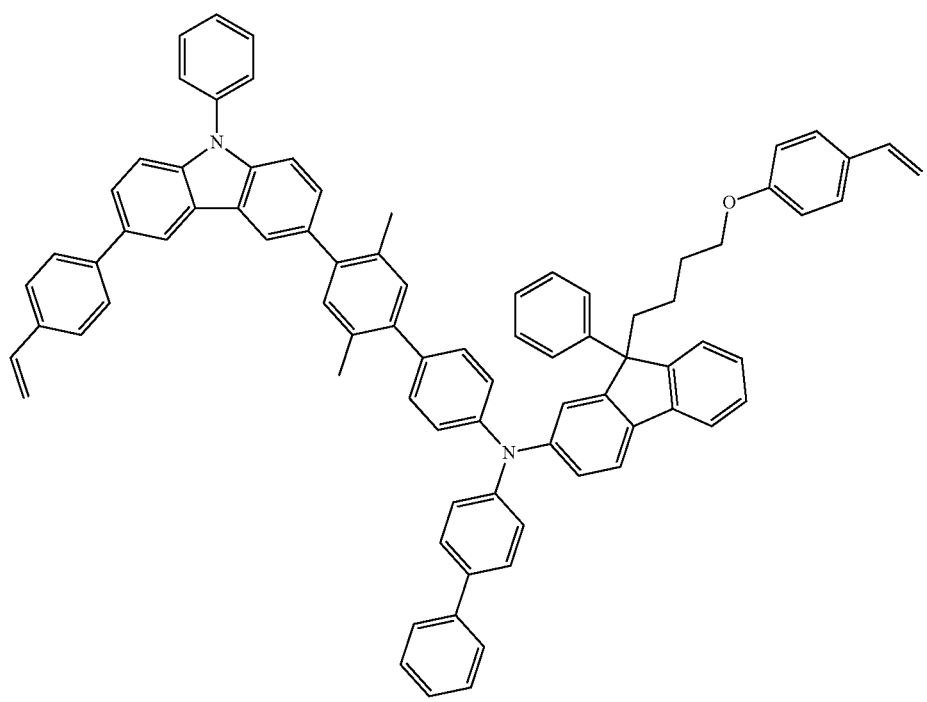

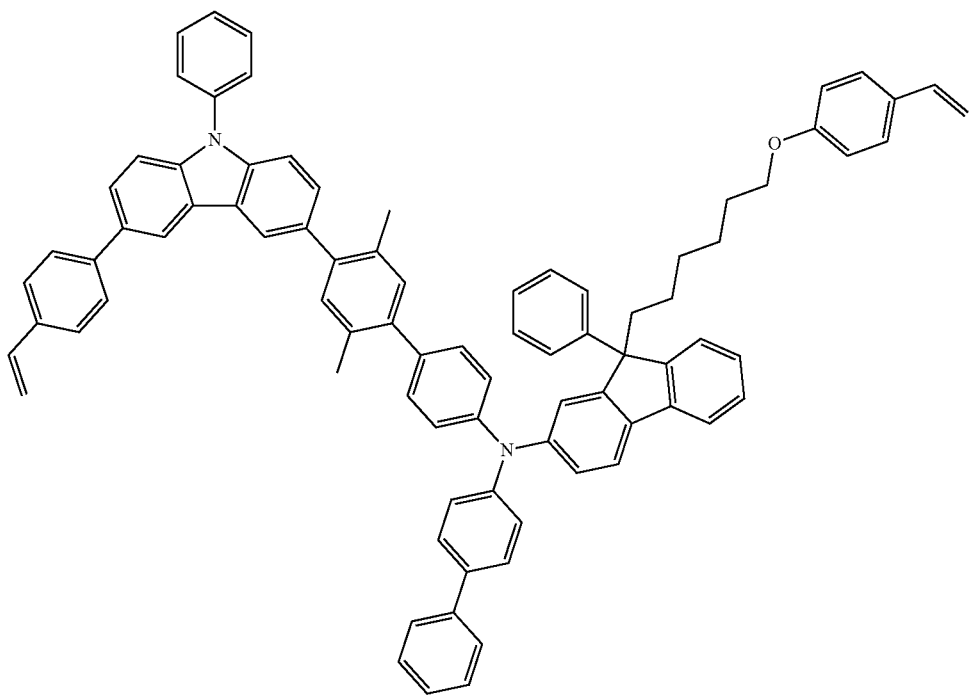
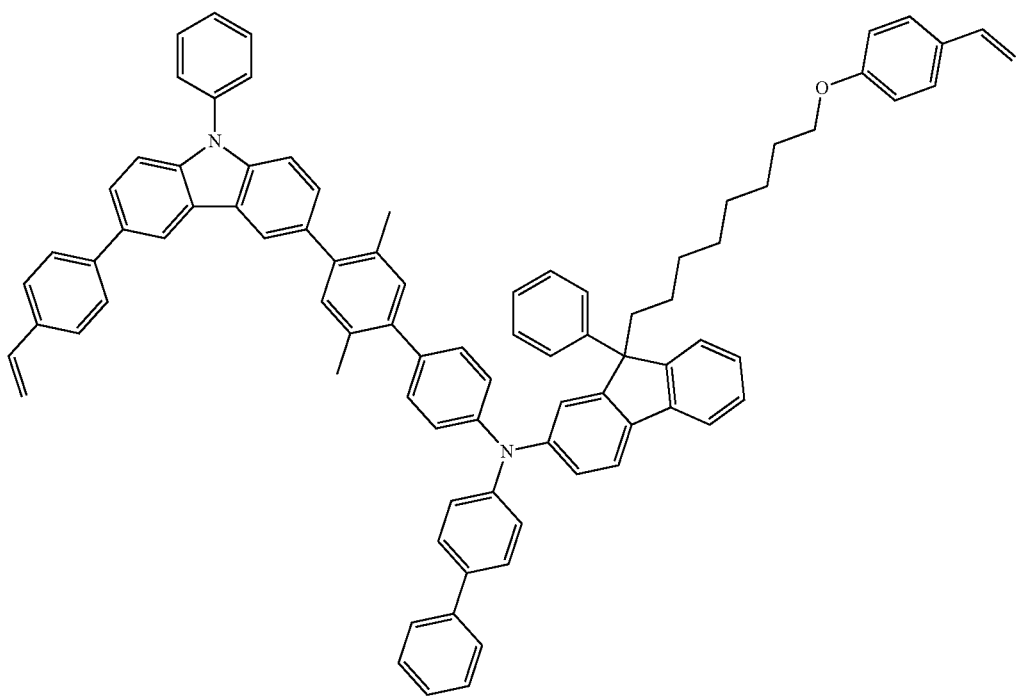

63 64
-continued
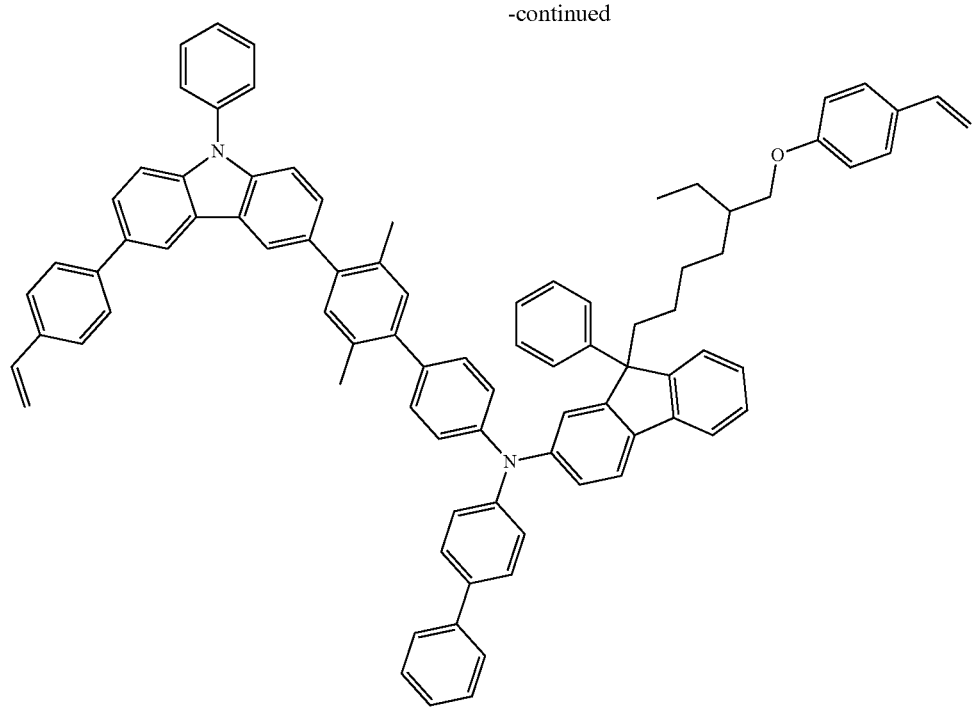
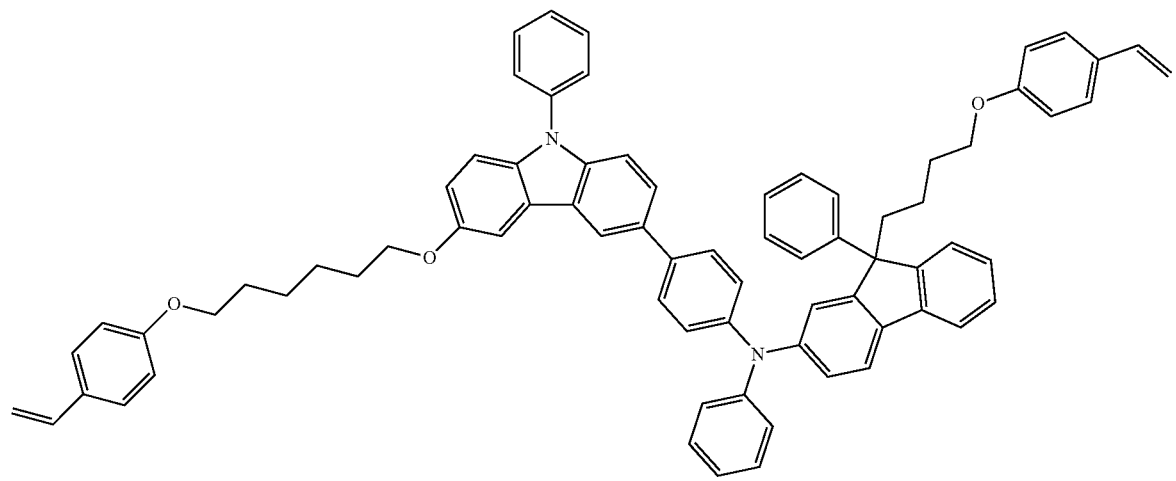
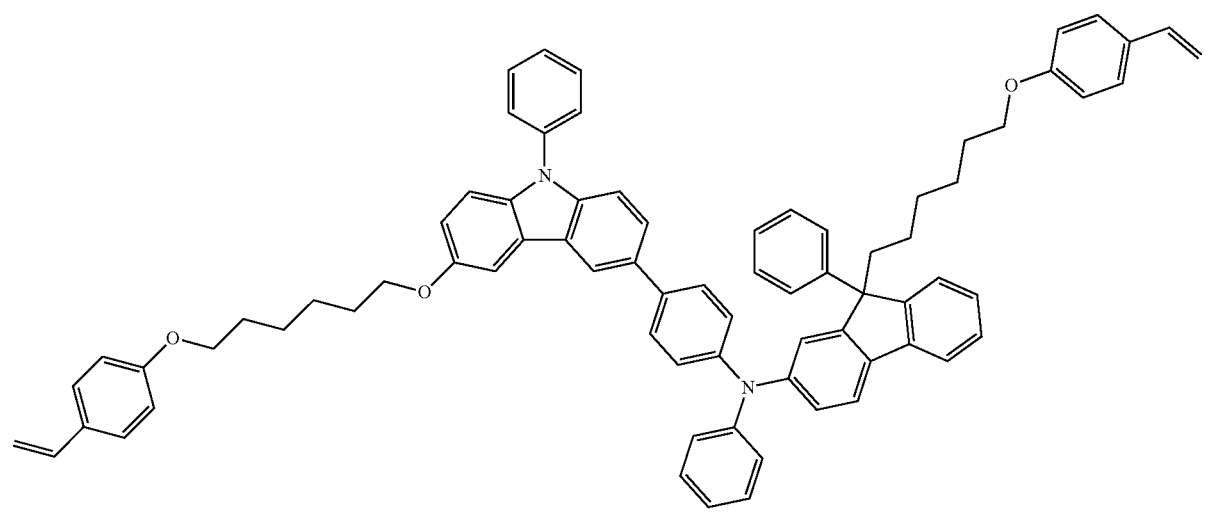

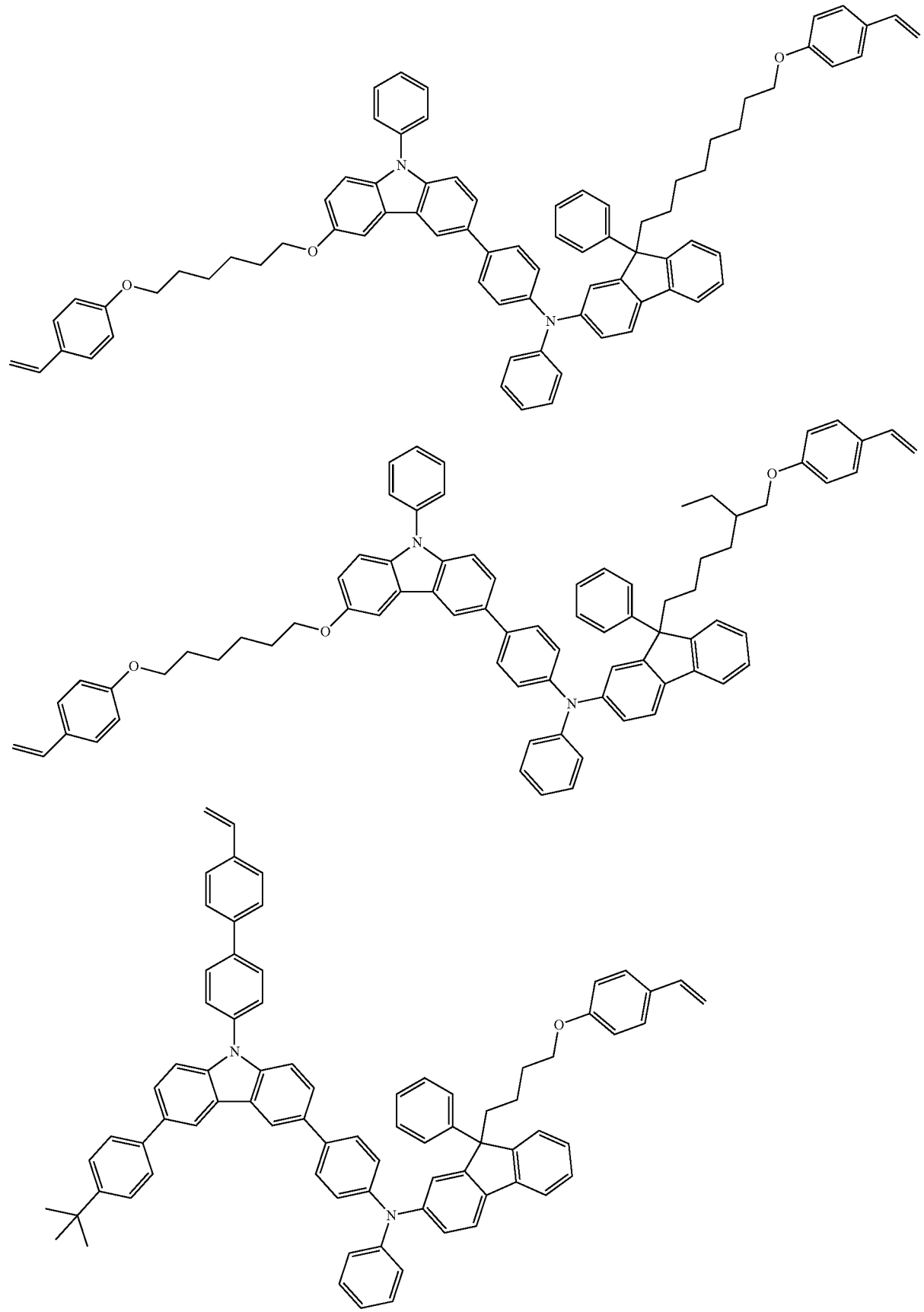

-continued
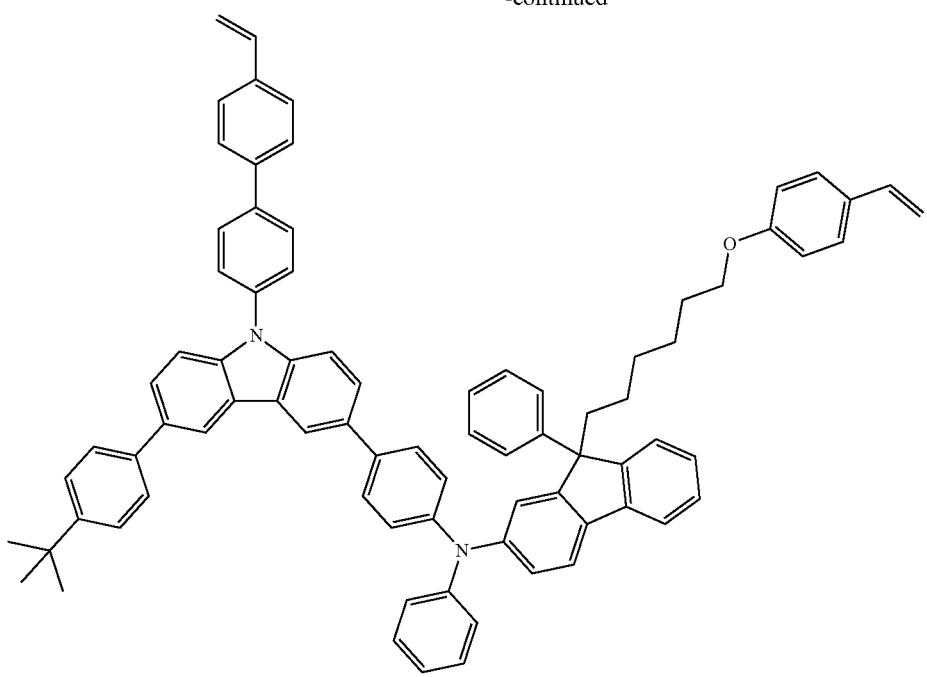
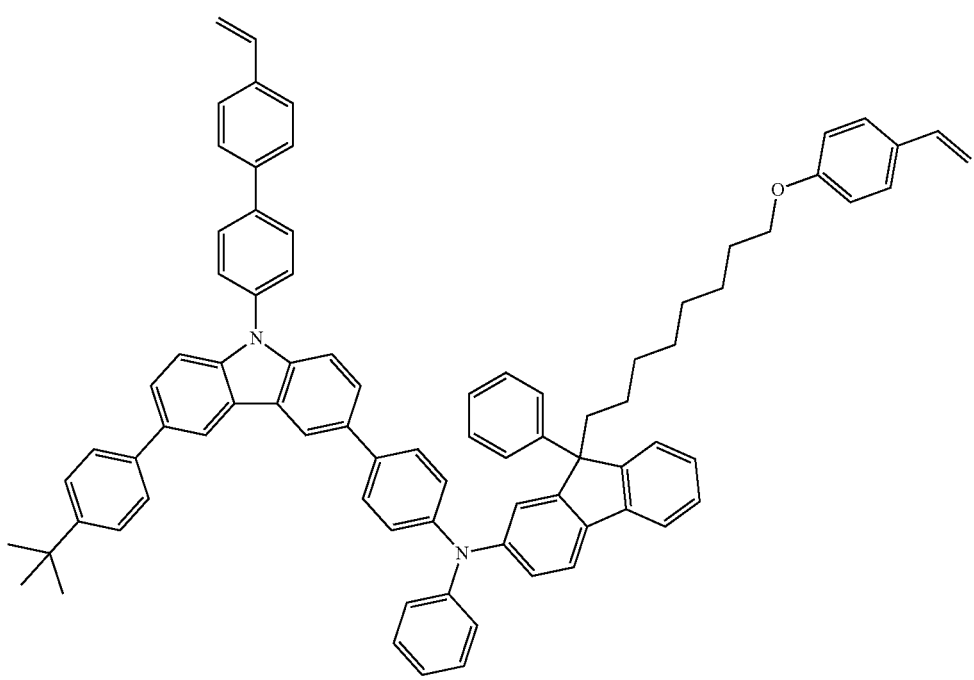

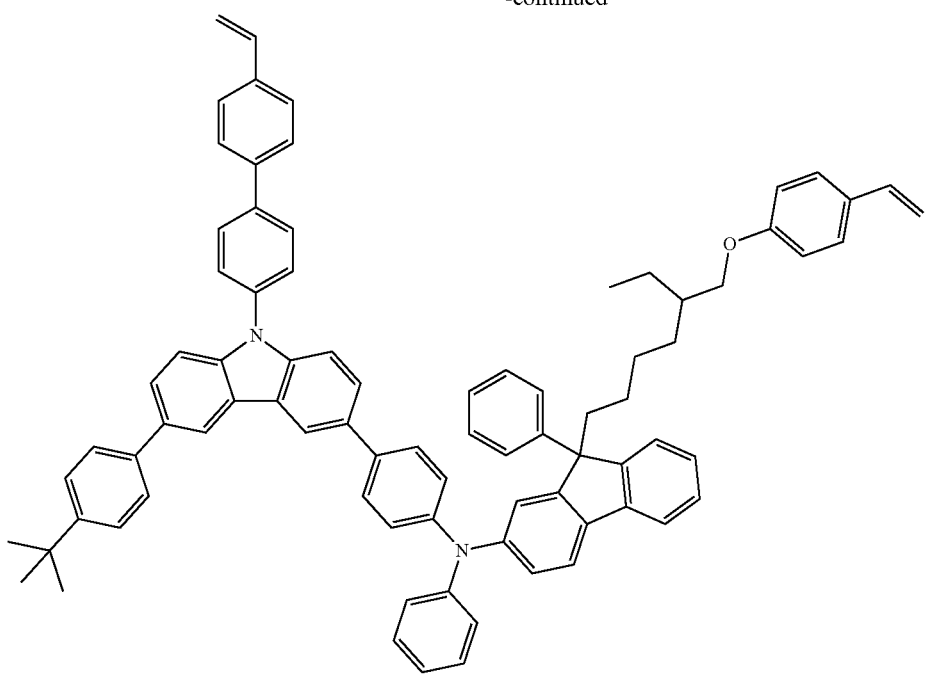
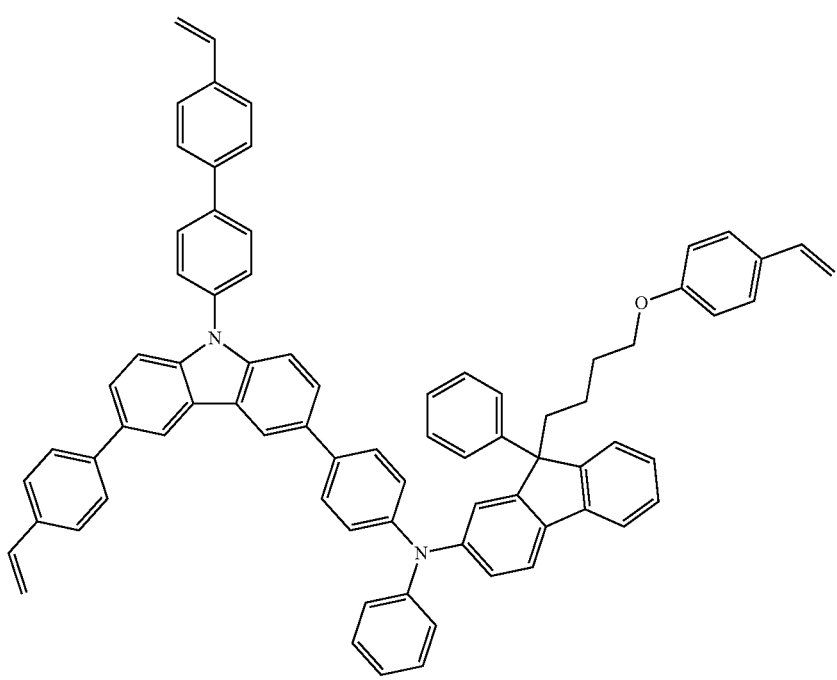

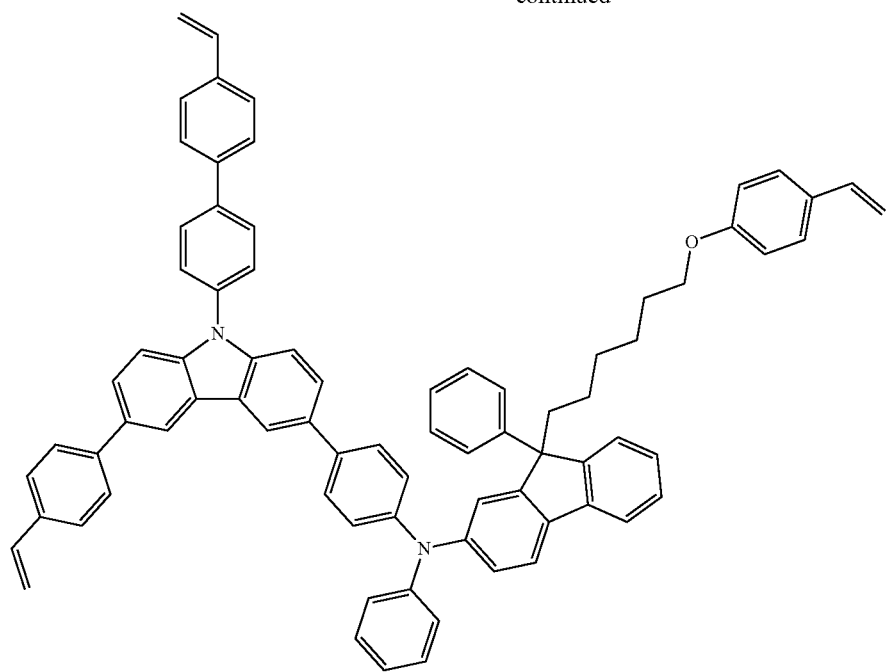
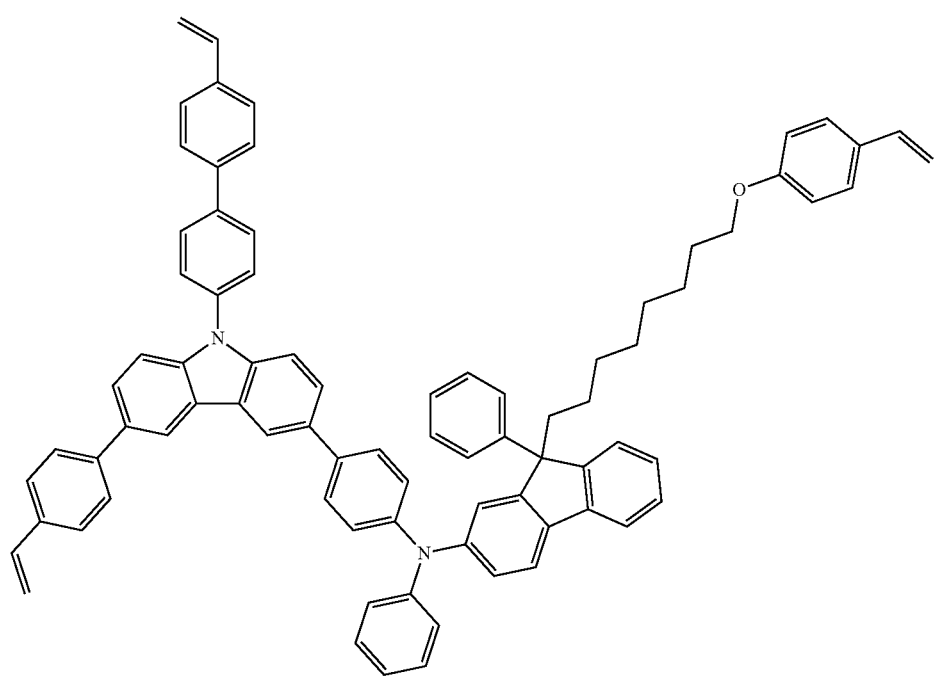

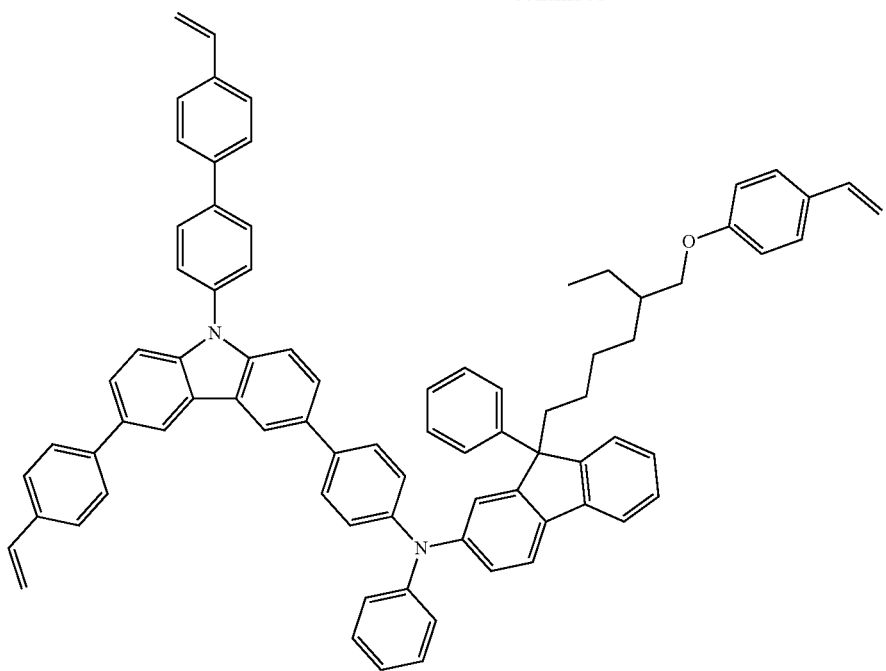
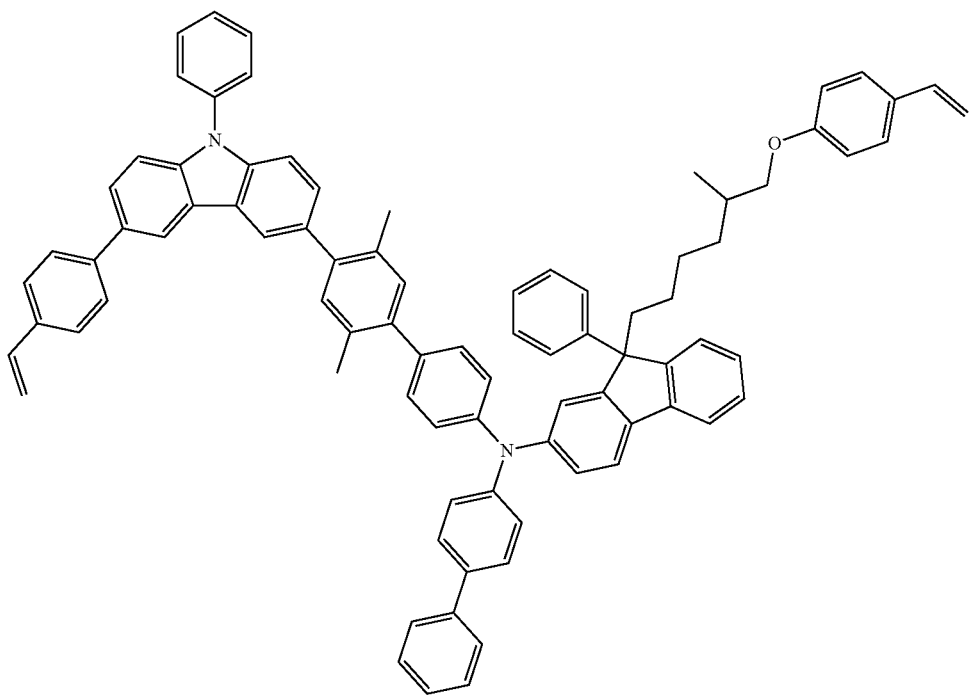

-continued
75
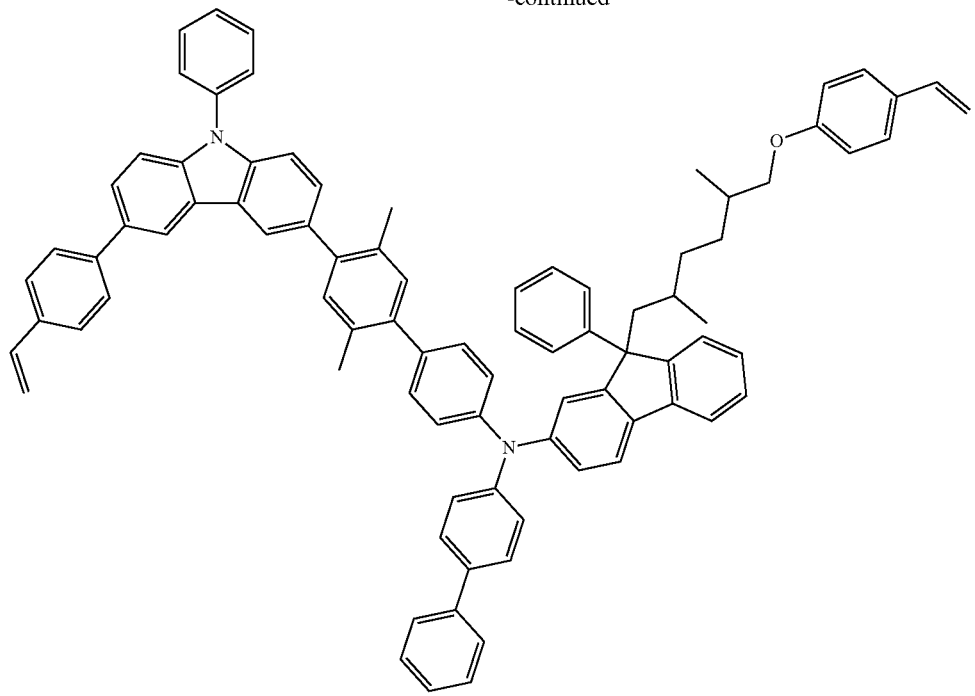
76
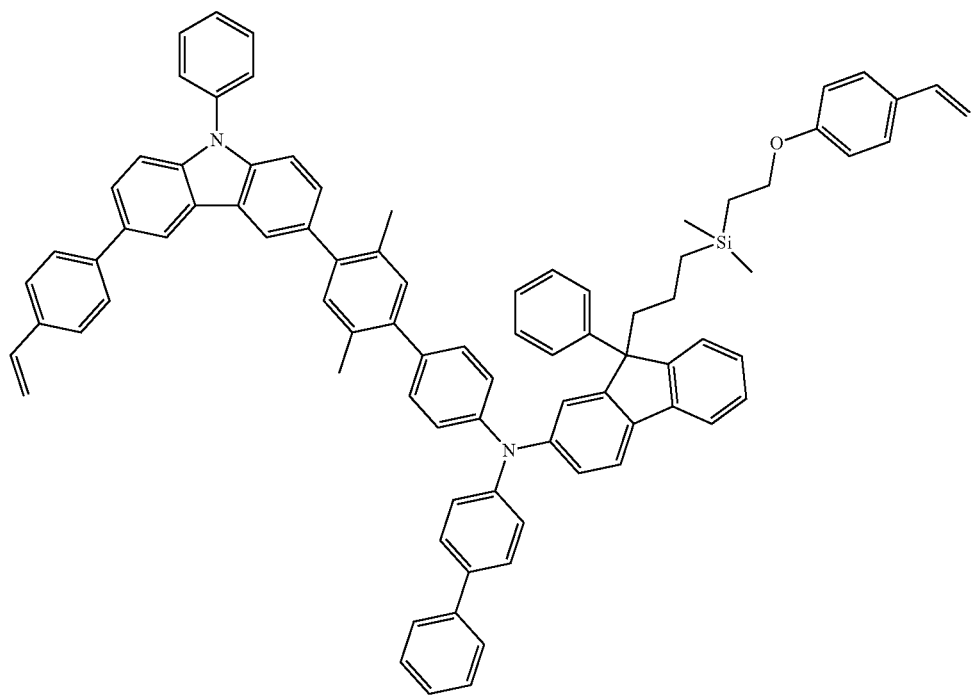 [SMILES: C=Cc1ccc(OCC[Si](C)(C)CCCC2(c3ccccc3)c3ccccc3-c3ccc(N(c4ccc(-c5ccccc5)cc4)c4ccc(-c5cc(C)c(-c6ccc7c(c6)c6cc(-c8ccc(C=C)cc8)ccc6n7-c6ccccc6)cc5C)cc4)cc32)cc1]

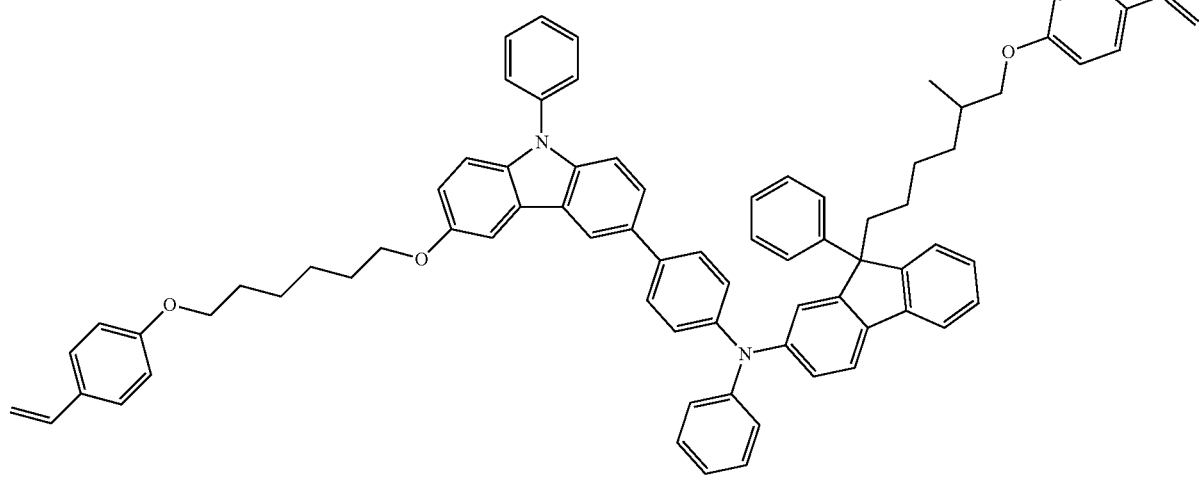
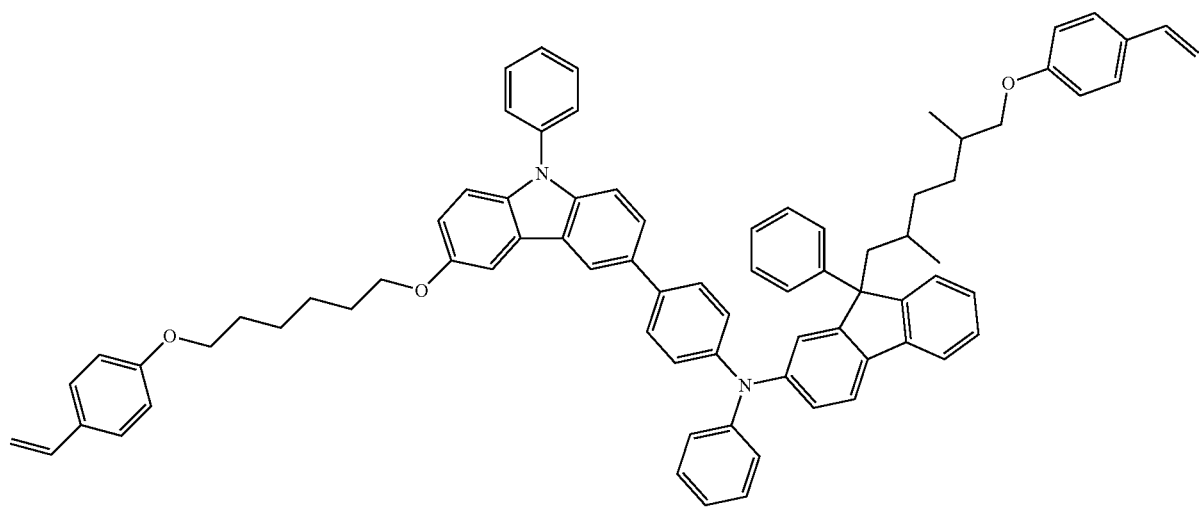
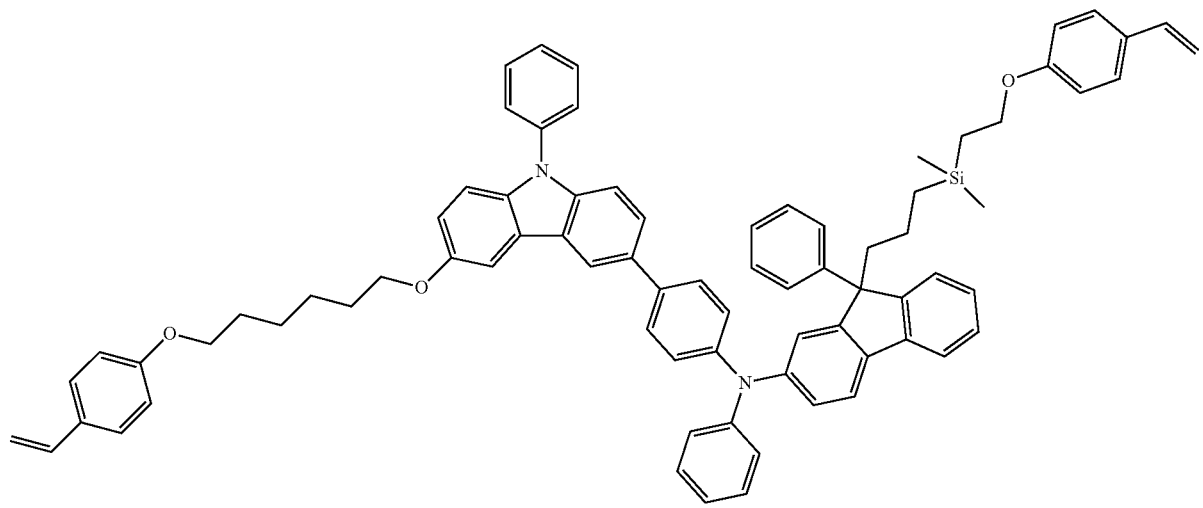

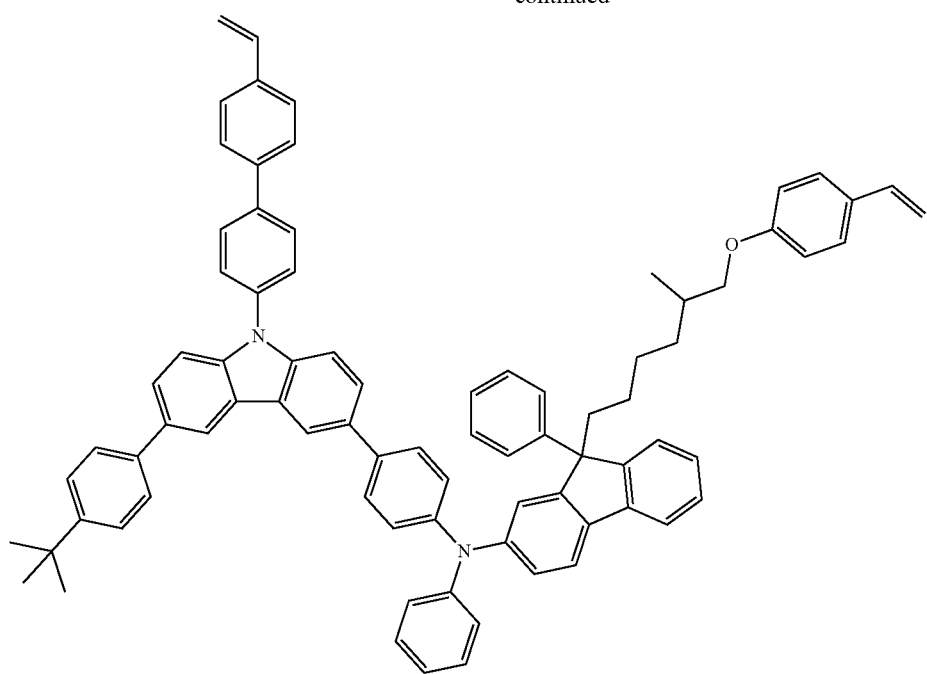
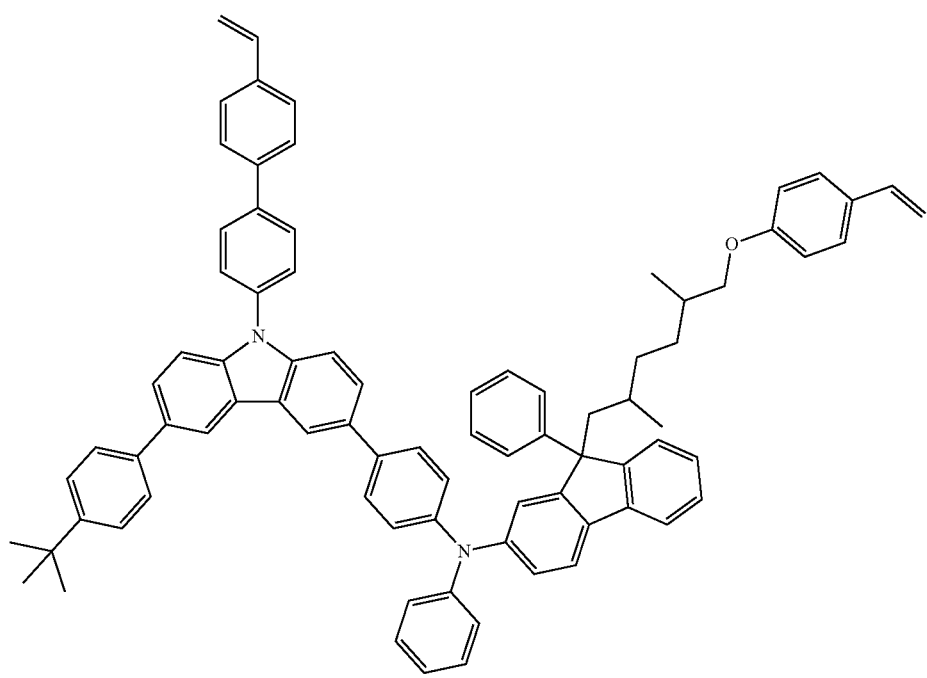 [SMILES: C=Cc1ccc(OCC[Si](C)(C)CCCC2(c3ccccc3)c3ccccc3-c3ccc(N(c4ccccc4)c4ccc(-c5ccc6c(c5)c5cc(-c7ccc(C(C)(C)C)cc7)ccc5n6-c5ccc(-c6ccc(C=C)cc6)cc5)cc4)cc32)cc1]

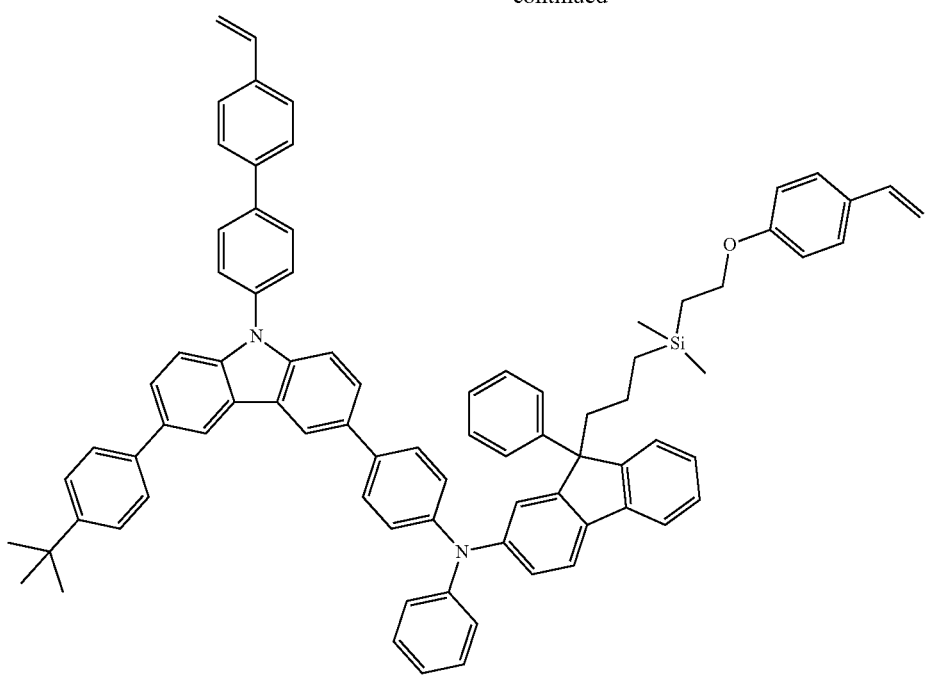
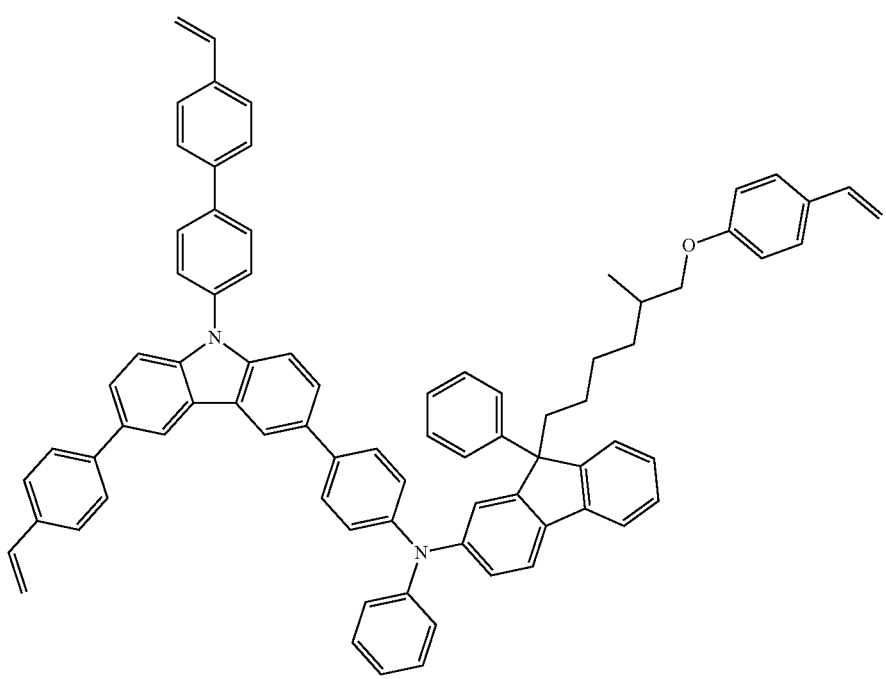

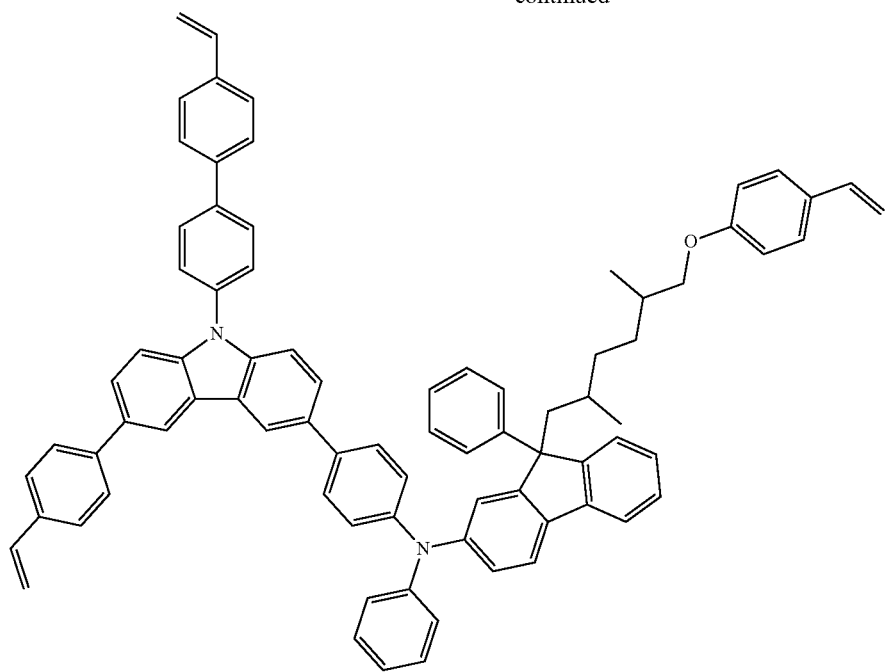
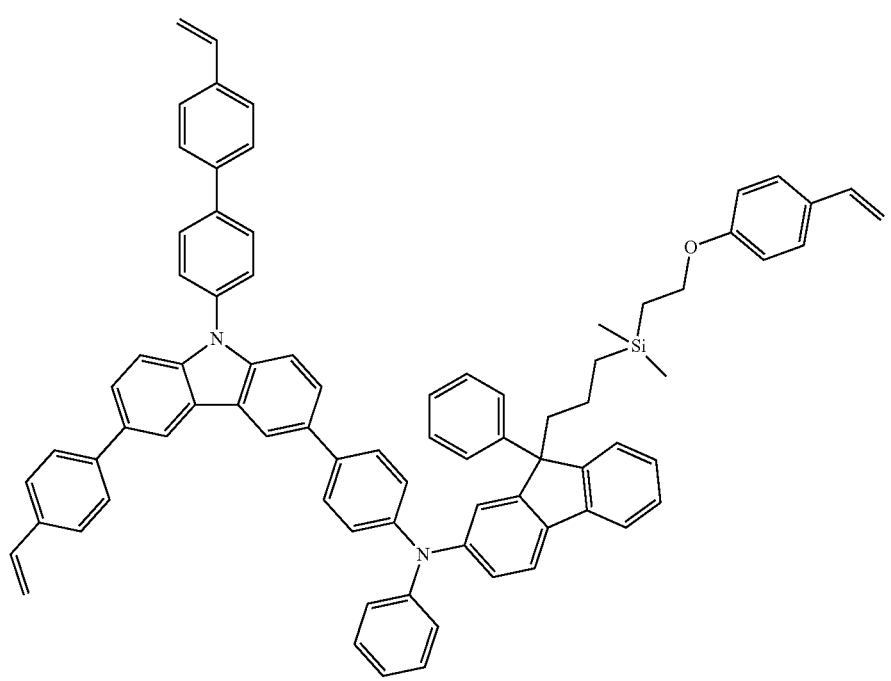 [SMILES: C=Cc1ccc(OCC[Si](C)(C)CCCC2(c3ccccc3)c3ccccc3-c3ccc(N(c4ccccc4)c4ccc(-c5ccc6c(c5)c5cc(-c7ccc(C=C)cc7)ccc5n6-c5ccc(-c6ccc(C=C)cc6)cc5)cc4)cc32)cc1]

85
86
-continued
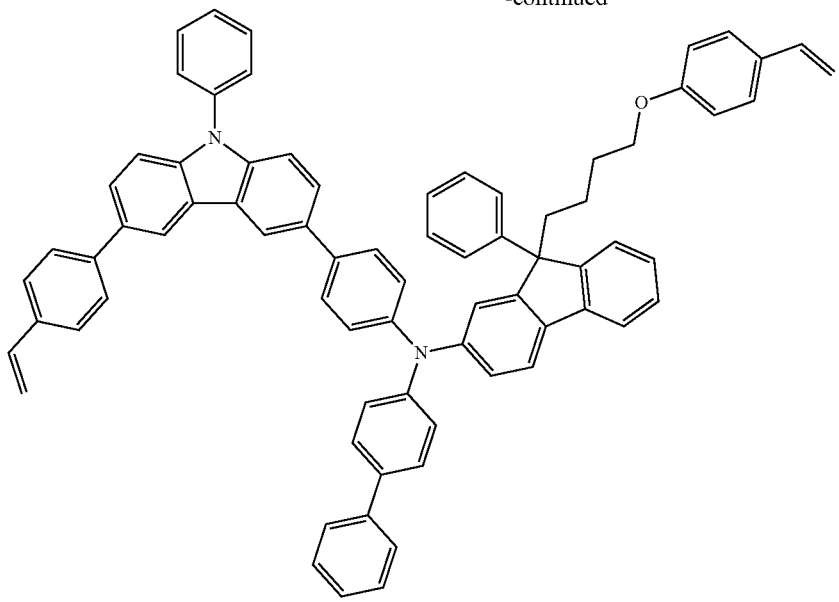
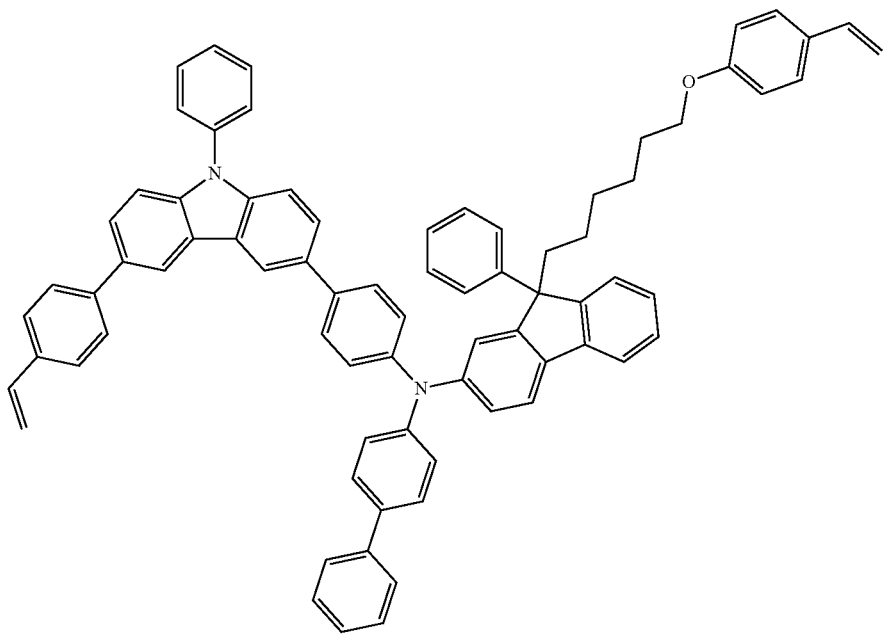 [SMILES: C=Cc1ccc(OCC[Si](C)(C)CCCC2(c3ccccc3)c3ccccc3-c3ccc(N(c4ccc(-c5ccccc5)cc4)c4ccc(-c5ccc6c(c5)c5cc(-c7ccc(C=C)cc7)ccc5n6-c5ccccc5)cc4)cc32)cc1]

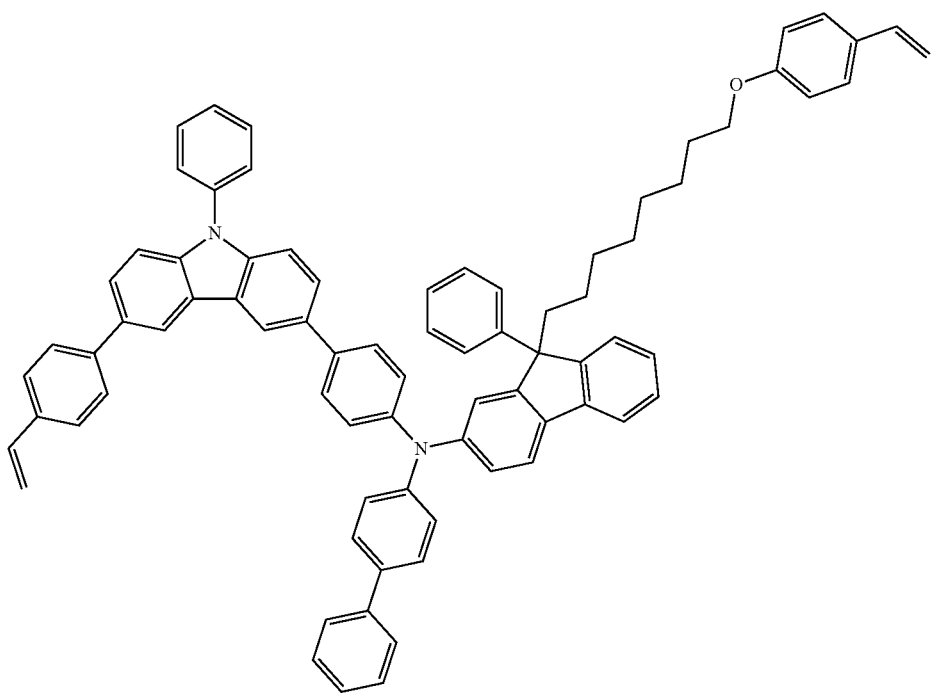
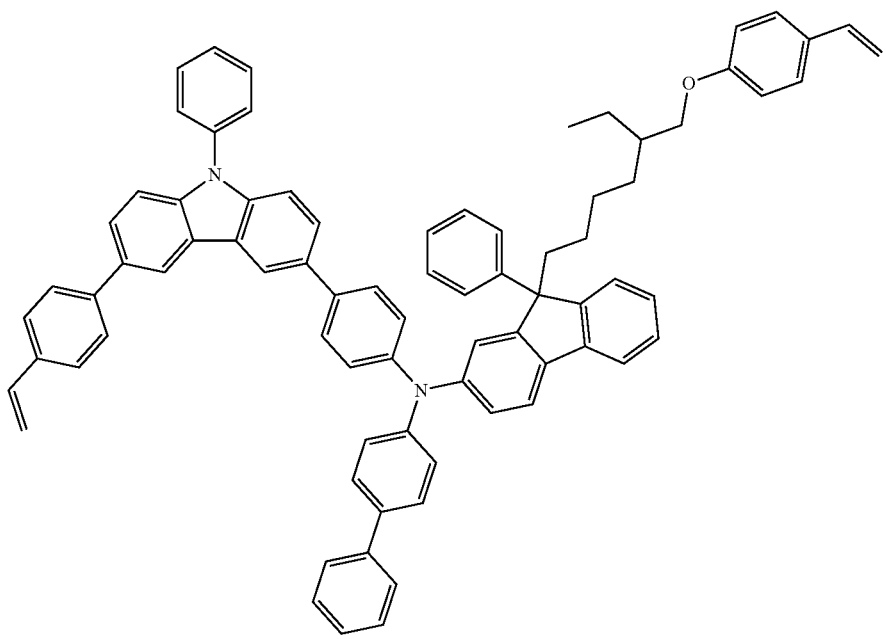

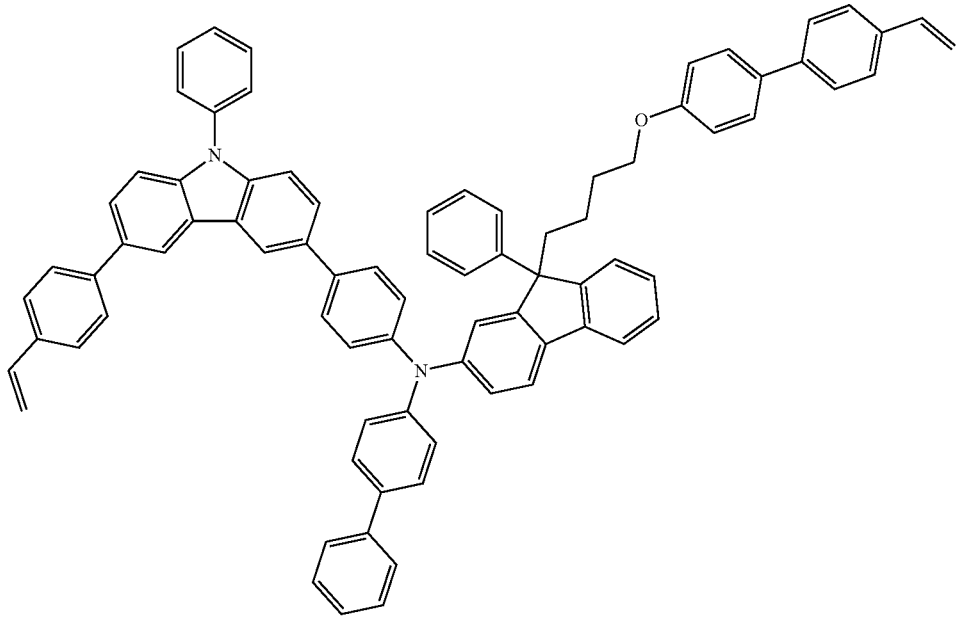
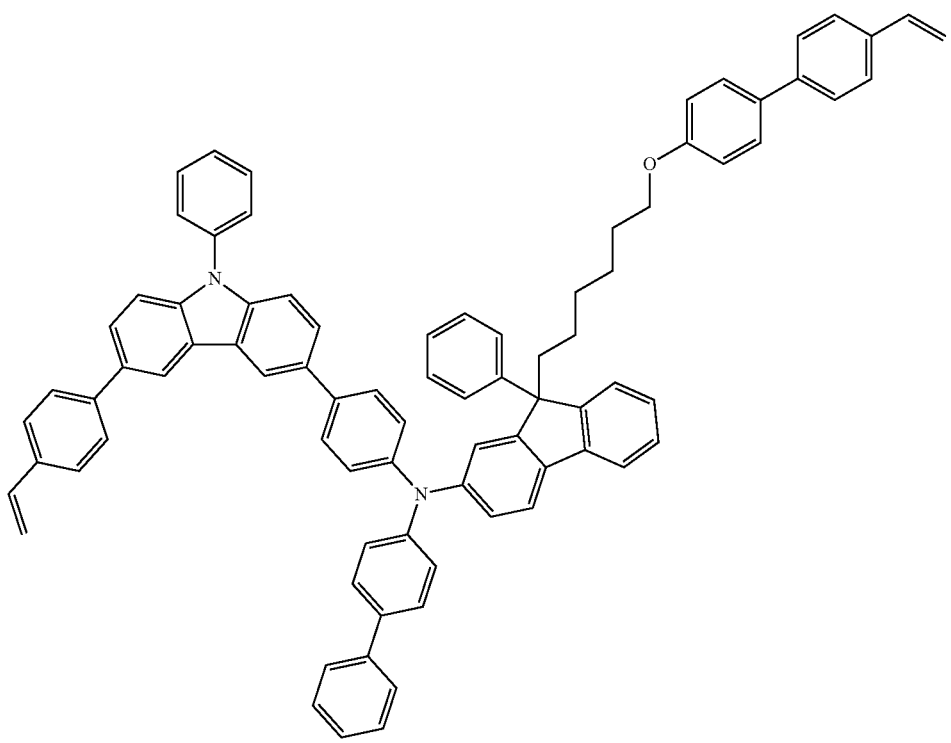

-continued
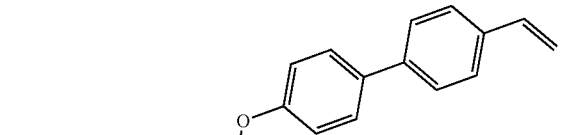
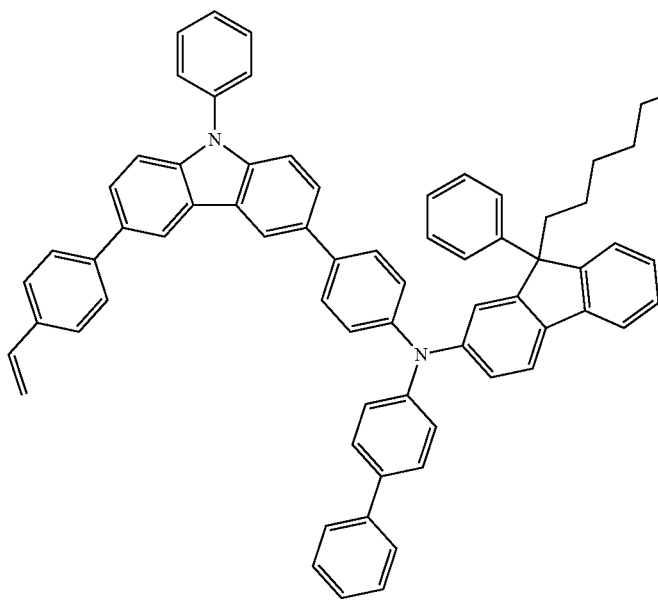
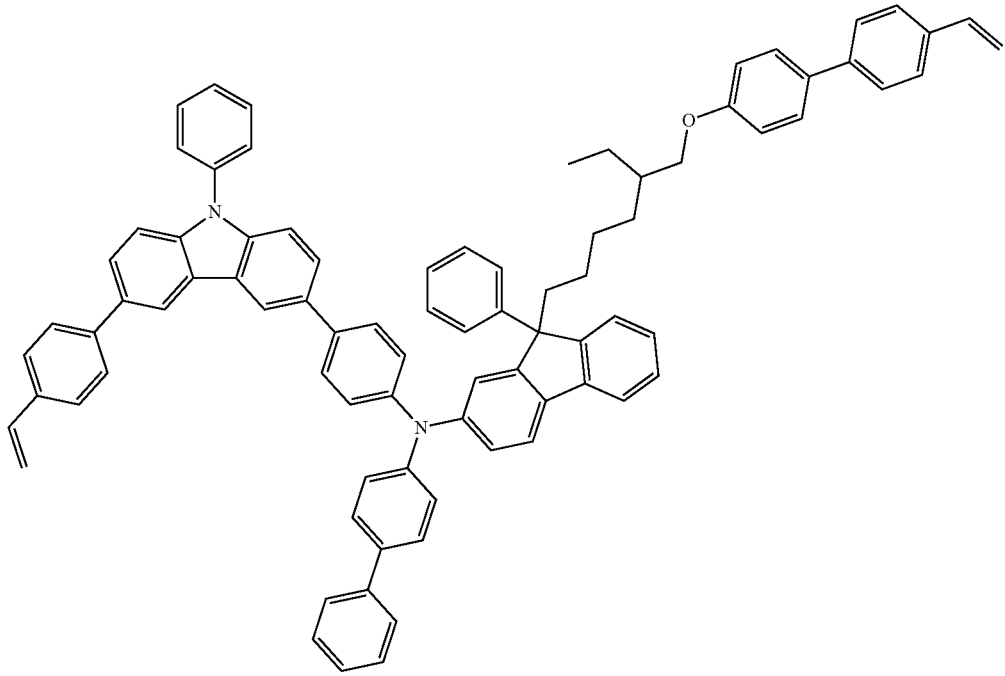

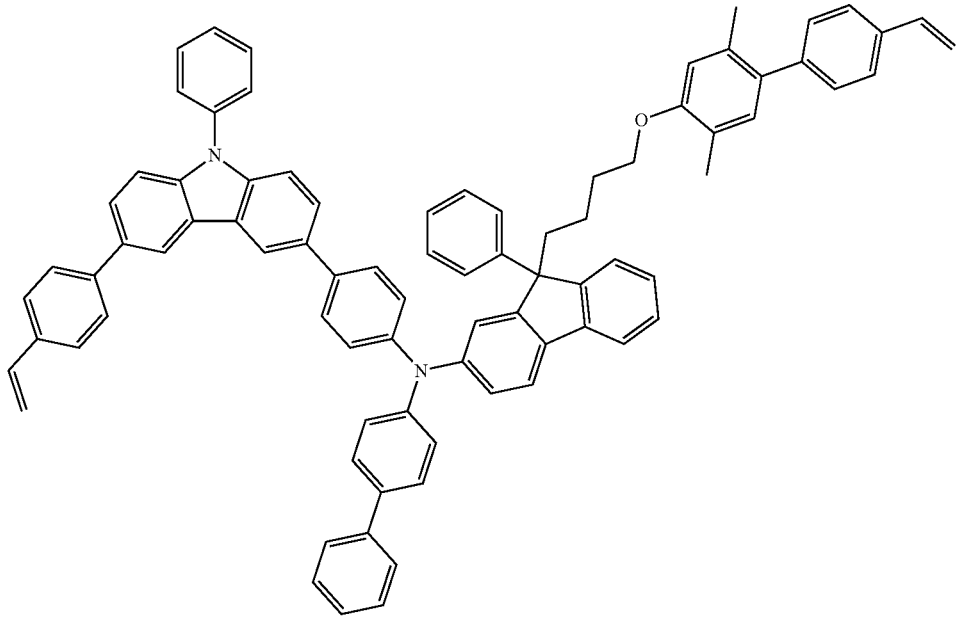
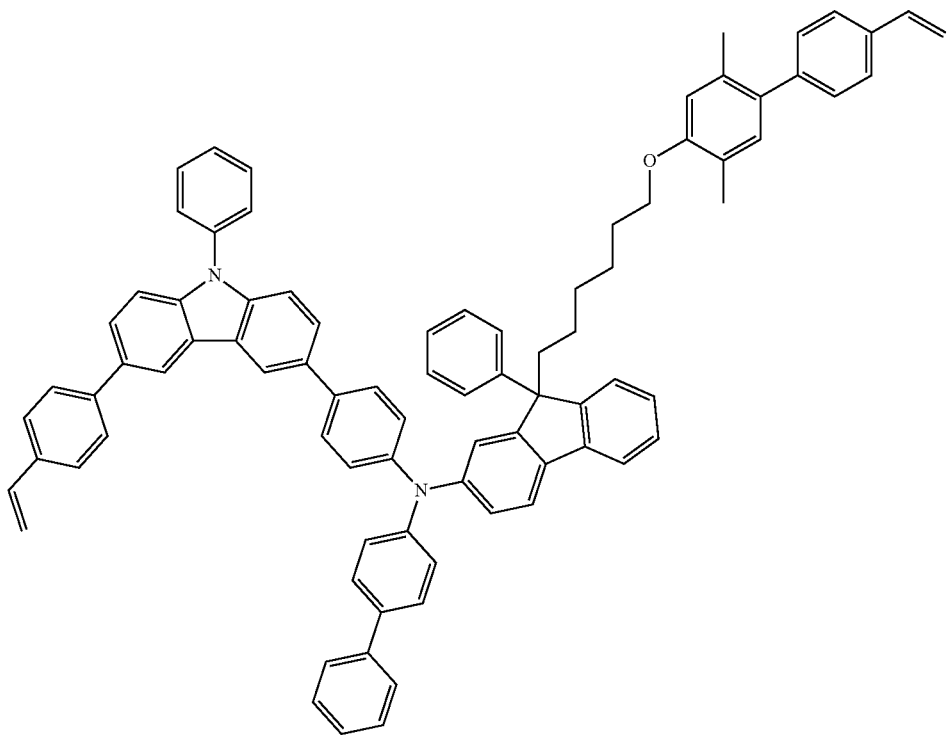

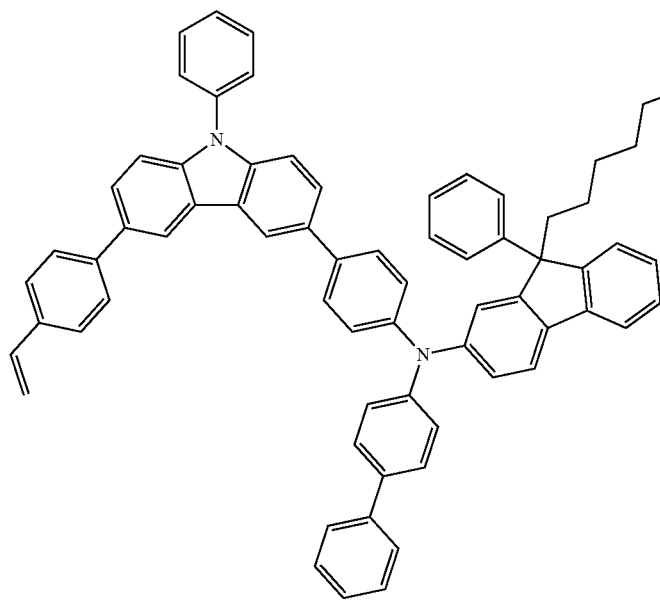
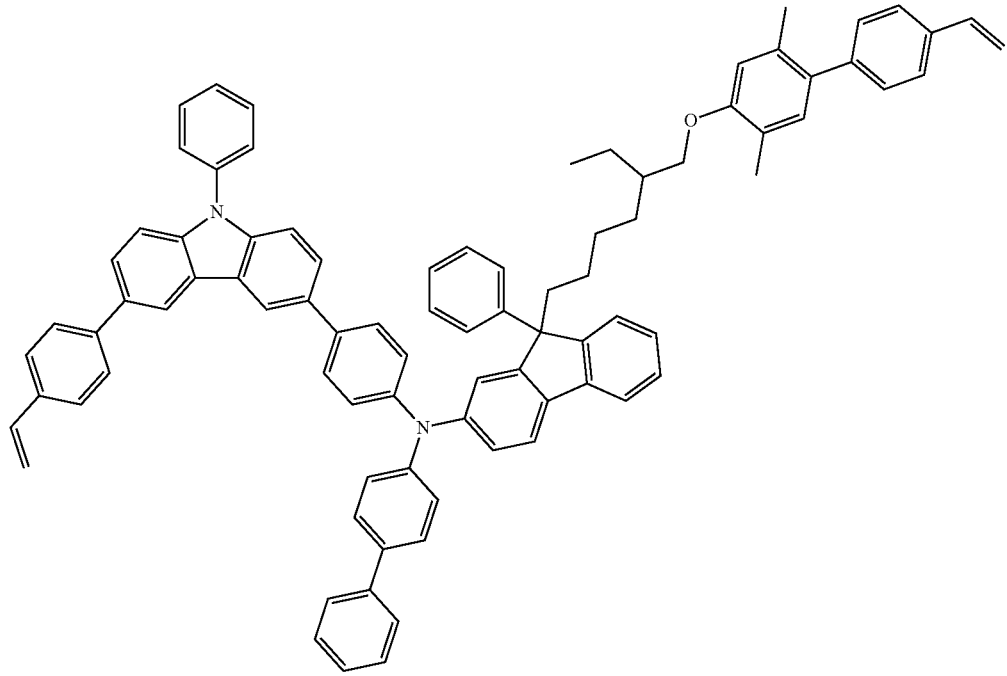

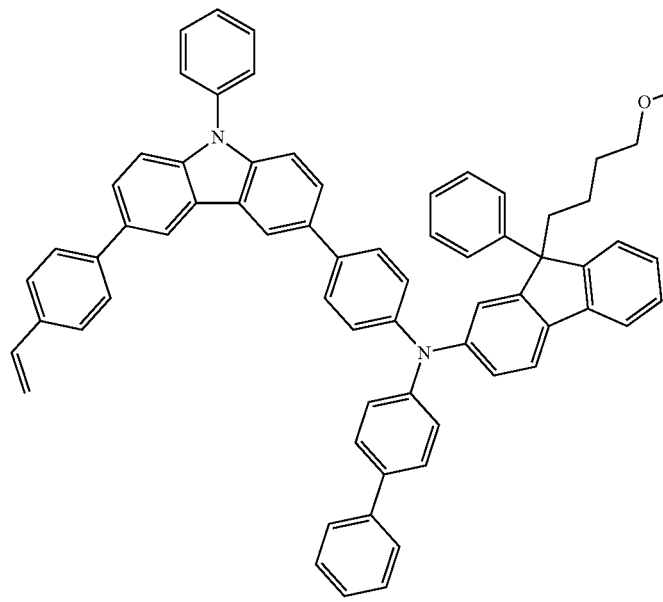
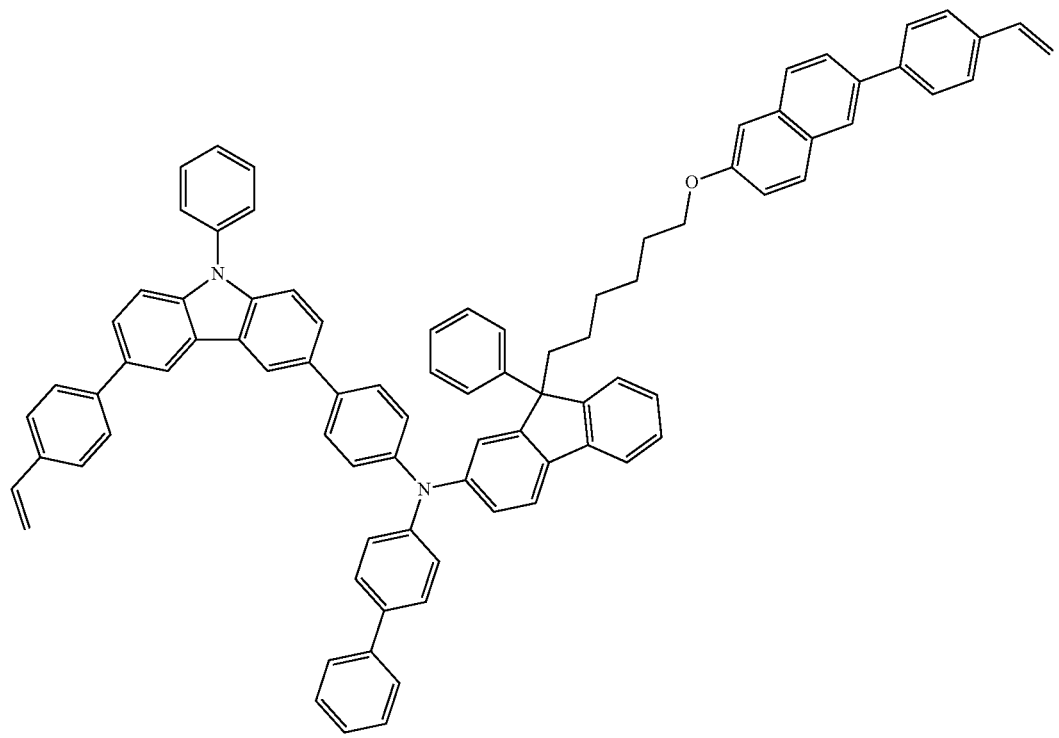

-continued
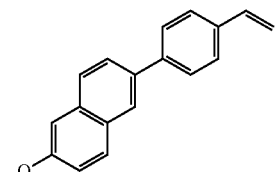
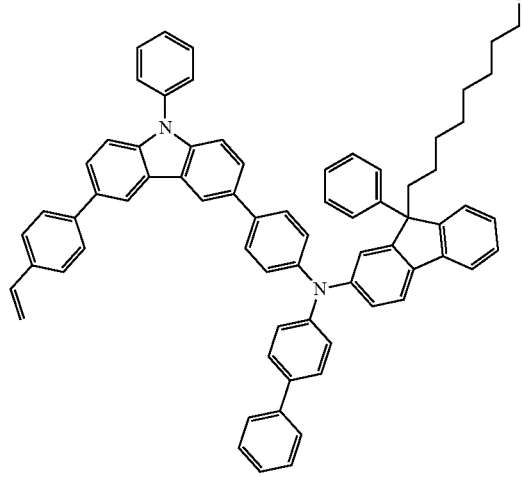
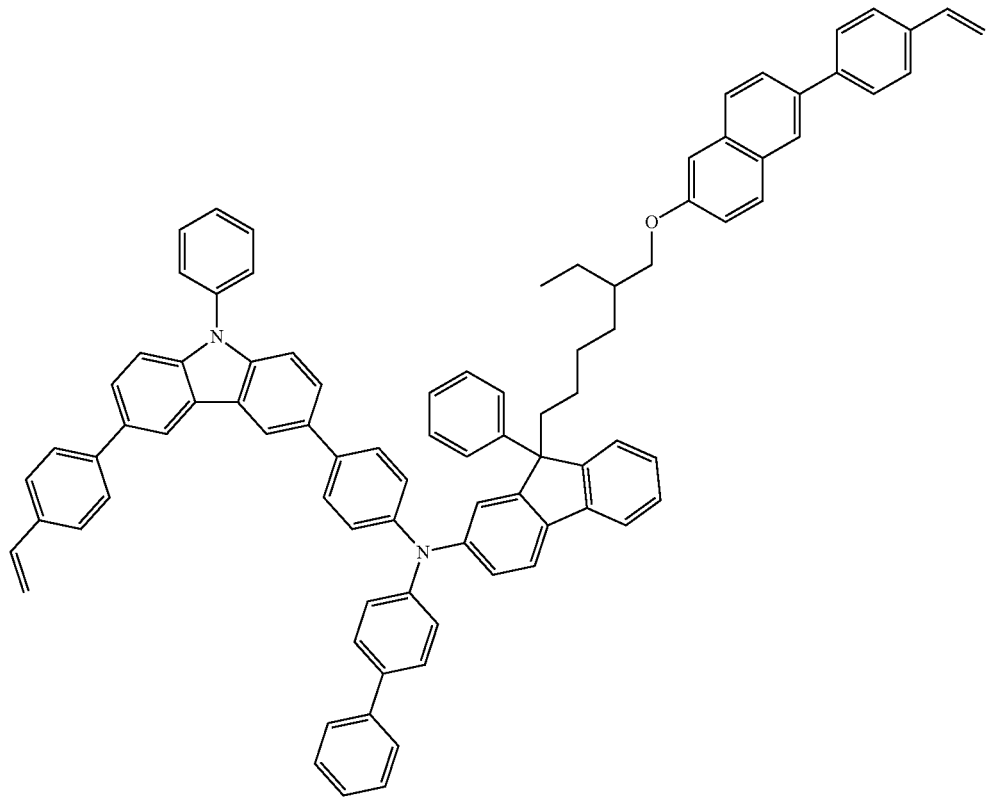

101
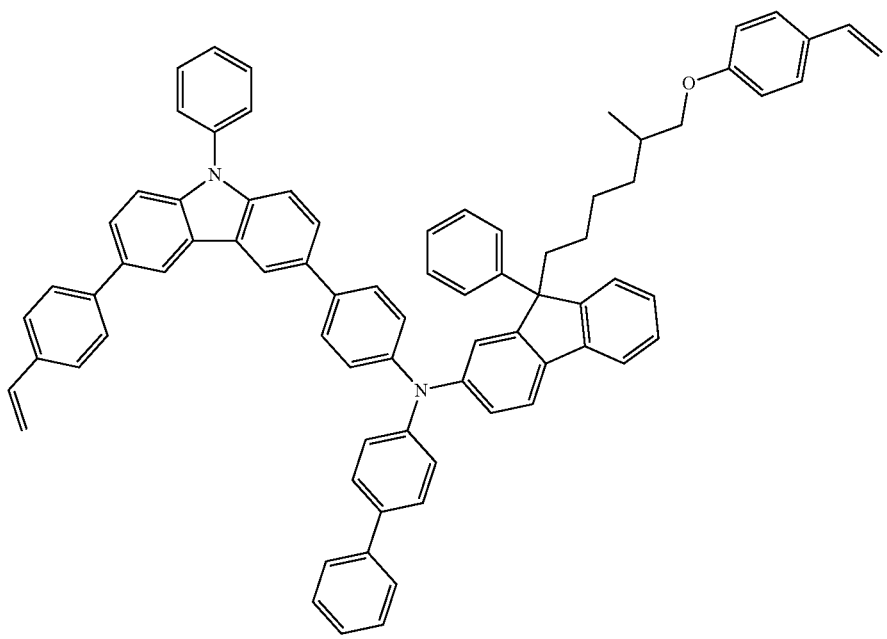
102
-continued
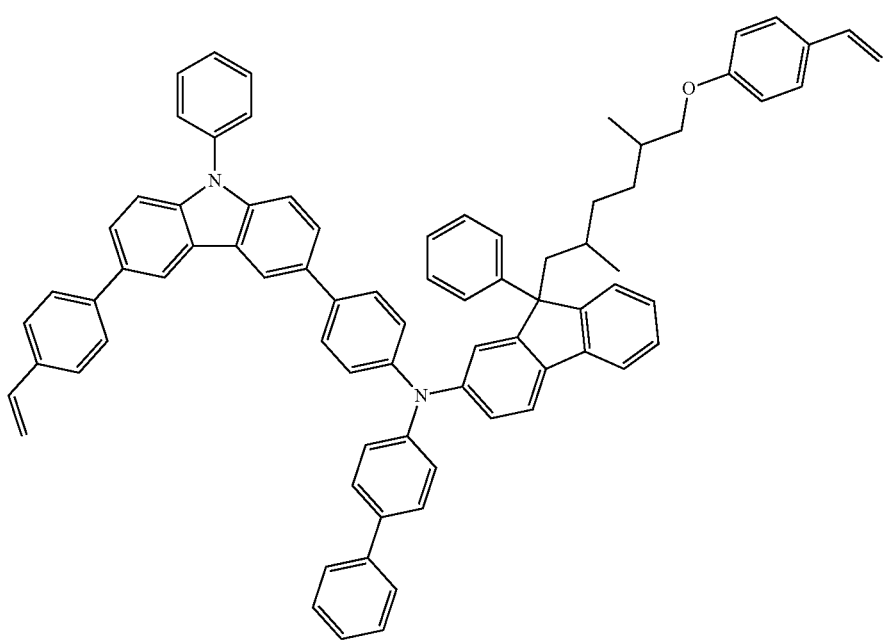

103
104
-continued
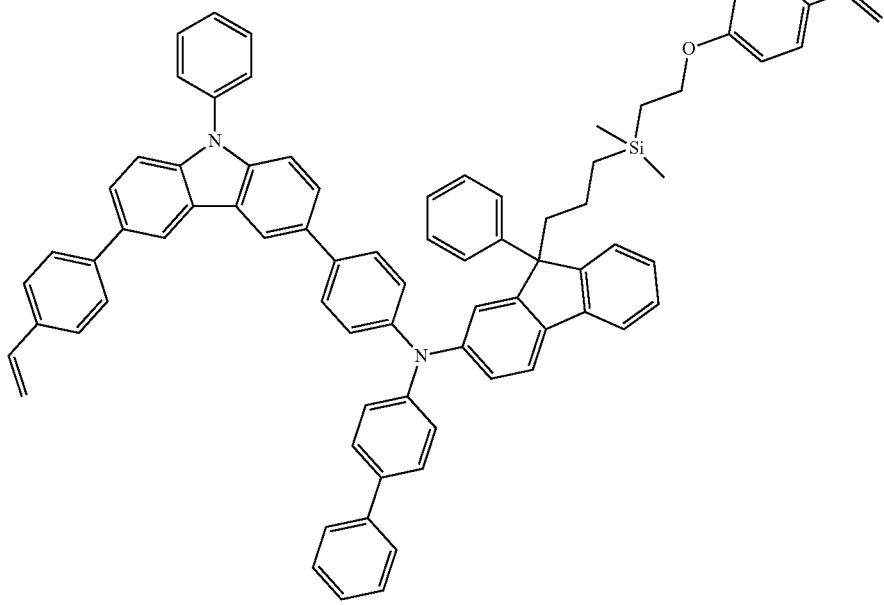
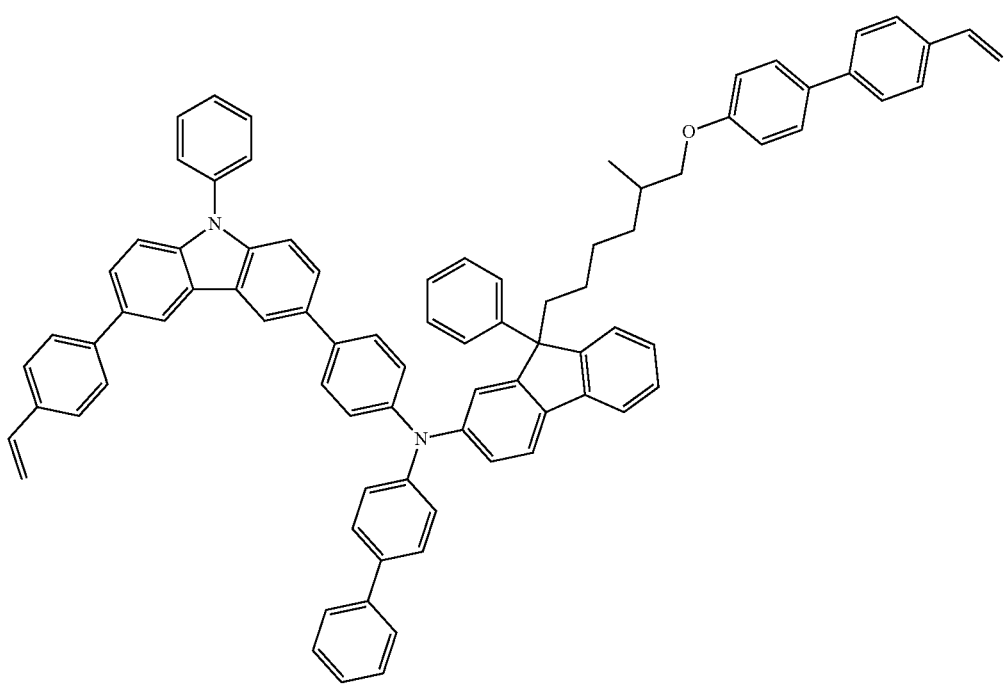

107
108
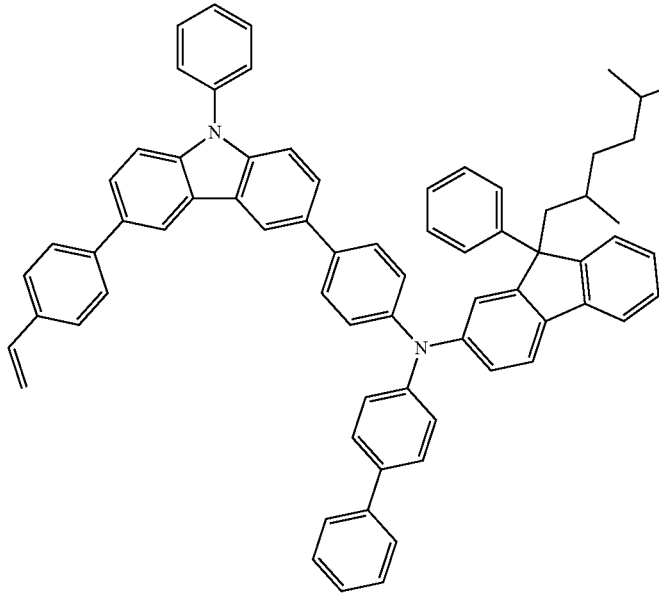
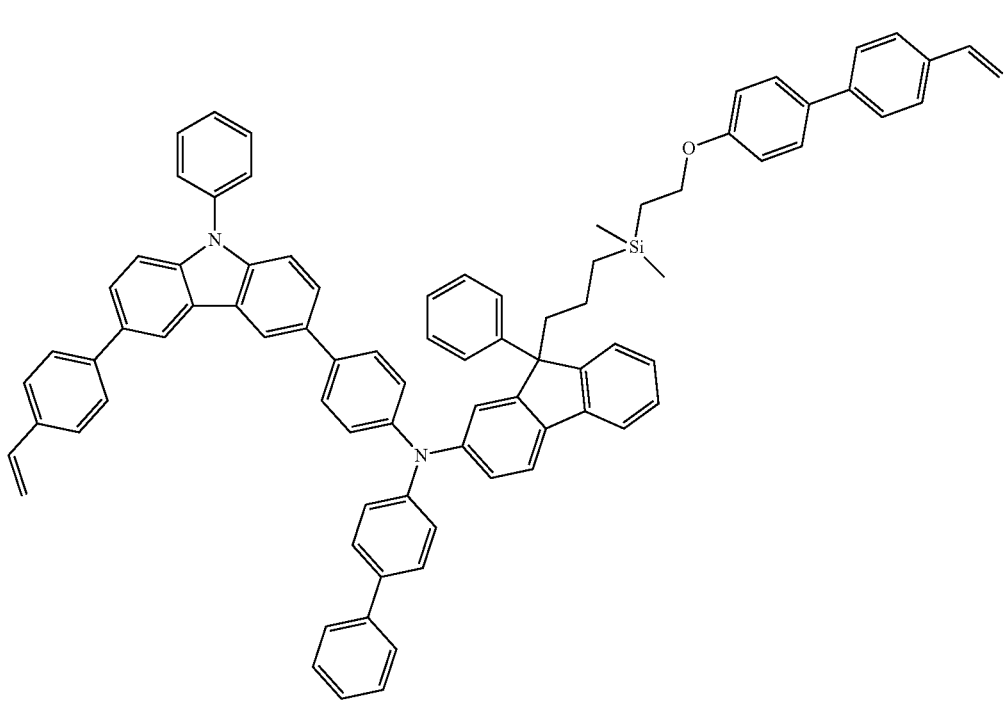 [SMILES: C=Cc1ccc(-c2ccc(OCC[Si](C)(C)CCCC3(c4ccccc4)c4ccccc4-c4ccc(N(c5ccc(-c6ccccc6)cc5)c5ccc(-c6ccc7c(c6)c6cc(-c8ccc(C=C)cc8)ccc6n7-c6ccccc6)cc5)cc43)cc2)cc1]

109 110
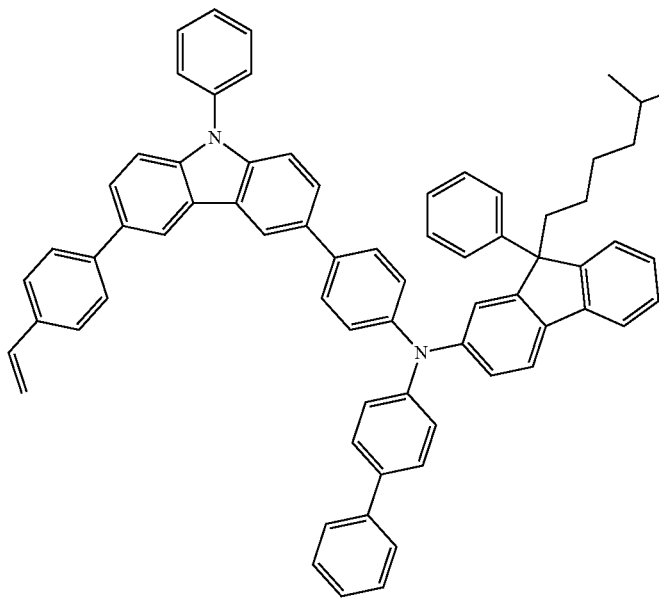
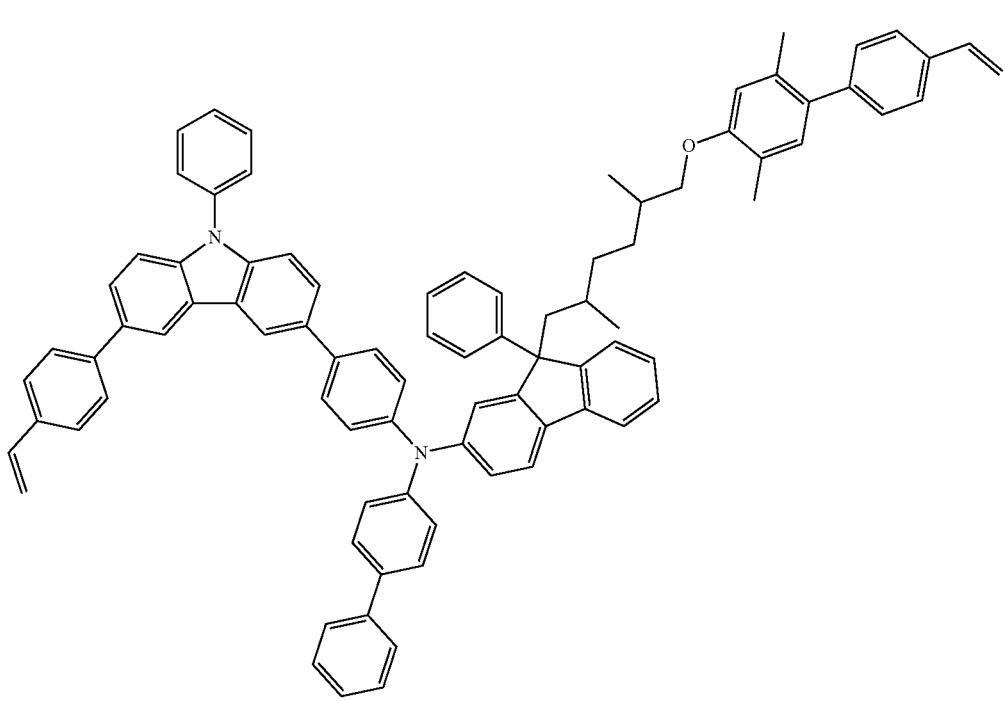 [SMILES: C=Cc1ccc(-c2ccc3c(c2)c2cc(-c4ccc(N(c5ccc(-c6ccccc6)cc5)c5ccc6c(c5)C(CCC[Si](C)(C)CCOc5cc(C)c(-c7ccc(C=C)cc7)cc5C)(c5ccccc5)c5ccccc5-6)cc4)ccc2n3-c2ccccc2)cc1]

111 112
-continued
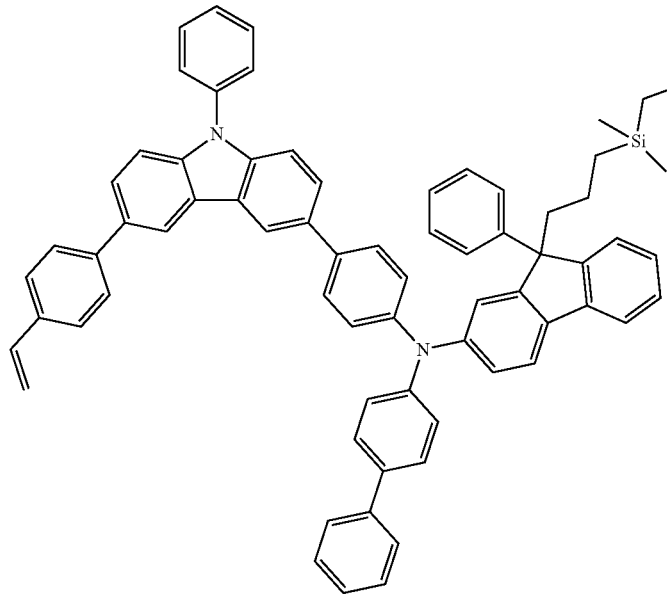
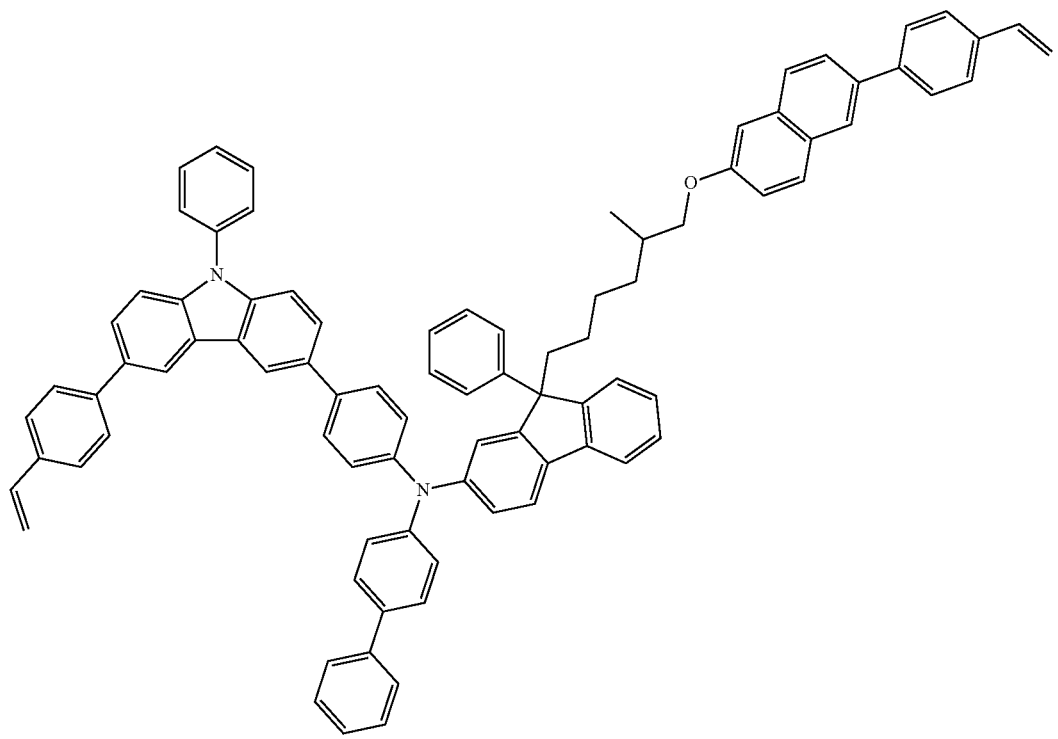

-continued
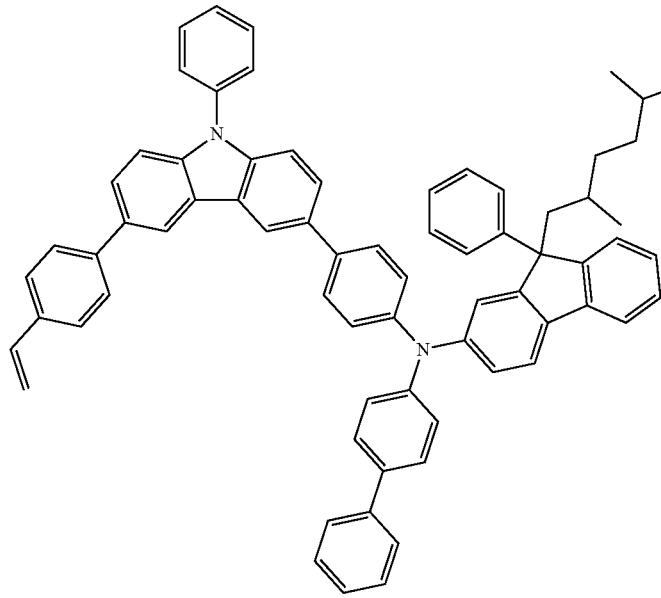
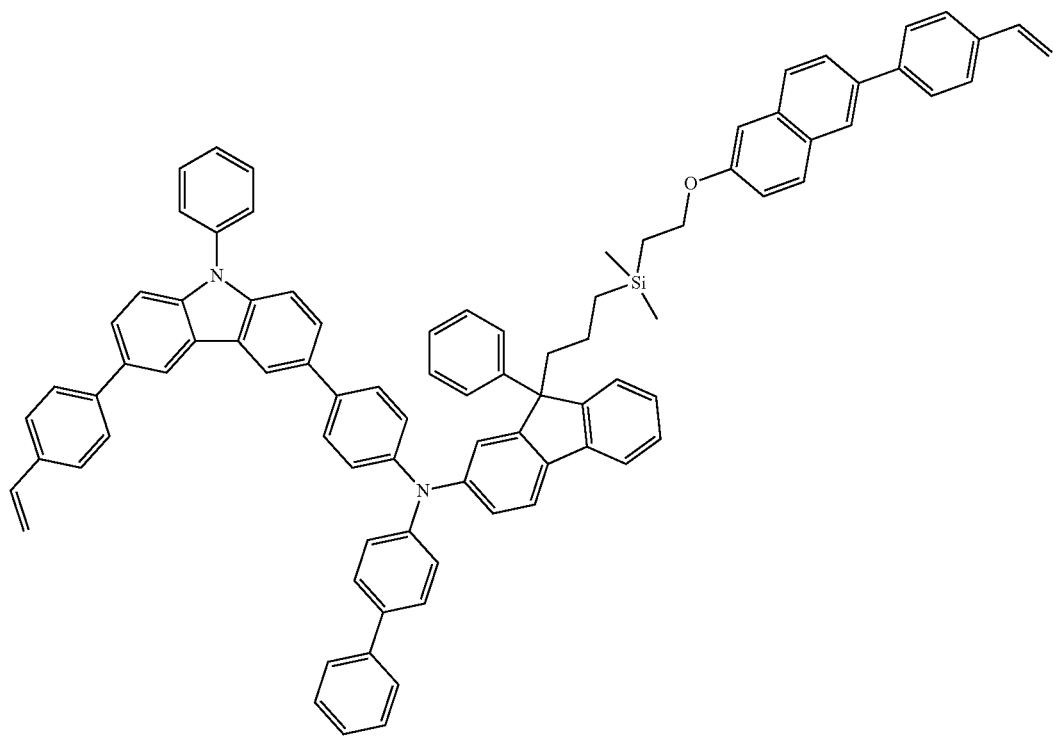 [SMILES: C=Cc1ccc(-c2ccc3cc(OCC[Si](C)(C)CCCC4(c5ccccc5)c5ccccc5-c5ccc(N(c6ccc(-c7ccccc7)cc6)c6ccc(-c7ccc8c(c7)c7cc(-c9ccc(C=C)cc9)ccc7n8-c7ccccc7)cc6)cc54)ccc3c2)cc1]

-continued
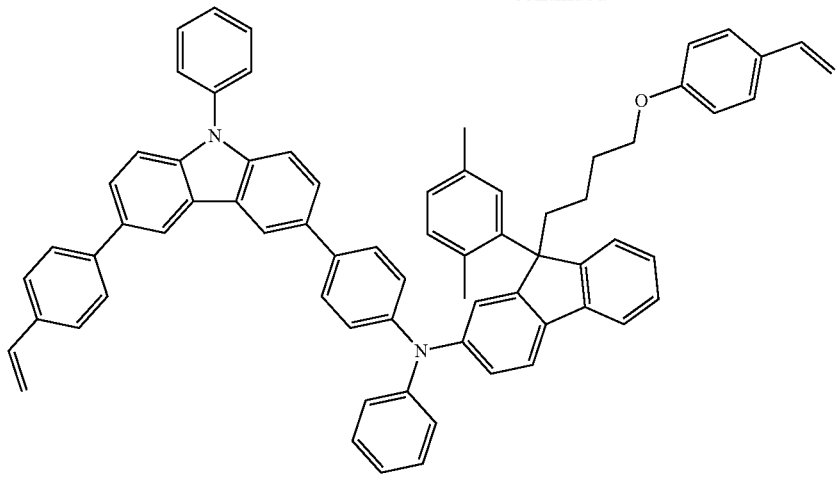
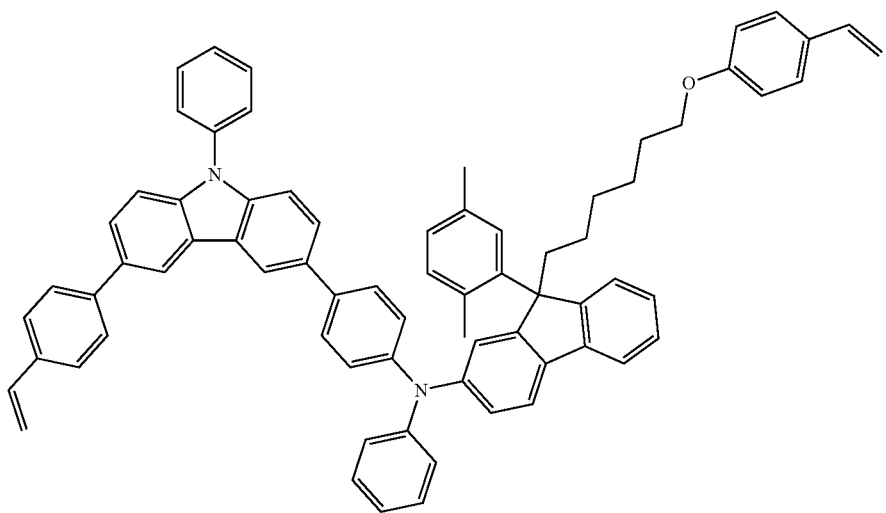
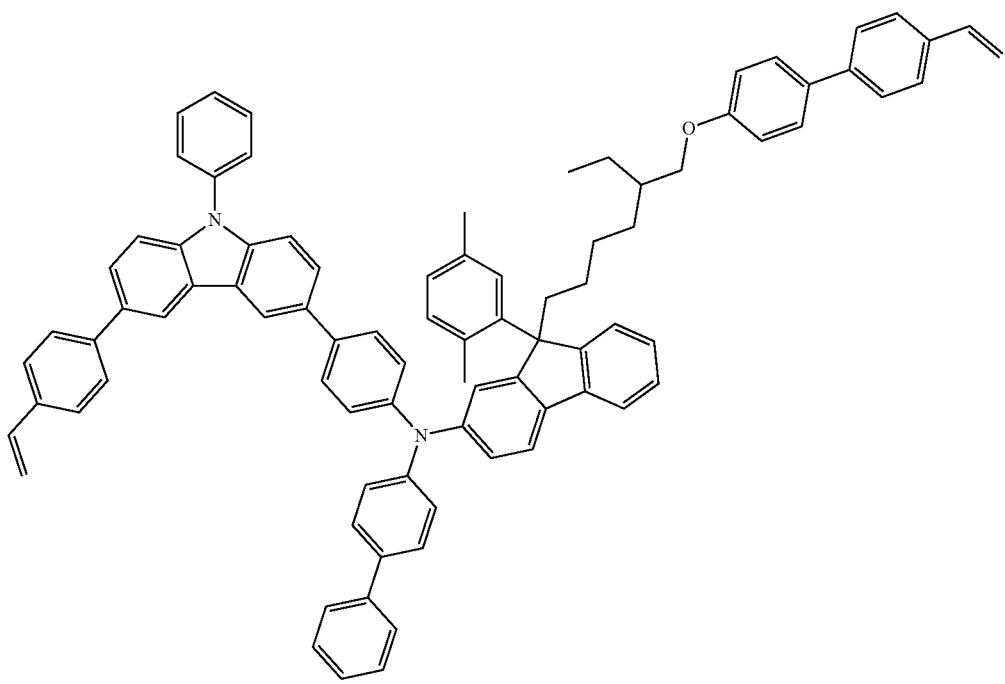

-continued
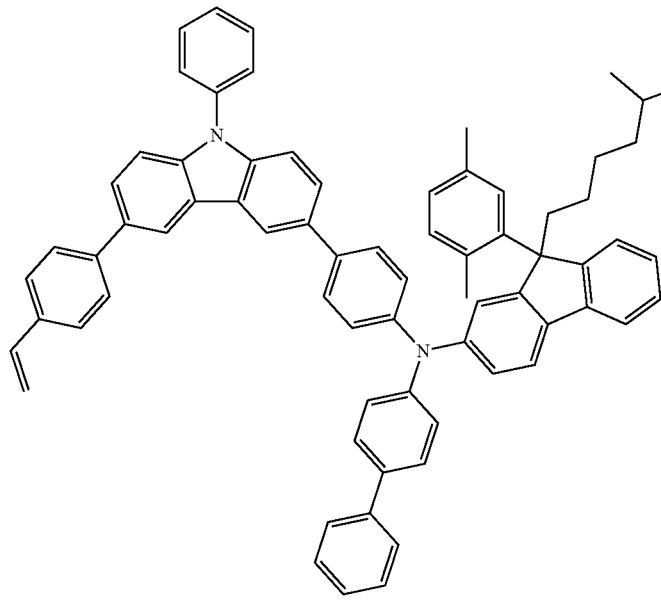
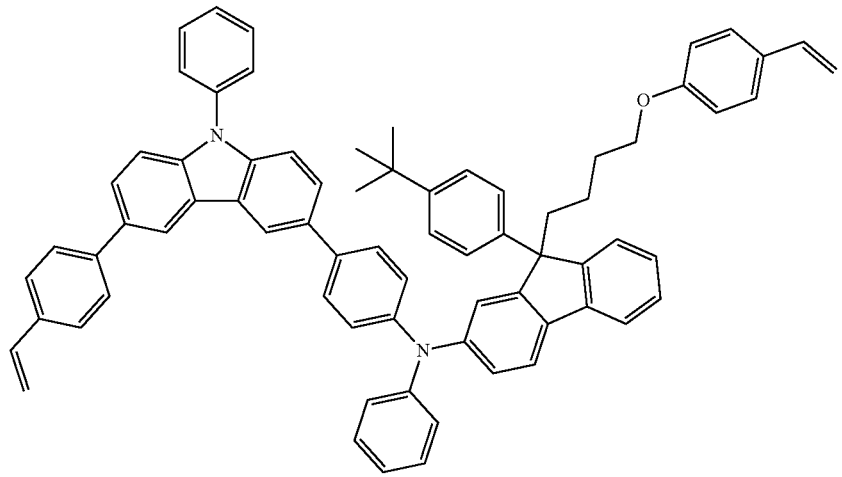
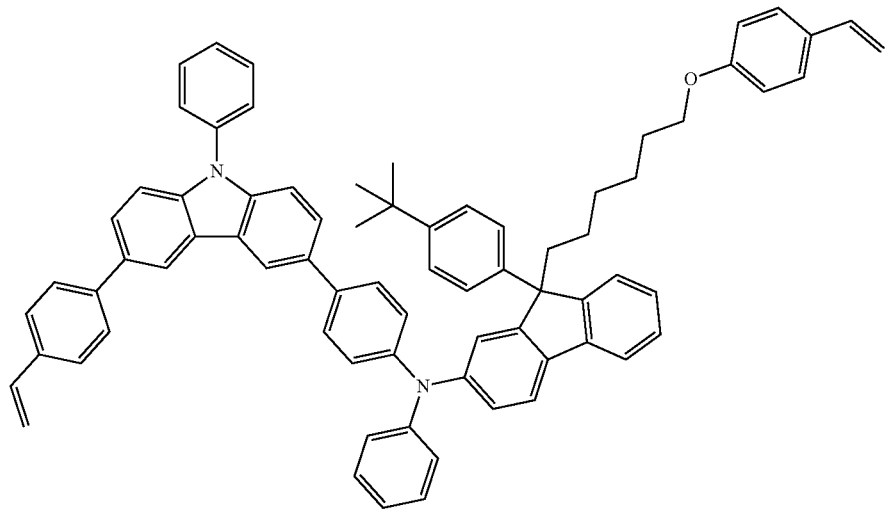

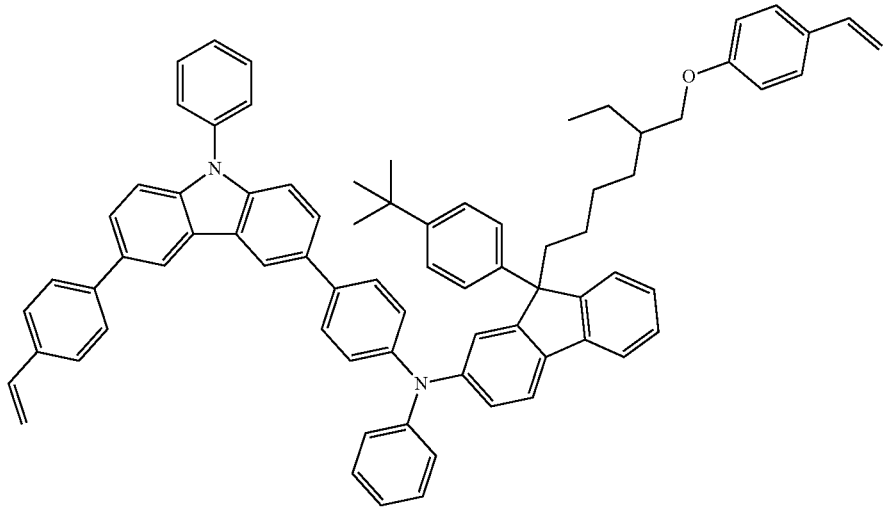
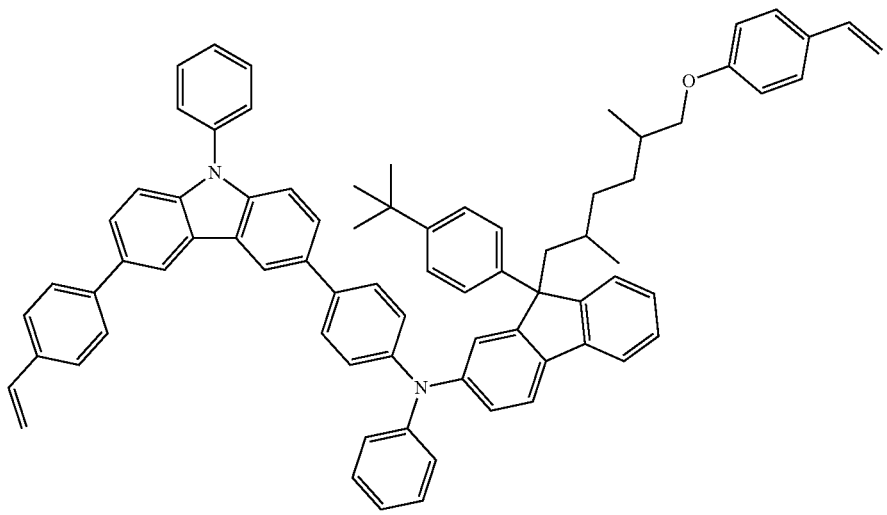

-continued
| 121 | 122 |
|---|---|
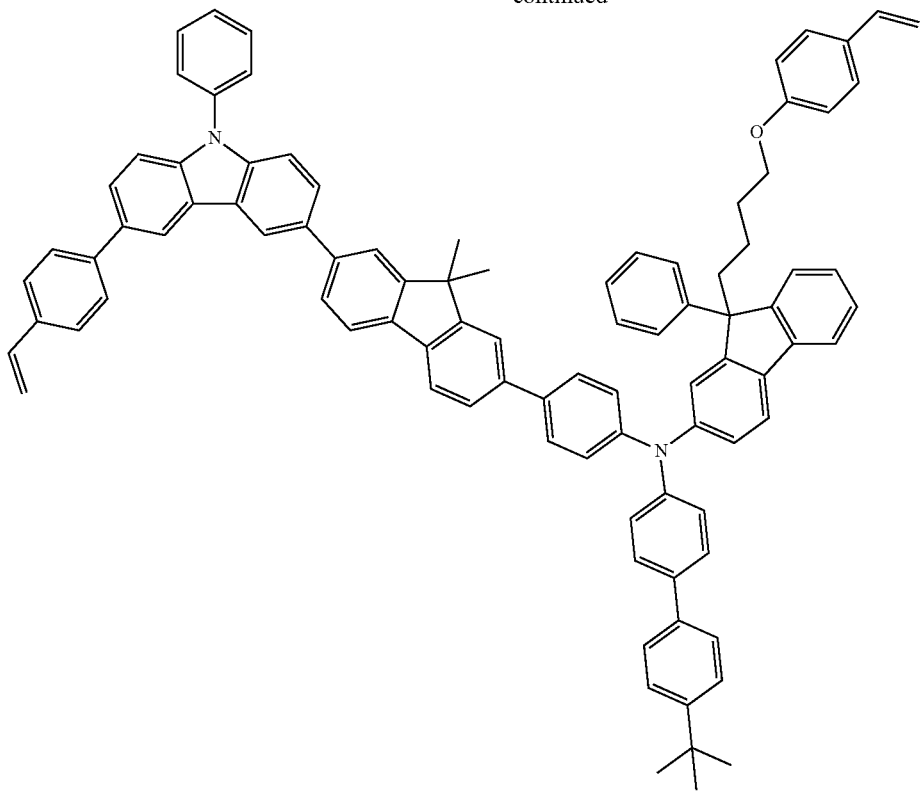
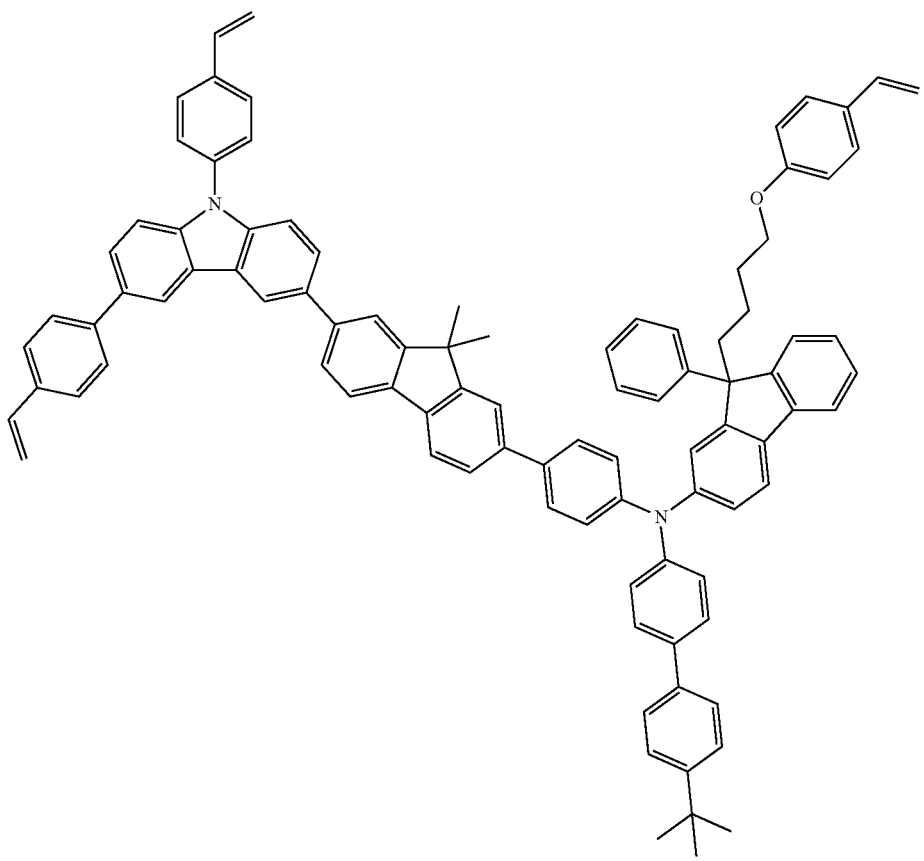

123 124
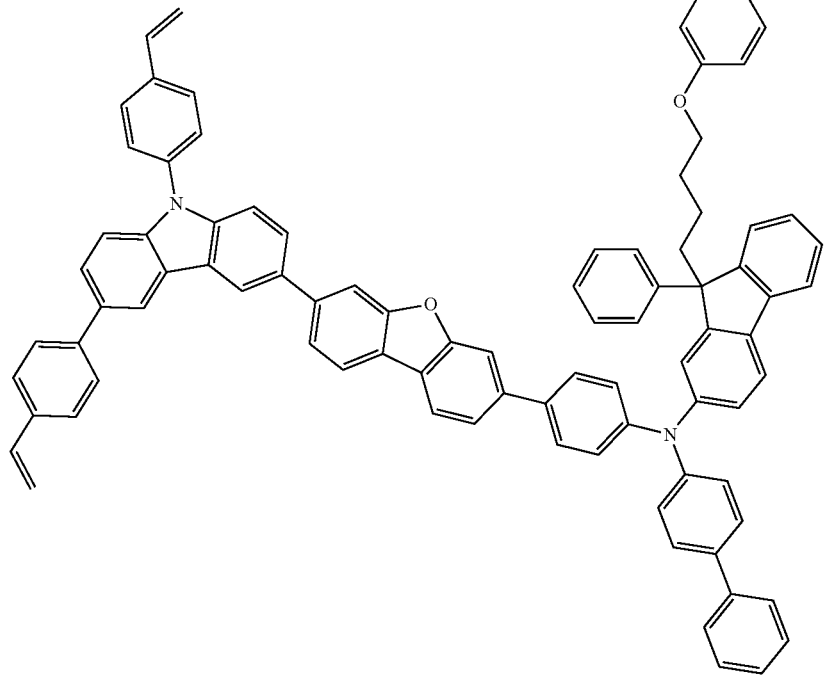
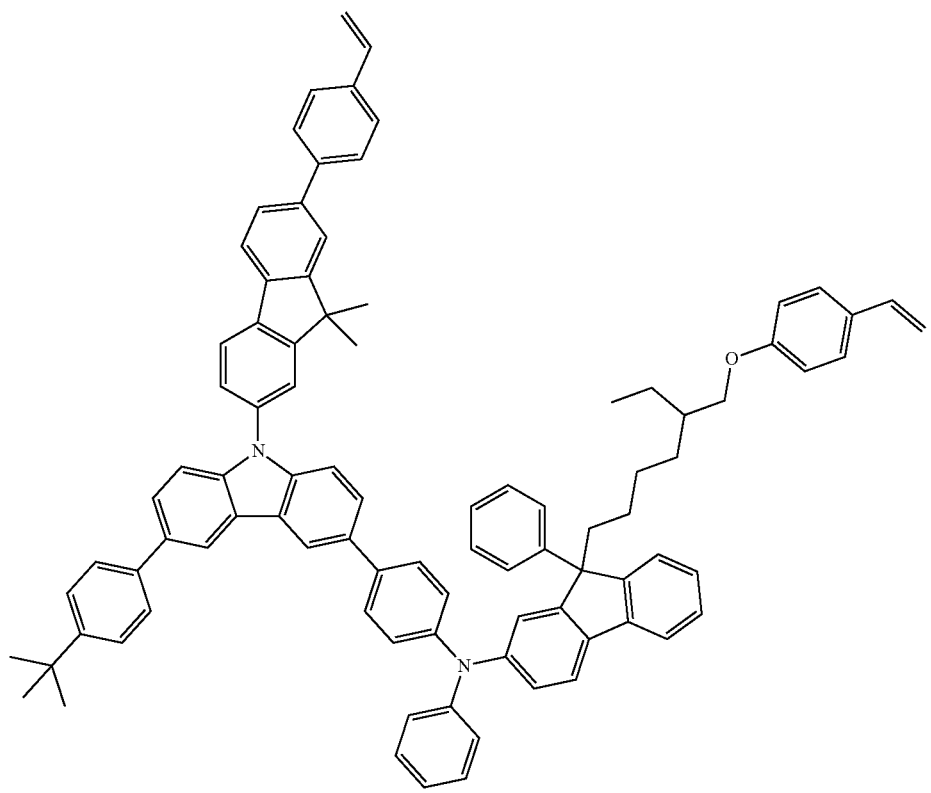

-continued
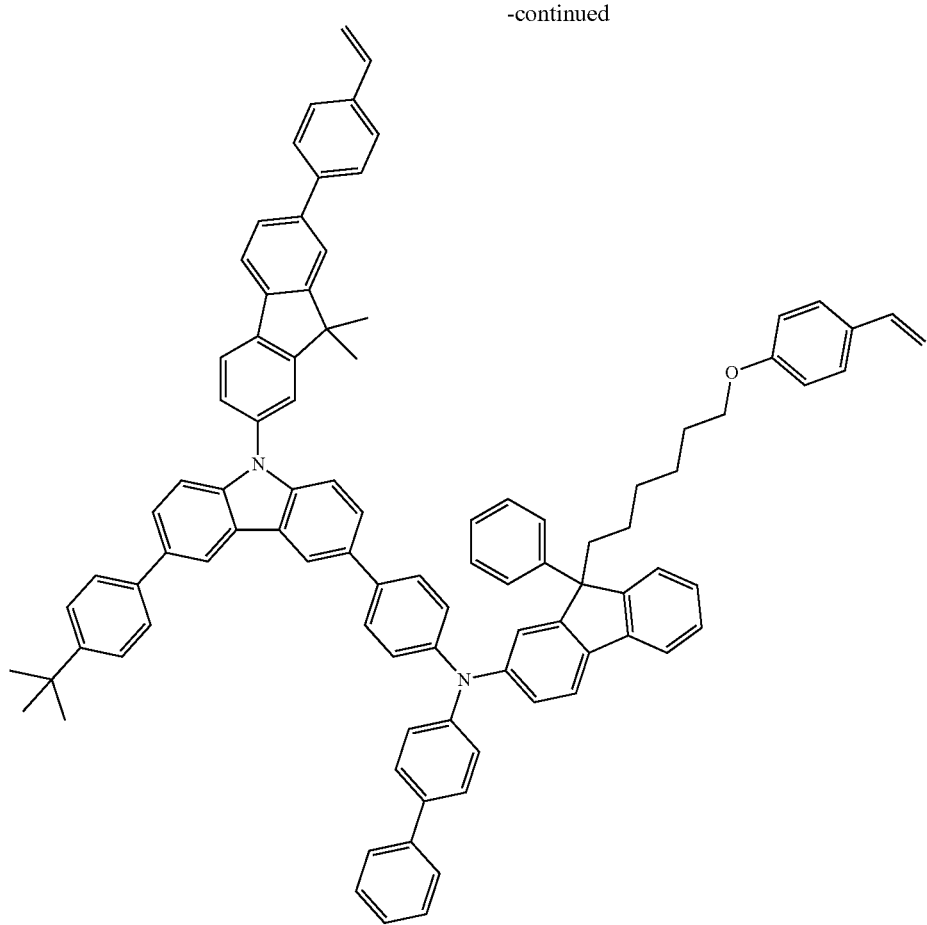
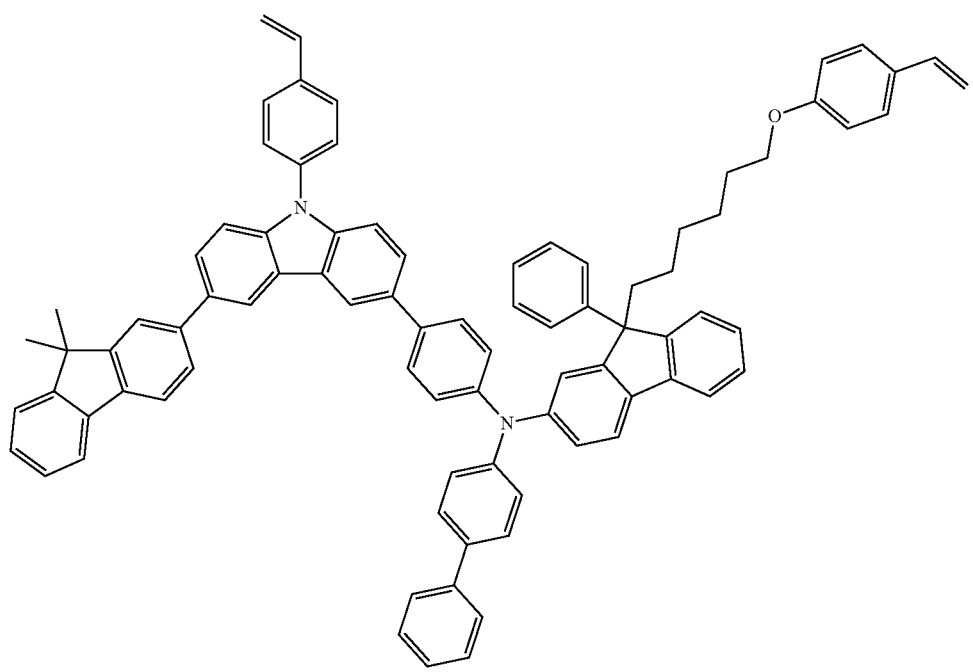

127
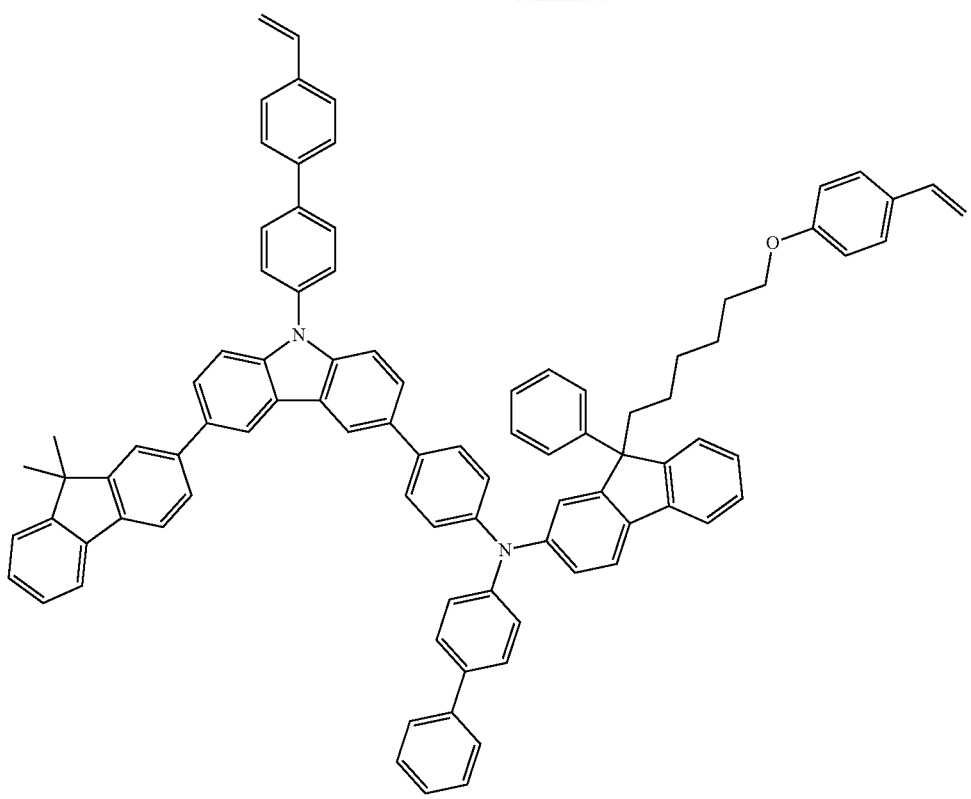
128
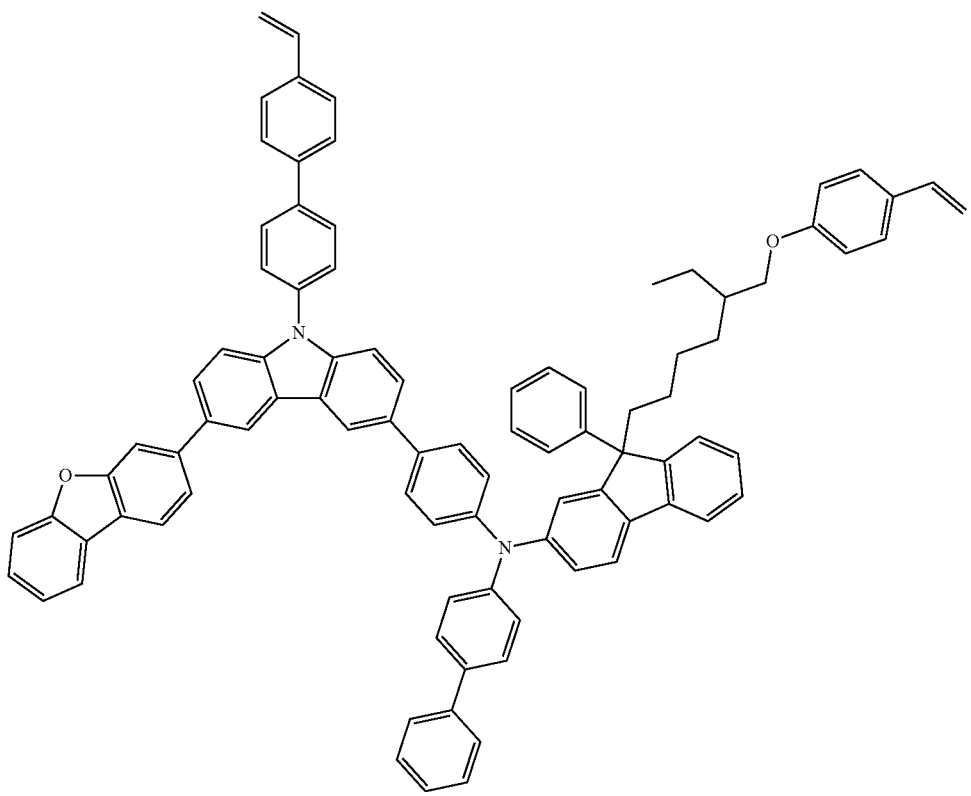

129
130
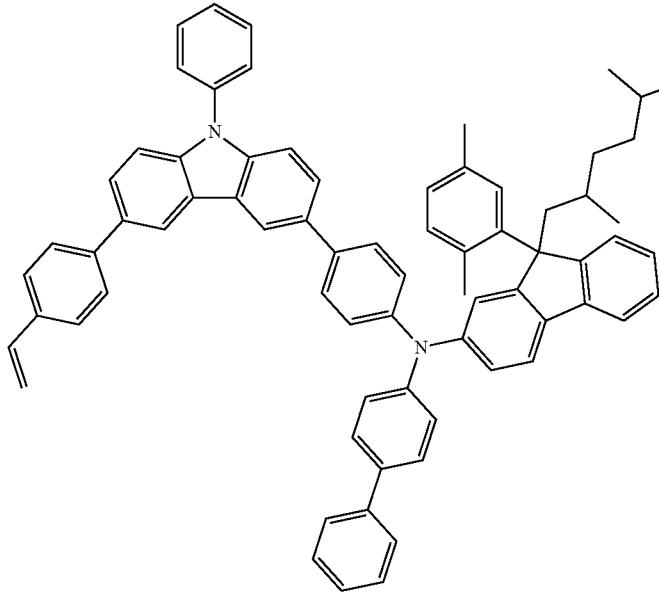
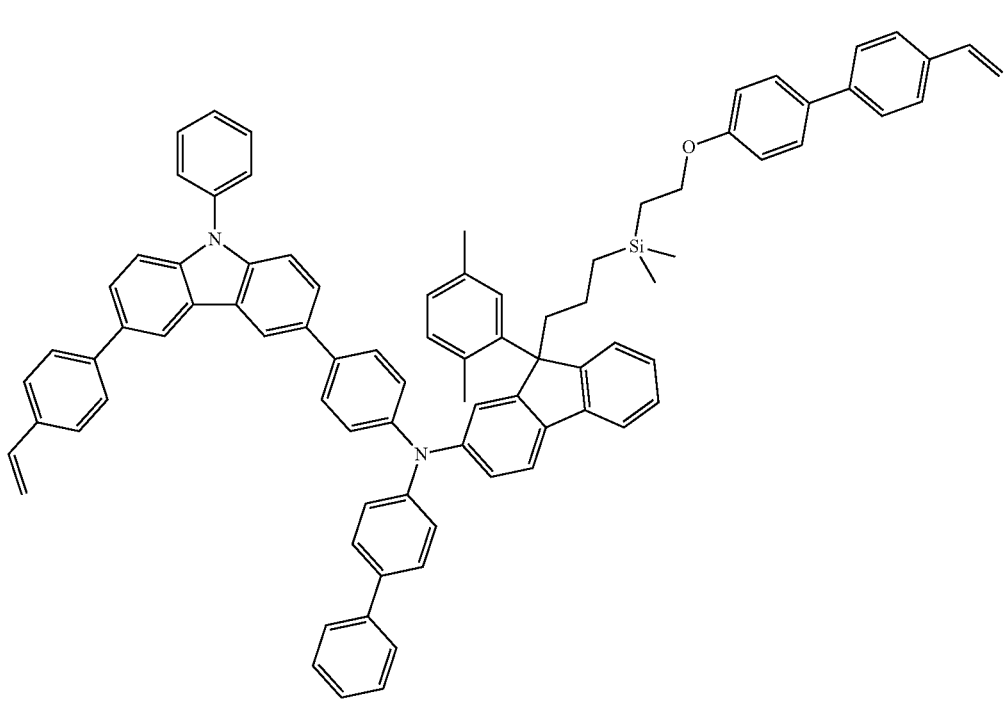 [SMILES: C=Cc1ccc(-c2ccc(OCC[Si](C)(C)CCCC3(c4cc(C)ccc4C)c4ccccc4-c4ccc(N(c5ccc(-c6ccccc6)cc5)c5ccc(-c6ccc7c(c6)c6cc(-c8ccc(C=C)cc8)ccc6n7-c6ccccc6)cc5)cc43)cc2)cc1]

131
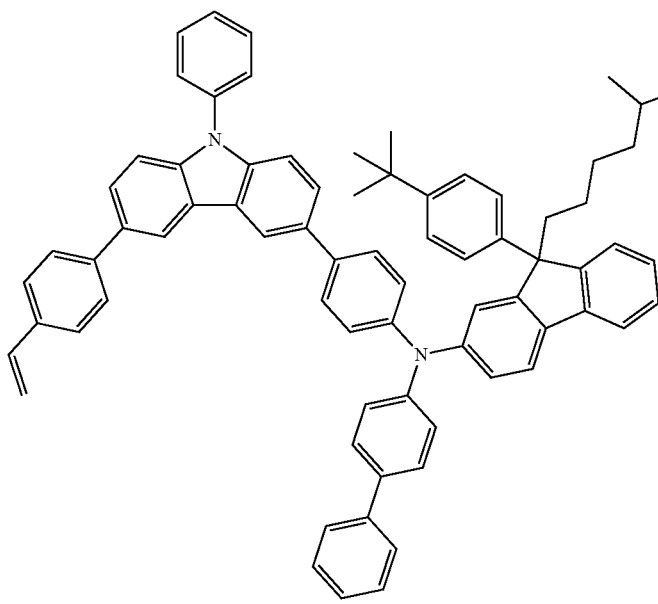
132
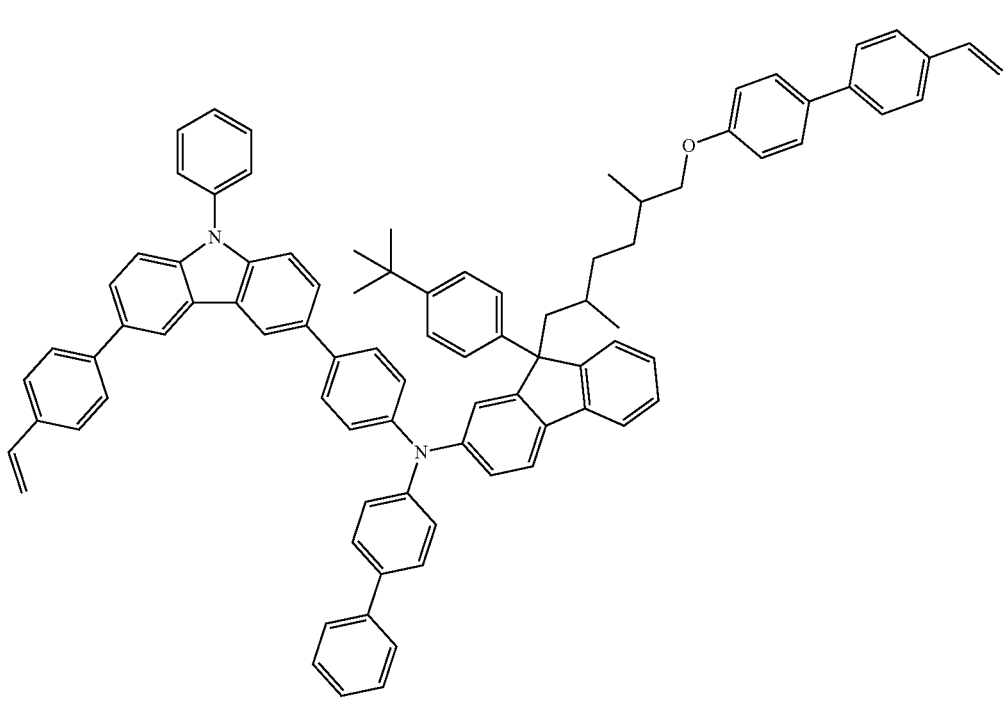

133
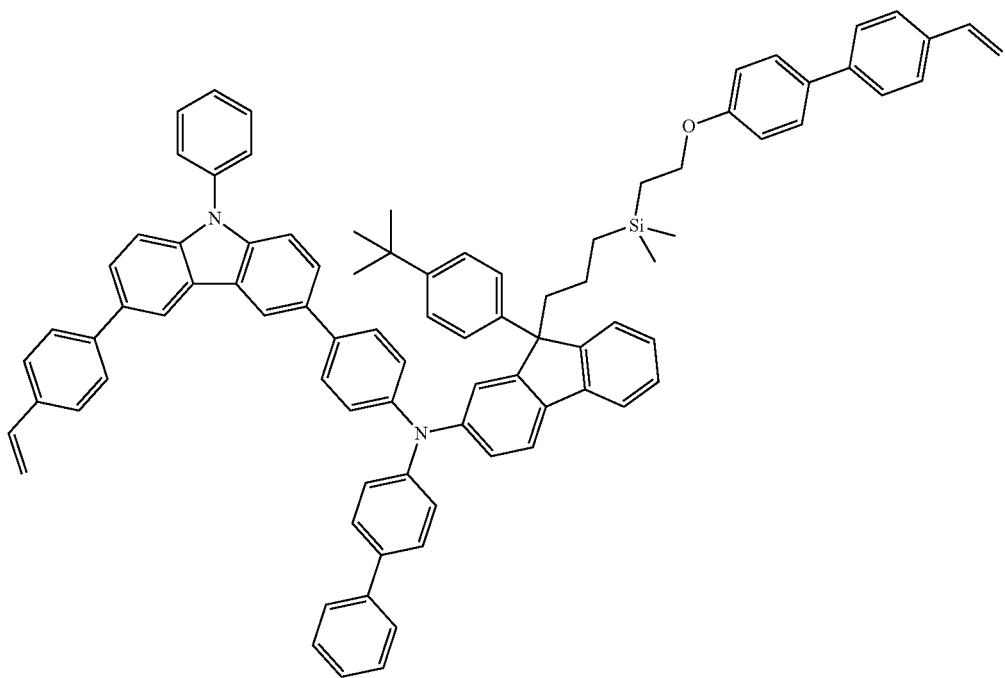 [SMILES: C=Cc1ccc(-c2ccc(OCC[Si](C)(C)CCCC3(c4ccc(C(C)(C)C)cc4)c4ccccc4-c4ccc(N(c5ccc(-c6ccccc6)cc5)c5ccc(-c6ccc7c(c6)c6cc(-c8ccc(C=C)cc8)ccc6n7-c6ccccc6)cc5)cc43)cc2)cc1]
134
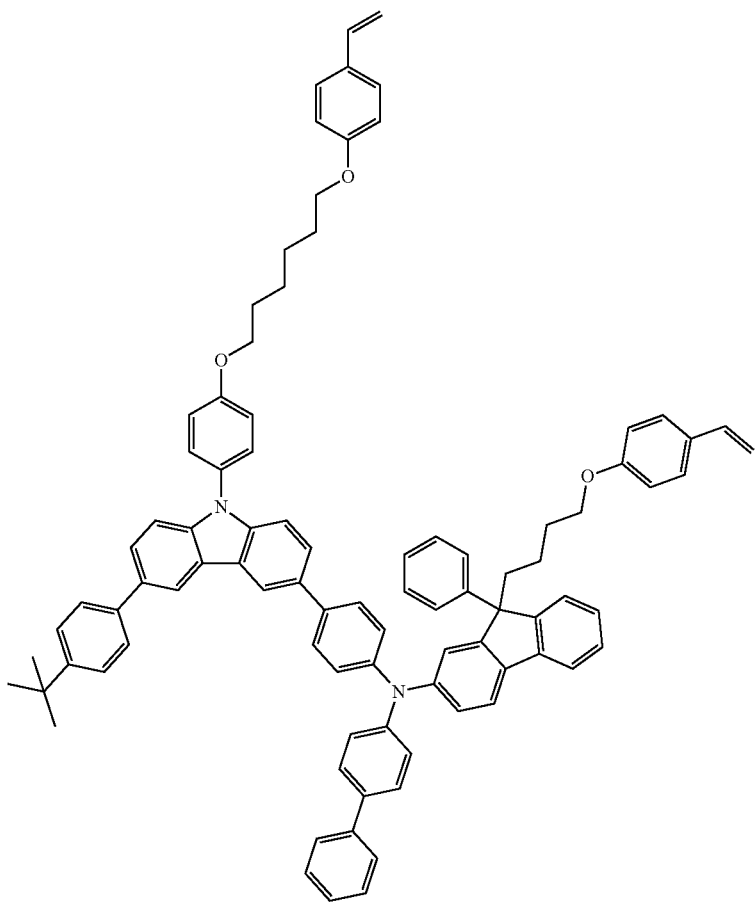

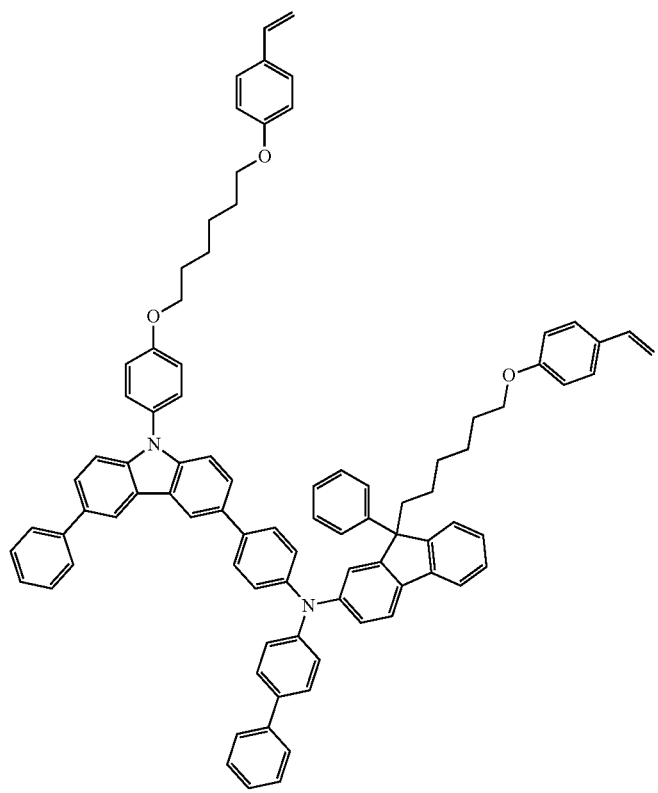
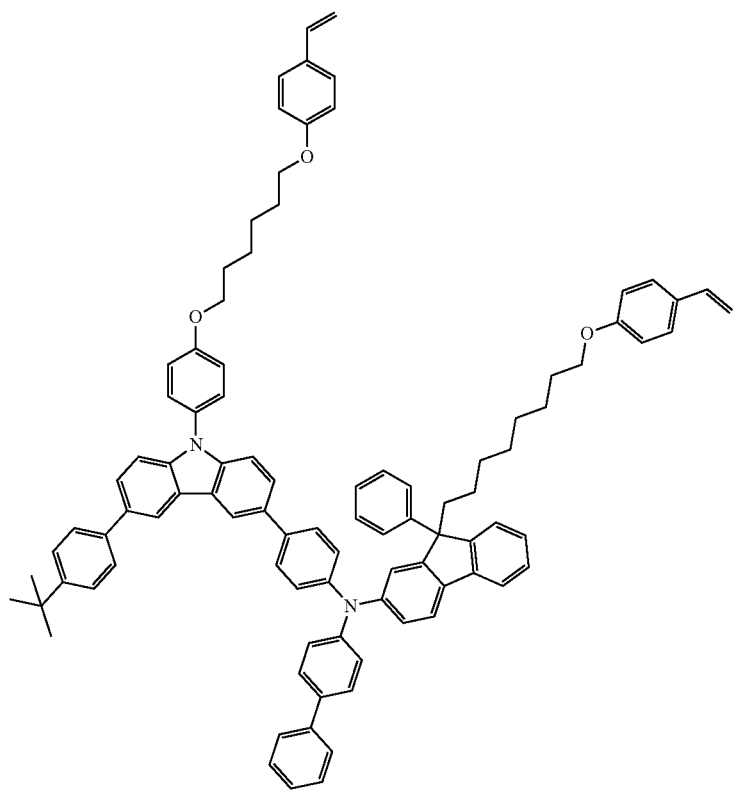 [SMILES: C=Cc1ccc(OCCCCCCCCC2(c3ccccc3)c3ccccc3-c3ccc(N(c4ccc(-c5ccccc5)cc4)c4ccc(-c5ccc6c(c5)c5cc(-c7ccc(C(C)(C)C)cc7)ccc5n6-c5ccc(OCCCCCCOc6ccc(C=C)cc6)cc5)cc4)cc32)cc1]

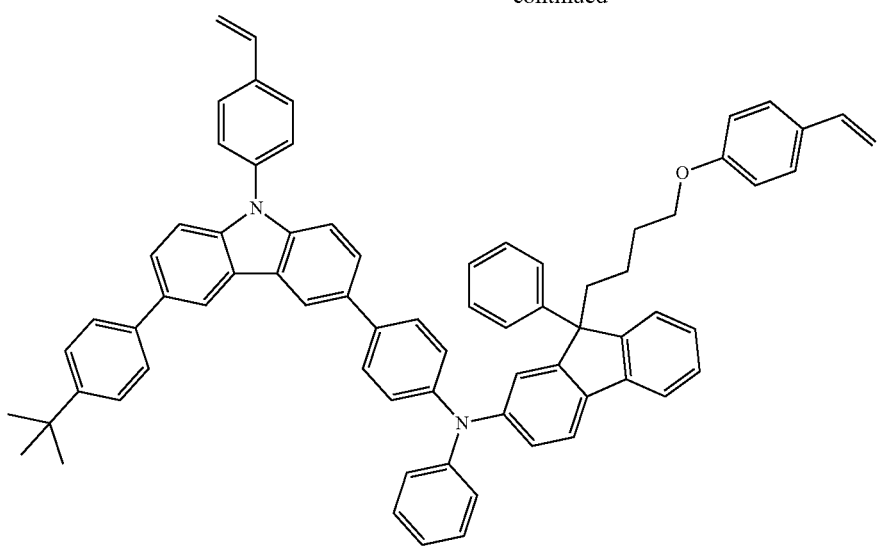
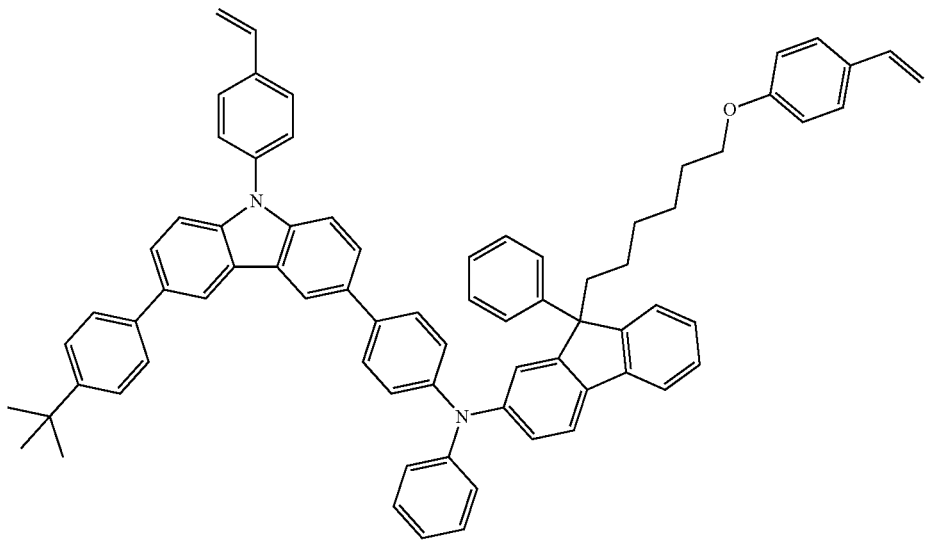
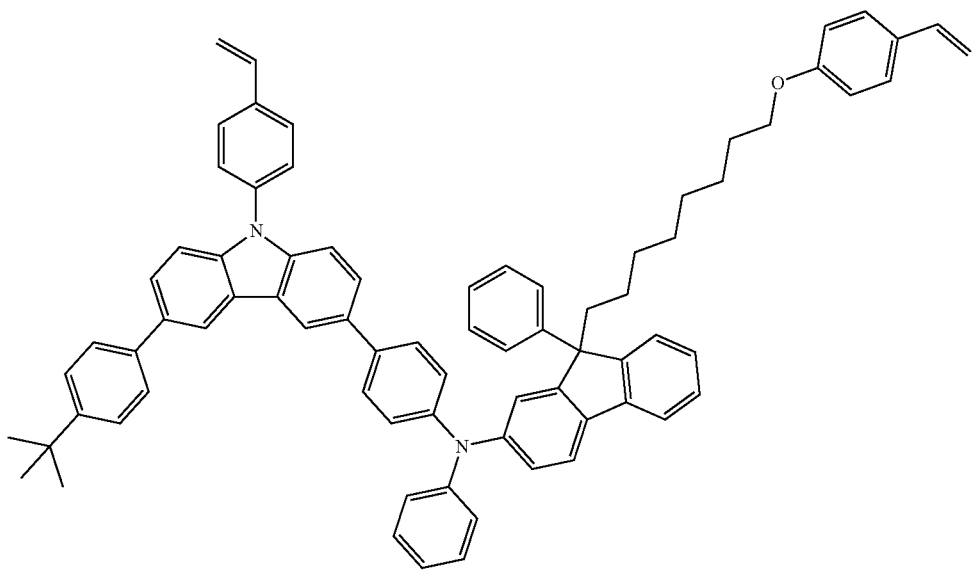

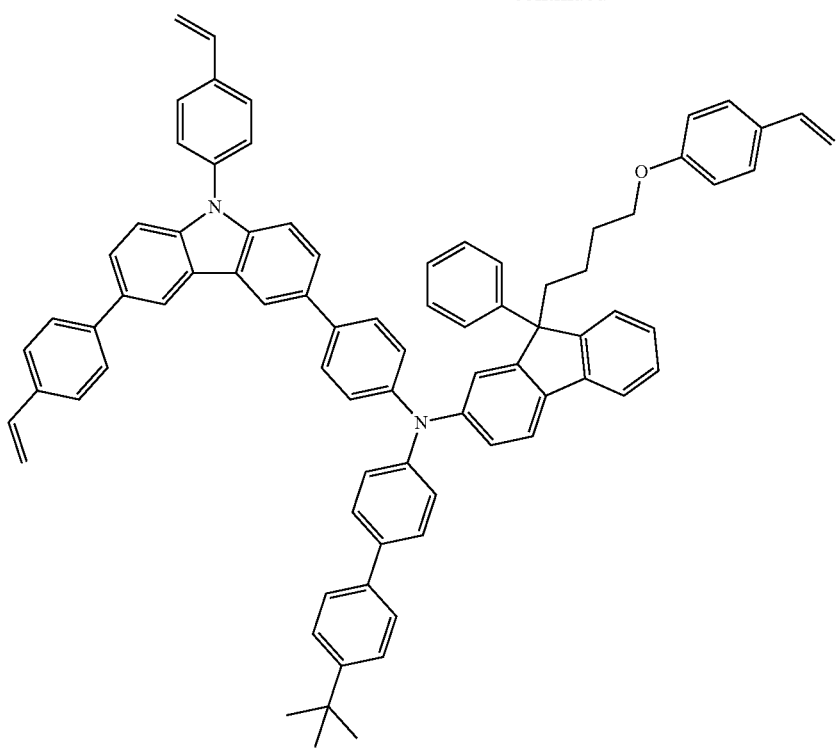
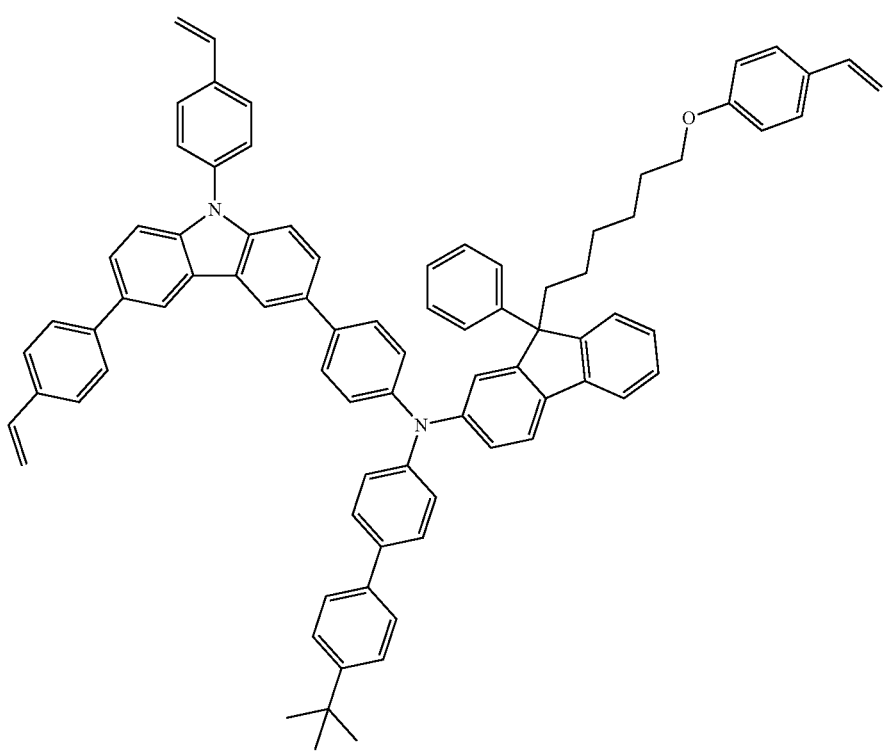

141 142
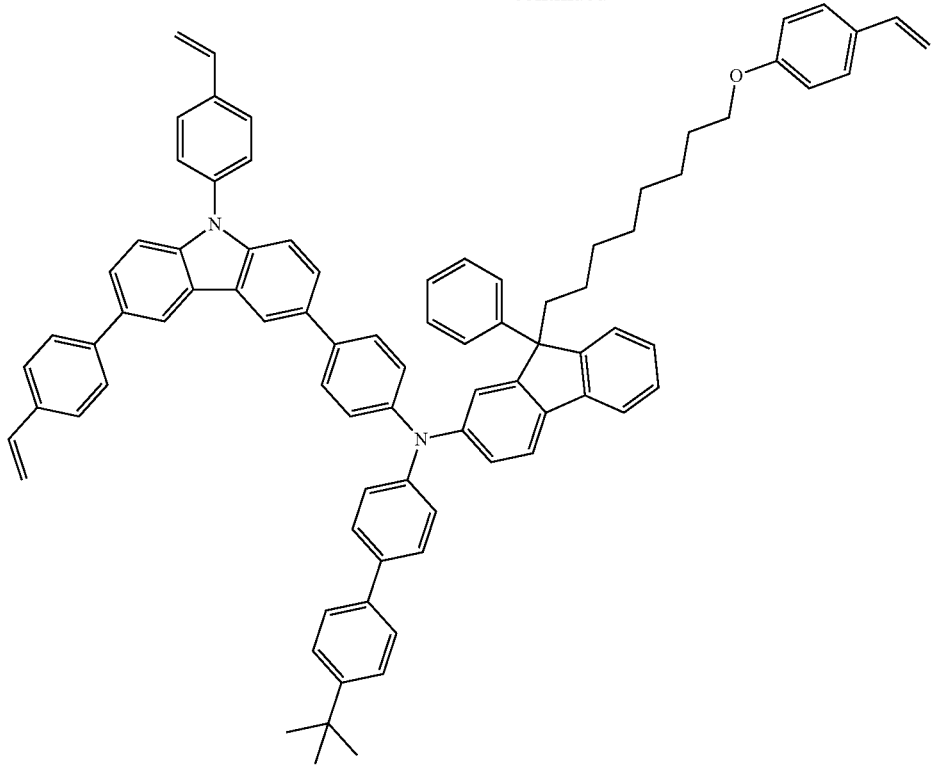 [SMILES: C=Cc1ccc(OCCCCCCCCC2(c3ccccc3)c3ccccc3-c3ccc(N(c4ccc(-c5ccc(C(C)(C)C)cc5)cc4)c4ccc(-c5ccc6c(c5)c5cc(-c7ccc(C=C)cc7)ccc5n6-c5ccc(C=C)cc5)cc4)cc32)cc1]
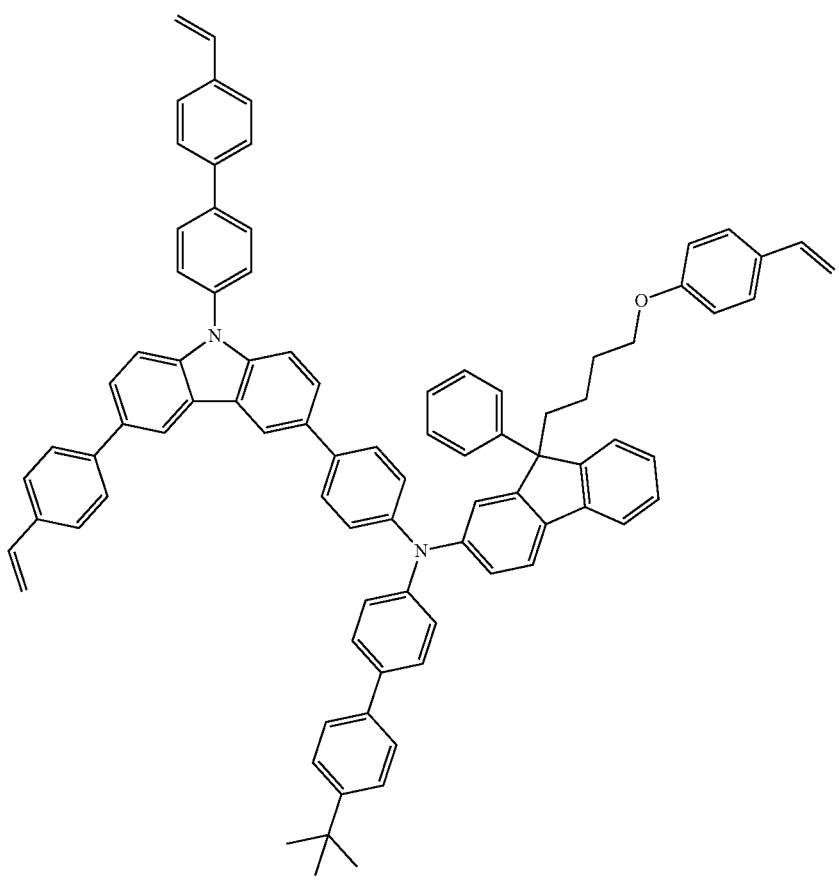

-continued
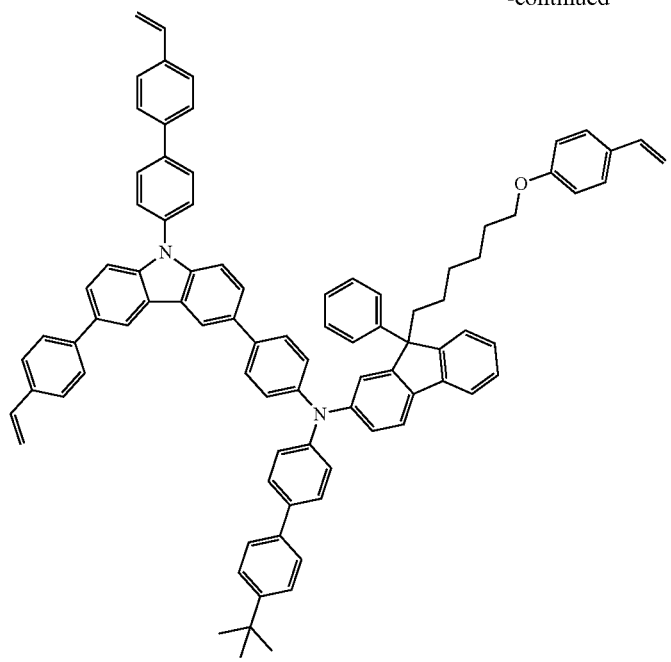
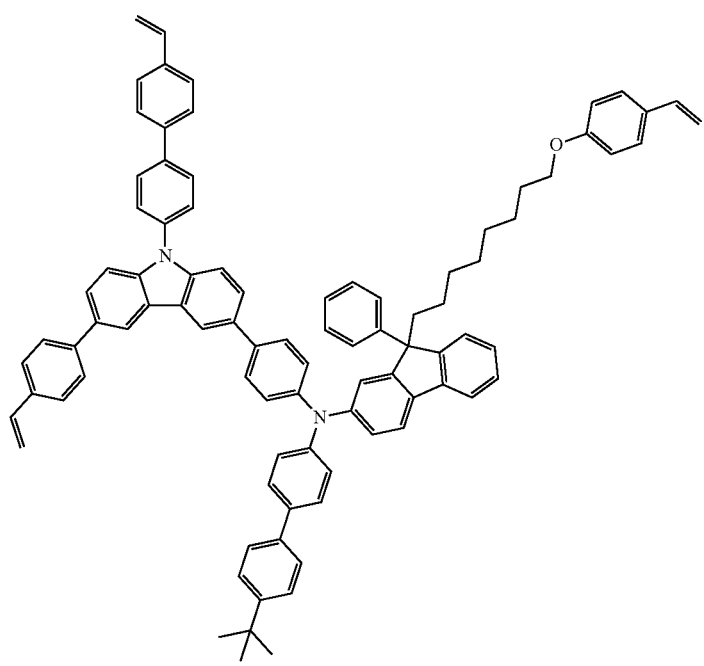 [SMILES: C=Cc1ccc(OCCCCCCCCC2(c3ccccc3)c3ccccc3-c3ccc(N(c4ccc(-c5ccc(C(C)(C)C)cc5)cc4)c4ccc(-c5ccc6c(c5)c5cc(-c7ccc(C=C)cc7)ccc5n6-c5ccc(-c6ccc(C=C)cc6)cc5)cc4)cc32)cc1]

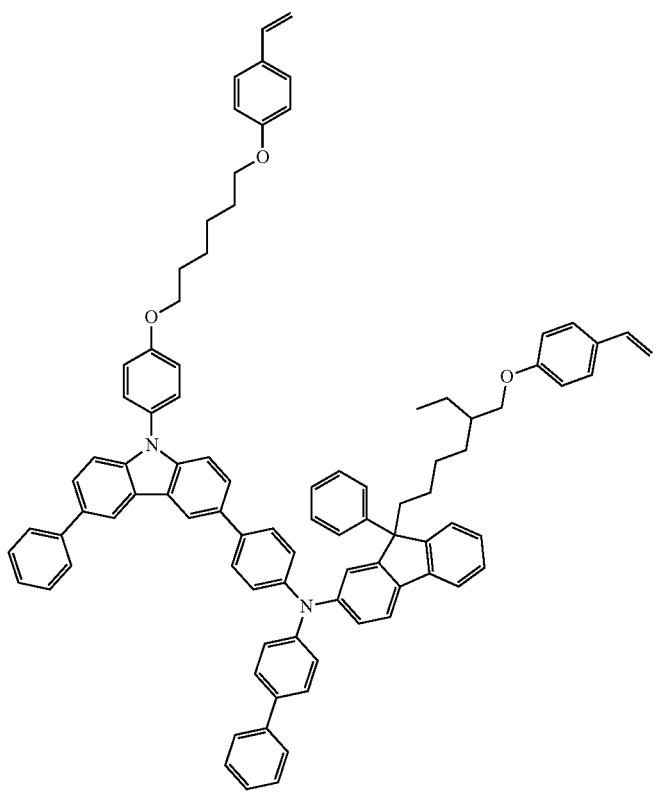
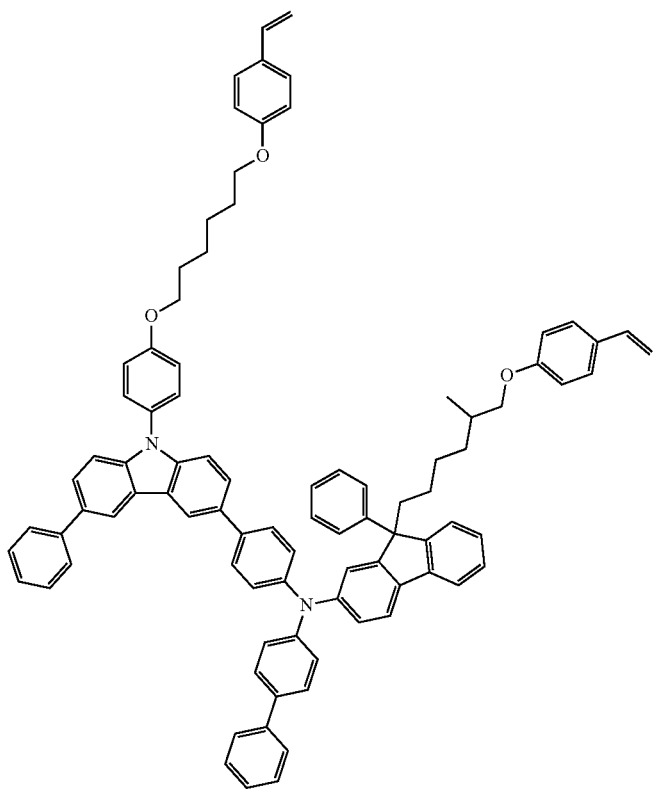

-continued
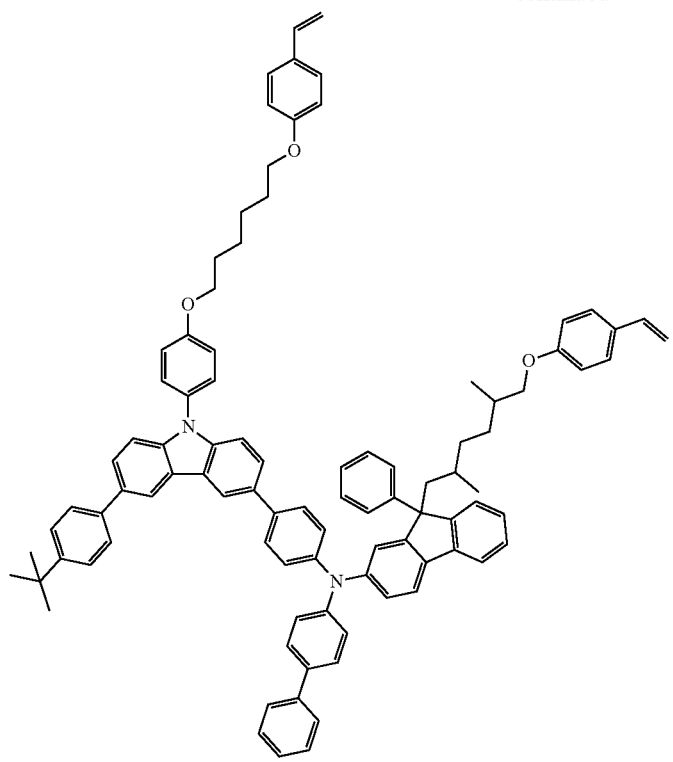
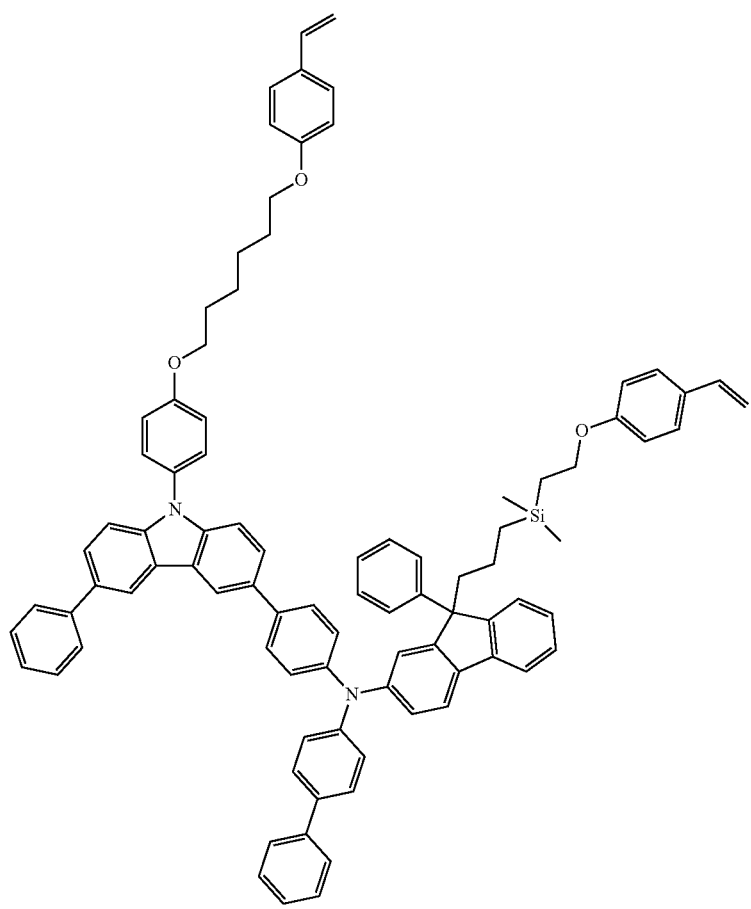

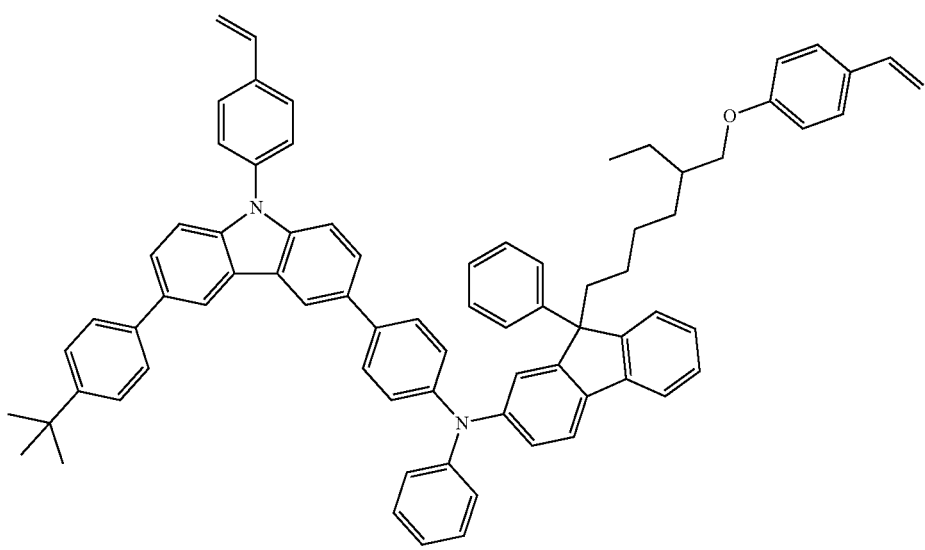
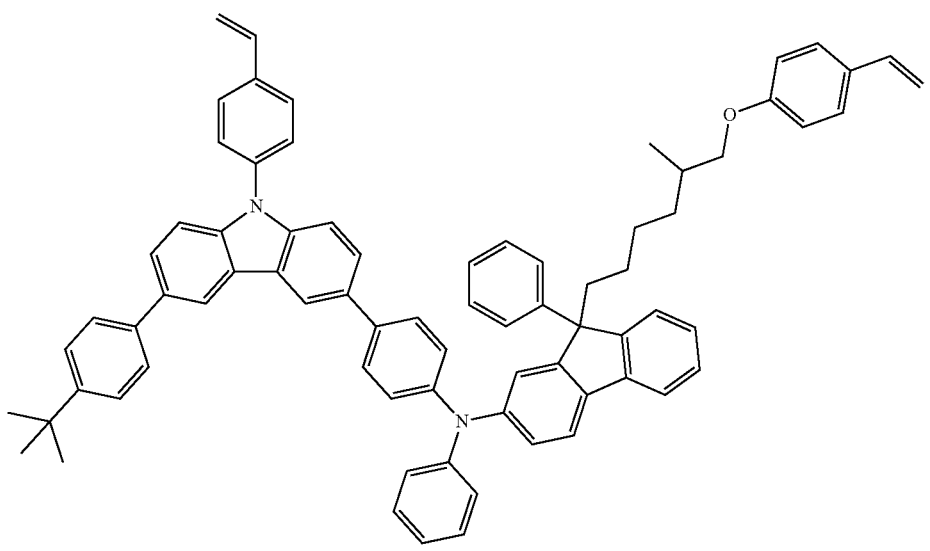
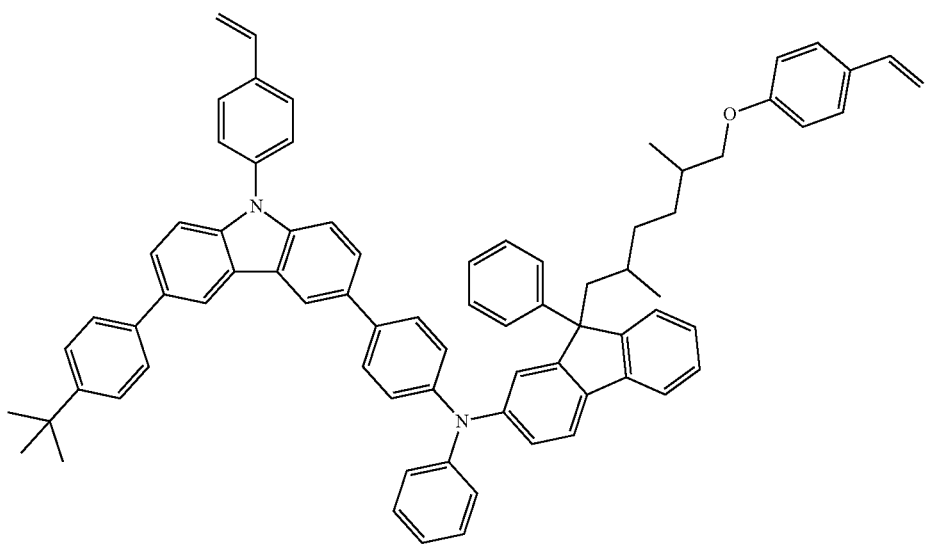

151
-continued
152
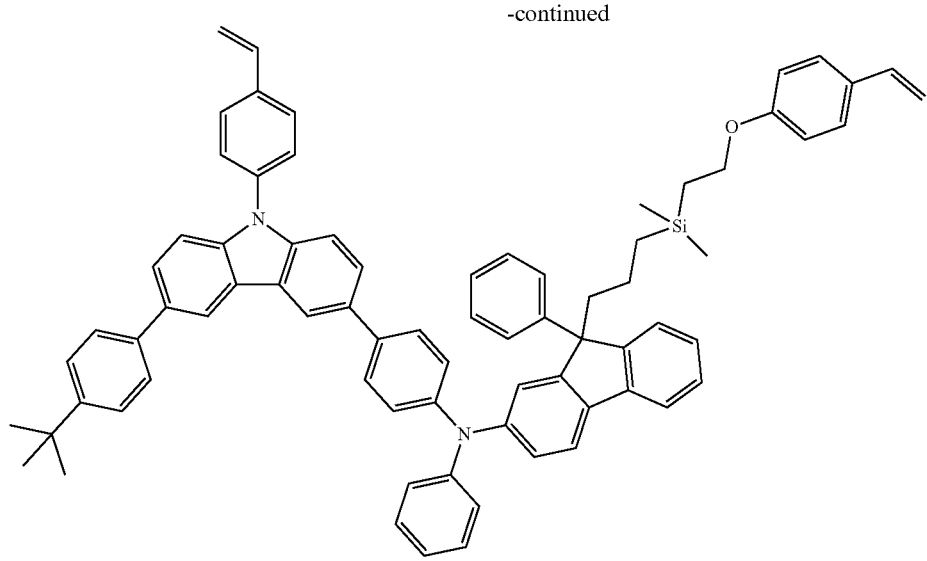
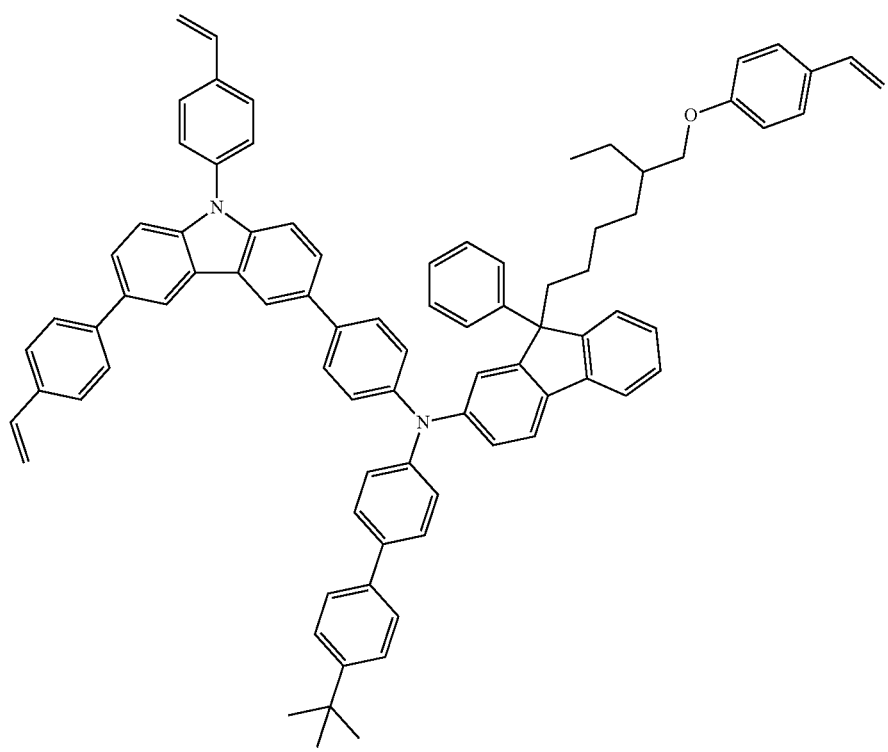

153 154
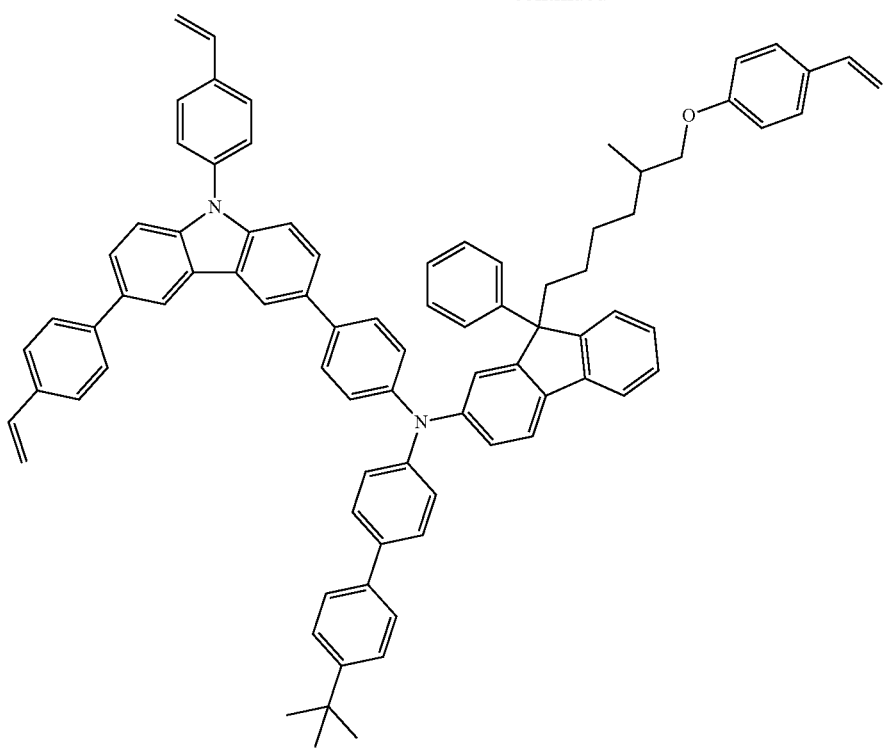
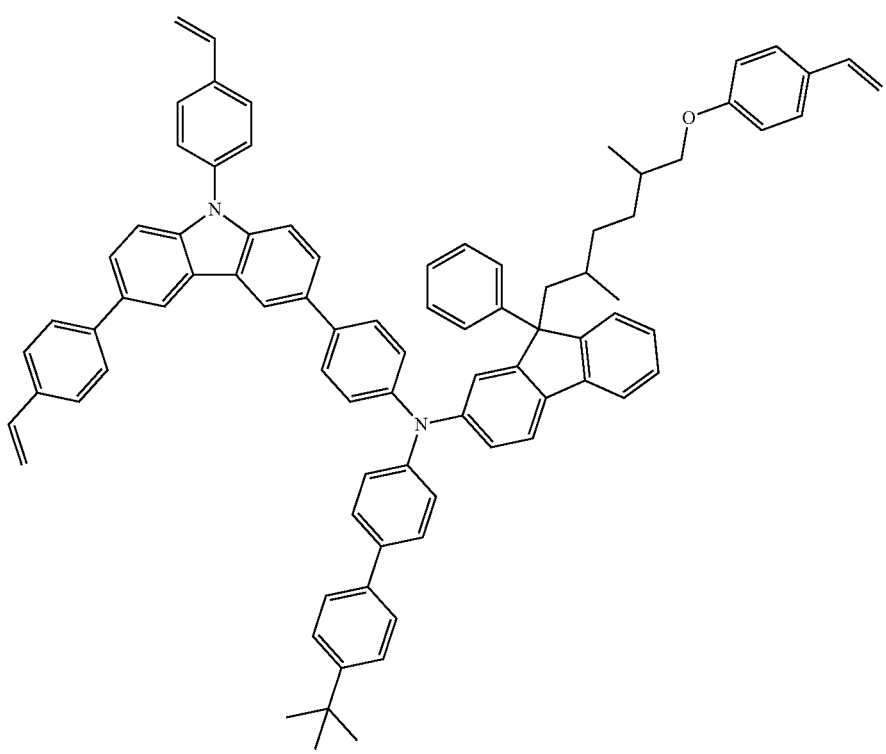

155 156
-continued
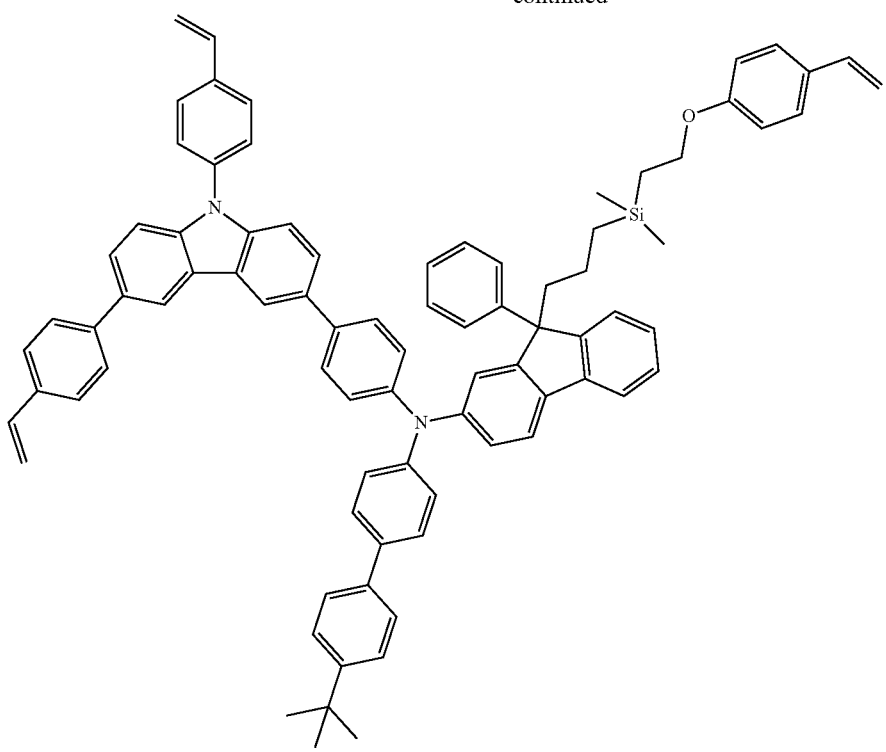
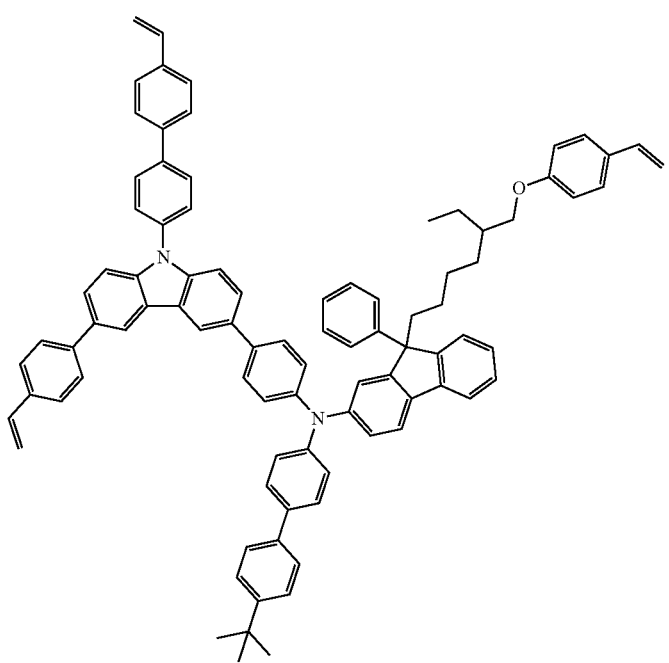

-continued
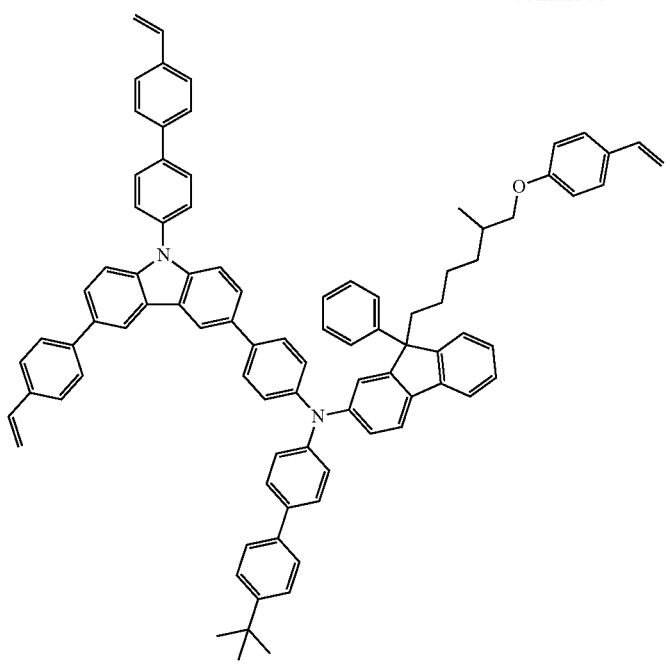
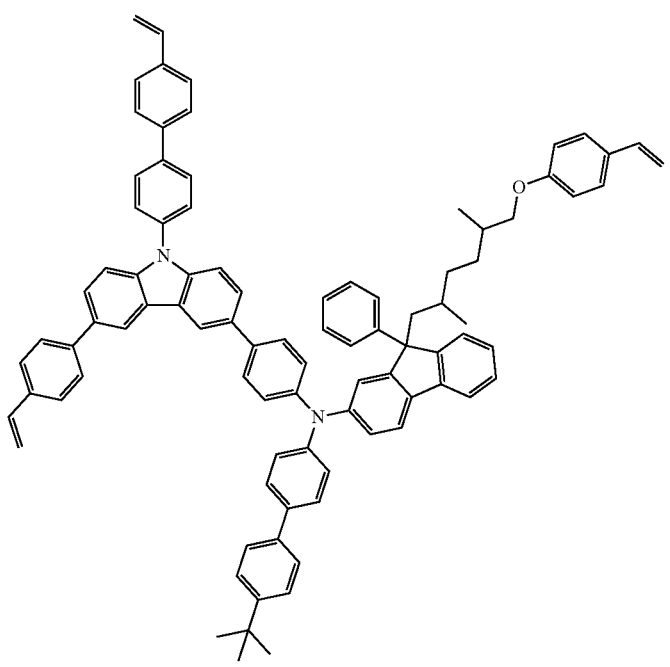

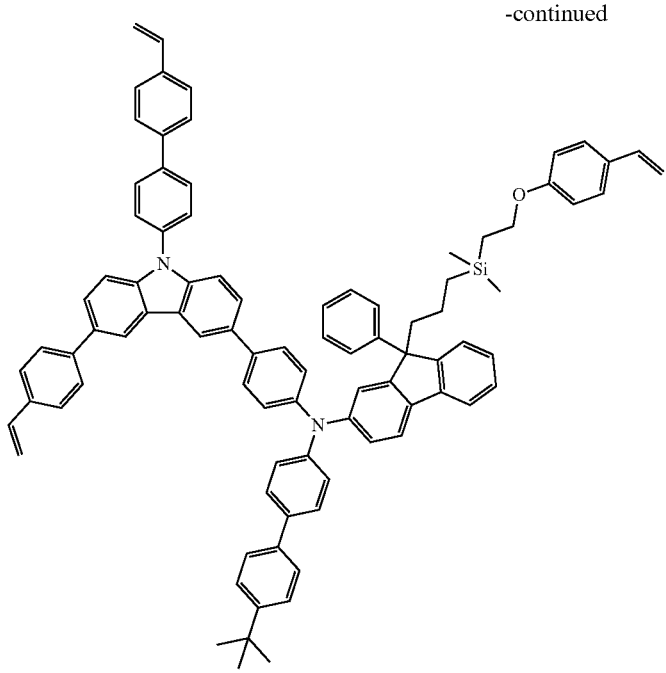

The compound according to one embodiment of the present specification may be prepared using preparation methods to describe below. In the preparation examples to describe below, representative examples are described, however, substituents may be added or excluded as necessary, and positions of the substituents may vary. In addition, based on technologies known in the art, starting materials, reaction materials, reaction conditions or the like may vary.

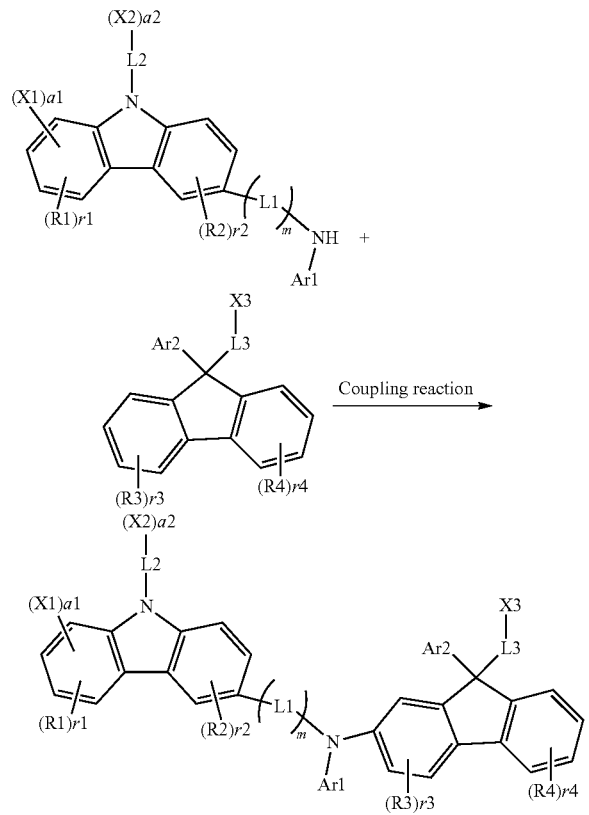

In the formula, X1 to X3, Ar1, Ar2, L1 to L3, R1 to R4, a1, a2, r1 to r3, and m have the same definitions as in Chemical Formula 1.

One embodiment of the present specification provides a coating composition including the compound.

According to one embodiment of the present specification, the coating composition may further include a solvent.

In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited thereto as long as it is a solvent capable of dissolving or dispersing the compound according to one embodiment of the present specification.

In another embodiment, the solvent may be used either alone as one type, or as a mixture mixing two or more solvent types.

In another embodiment, the solvent preferably has a boiling point of 40° C. to 250° C. and more preferably 60° C. to 230° C., however, the boiling point is not limited thereto.

In another embodiment, viscosity of the single or mixed solvent is preferably from 1 CP to 10 CP and more preferably from 3 CP to 8 CP, but is not limited thereto.

In another embodiment, the coating composition preferably has a concentration of 0.1 wt/v % to 20 wt/v % and more preferably 0.5 wt/v % to 5 wt/v %, however, the concentration is not limited thereto.

In one embodiment of the present specification, the coating composition may further include one, two or more types of additives selected from the group consisting of thermal polymerization initiators and photopolymerization initiators.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5, 5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethyl-benzoylphenylethoxyphosphine oxide, bis(2,4,6-trimethyl-benzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like, but are not limited thereto.

In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

Another embodiment of the present specification provides an organic light emitting device formed using the coating composition.

In one embodiment of the present specification, the organic light emitting device comprises a first electrode; a second electrode provided opposite to the first electrode; and one or more organic material layers provided between the first electrode and the second electrode, wherein one or more layers of the organic material layers are formed using the coating composition including the compound, or a cured material thereof.

In one embodiment of the present specification, the first electrode is a cathode, and the second electrode is an anode.

In another embodiment, the first electrode is an anode, and the second electrode is a cathode.

In one embodiment of the present specification, the organic material layer formed using the coating composition is a hole transfer layer, a hole injection layer, or a layer carrying out hole transfer and hole injection at the same time.

In one embodiment of the present specification, the organic material layer including the coating composition or a cured material thereof is a light emitting layer.

In one embodiment of the present specification, the coating composition may further include an ionic compound represented by an anion group represented by the following Chemical Formula 11; and a cation group represented by the following Chemical Formula 12.

[Chemical Formula 11]

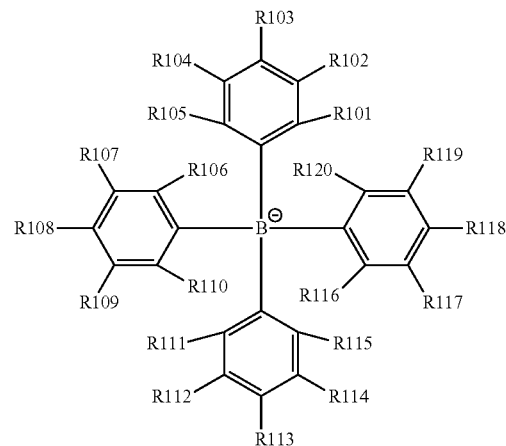

In Chemical Formula 11, at least one of R101 to R120 is F; a cyano group; or a substituted or unsubstituted fluoroalkyl group, at least one of the remaining R101 to R120 is a curing group, and the remaining R101 to R120 are the same as or different from each other, and each independently hydrogen; deuterium; a nitro group; a substituted or unsubstituted alkyl group; a substituted or unsubstituted alkenyl group; a substituted or unsubstituted amine group; a substituted or unsubstituted aryl group; or a substituted or unsubstituted heterocyclic group,

[Chemical Formula 12]

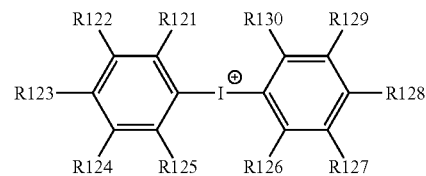

in Chemical Formula 12,

R121 to R130 are the same as or different from each other, and each independently hydrogen; deuterium; a nitro group;

a halogen group; a substituted or unsubstituted alkyl group; a substituted or unsubstituted cycloalkyl group; a substituted or unsubstituted alkenyl group; a substituted or unsubstituted aryl group; or a substituted or unsubstituted heterocyclic group, or a curing group.

In the present specification, the "curing group" may mean a reactive substituent crosslinking compounds by being exposed to heat and/or light. The crosslinking may be produced by linking radicals produced while carbon-carbon multiple bonds or cyclic structures are decomposed by heat treatment or light irradiation.

In one embodiment of the present specification, the curing group is any one selected from among the following structures.

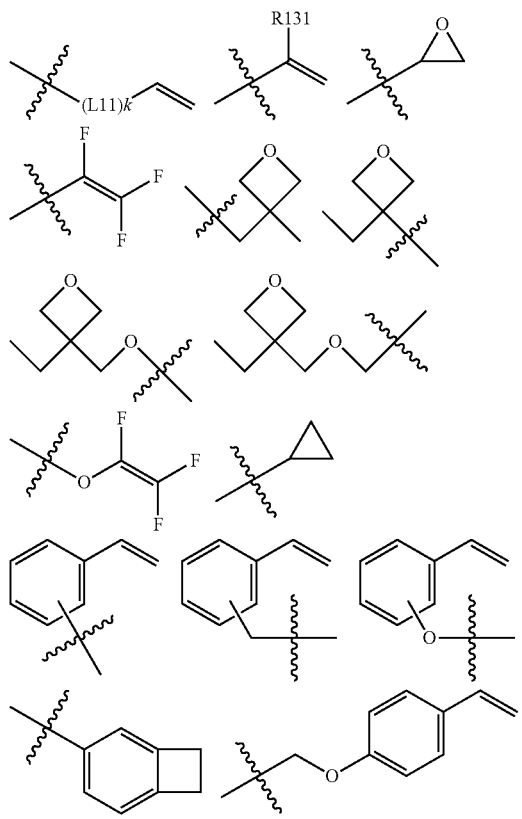

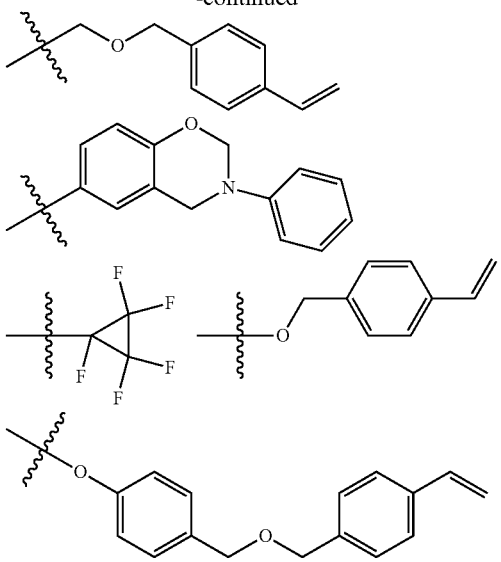

In the structures,

L11 is a direct bond; —O—; —S—; a substituted or unsubstituted alkylene group; a substituted or unsubstituted arylene group; or a substituted or unsubstituted heteroarylene group, k is 1 or 2, when k is 2, L11s are the same as or different from each other, and R131 is a substituted or unsubstituted alkyl group.

In one embodiment of the present specification, the curing group of Chemical Formula 11 is a vinyl group.

In one embodiment of the present specification, R103, R108, R113 and R118 of Chemical Formula 11 are the same as or different from each other, and each independently a vinyl group or F.

In one embodiment of the present specification, at least one of R103, R108, R113 and R118 of Chemical Formula 11 is a curing group.

In one embodiment of the present specification, at least one of R103, R108, R113 and R118 of Chemical Formula 11 is a vinyl group.

In one embodiment of the present specification, at least one of R103, R108, R113 and R118 of Chemical Formula 11 is a vinyl group, and the rest are F.

In one embodiment of the present specification, the anion group represented by Chemical Formula 11 is any one selected from among the following structures.

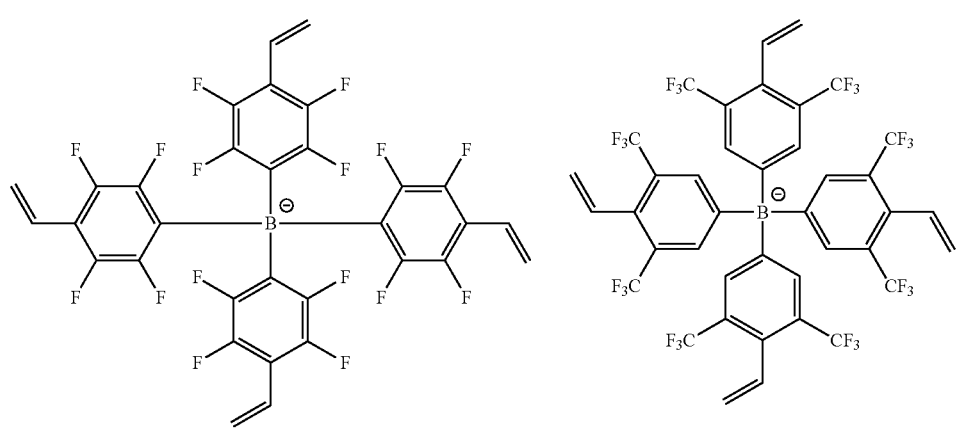

165 166
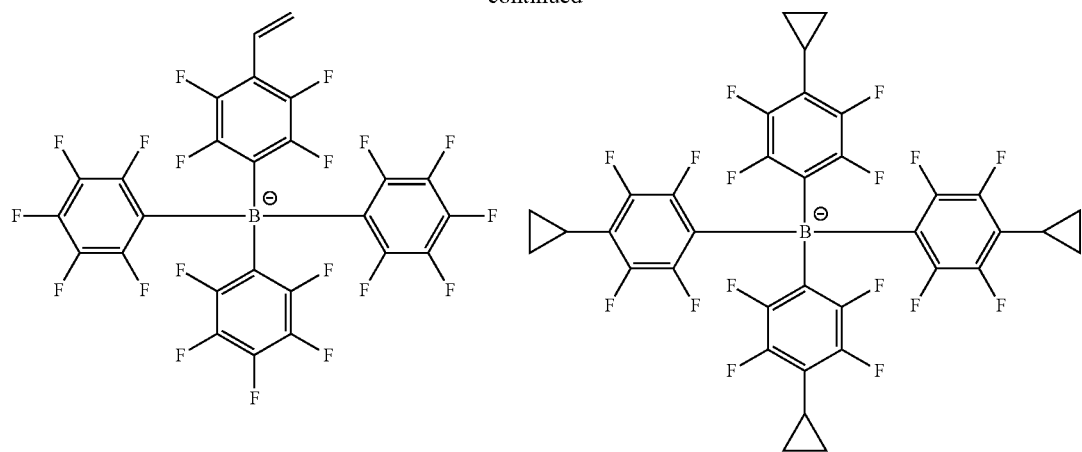
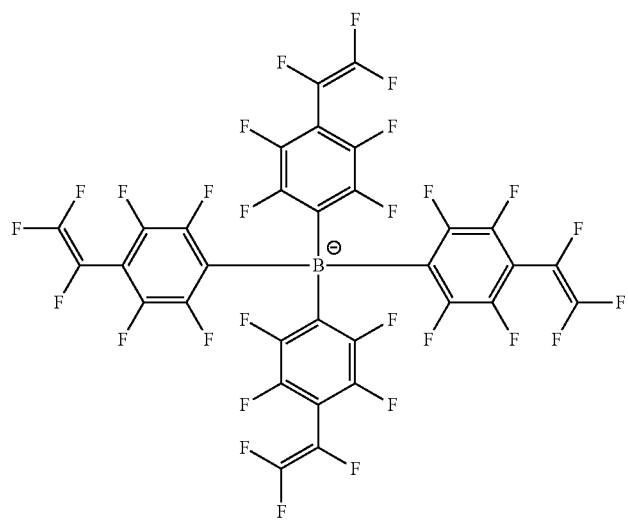
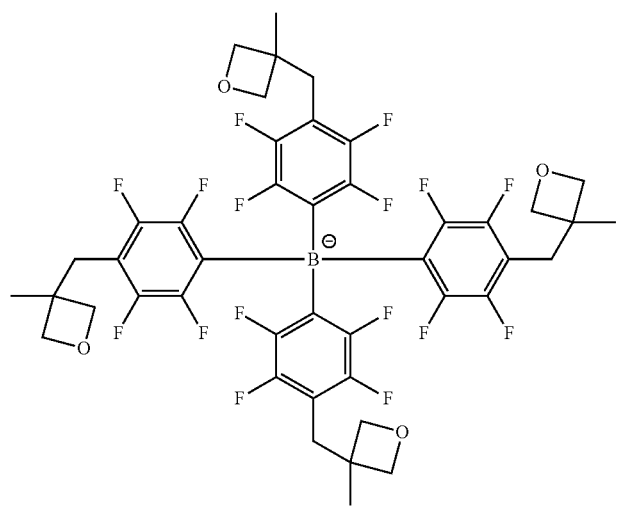

-continued
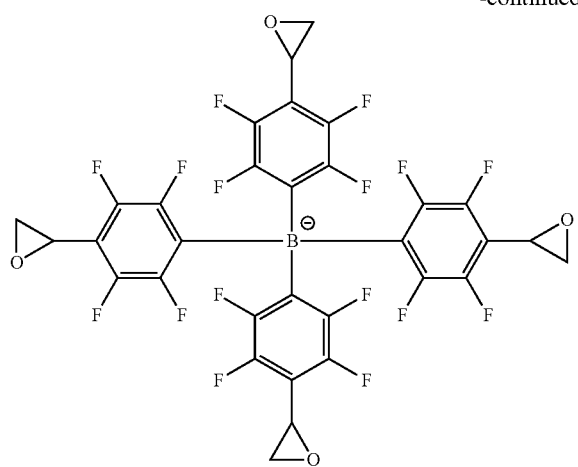
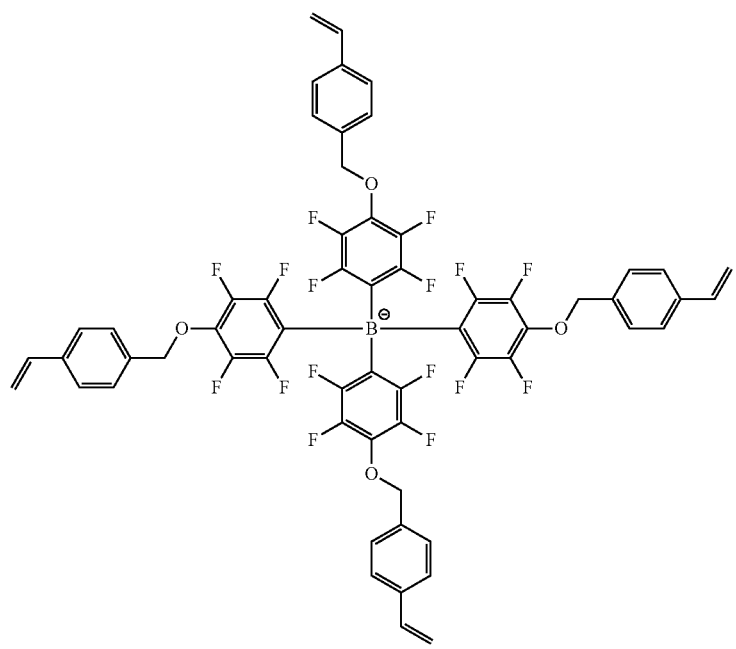
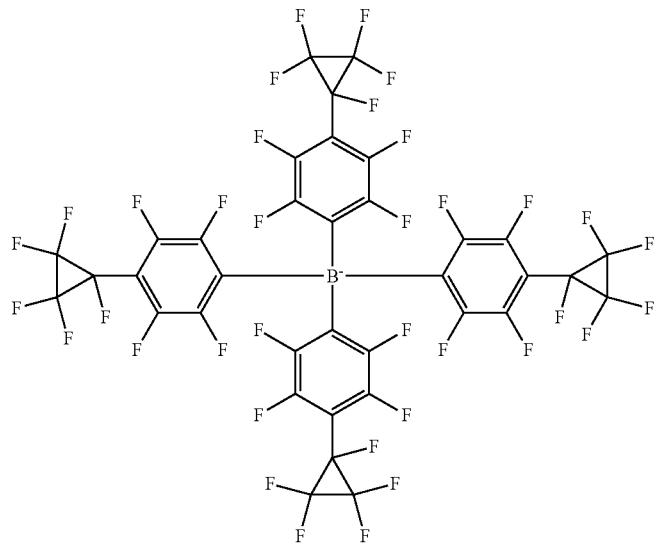

In one embodiment of the present specification, the cation group represented by Chemical Formula 12 is any one selected from among the following structures.

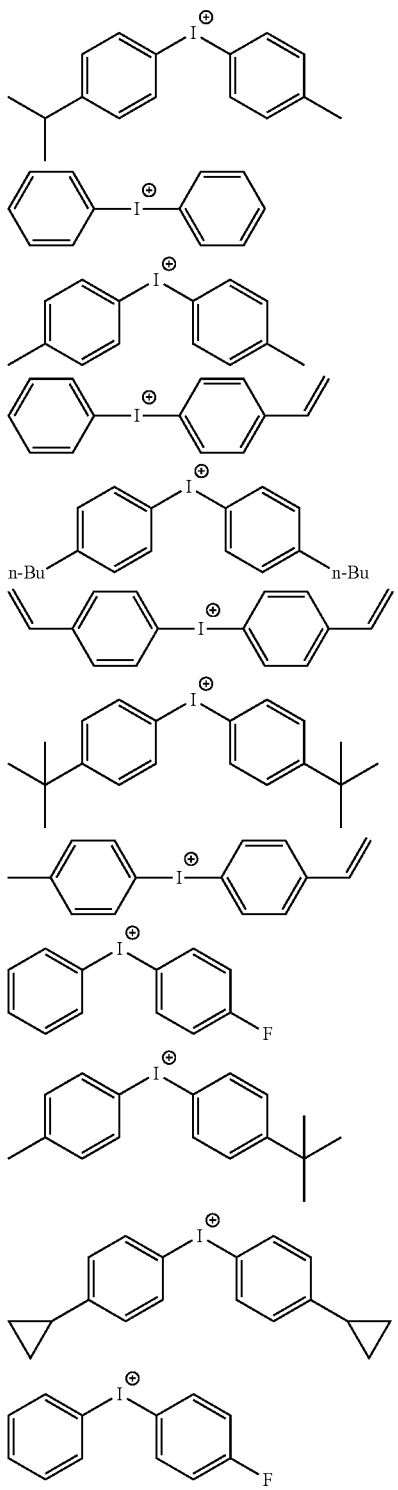

In one embodiment of the present specification, the organic light emitting device may further include one, two or more layers selected from the group consisting of a hole injection layer, a hole transfer layer, an electron transfer layer, an electron injection layer, an electron injection and transfer layer, an electron blocking layer and a hole blocking layer.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present specification may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

For example, a structure of the organic light emitting device according to one embodiment of the present specification is illustrated in the FIGURE.

The FIGURE illustrates a structure of the organic light emitting device in which an anode (201), a hole injection layer (301), a hole transfer layer (401), a light emitting layer (501), an electron injection and transfer layer (601) and a cathode (701) are consecutively laminated on a substrate (101).

The FIGURE illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

Another embodiment of the present specification provides a method for manufacturing an organic light emitting device formed using the coating composition.

Specifically, in one embodiment of the present specification, the method for manufacturing an organic light emitting device includes preparing a substrate; forming a cathode or an anode on the substrate; forming one or more organic material layers on the cathode or the anode; and forming an anode or a cathode on the organic material layer, wherein the forming of organic material layers includes forming one or more organic material layers using the coating composition.

In one embodiment of the present specification, the organic material layer formed using the coating composition is formed using spin coating or inkjetting.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer formed using the coating composition includes coating the coating composition on the cathode or the anode; and heat treating or light treating the coated coating composition.

In one embodiment of the present specification, the time of heat treating the organic material layer formed using the coating composition is preferably within 1 hour and more preferably within 30 minutes.

In one embodiment of the present specification, the atmosphere of heat treating the organic material layer formed using the coating composition is preferably inert gas such as argon or nitrogen.

When the forming of organic material layers using the coating composition includes the heat treating or light treating, a plurality of fluorene groups included in the coating composition form crosslinking, and an organic material layer including a thin-filmed structure may be provided. In this case, being dissolved by a solvent deposited on a surface of the organic material layer formed using the coating composition, or being morphologically influenced or decomposed may be prevented.

Accordingly, when the organic material layer formed using the coating composition is formed including the heat treating or light treating, resistance for a solvent increases, and a multilayer may be formed by repeatedly performing solution deposition and crosslinking method, and as a result, lifetime properties of a device may be enhanced due to increased stability.

In one embodiment of the present specification, the coating composition including the compound may use a coating composition mixed to a polymer binder and dispersed.

In one embodiment of the present specification, as the polymer binder, those that do not extremely inhibit charge transfer are preferred, and those that do not have strong absorption for visible light are preferably used. Examples of the polymer binder may include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, the compound according to one embodiment of the present specification may be included alone in the organic material layer, or may be included as a copolymer using a coating composition mixed with other monomers. In addition, a copolymer or a mixture may be included using a coating composition mixed with other polymers.

As the anode material, materials having large work function are normally preferred so that hole injection to an organic material layer is smooth. Specific examples of the anode material capable of being used in the present specification include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection layer is a layer that injects holes from an electrode, and the hole injection material is preferably a compound that has an ability to transfer holes and thereby has a hole injection effect in an anode and an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including Alq$_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, aluminum complexes and the like are included, however, the material is not limited thereto.

The organic light emitting device according to the present specification may be a top-emission type, a bottom-emission type or a dual-emission type depending on the materials used.

In one embodiment of the present specification, the compound may be included in an organic solar cell or an organic transistor in addition to the organic light emitting device.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

PREPARATION EXAMPLE

Preparation Example 1. Preparation of Compound A

1) Preparation of Intermediate A-1

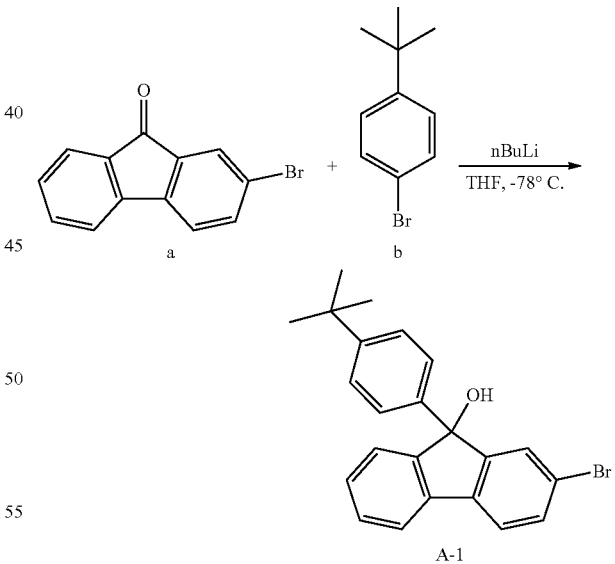

A-1 b (61.8 g, 290 mmol, 1.5 eq.) was dissolved in tetrahydrofuran (THF) (385 ml, 0.5 M), and the temperature was lowered to −78° C. nBuLi (2.5 M in hexane) (116 ml, 290 mol, 1.5 eq.) was slowly introduced thereto, and the result was stirred for 30 minutes at −78° C. a (50 g, 193 mmol, 1.0 eq.) was introduced thereto, and the result was stirred overnight. After that, the reaction was stopped using 1 N HCl (aq), and the organic layer was extracted with ethyl acetate [EA]. The organic layer was dried with magnesium sulfate, and after removing the solvent, the result was purified using column chromatography to obtain Intermediate Compound A-1.

2) Preparation of Intermediate A-2

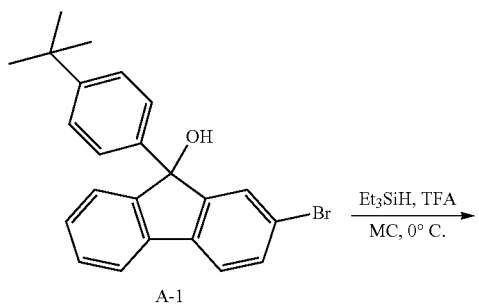

A-1 (30 g, 76.3 mmol, 1.0 eq.) was dissolved in methylene chloride (MC) (255 ml, 0.3 M), and the temperature was lowered to 0° C. Et₃SiH (18.3 ml, 114.5 mmol, 1.5 eq.) was introduced thereto, and then trifluoroacetic acid (TFA) (8.9 ml, 305 mmol, 4.0 eq.) was slowly introduced thereto. After that, the reaction was stopped using a saturated aqueous NaHCO₃ solution, and the organic layer was extracted with MC. The organic layer was dried with magnesium sulfate, and after removing the solvent, the result was purified using column chromatography to obtain Intermediate Compound A-2.

3) Preparation of Intermediate A-3

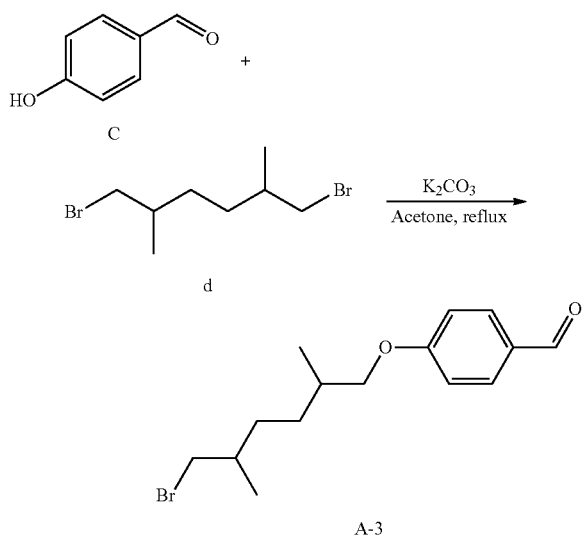

c (30 g, 245 mmol, 1.0 eq.) was dissolved in acetone (490 ml, 0.5 M), K₂CO₃ (67.7 g, 490 mmol, 2.0 eq.) was introduced thereto, and the result was refluxed for 30 minutes. d (133 g, 490 mmol, 2.0 eq.) was introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound A-3.

4) Preparation of Intermediate A-4

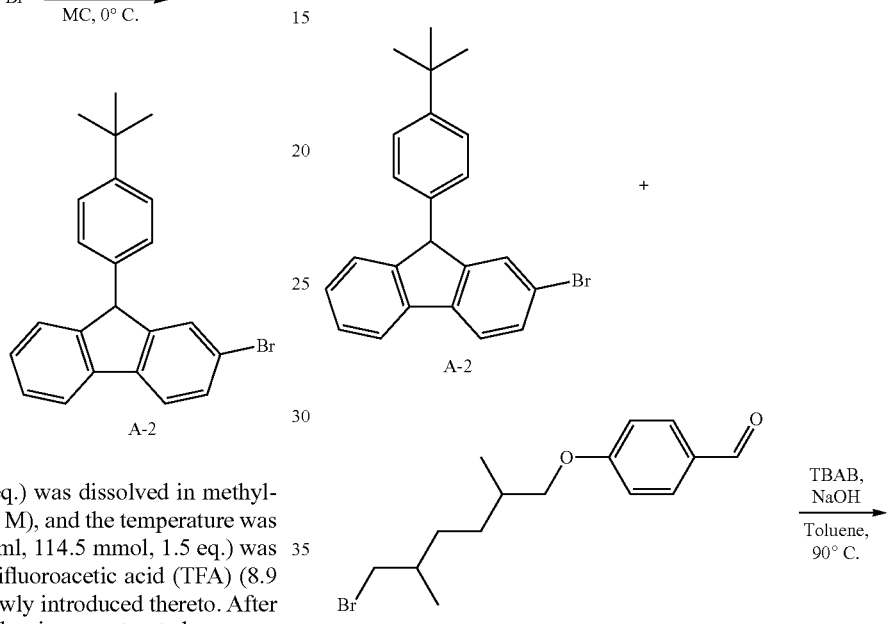

A-2 (20 g, 53 mmol, 1.0 eq.), tetrabutylammonium bromide (TBAB) (1.7 g, 5.3 mmol, 0.1 eq.) and toluene (176 ml, 0.3 M) were introduced, and stirred at 60° C. 50 wt % NaOH (3.18 ml, 159 mmol, 3.0 eq.) was slowly introduced thereto. A-3 (19.9 g, 63.6 mmol, 1.2 eq.) was introduced thereto, and the result was stirred overnight at 90° C. After that, the reaction was stopped using a saturated aqueous NH₄Cl solution, and the organic layer was extracted with ethyl acetate [EA]. The organic layer was dried with magnesium sulfate, and after removing the solvent, the result was purified using column chromatography to obtain Intermediate Compound A-4.

5) Preparation of Intermediate A-5

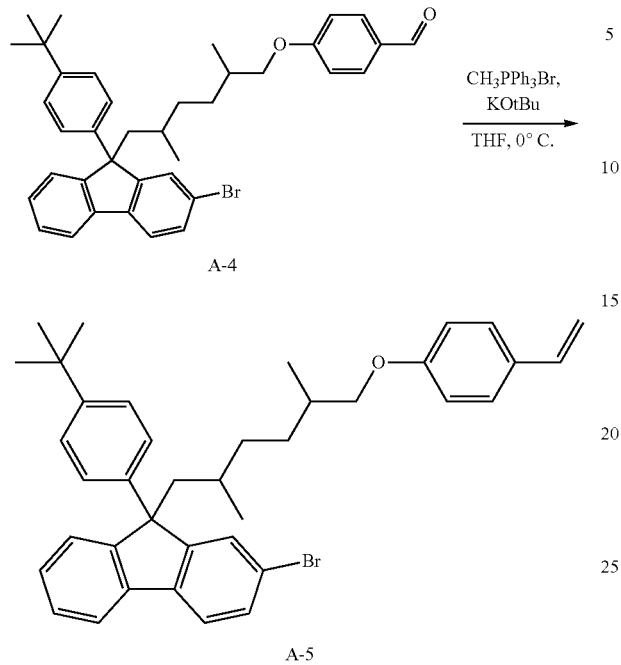

CH₃PPh₃Br (38.6 g, 108 mmol, 3.0 eq.), KOtBu (12.1 g, 108 mmol, 3.0 eq.) and tetrahydrofuran (THF) (180 ml, 0.2 M) were introduced, and stirred for 30 minutes at 0° C. A-4 (20 g, 36 mmol, 1.0 eq.) was introduced thereto, and the result was stirred for 2 hours. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound A-5.

6) Preparation of Intermediate A-6

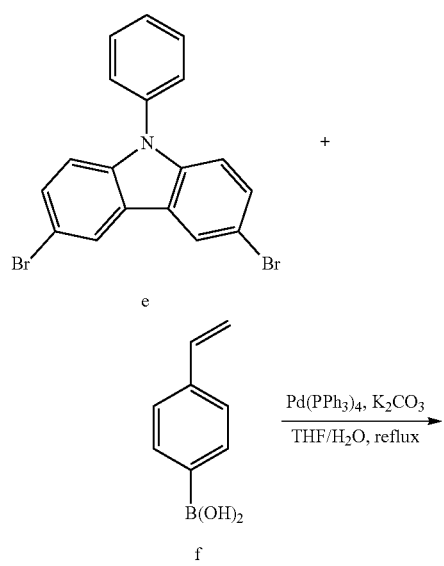

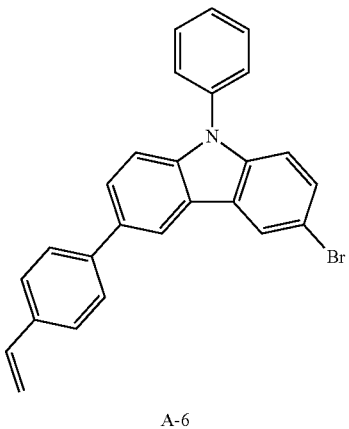

e (30 g, 74.8 mmol, 1.0 eq.) and f (13.3 g, 89.8 mmol, 1.2 eq.) were dissolved in tetrahydrofuran (THF) (250 ml, 0.3 M). K₂CO₃ (20.7 g, 150 mmol, 2.0 eq.) and H₂O (25 ml) were introduced thereto, and the result was refluxed. Pd(PPh₃)₄ (4.32 g, 3.74 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound A-6.

7) Preparation of Intermediate A-7

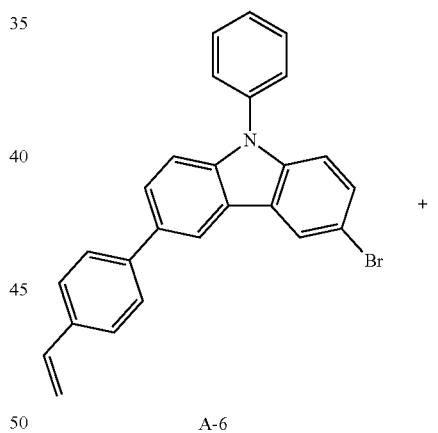

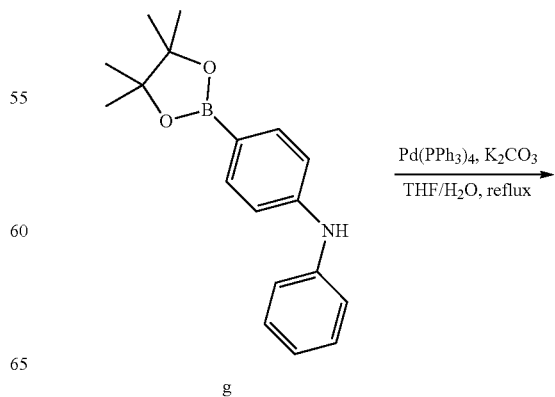

-continued

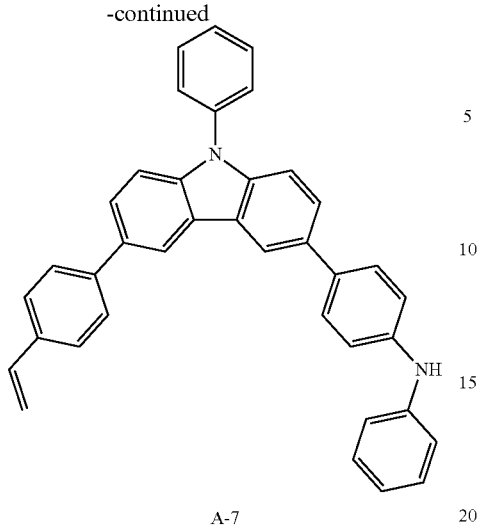

A-7

A-6 (30 g, 70.7 mmol, 1.0 eq.) and g (25 g, 84.8 mmol, 1.2 eq.) were dissolved in THF (235 ml, 0.3 M). K₂CO₃ (19.5 g, 141 mmol, 2.0 eq.) and H₂O (25 ml) were introduced thereto, and the result was refluxed. Pd(PPh₃)₄ (4.09 g, 3.54 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound A-7.

8) Preparation of Compound A

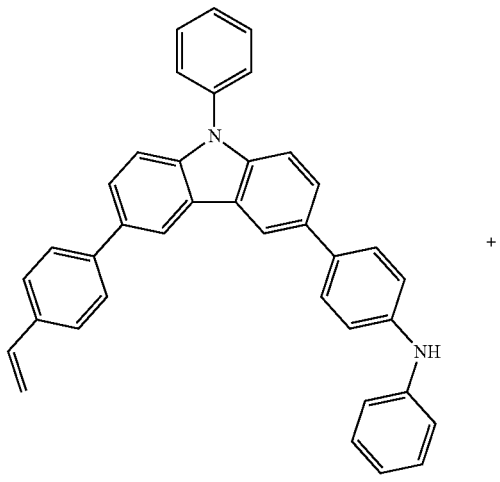

A-7

+

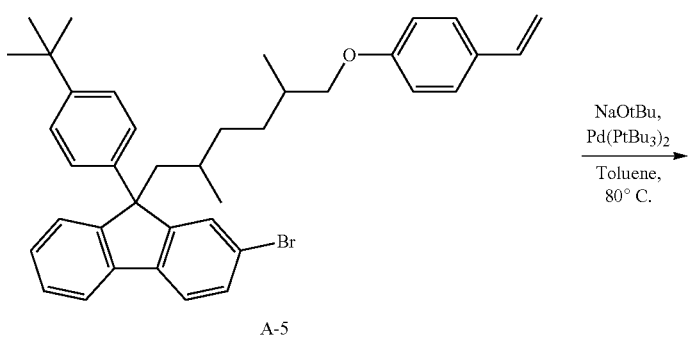

A-5

NaOtBu,
Pd(PtBu₃)₂
——————→
Toluene,
80° C.

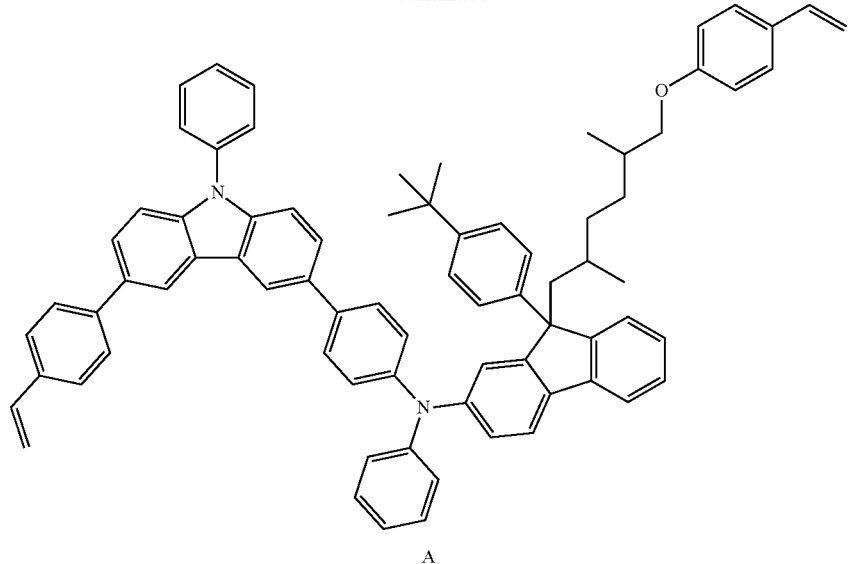

A

A-7 (10 g, 19.5 mmol, 1.0 eq.), A-5 (14.2 g, 23.4 mmol, 1.2 eq.), NaOtBu (5.6 g, 58.5 mmol, 3.0 eq.) and toluene (65 ml, 0.3 M) were introduced, and stirred at 80° C. Pd(PtBu$_3$)$_2$ (0.30 g, 0.585 mmol, 0.03 eq.) was introduced thereto, and the result was stirred for 4 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain white solid Compound A. NMR data values of Compound A are as follows.

1H NMR (500 MHz): δ=8.4-8.2 (d, 1H), 8.2-8.1 (d, 1H), 8.0-7.7 (m, 6H), 7.7-7.5 (m, 14H), 7.4-7.1 (m, 9H), 7.1-6.9 (m, 8H), 6.8-6.5 (m, 2H), 5.8-5.6 (d, 2H), 5.3-5.2 (d, 2H), 4.1-3.6 (q, 2H), 2.3-2.2 (d, 2H), 2.2-1.8 (m, 1H), 1.45-1.35 (m, 1H), 1.35-1.3 (s, 9H), 1.2-1.0 (m, 4H), 1.0-0.5 (d, 6H)

Preparation Example 2. Preparation of Compound B

1) Preparation of Intermediate B-1

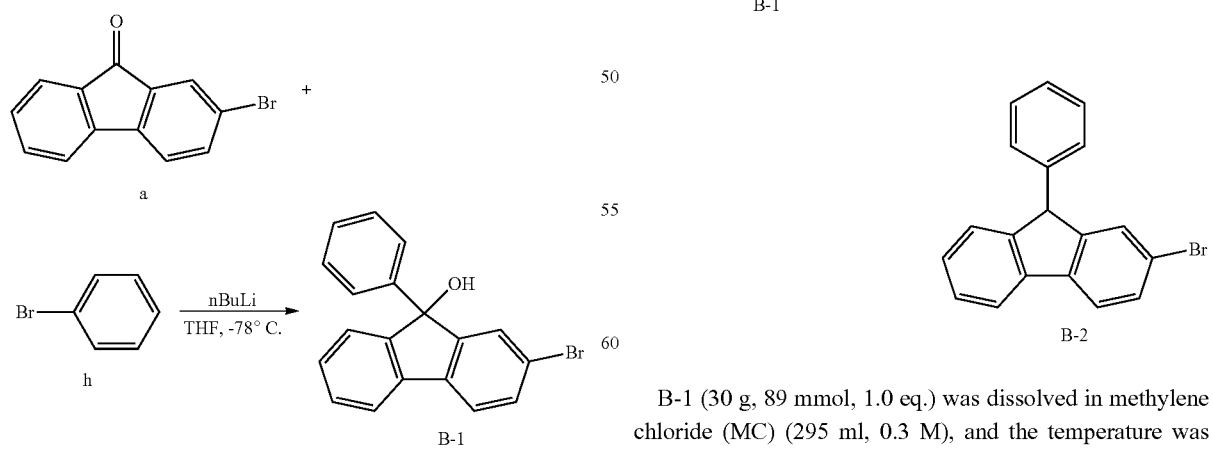

h (45.5 g, 290 mmol, 1.5 eq.) was dissolved in tetrahydrofuran (THF) (385 ml, 0.5 M), and the temperature was lowered to −78° C. nBuLi (2.5 M in hexane) (116 ml, 290 mol, 1.5 eq.) was slowly introduced thereto, and the result was stirred for 30 minutes at −78° C. a (50 g, 193 mmol, 1.0 eq.) was introduced thereto, and the result was stirred overnight. After that, the reaction was stopped using 1 N HCl (aq), and the organic layer was extracted with ethyl acetate [EA]. The organic layer was dried with magnesium sulfate, and after removing the solvent, the result was purified using column chromatography to obtain Intermediate Compound B-1.

2) Preparation of Intermediate B-2

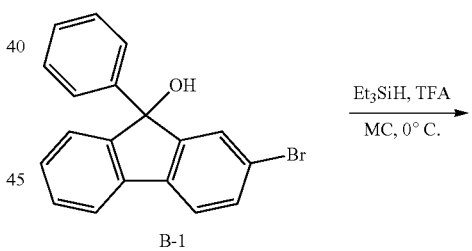

B-1 (30 g, 89 mmol, 1.0 eq.) was dissolved in methylene chloride (MC) (295 ml, 0.3 M), and the temperature was lowered to 0° C. Et$_3$SiH (21.3 ml, 133.4 mmol, 1.5 eq.) was introduced thereto, and then TFA (10.6 ml, 362 mmol, 4.0 eq.) was slowly introduced thereto. After that, the reaction was stopped using a saturated aqueous NaHCO₃ solution, and the organic layer was extracted with MC. The organic layer was dried with magnesium sulfate, and after removing the solvent, the result was purified using column chromatography to obtain Intermediate Compound B-2.

3) Preparation of Intermediate B-3

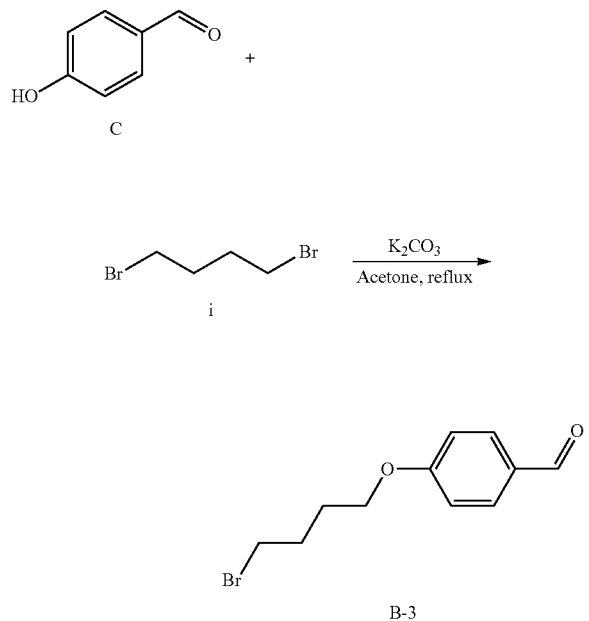

c (30 g, 245 mmol, 1.0 eq.) was dissolved in acetone (490 ml, 0.5 M), K₂CO₃ (67.7 g, 490 mmol, 2.0 eq.) was introduced thereto, and the result was refluxed for 30 minutes. i (106 g, 490 mmol, 2.0 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound B-3.

4) Preparation of Intermediate B-4

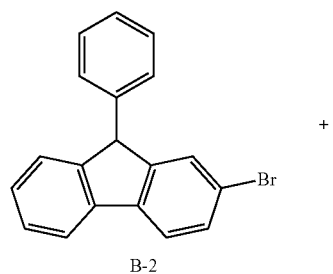

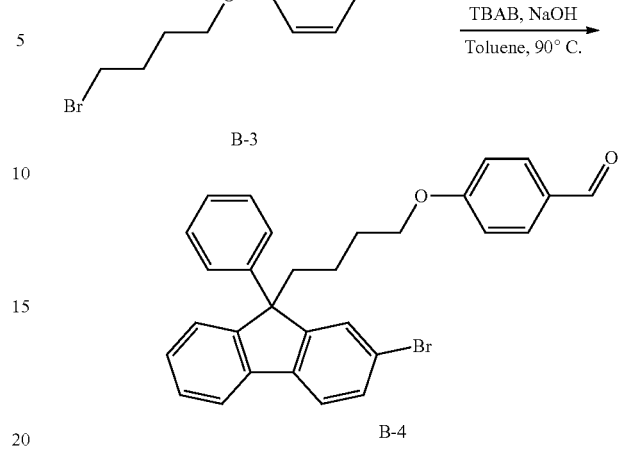

B-2 (20 g, 62 mmol, 1.0 eq.), TBAB (2 g, 6.2 mmol, 0.1 eq.) and toluene (205 ml, 0.3 M) were introduced, and stirred at 60° C. 50 wt % NaOH (3.72 ml, 186 mmol, 3.0 eq.) was slowly introduced thereto. B-3 (19.1 g, 74.4 mmol, 1.2 eq.) was introduced thereto, and the result was stirred overnight at 90° C. After that, the reaction was stopped using a saturated aqueous NH₄Cl solution, and the organic layer was extracted with ethyl acetate [EA]. The organic layer was dried with magnesium sulfate, and after removing the solvent, the result was purified using column chromatography to obtain Intermediate Compound B-4.

5) Preparation of Intermediate B-5

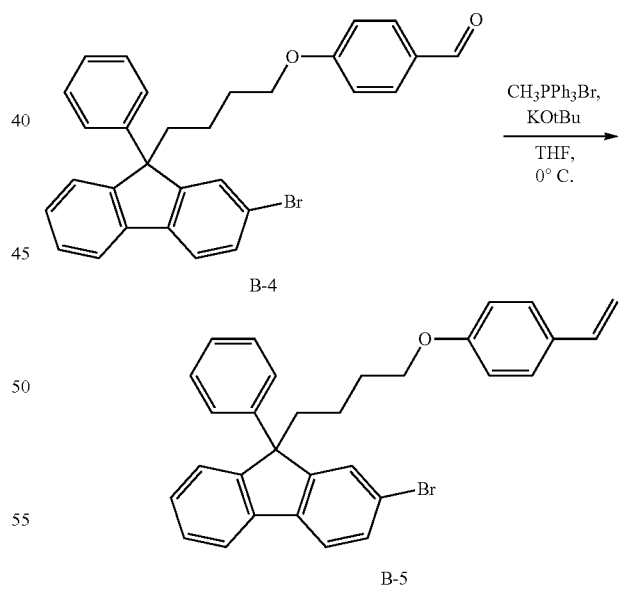

CH₃PPh₃Br (43 g, 121 mmol, 3.0 eq.), KOtBu (13.6 g, 121 mmol, 3.0 eq.) and THF (200 ml, 0.2 M) were introduced, and stirred for 30 minutes at 0° C. B-4 (20 g, 40 mmol, 1.0 eq.) was introduced thereto, and the result was stirred for 2 hours. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound B-5.

6) Preparation of Intermediate B-6

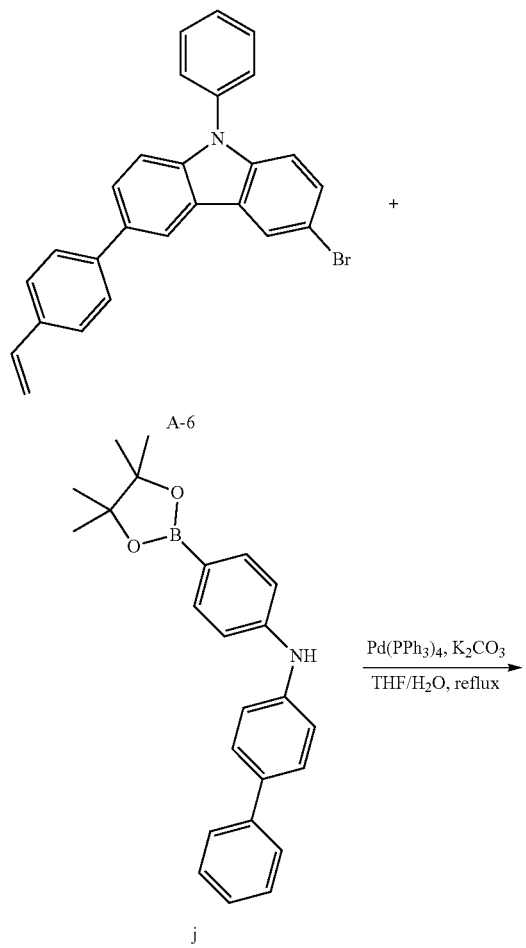

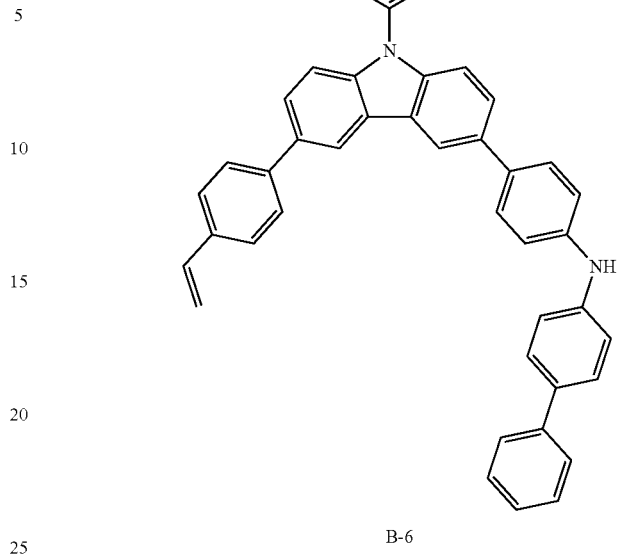

A-6 (30 g, 70.7 mmol, 1.0 eq.) and j (31.5 g, 84.8 mmol, 1.2 eq.) were dissolved in tetrahydrofuran (THF) (235 ml, 0.3 M). $K_2CO_3$ (19.5 g, 141 mmol, 2.0 eq.) and $H_2O$ (25 ml) were introduced thereto, and the result was refluxed. $Pd(PPh_3)_4$ (4.09 g, 3.54 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound B-6.

8) Preparation of Compound B

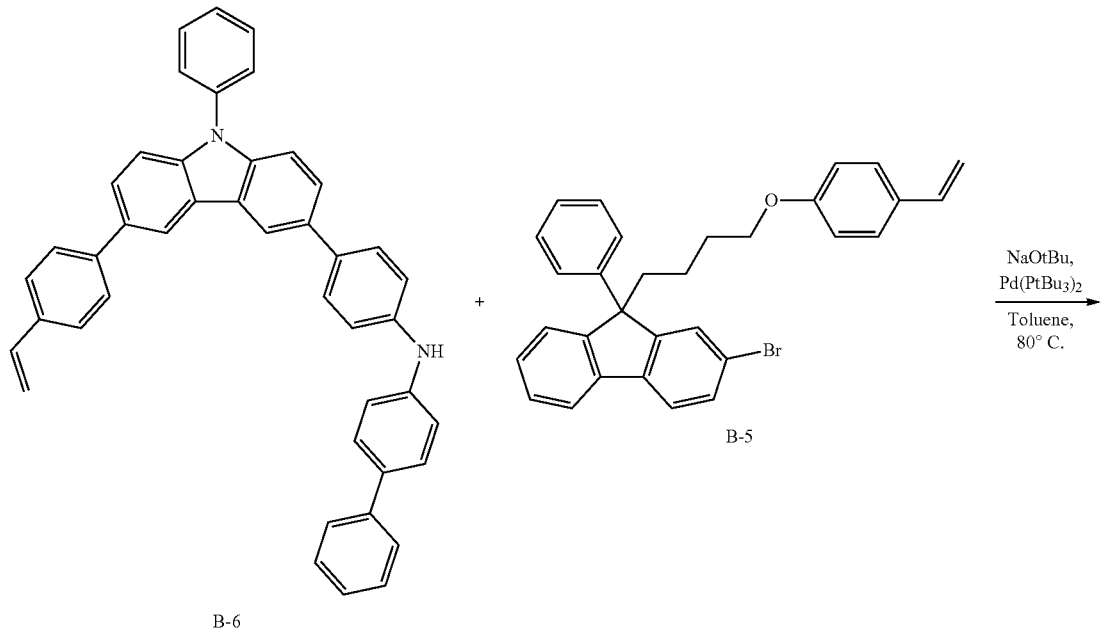

-continued

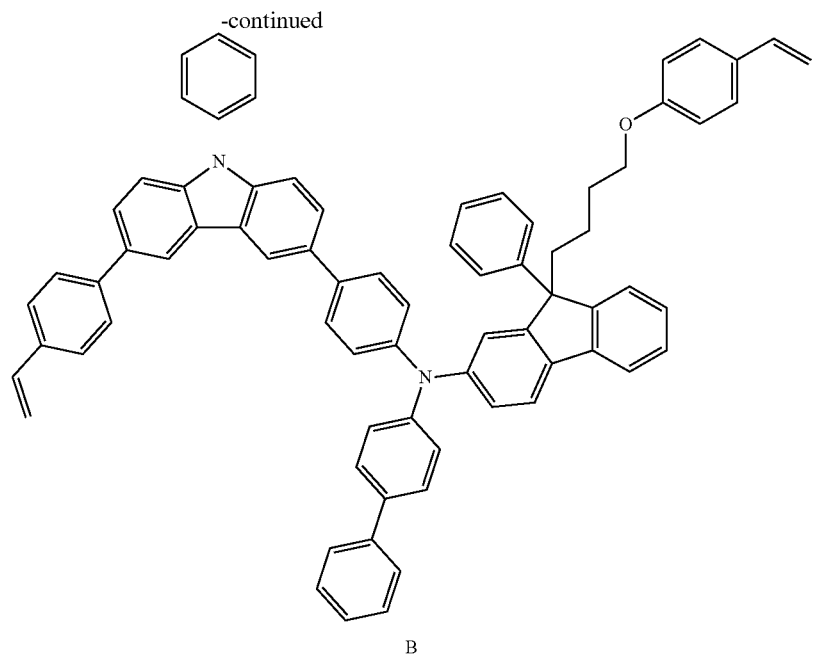

B

B-6 (10 g, 17 mmol, 1.0 eq.), B-5 (10.1 g, 20.4 mmol, 1.2 eq.), NaOtBu (4.9 g, 51 mmol, 3.0 eq.) and toluene (57 ml, 0.3 M) were introduced, and stirred at 80° C. Pd(PtBu$_3$)$_2$ (0.26 g, 0.51 mmol, 0.03 eq.) was introduced thereto, and the result was stirred for 4 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain white solid Compound B. NMR data values of Compound B are as follows.

1H NMR (500 MHz): δ=8.4-8.3 (d, 1H), 8.2-8.1 (d, 1H), 8.1-7.9 (d, 1H), 7.9-7.85 (m, 4H), 7.8-7.7 (m, 3H), 7.7-7.1 (m, 20H), 7.1-6.9 (m, 2H), 6.8-6.6 (d, 2H), 5.8-5.6 (d, 2H), 5.3-5.2 (d, 2H), 4.1-4.0 (t, 2H), 2.3-2.1 (t, 2H), 1.8-1.6 (q, 2H), 1.3-1.1 (q, 2H)

Preparation Example 3. Preparation of Compound C

1) Preparation of Intermediate C-1

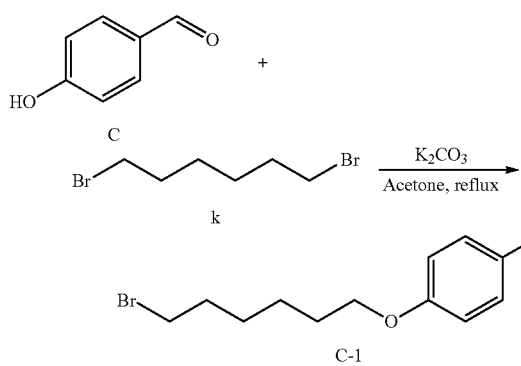

c (30 g, 245 mmol, 1.0 eq.) was dissolved in acetone (490 ml, 0.5 M), K$_2$CO$_3$ (67.7 g, 490 mmol, 2.0 eq.) was introduced thereto, and the result was refluxed for 30 minutes. k (119 g, 490 mmol, 2.0 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-1.

2) Preparation of Intermediate C-2

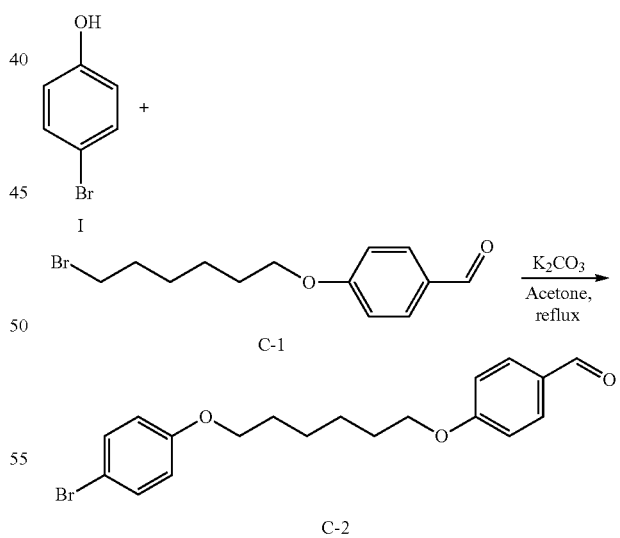

1 (30 g, 173 mmol, 1.0 eq.) was dissolved in acetone (345 ml, 0.5 M), K$_2$CO$_3$ (47.9 g, 347 mmol, 2.0 eq.) was introduced thereto, and the result was refluxed for 30 minutes. C-1 (99 g, 347 mmol, 2.0 eq.) of the reaction formula was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-2.

3) Preparation of Intermediate C-3

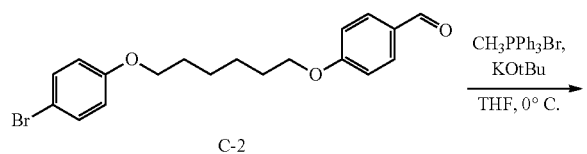

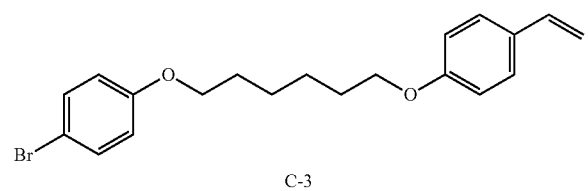

CH₃PPh₃Br (56.8 g, 159 mmol, 3.0 eq.), KOtBu (17.8 g, 159 mmol, 3.0 eq.) and tetrahydrofuran (THF) (265 ml, 0.2 M) were introduced, and stirred for 30 minutes at 0° C. C-2 (20 g, 53 mmol, 1.0 eq.) was introduced thereto, and the result was stirred for 2 hours. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-3.

4) Preparation of Intermediate C-4

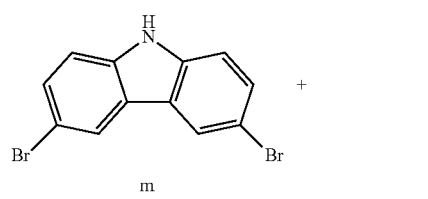

m (30 g, 92.3 mmol, 1.0 eq.) and n (19.7 g, 110.7 mmol, 1.2 eq.) were dissolved in THF (308 ml, 0.3 M). K₂CO₃ (25.5 g, 184.6 mmol, 2.0 eq.) and H₂O (30 ml) were introduced thereto, and the result was refluxed. Pd(PPh₃)₄ (5.33 g, 4.615 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-4.

5) Preparation of Intermediate C-5

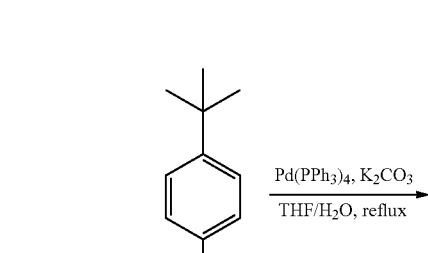

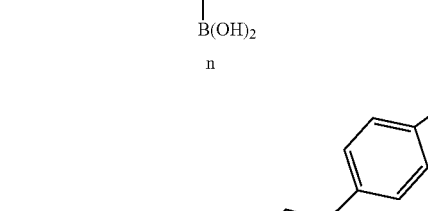

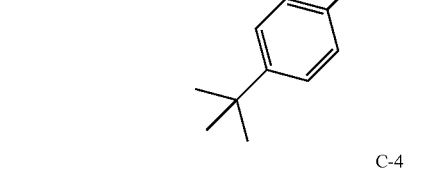

C-4 (10 g, 26.4 mmol, 1.0 eq.), C-3 (11.9 g, 31.7 mmol, 1.2 eq.), NaOtBu (7.6 g, 79.2 mmol, 3.0 eq.) and toluene (88 ml, 0.3 M) were introduced, and stirred at 80° C. Pd(PtBu$_3$)$_2$ (0.405 g, 0.792 mmol, 0.03 eq.) was introduced thereto, and the result was stirred for 6 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-5.

6) Preparation of Intermediate C-6

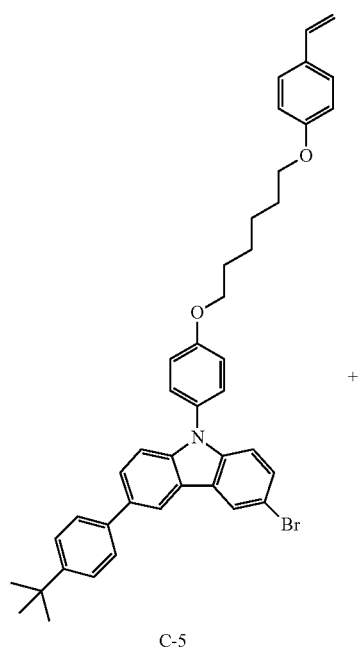

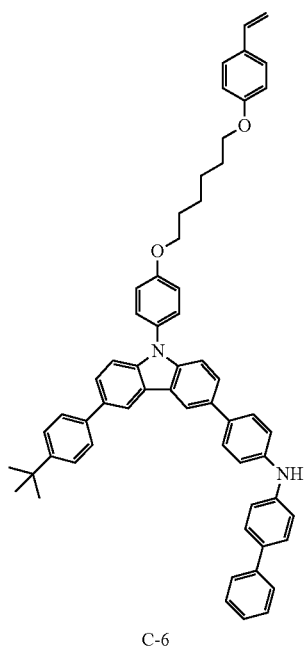

C-5 (15 g, 22.3 mmol, 1.0 eq.) and j (9.93 g, 26.8 mmol, 1.2 eq.) were dissolved in tetrahydrofuran (THF) (75 ml, 0.3 M). K$_2$CO$_3$ (6.16 g, 44.6 mmol, 2.0 eq.) and H$_2$O (7.5 ml) were introduced thereto, and the result was refluxed. Pd(PPh$_3$)$_4$ (1.29 g, 1.115 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound C-6.

7) Preparation of Compound C

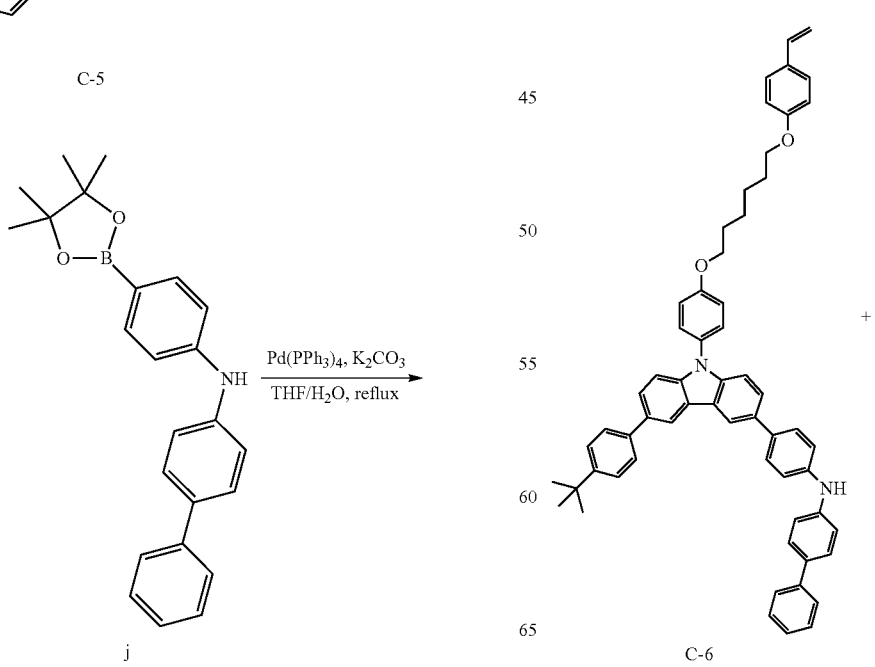

-continued

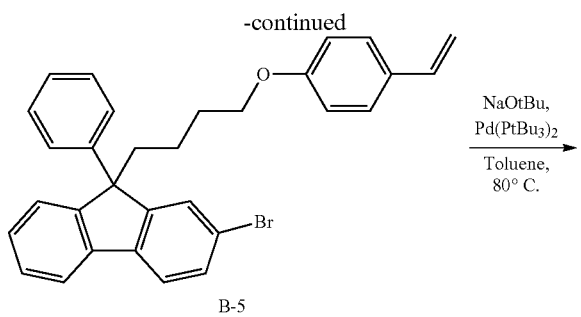

B-5

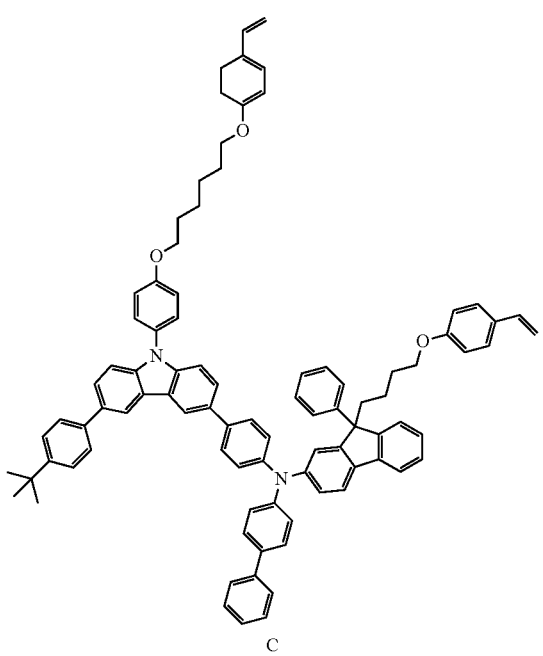

C

C-6 (10 g, 11.9 mmol, 1.0 eq.), B-5 (7.1 g, 14.3 mmol, 1.2 eq.), NaOtBu (3.43 g, 35.7 mmol, 3.0 eq.) and toluene (40 ml, 0.3 M) were introduced, and stirred at 80° C. Pd(PtBu₃)₂ (0.30 g, 0.595 mmol, 0.03 eq.) was introduced thereto, and the result was stirred for 4 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain white solid Compound C. NMR data values of Compound C are as follows.

1H NMR (500 MHz): δ=8.4-8.3 (d, 1H), 8.2-8.1 (d, 1H), 8.1-7.9 (d, 1H), 7.9-7.85 (m, 4H), 7.8-7.7 (m, 3H), 7.7-7.1 (m, 20H), 7.1-6.9 (m, 2H), 6.8-6.6 (d, 2H), 5.8-5.6 (d, 2H), 5.3-5.2 (d, 2H), 4.1-4.0 (t, 2H), 2.3-2.1 (t, 2H), 1.8-1.6 (q, 2H), 1.3-1.1 (q, 2H)

Preparation Example 4. Preparation of Compound D

1) Preparation of Intermediate D-1

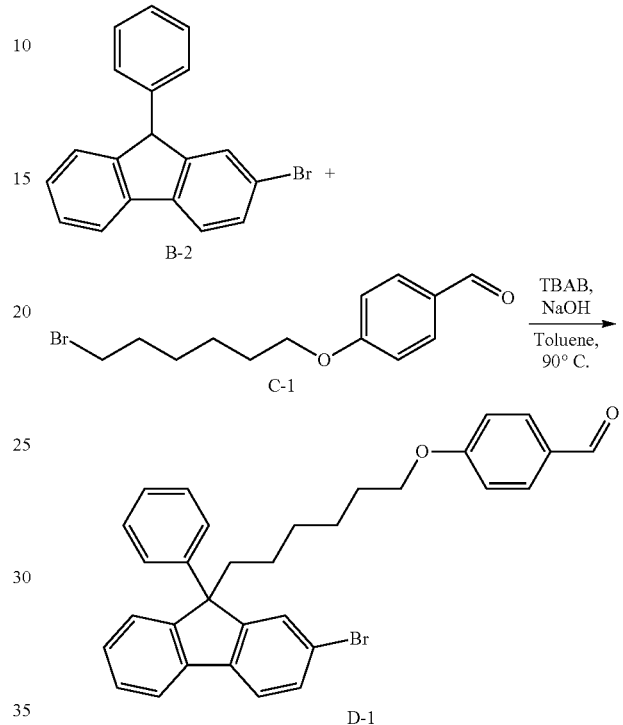

B-2 (20 g, 62 mmol, 1.0 eq.), TBAB (2 g, 6.2 mmol, 0.1 eq.) and toluene (205 ml, 0.3 M) were introduced, and stirred at 60° C. 50 wt % NaOH (3.72 ml, 186 mmol, 3.0 eq.) was slowly introduced thereto. C-1 (21.2 g, 74.4 mmol, 1.2 eq.) was introduced thereto, and the result was stirred overnight at 90° C. After that, the reaction was stopped using a saturated aqueous NH₄Cl solution, and the organic layer was extracted with ethyl acetate [EA]. The organic layer was dried with magnesium sulfate, and after removing the solvent, the result was purified using column chromatography to obtain Intermediate Compound D-1.

2) Preparation of Intermediate D-2

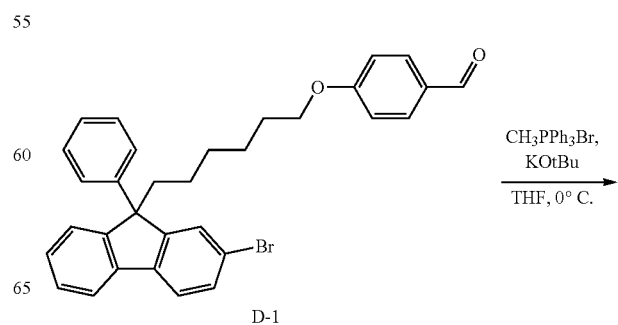

-continued

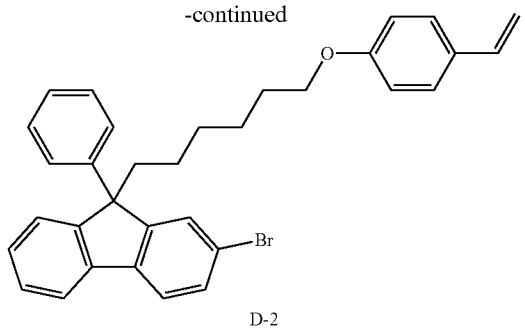

D-2

CH₃PPh₃Br (40.8 g, 114.3 mmol, 3.0 eq.), KOtBu (12.8 g, 114.3 mmol, 3.0 eq.) and tetrahydrofuran (THF) (570 ml, 0.2 M) were introduced, and stirred for 30 minutes at 0° C. D-1 (20 g, 38.1 mmol, 1.0 eq.) were introduced, and stirred for 2 hours. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound D-2.

3) Preparation of Intermediate D-3

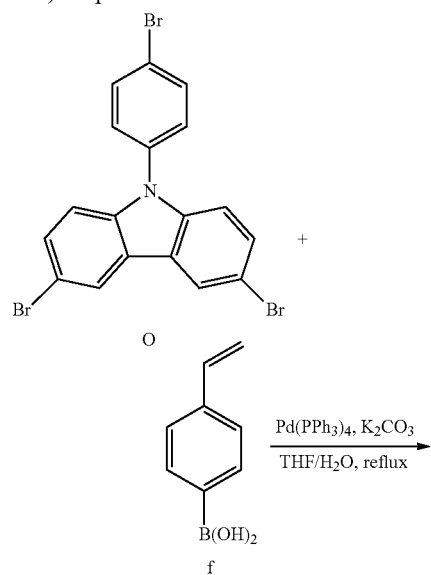

o (20 g, 41.7 mmol, 1.0 eq.) and f (13.6 g, 91.7 mmol, 2.2 eq.) were dissolved in tetrahydrofuran (THF) (140 ml, 0.3 M). K₂CO₃ (23 g, 167 mmol, 4.0 eq.) and H₂O (14 ml) were introduced thereto, and the result was refluxed. Pd(PPh₃)₄ (4.82 g, 4.17 mmol, 0.1 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound D-3.

4) Preparation of Intermediate D-4

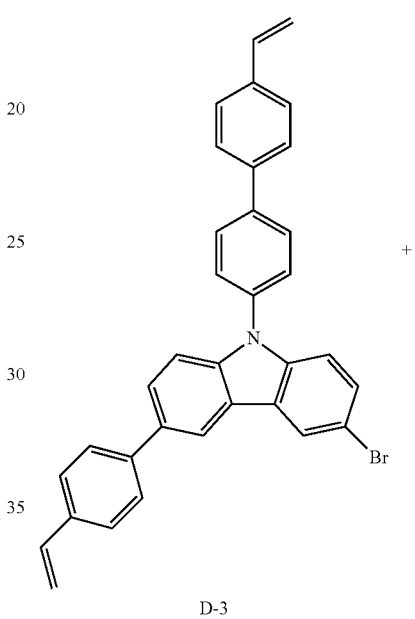

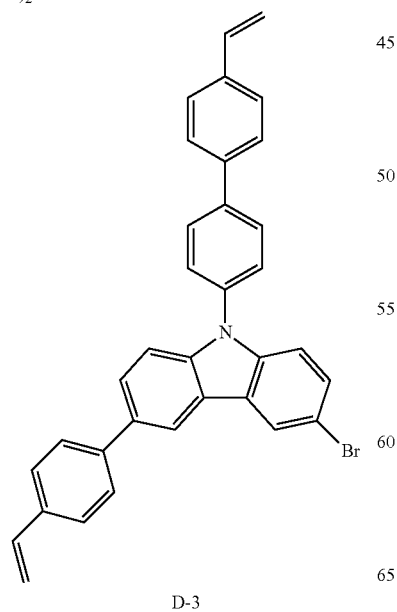

D-3

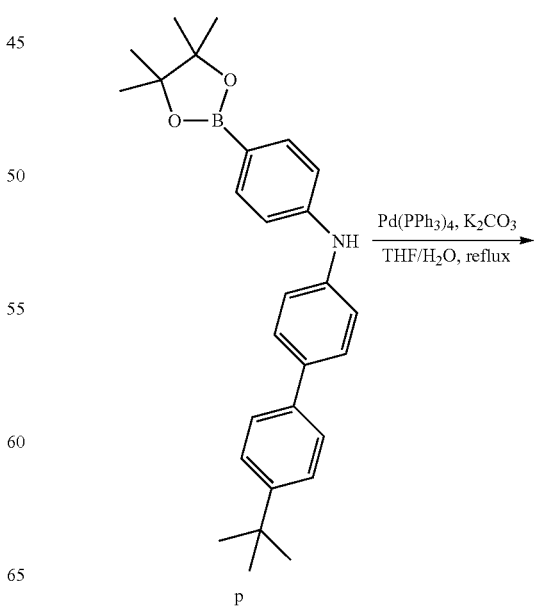

p

-continued

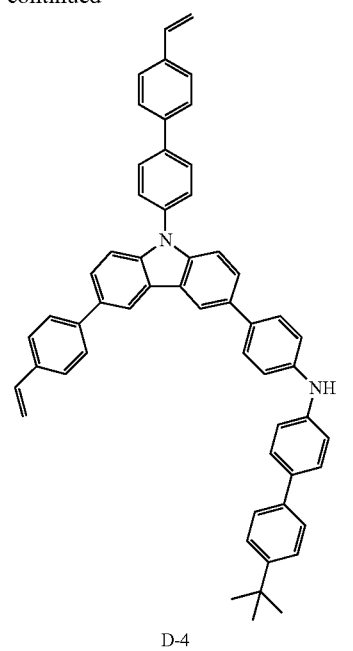

D-4

D-3 (15 g, 28.5 mmol, 1.0 eq.) and p (14.6 g, 34.2 mmol, 1.2 eq.) were dissolved in tetrahydrofuran (THF) (95 ml, 0.3 M). $K_2CO_3$ (7.88 g, 57 mmol, 2.0 eq.) and $H_2O$ (9.5 ml) were introduced thereto, and the result was refluxed. $Pd(PPh_3)_4$ (1.65 g, 1.425 mmol, 0.05 eq.) was slowly introduced thereto, and the result was refluxed overnight. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound D-4.

5) Preparation of Compound D

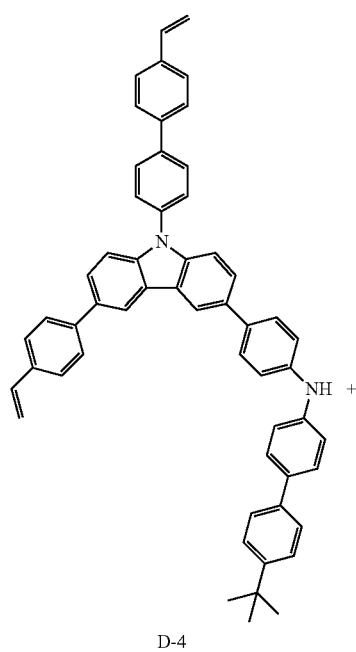

D-4

-continued

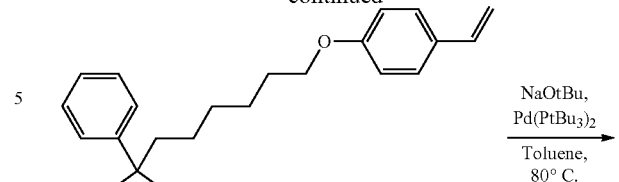

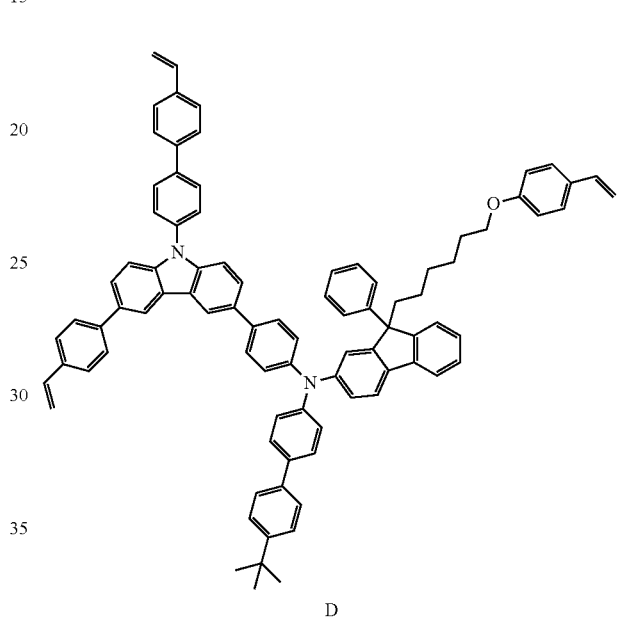

D

D-4 (10 g, 13.4 mmol, 1.0 eq.), D-2 (8.4 g, 16.1 mmol, 1.2 eq.), NaOtBu (3.86 g, 40.2 mmol, 3.0 eq.) and toluene (45 ml, 0.3 M) were introduced, and stirred at 80° C. $Pd(PtBu_3)_2$ (0.21 g, 0.402 mmol, 0.03 eq.) was introduced thereto, and the result was stirred for 4 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain solid Compound D. NMR data values of Compound D are as follows.

1H NMR (500 MHz): δ=8.4-8.3 (d, 1H), 8.2-8.1 (d, 1H), 8.1-7.95 (d, 1H), 7.95-7.8 (m, 8H), 7.8-7.7 (d, 1H), 7.7-7.5 (m, 15H), 7.5-7.1 (m, 17H), 7.1-6.9 (m, 1H), 6.8-6.6 (d, 2H), 5.8-5.6 (d, 2H), 5.3-5.2 (d, 2H), 4.1-4.0 (t, 2H), 2.3-2.1 (m, 2H), 1.8-1.6 (m, 2H), 1.5-1.4 (m, 2H), 1.4-1.3 (s, 9H), 1.3-1.2 (m, 2H)

Preparation Example 5. Preparation of Compound E

1) Preparation of Intermediate E-1

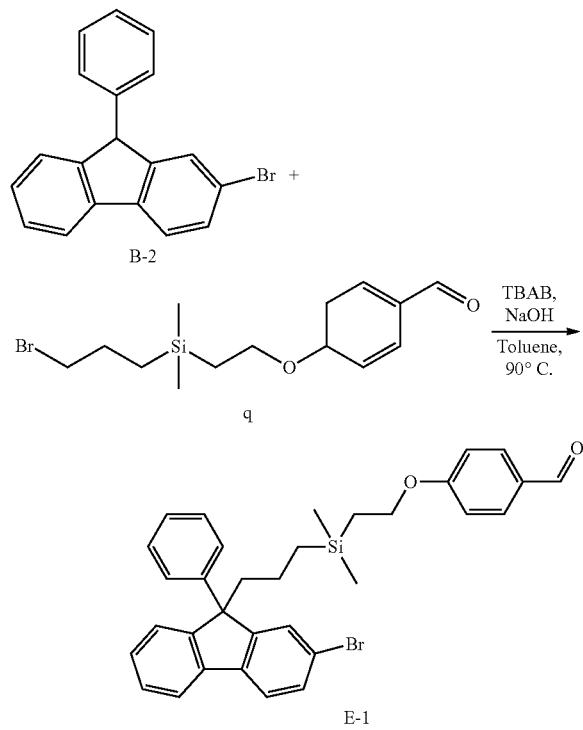

B-2 (20 g, 62 mmol, 1.0 eq.), tetrabutylammonium bromide (TBAB) (2 g, 6.2 mmol, 0.1 eq.) and toluene (205 ml, 0.3 M) were introduced, and stirred at 60° C. 50 wt % NaOH (3.72 ml, 186 mmol, 3.0 eq.) was slowly introduced thereto. q (24.5 g, 74.4 mmol, 1.2 eq.) of the reaction formula was introduced thereto, and the result was stirred overnight at 90° C. After that, the reaction was stopped using a saturated aqueous NH$_4$Cl solution, and the organic layer was extracted with ethyl acetate [EA]. The organic layer was dried with magnesium sulfate, and after removing the solvent, the result was purified using column chromatography to obtain Intermediate Compound E-1.

2) Preparation of Intermediate E-2

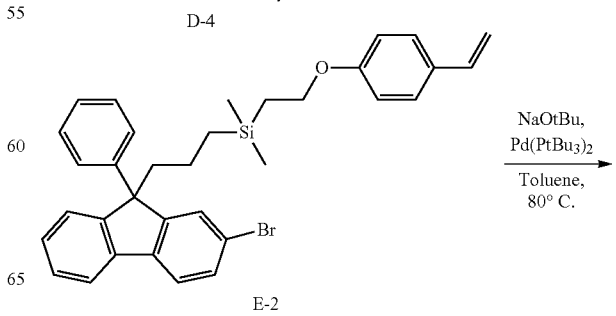

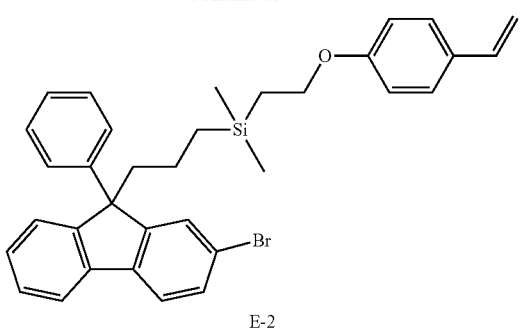

CH$_3$PPh$_3$Br (37.6 g, 105.3 mmol, 3.0 eq.), KOtBu (11.8 g, 105.3 mmol, 3.0 eq.) and tetrahydrofuran (THF) (526 ml, 0.2 M) were introduced, and stirred for 30 minutes at 0° C. E-1 (20 g, 35.1 mmol, 1.0 eq.) were introduced thereto, and the result was stirred for 2 hours. After that, water was introduced thereto to stop the reaction, and the organic layer was extracted with ethyl acetate [EA]. The organic layer was dried with magnesium sulfate, and after removing the solvent, the result was purified using column chromatography to obtain Intermediate Compound E-2.

3) Preparation of Compound E

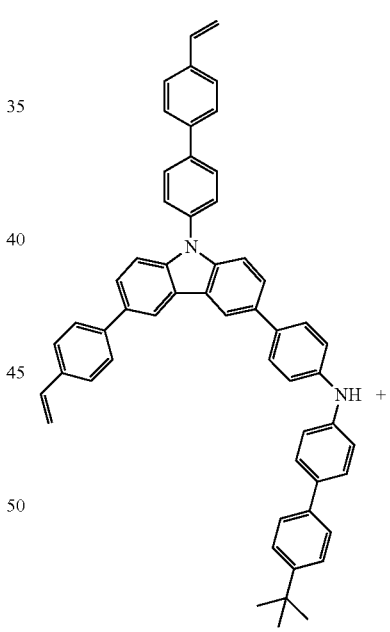

-continued

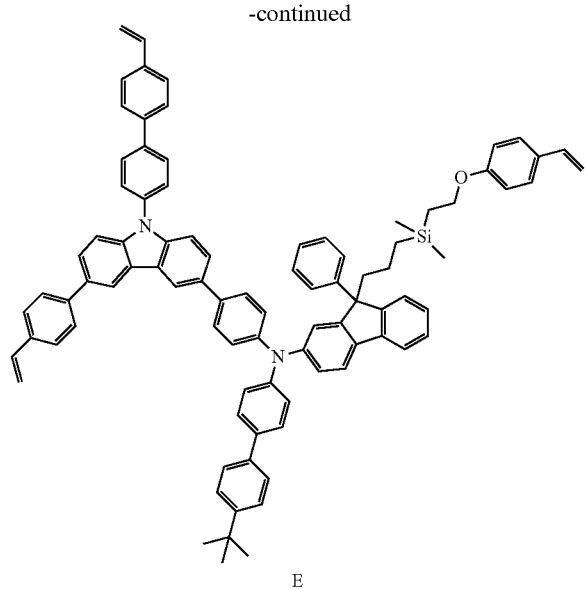

E

D-4 (10 g, 13.4 mmol, 1.0 eq.), E-2 (9.1 g, 16.1 mmol, 1.2 eq.), NaOtBu (3.86 g, 40.2 mmol, 3.0 eq.) and toluene (45 ml, 0.3 M) were introduced, and stirred at 80° C. Pd(PtBu$_3$)$_2$ (0.21 g, 0.402 mmol, 0.03 eq.) was introduced thereto, and the result was stirred for 4 hours at 80° C. After that, water was introduced thereto to stop the reaction, and the organic layer was extracted with ethyl acetate [EA]. The organic layer was dried with magnesium sulfate, and after removing the solvent, the result was purified using column chromatography to obtain solid Compound E. NMR data values of Compound E are as follows.

1H NMR (500 MHz): δ=8.4-8.3 (d, 1H), 8.2-8.1 (d, 1H), 8.1-7.95 (d, 1H), 7.95-7.8 (m, 8H), 7.8-7.7 (d, 1H), 7.7-7.5 (m, 15H), 7.5-7.1 (m, 17H), 7.1-6.9 (m, 1H), 6.8-6.6 (d, 2H), 5.8-5.6 (d, 2H), 5.3-5.2 (d, 2H), 4.1-4.0 (t, 2H), 2.3-2.1 (m, 2H), 1.4-1.3 (s, 9H), 1.3-1.0 (m, 4H), 0.8-0.3 (m, 2H), 0.3-0.1 (m, 6H)

<Example>—Manufacture of Organic Light Emitting Device Example 1

A glass substrate on which indium tin oxide (ITO) was deposited as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone for 30 minutes each, dried, and then transferred to a glove box.

On the transparent ITO electrode prepared as above, a hole injection layer having a thickness of 300 Å was formed by spin coating a coating composition mixing Compound A (20 mg), the following Chemical Formula F (1 mg) and toluene (1 mg), and the coating composition was cured for 1 hour on a hot plate in the air. After that, the result was transferred to a vacuum deposition apparatus, and a hole transfer layer was formed on the hole injection layer by vacuum depositing the following a-NPD.

After depositing a-NPD to a thickness of 40 nm, a light emitting layer was formed on the hole transfer layer by vacuum depositing the following Alq$_3$ to 50 nm. On the light emitting layer, the following BCP was vacuum deposited to a thickness of 35 nm to form an electron injection and transfer layer. A cathode was formed on the electron injection and transfer layer by depositing LiF to a thickness of 0.5 nm and aluminum to a thickness of 100 nm.

In the above-mentioned process, the deposition rates of the organic materials were maintained at 0.4 Å/sec to 0.7 Å/sec, the deposition rates of the LiF and the aluminum of the cathode were maintained at 0.3 Å/sec and 2 Å/sec, respectively, and the degree of vacuum during the deposition was maintained at $2 \times 10^{-7}$ torr to $3 \times 10^{-5}$ torr.

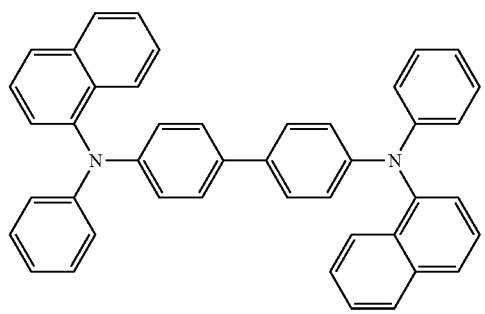

[a-NPD]

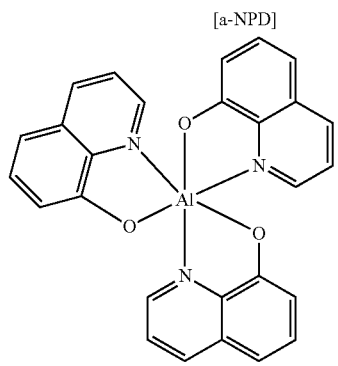

[Alq$_3$]

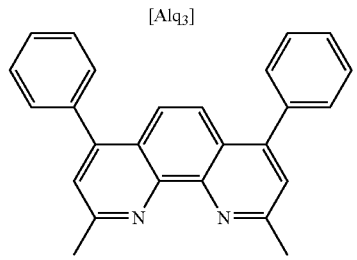

[BCP]

[Chemical Formula F]

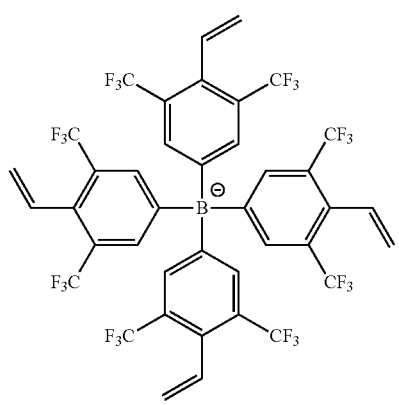

-continued

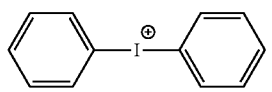

[Chemical Formula G]

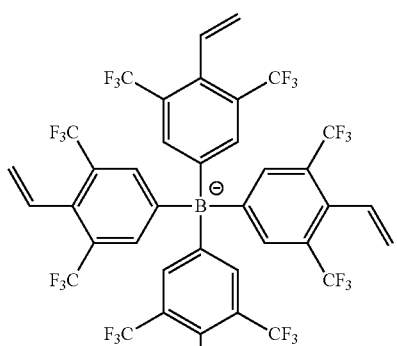

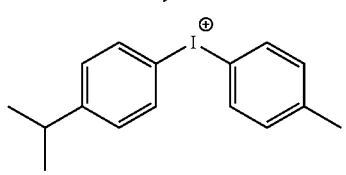

[Chemical Formula H]

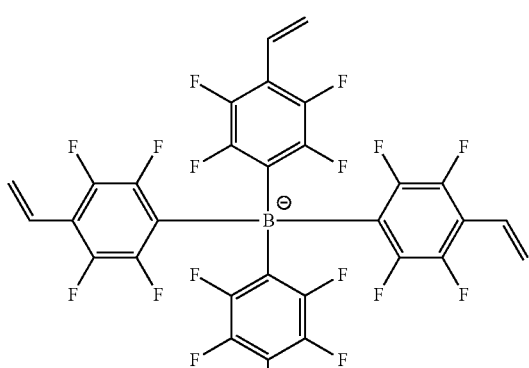

[Chemical Formula I]

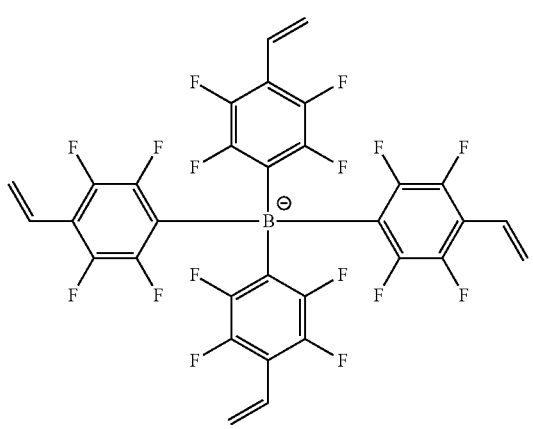

-continued

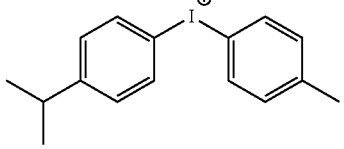

[Chemical Formula J]

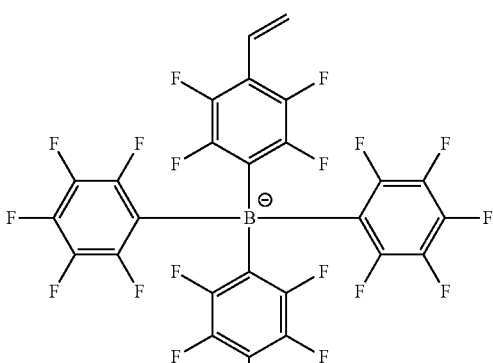

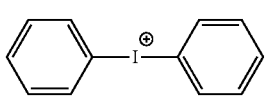

[Chemical Formula K]

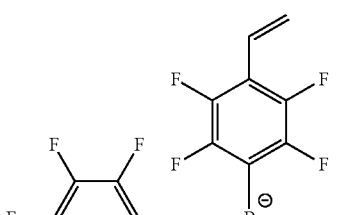

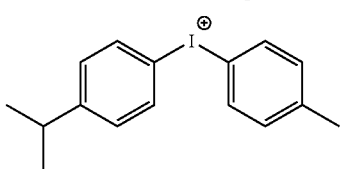

Example 2

An organic light emitting device was manufactured in the same manner as in Example 1 except that Compound B was used instead of Compound A in Example 1.

Example 3

An organic light emitting device was manufactured in the same manner as in Example 1 except that Compound C was used instead of Compound A in Example 1.

Example 4

An organic light emitting device was manufactured in the same manner as in Example 1 except that Compound D was used instead of Compound A in Example 1.

Example 5

An organic light emitting device was manufactured in the same manner as in Example 1 except that Compound E was used instead of Compound A in Example 1.

Example 6

An organic light emitting device was manufactured in the same manner as in Example 1 except that Compound D was used instead of Compound A and Chemical Formula G was used instead of Chemical Formula F in Example 1.

Example 7

An organic light emitting device was manufactured in the same manner as in Example 1 except that Chemical Formula H was used instead of Chemical Formula F in Example 1.

Example 8

An organic light emitting device was manufactured in the same manner as in Example 7 except that Compound B was used instead of Compound A in Example 7.

Example 9

An organic light emitting device was manufactured in the same manner as in Example 7 except that Compound C was used instead of Compound A in Example 7.

Example 10

An organic light emitting device was manufactured in the same manner as in Example 1 except that Compound D was used instead of Compound A and Chemical Formula I was used instead of Chemical Formula F in Example 1.

Example 11

An organic light emitting device was manufactured in the same manner as in Example 1 except that Chemical Formula J was used instead of Chemical Formula F in Example 1.

Example 12

An organic light emitting device was manufactured in the same manner as in Example 11 except that Compound B was used instead of Compound A in Example 11.

Example 13

An organic light emitting device was manufactured in the same manner as in Example 11 except that Compound C was used instead of Compound A in Example 11.

Example 14

An organic light emitting device was manufactured in the same manner as in Example 1 except that Compound D was used instead of Compound A and Chemical Formula K was used instead of Chemical Formula F in Example 1.

Comparative Example 1

An organic light emitting device was manufactured in the same manner as in Example 1 except that Compound M was used instead of Compound A in Example 1.

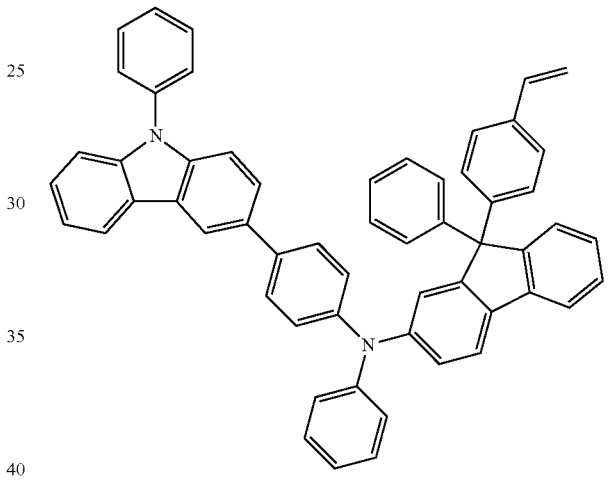

[Compound M]

Comparative Example 2

An organic light emitting device was manufactured in the same manner as in Example 7 except that Compound N was used instead of Compound A in Example 7.

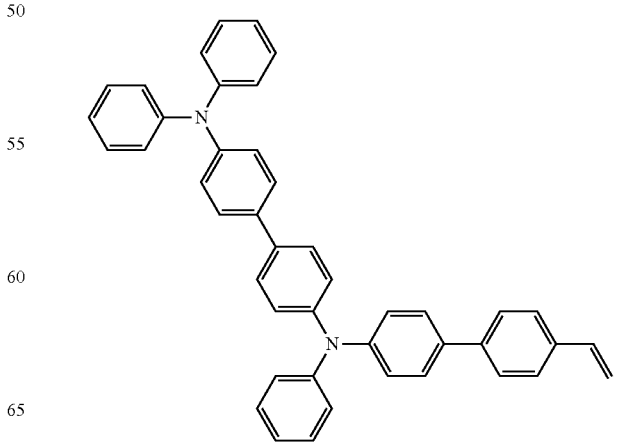

[Compound N]

Comparative Example 3
An organic light emitting device was manufactured in the same manner as in Example 7 except that Compound O was used instead of Compound A in Example 7.
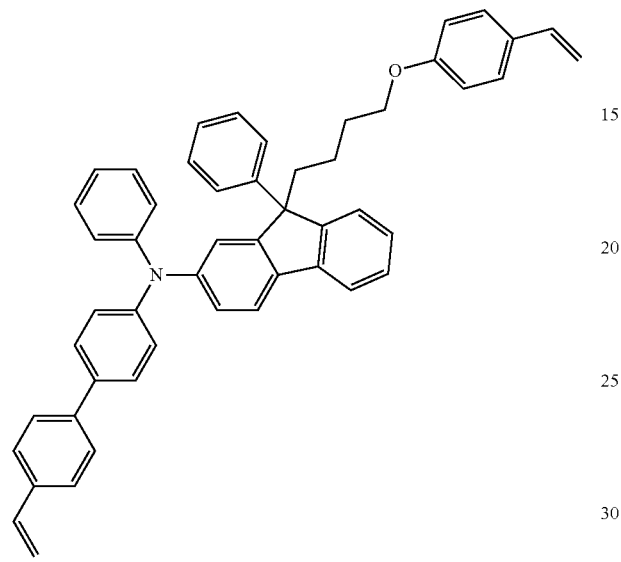
[Compound O]
Comparative Example 4
An organic light emitting device was manufactured in the same manner as in Example 1 except that Compound P was used instead of Compound A in Example 1.
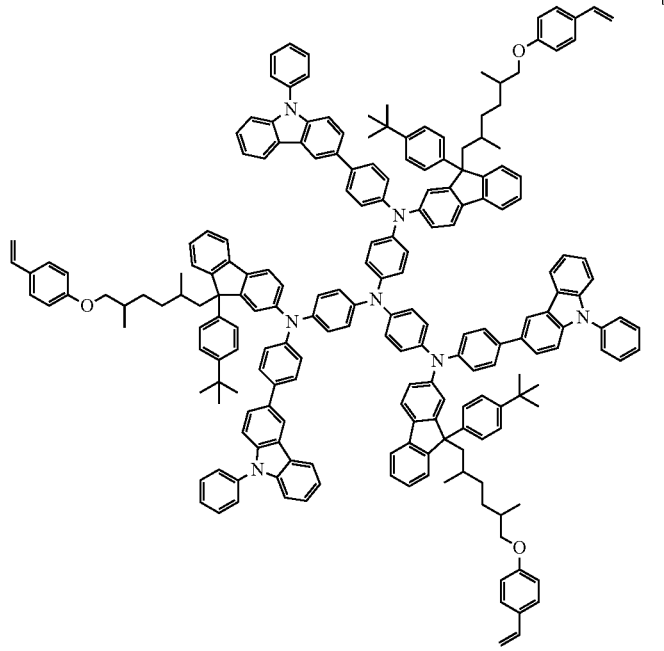
[Compound P]

For each of the organic light emitting devices manufactured in Examples 1 to 14 and Comparative Examples 1 to 4, driving voltage, current efficiency and quantum efficiency (QE) values were measured at current density of 10 mA/cm², and time taken for luminance becoming 90% with respect to initial luminance (T90) was measured at current density of 10 mA/cm². The results are shown in the following Table 1

For each of the organic light emitting devices manufactured in Examples 1 to 14 and Comparative Examples 1 to 4, driving voltage, current efficiency and quantum efficiency (QE) values were measured at current density of 10 mA/cm², and time taken for luminance becoming 90% with respect to initial luminance (T90) was measured at current density of 10 mA/cm². The results are shown in the following Table 1.

TABLE 1

| Device | Driving Voltage (V) | Current Efficiency (cd/A) | QE (%) | Lifetime T90 (10 mA/cm²) |
|---|---|---|---|---|
| Example 1 | 3.9 | 5.0 | 5.3 | 68.3 |
| Example 2 | 3.9 | 5.1 | 5.4 | 72.5 |
| Example 3 | 4.0 | 4.9 | 5.1 | 67.1 |
| Example 4 | 3.9 | 4.8 | 5.3 | 69.5 |
| Example 5 | 3.8 | 4.8 | 5.1 | 67.0 |
| Example 6 | 3.8 | 4.9 | 5.3 | 69.0 |
| Example 7 | 3.8 | 4.9 | 5.3 | 69.1 |
| Example 8 | 3.8 | 5.2 | 5.5 | 72.7 |
| Example 9 | 3.9 | 4.8 | 5.0 | 67.8 |
| Example 10 | 3.8 | 5.0 | 5.4 | 70.4 |
| Example 11 | 3.9 | 4.9 | 5.1 | 68.7 |
| Example 12 | 3.8 | 5.2 | 5.5 | 71.8 |
| Example 13 | 4.0 | 4.8 | 4.9 | 66.0 |
| Example 14 | 3.9 | 4.8 | 5.0 | 67.5 |
| Comparative Example 1 | 4.5 | 4.0 | 3.7 | 34.1 |
| Comparative Example 2 | 4.9 | 3.8 | 3.2 | 28.4 |
| Comparative Example 3 | 4.3 | 4.0 | 4.0 | 38.5 |
| Comparative Example 4 | 4.0 | 4.0 | 4.5 | 42.0 |

From the results of Table 1, it was identified that Examples 1 to 14 manufacturing an organic light emitting device using the compound of the present application had a lower driving voltage, and had excellent current efficiency and quantum efficiency, and also had excellent lifetime properties compared to the organic light emitting devices manufactured in Comparative Examples 1 to 4.

The invention claimed is:

1. A compound represented by the following Chemical Formula 1:

[Chemical Formula 1]

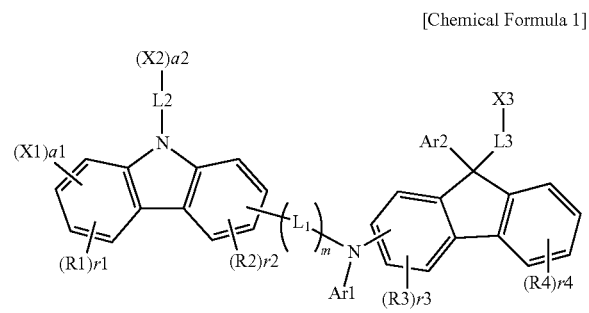

wherein, in Chemical Formula 1,

Ar1 and Ar2 are the same as or different from each other, and each independently a substituted or unsubstituted aryl group;

R1 to R4 are the same as or different from each other, and each independently hydrogen; deuterium; a halogen group; a nitrile group; a substituted or unsubstituted alkyl group; a substituted or unsubstituted aryl group; or a substituted or unsubstituted heterocyclic group;

r1 to r3 are the same as or different from each other, and each independently from 1 to 3;

r4 is from 1 to 4;

when r1 to r4 are each 2 or greater, the two or more R1 to R4 are each the same as or different from each other;

X3 is

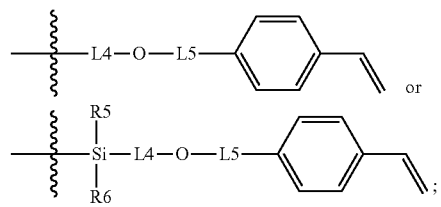

X1 and X2 are the same as or different from each other, and each independently

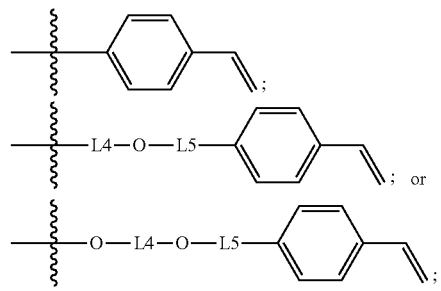

each

means a linking site;

L4 is a substituted or unsubstituted alkylene group;

L5 is a direct bond; or a substituted or unsubstituted arylene group;

R5 and R6 are the same as or different from each other, and each independently a substituted or unsubstituted alkyl group;

a1 and a2 are the same as or different from each other, and each independently 0 or 1;

when a2 is 0, L2 is a substituted or unsubstituted aryl group;

when a2 is 1, L2 is a direct bond; or a substituted or unsubstituted arylene group;

L1 is a substituted or unsubstituted arylene group; or a substituted or unsubstituted heteroarylene group;

m is 1 or 2, and when m is 2, L1 s are the same as or different from each other;

L3 is a direct bond; or a substituted or unsubstituted alkylene group; and

0≤a1+a2≤2.

2. The compound of claim 1, wherein Chemical Formula 1 is represented by the following Chemical Formula 2:

[Chemical Formula 2]

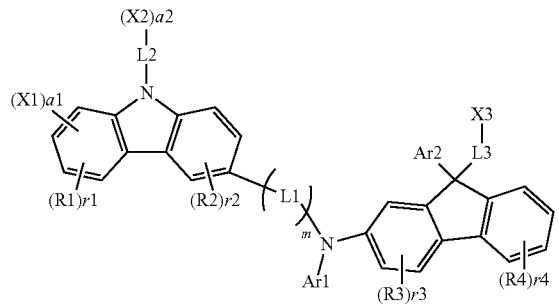

in Chemical Formula 2,

L1 to L3, Ar1, Ar2, R1 to R4, r1 to r4, X1 to X3, m, a1 and a2 have the same definitions as in Chemical Formula 1.

3. The compound of claim 1, wherein L1 is a substituted or unsubstituted phenylene group; a substituted or unsubstituted divalent fluorene group; or a substituted or unsubstituted divalent dibenzothiophene group.

4. The compound of claim 1, wherein Ar1 and Ar2 are the same as or different from each other, and each independently a substituted or unsubstituted phenyl group, or a substituted or unsubstituted biphenyl group.

5. The compound of claim 1, wherein the compound represented by Chemical Formula 1 is any one selected from among the following compounds:

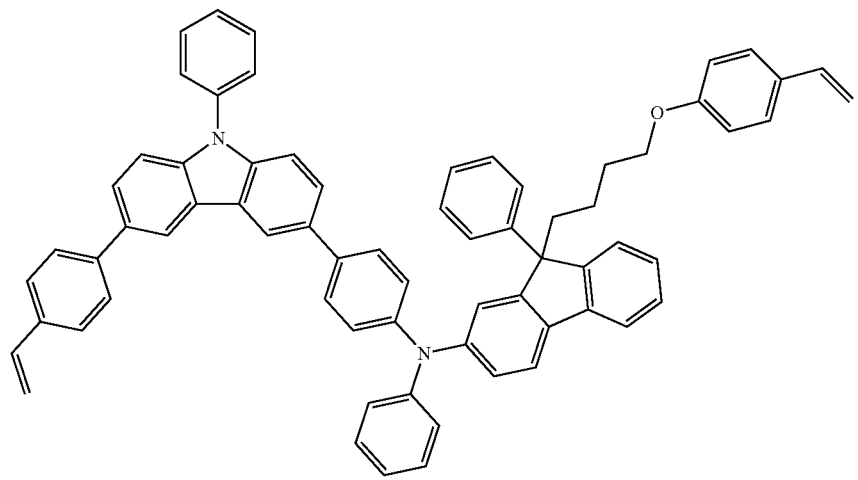

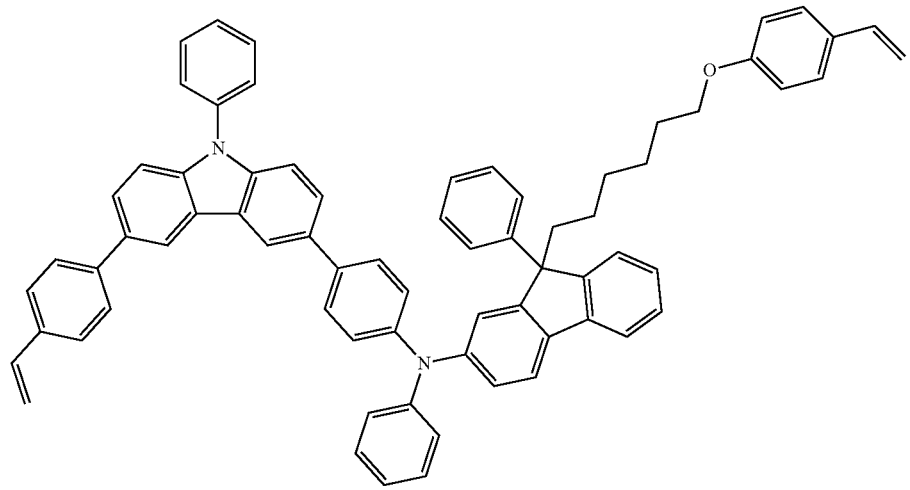

213 214
-continued
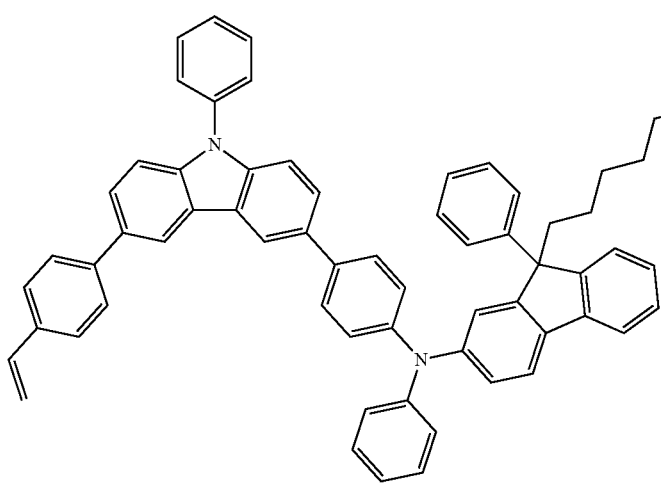
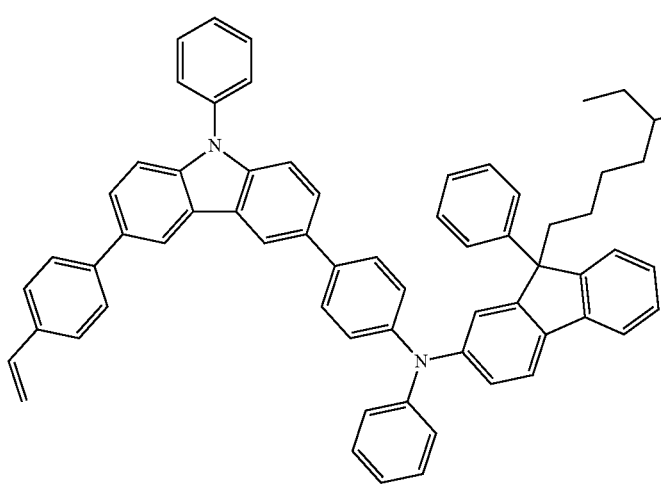
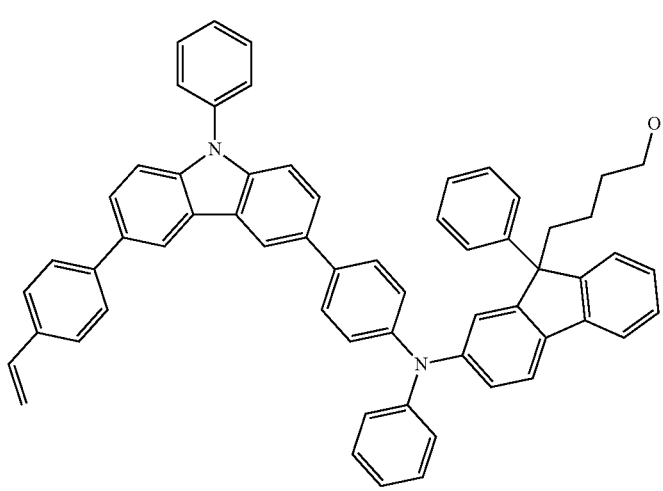

-continued
215
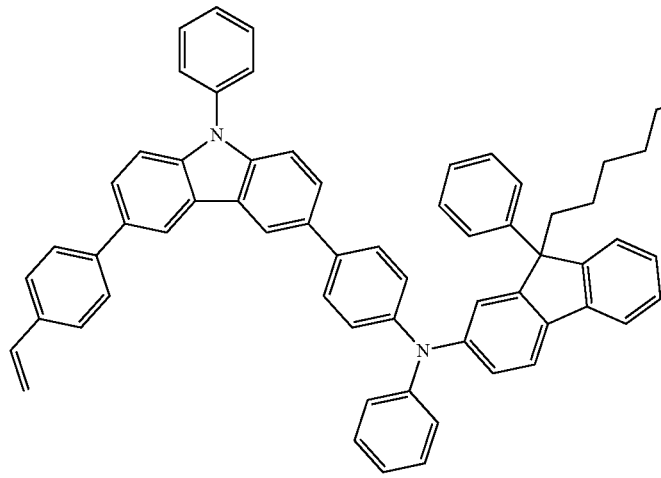
216
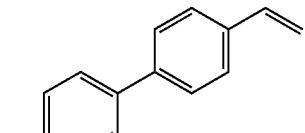
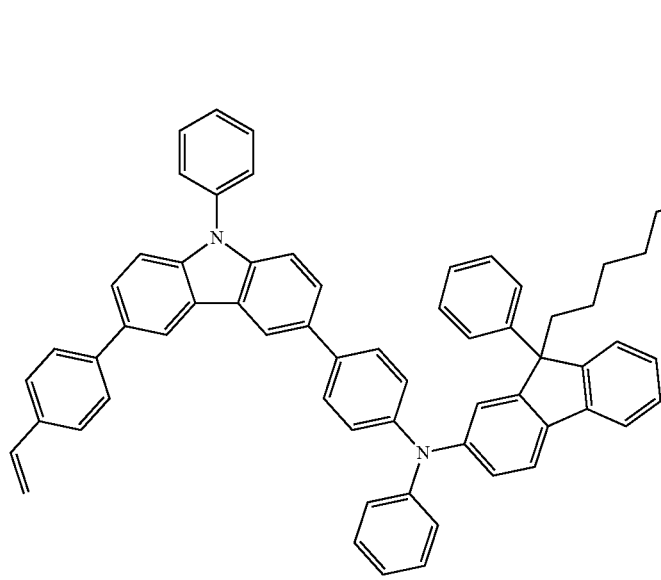
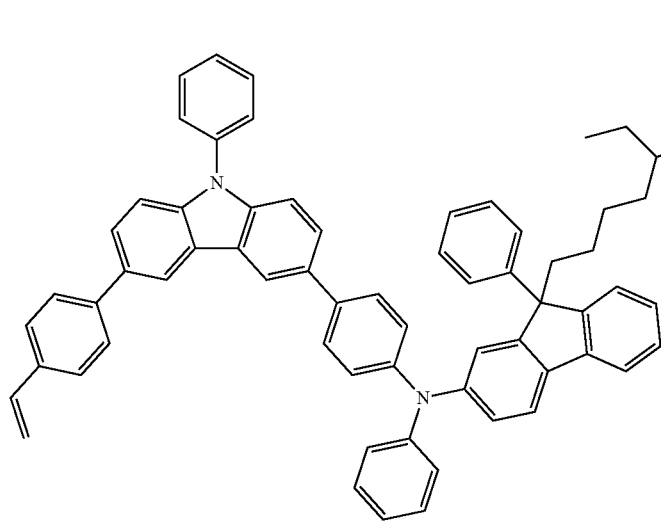

217
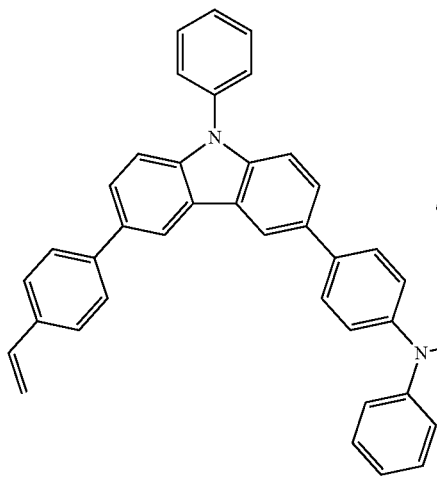
218
-continued
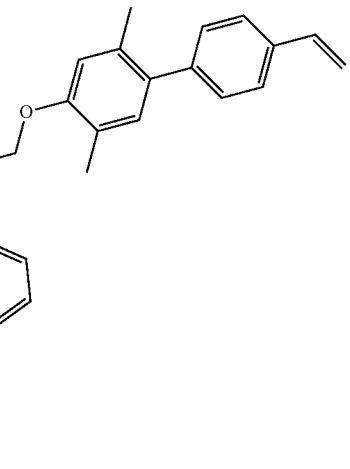
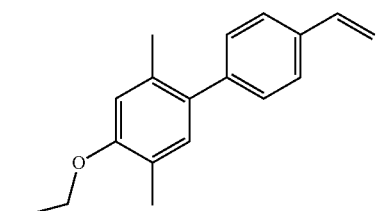
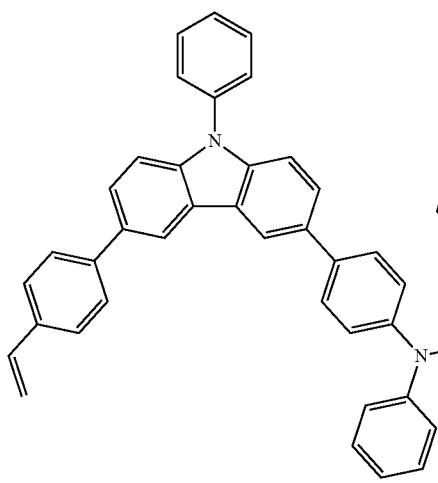
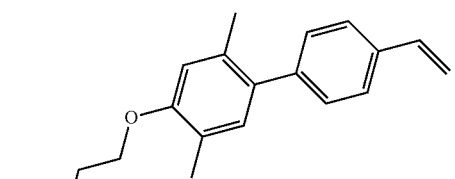
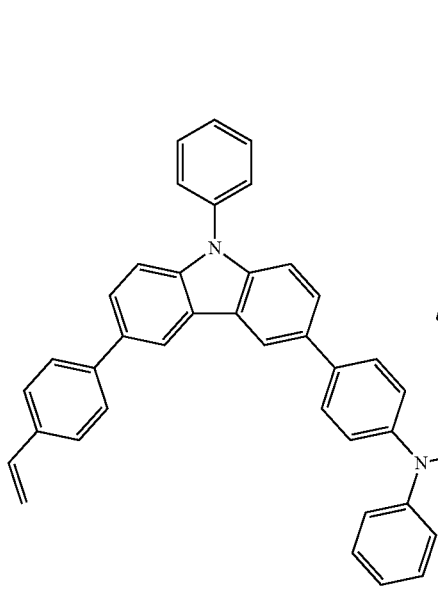

219 220
-continued
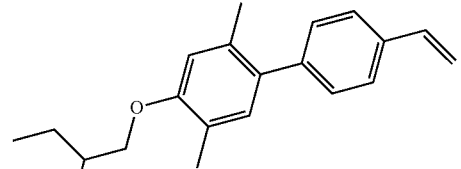
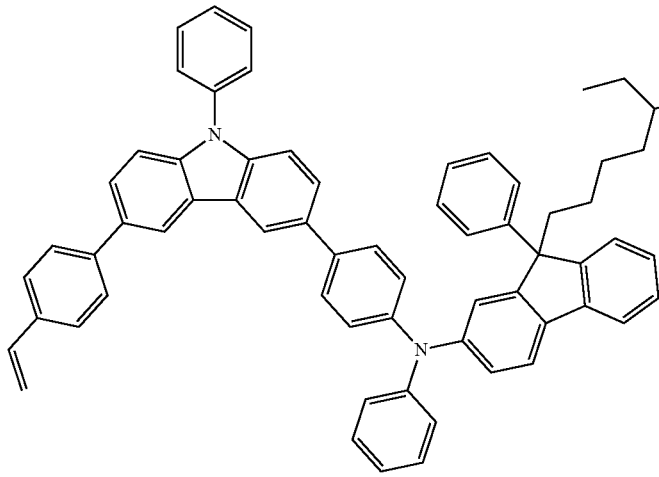
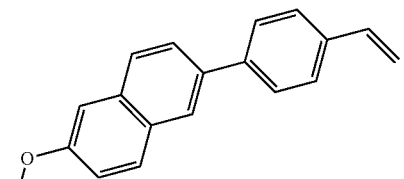
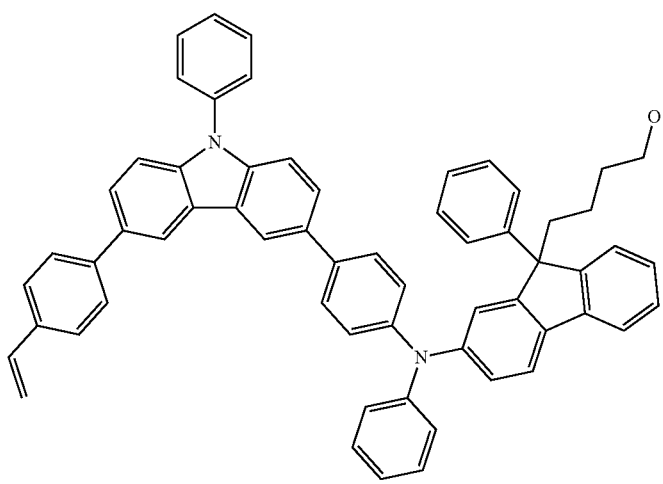
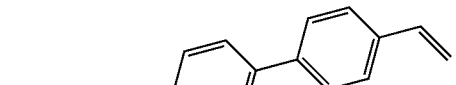
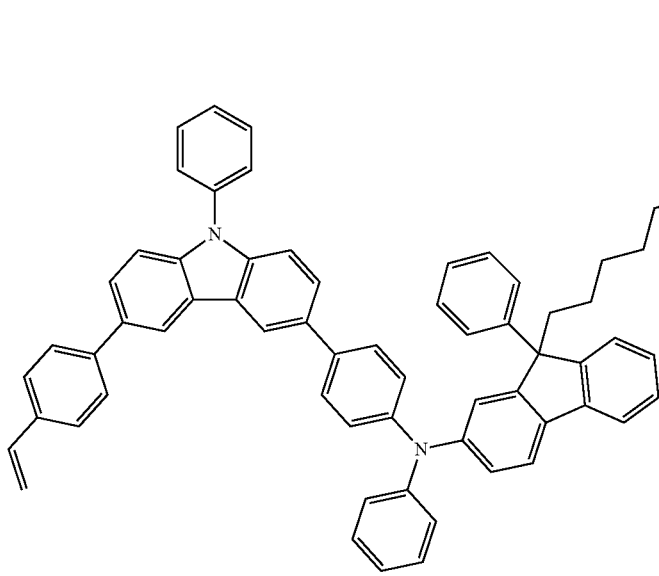

-continued
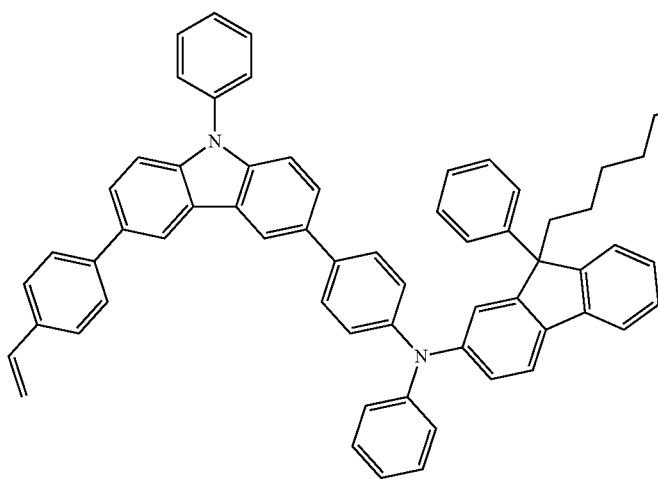
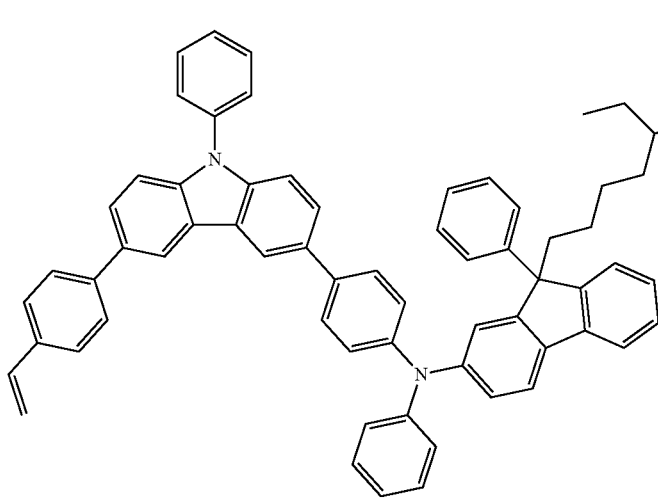
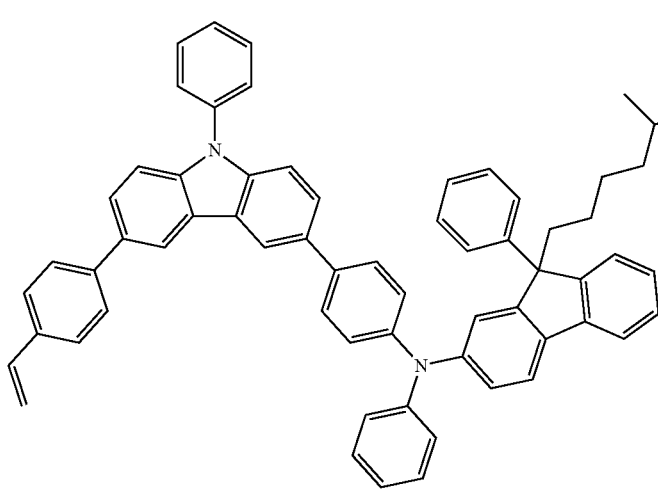

223
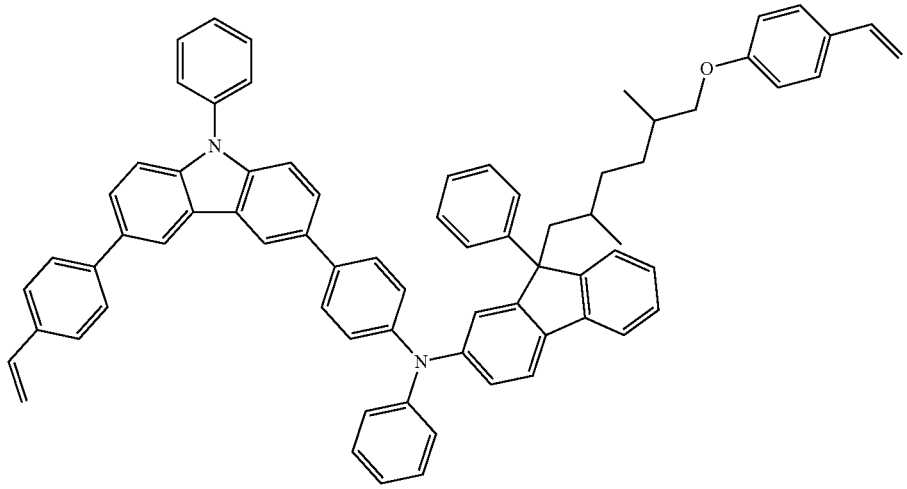
-continued
224
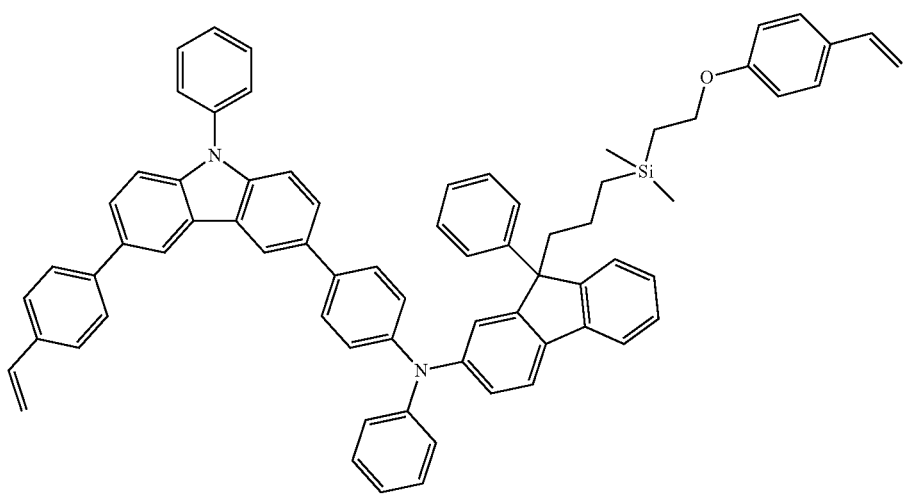
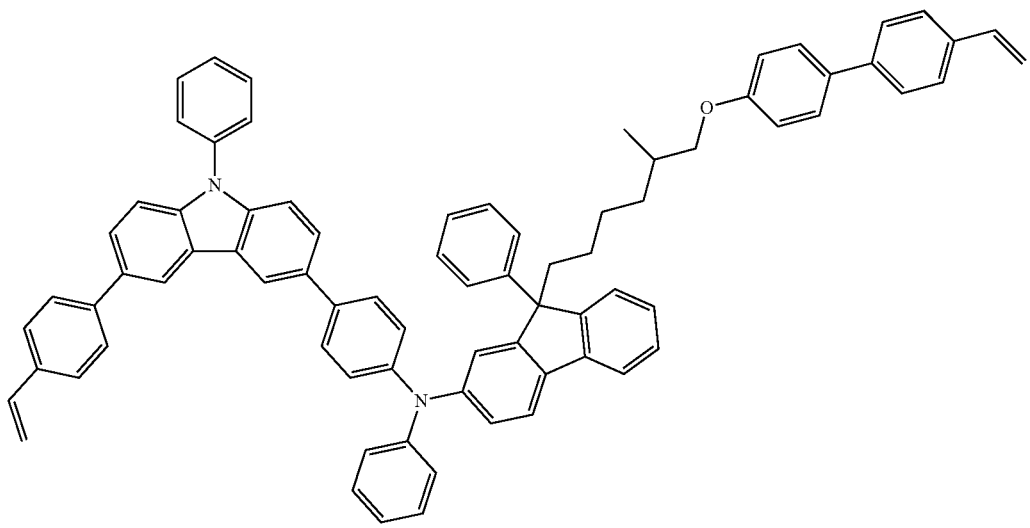

-continued
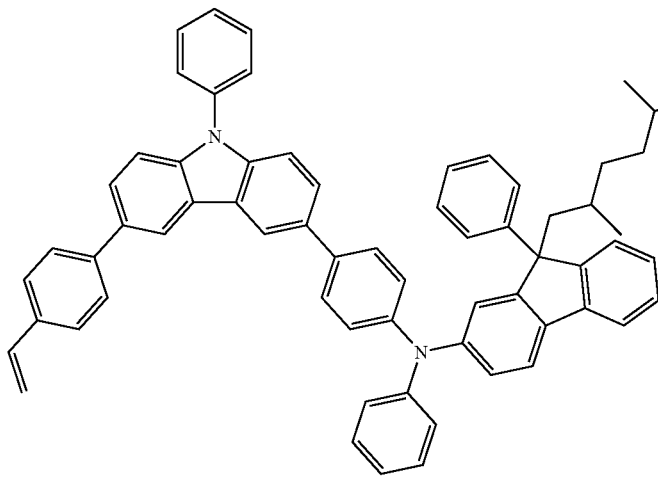
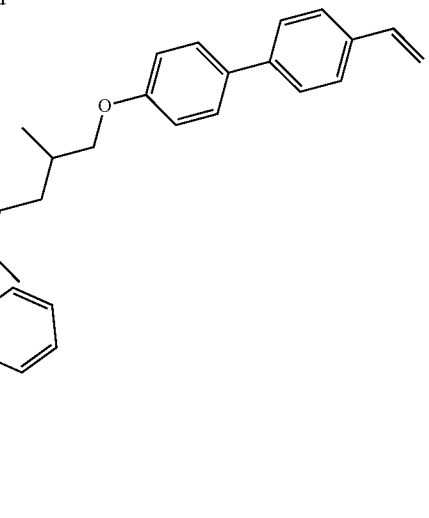
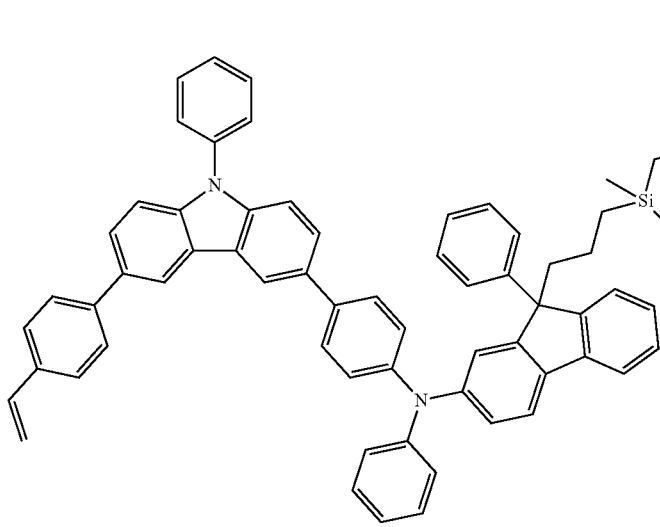
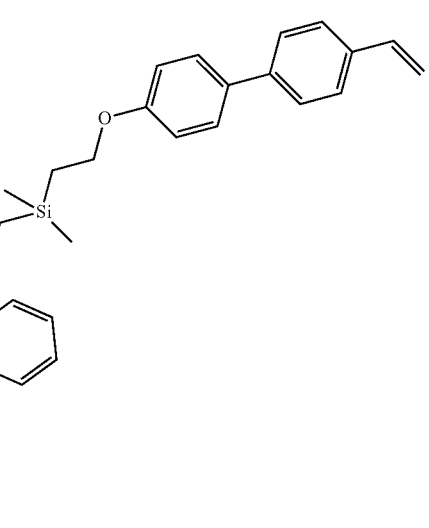
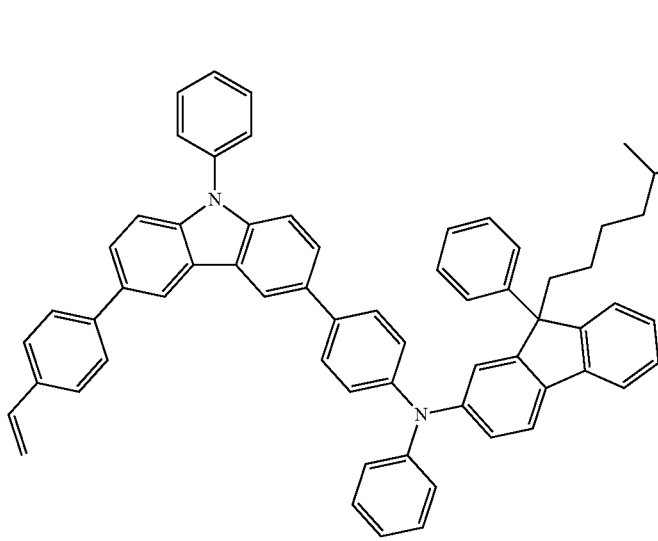
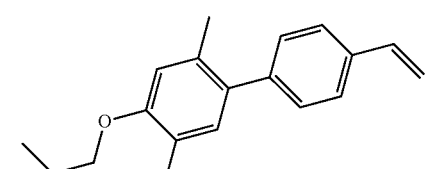

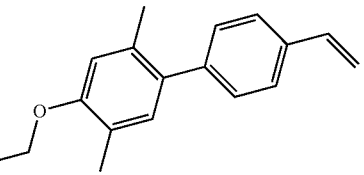
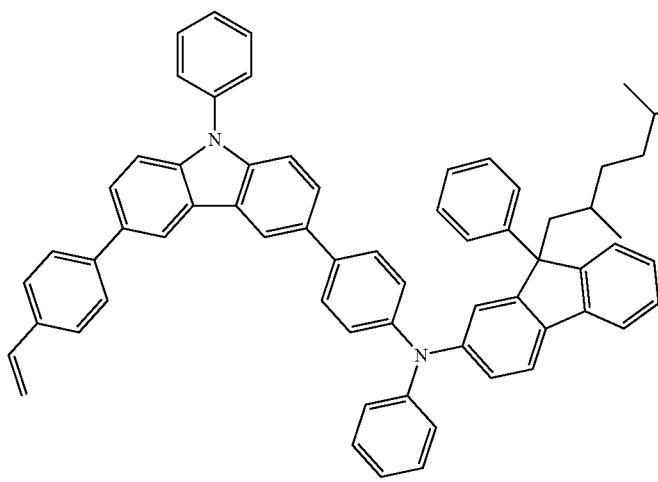
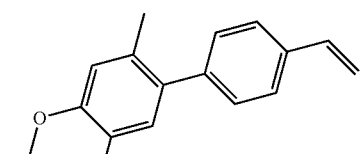
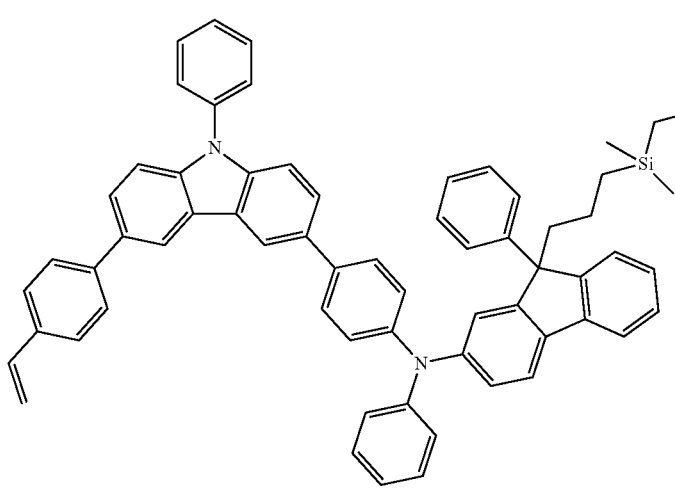
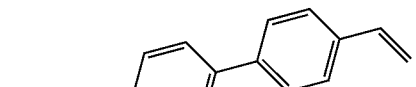
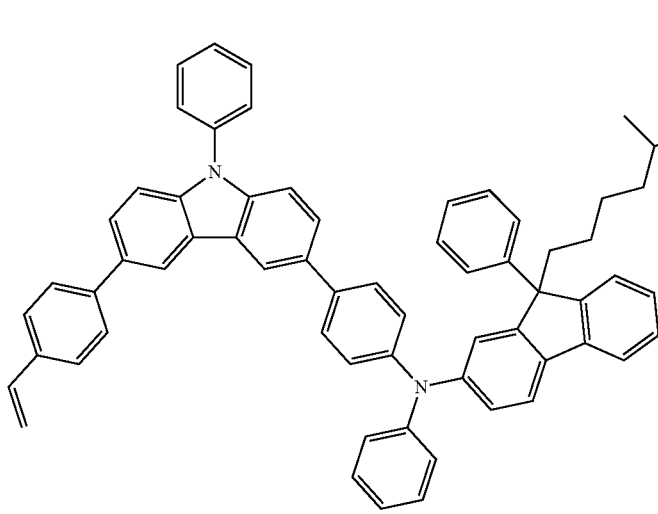

229
230
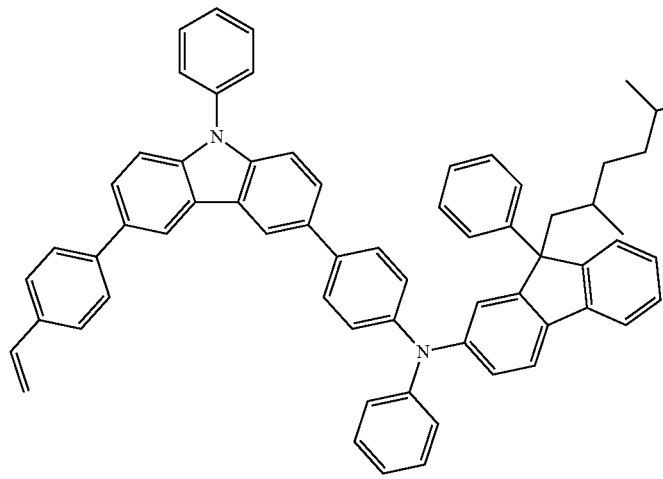
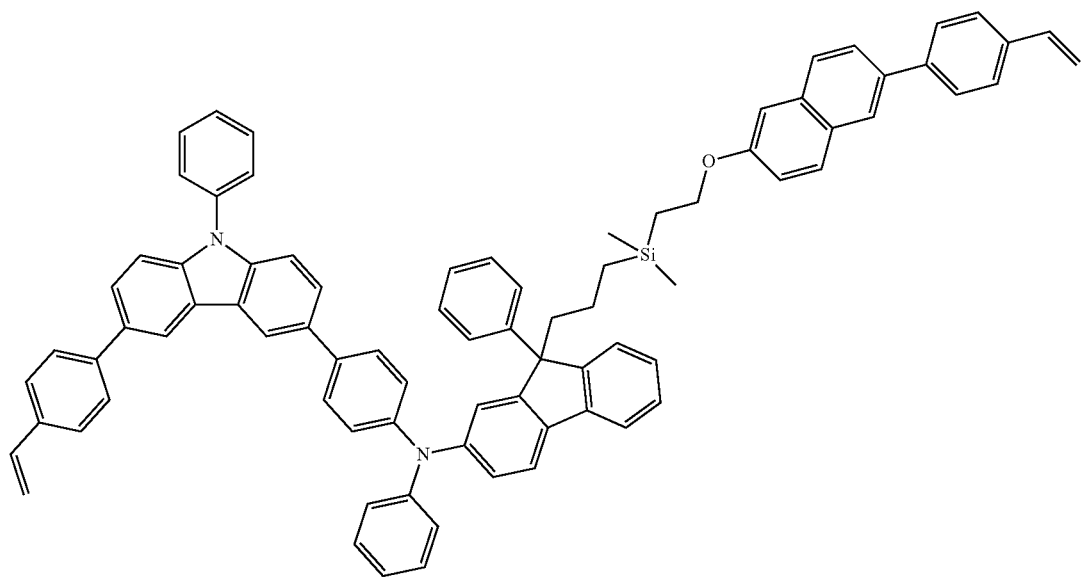

-continued
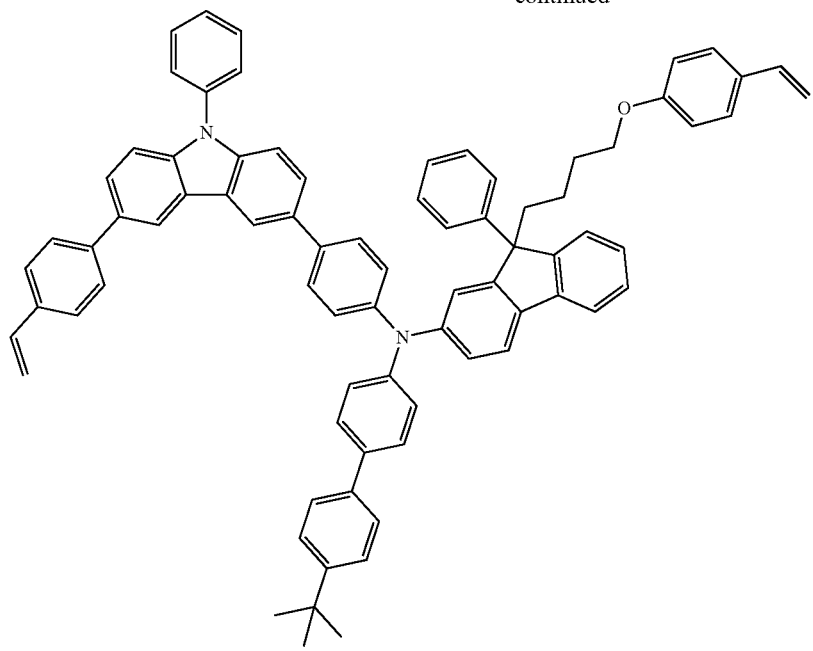
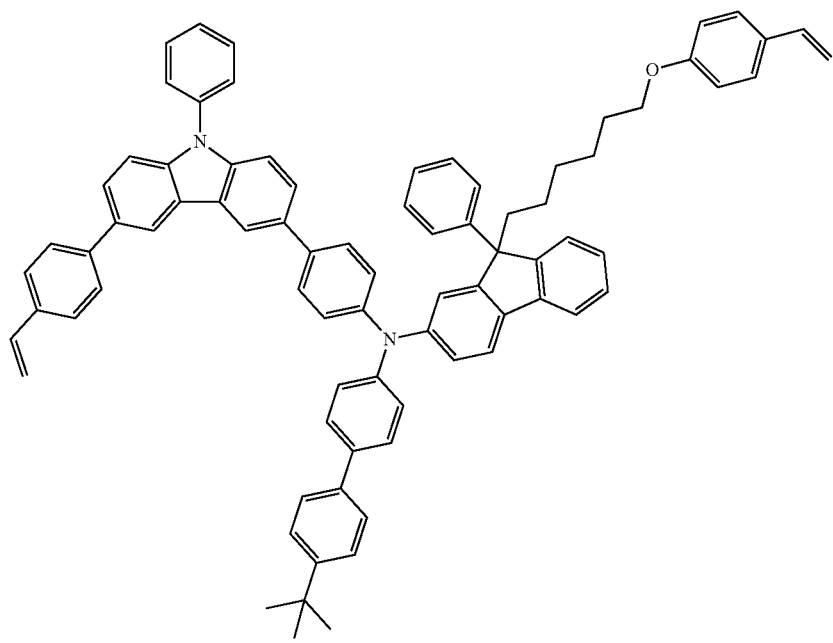

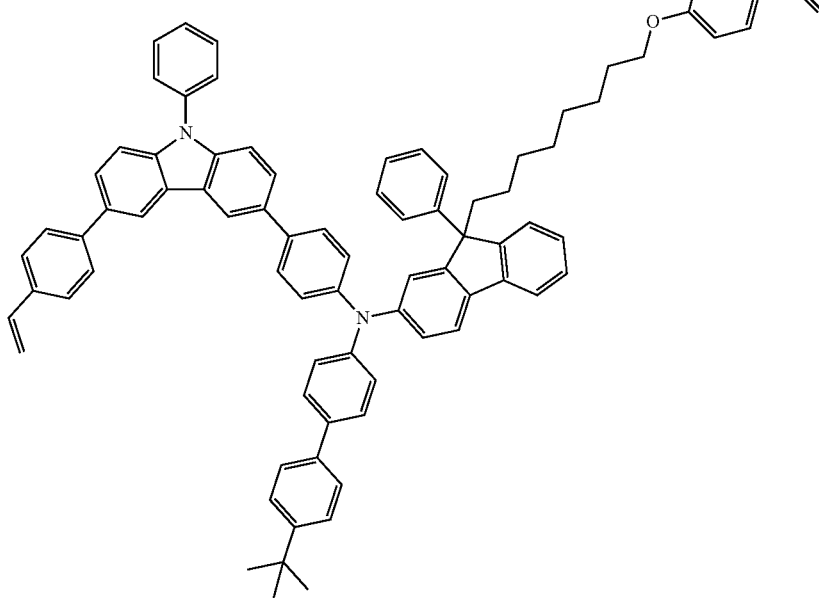
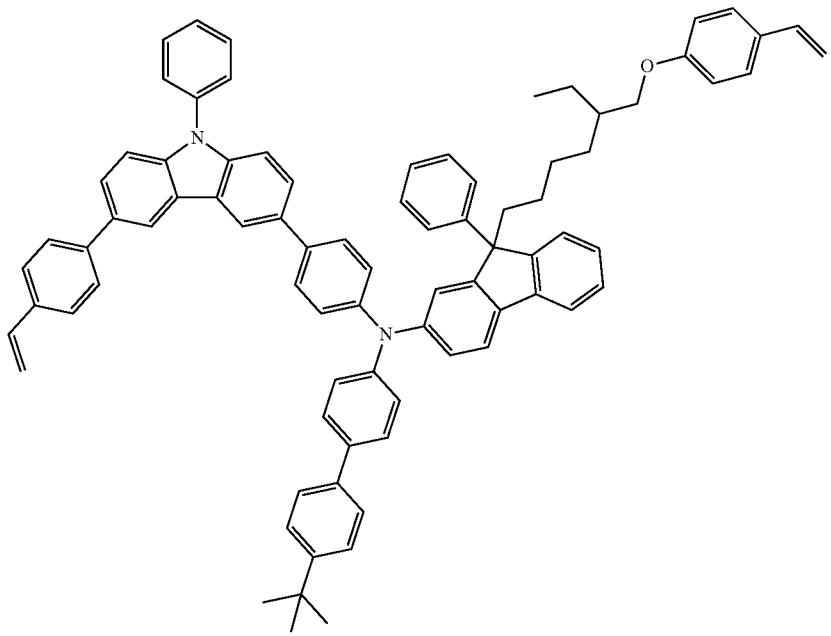

235 236
-continued
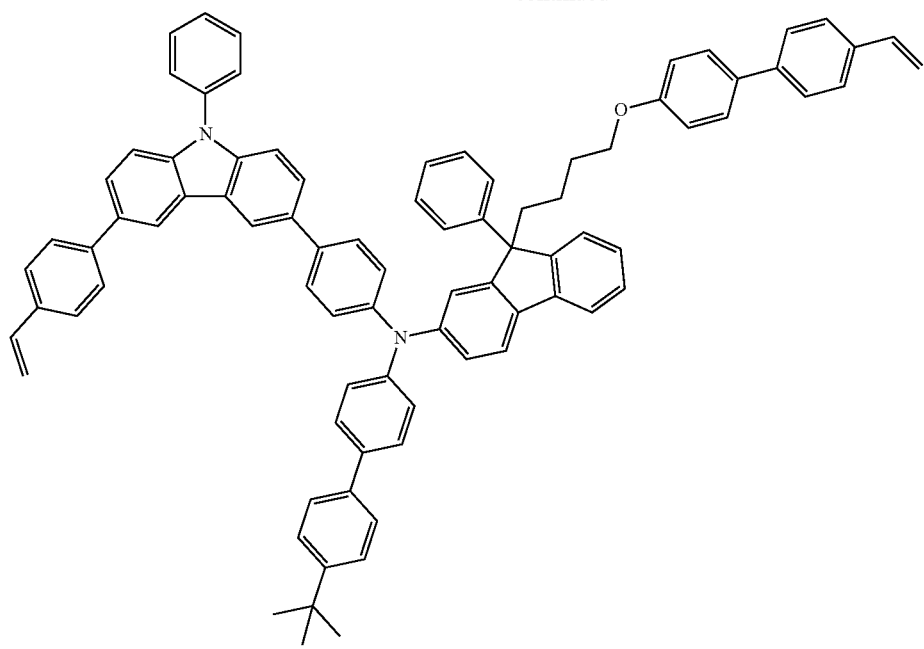
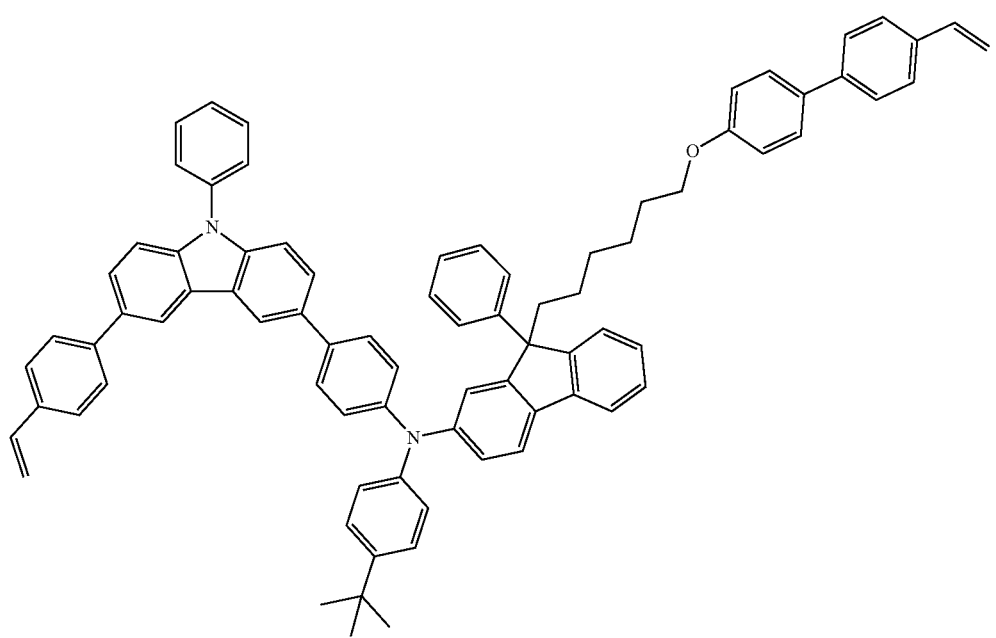

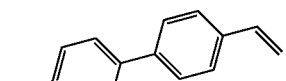
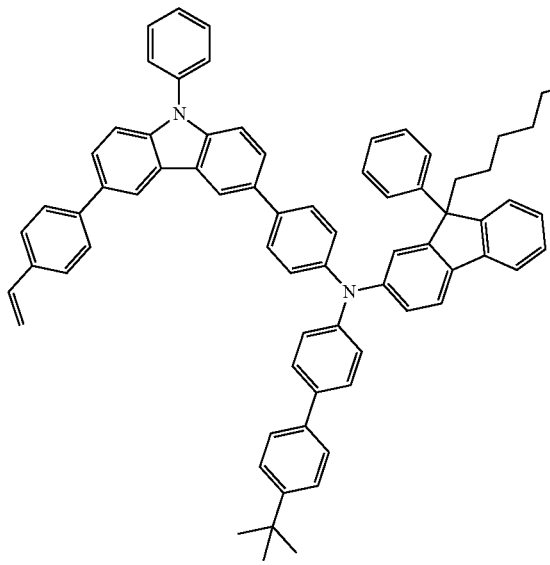
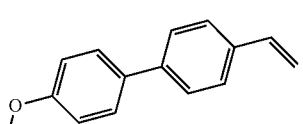
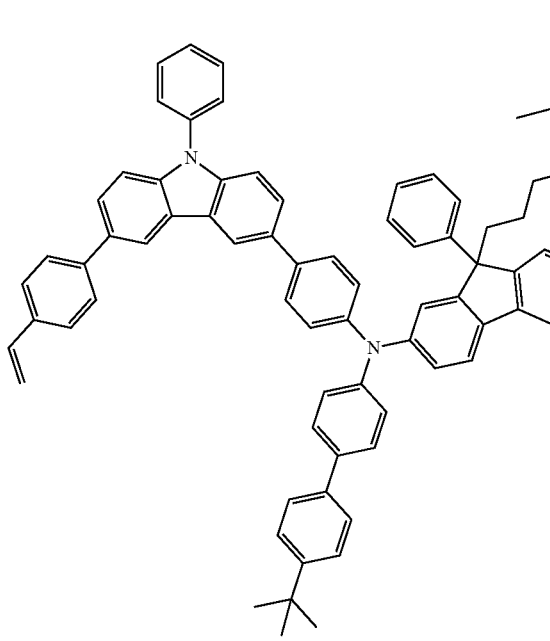

-continued
239
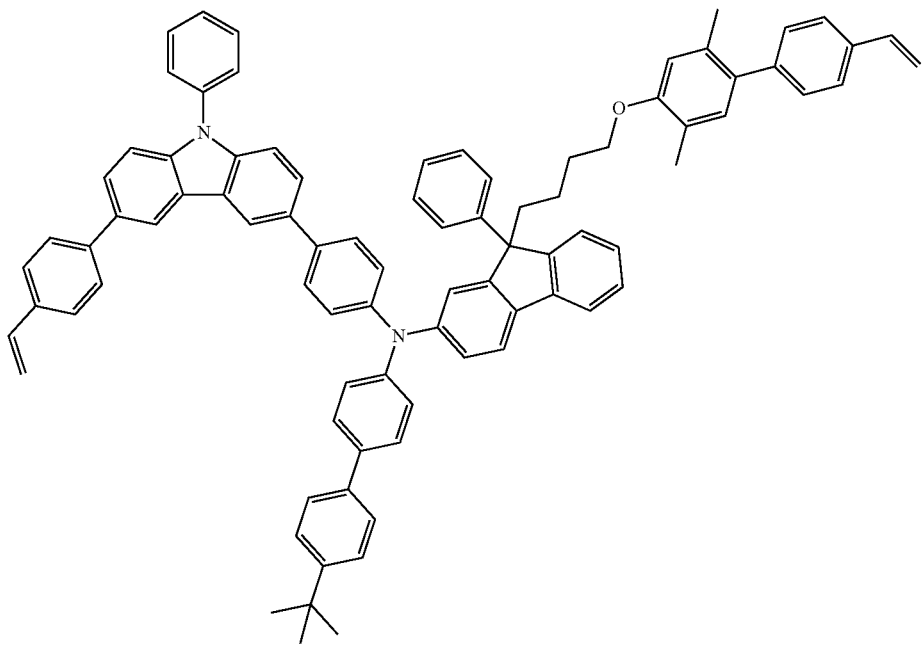
240
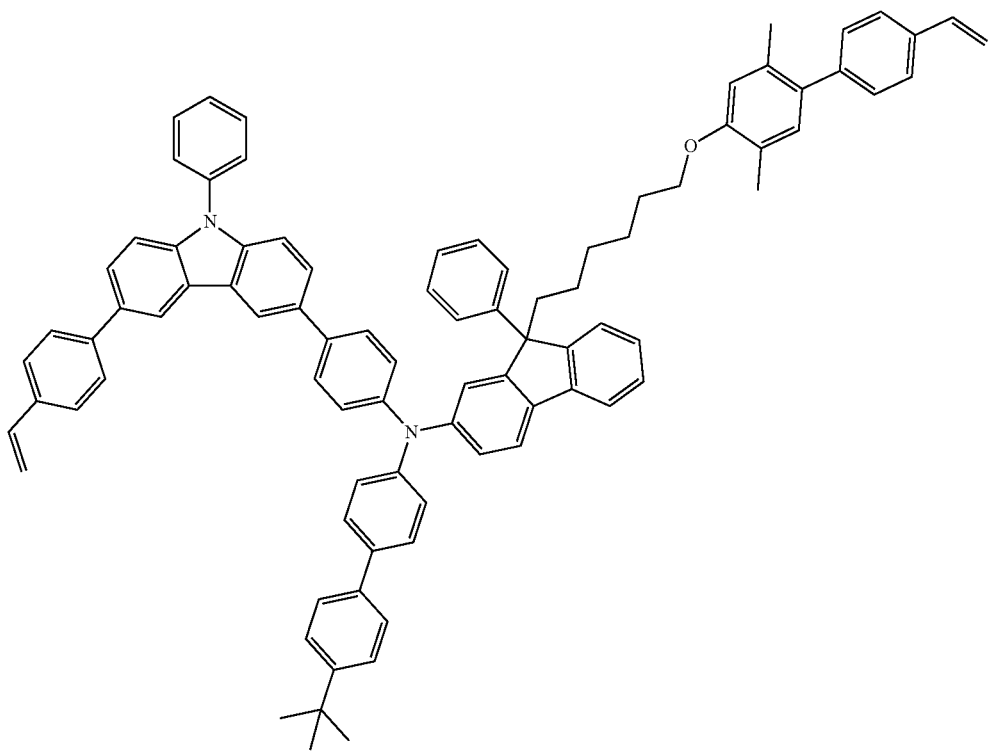

-continued
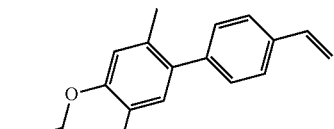
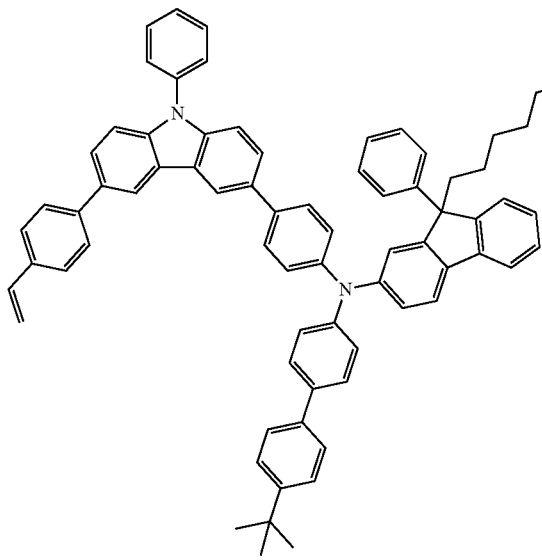
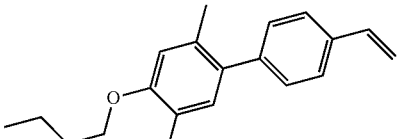
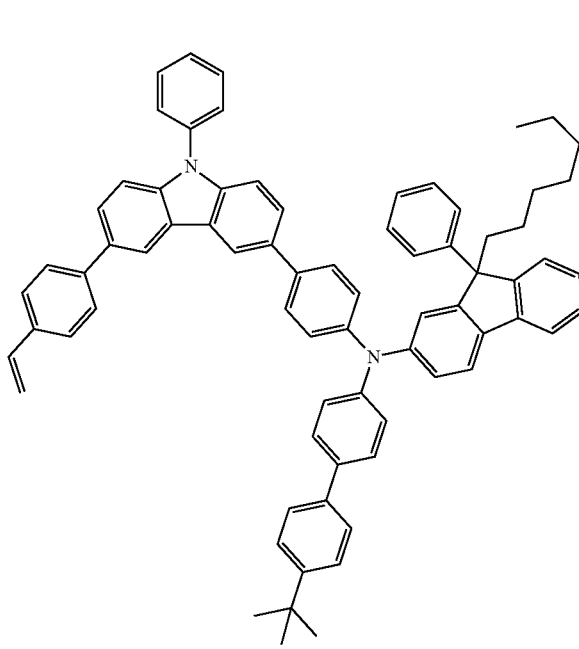

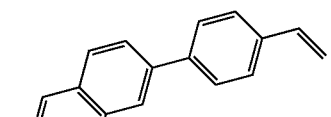
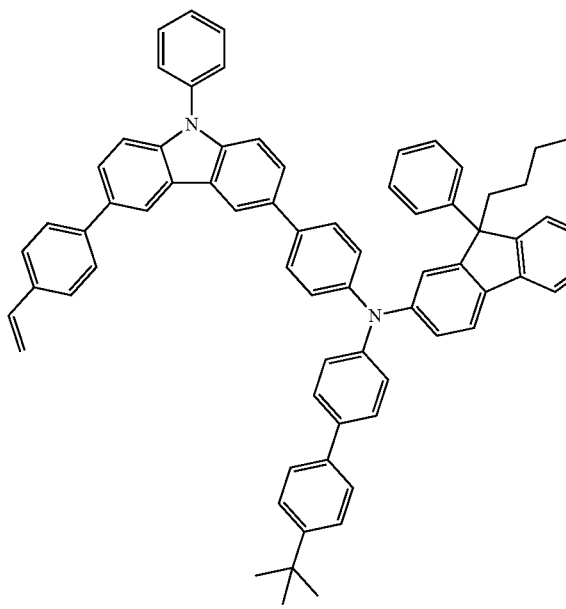
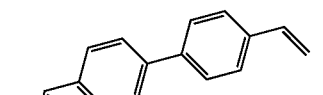
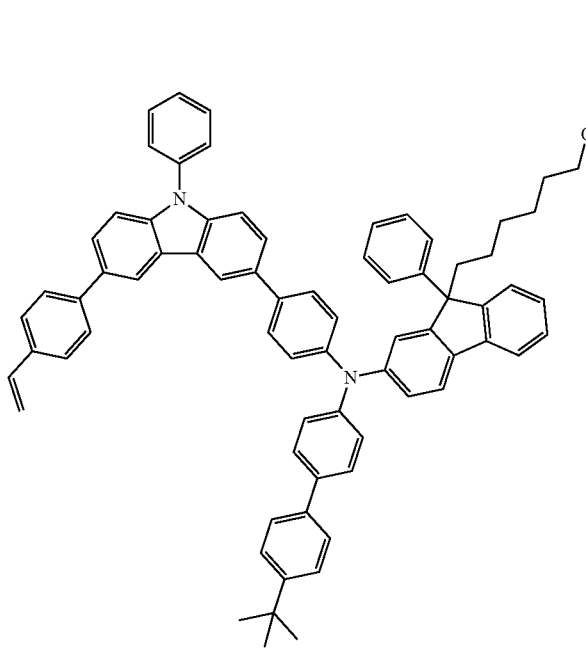

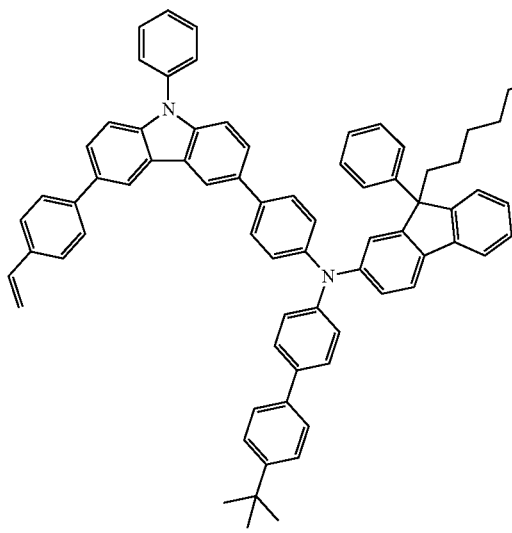
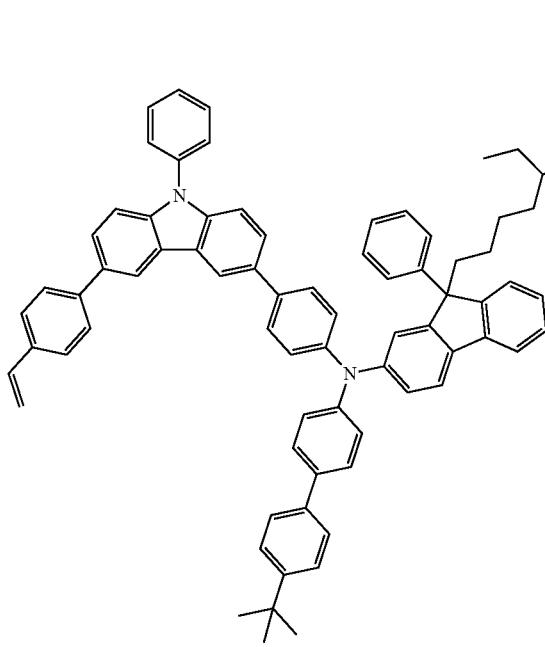

247
-continued
248
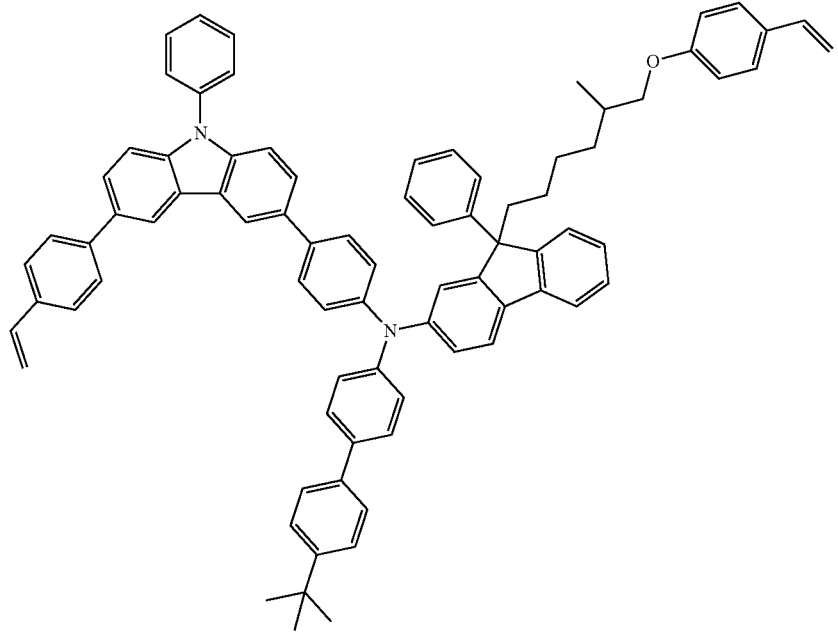
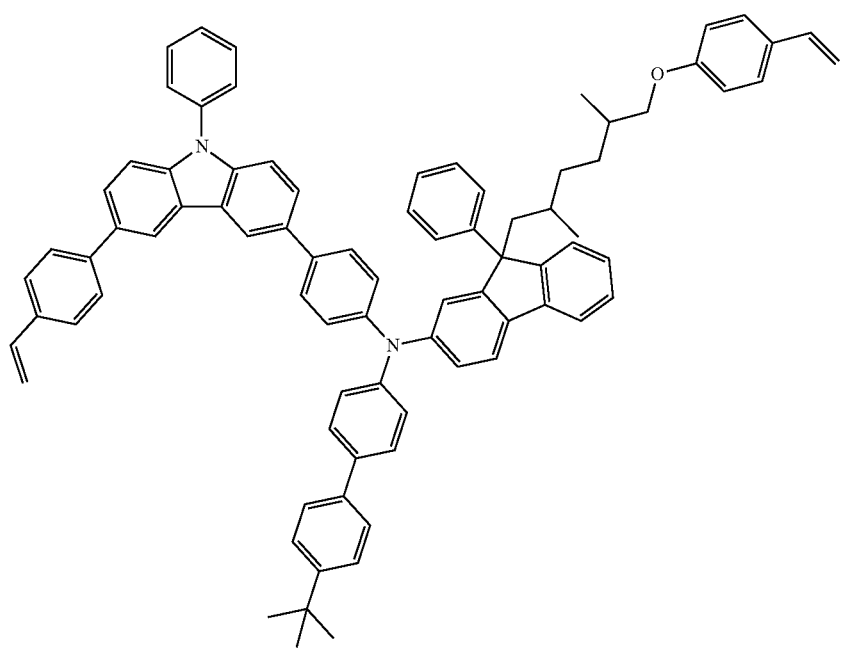

-continued
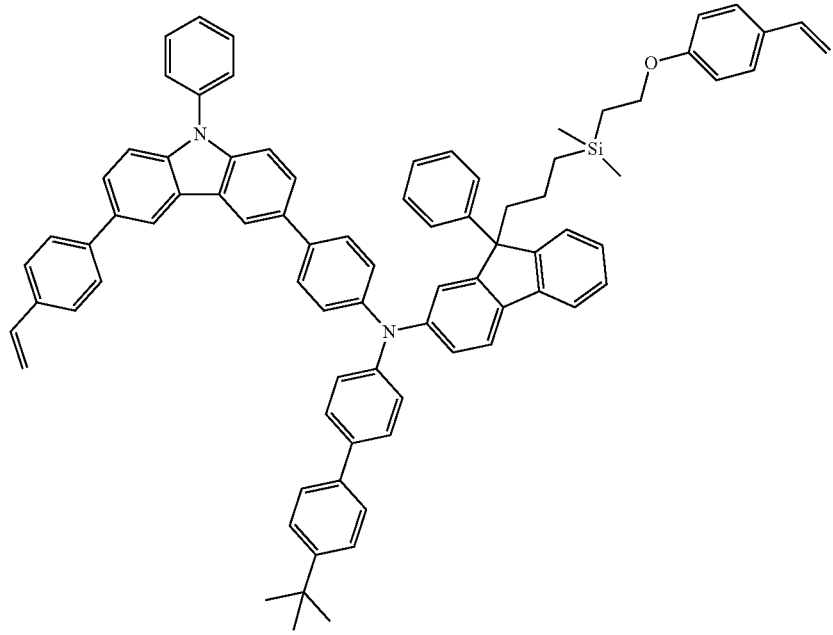
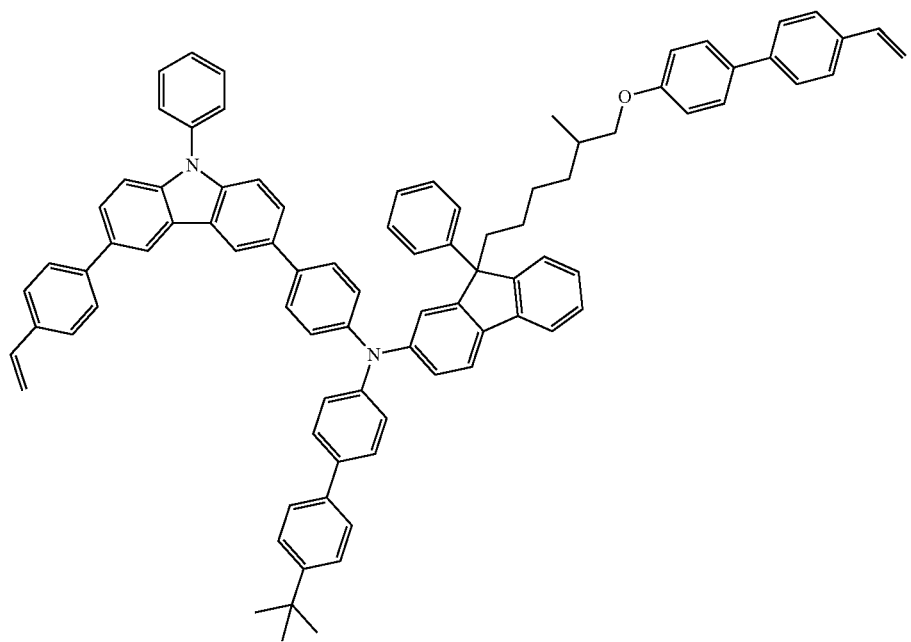

251 252
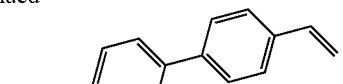
-continued
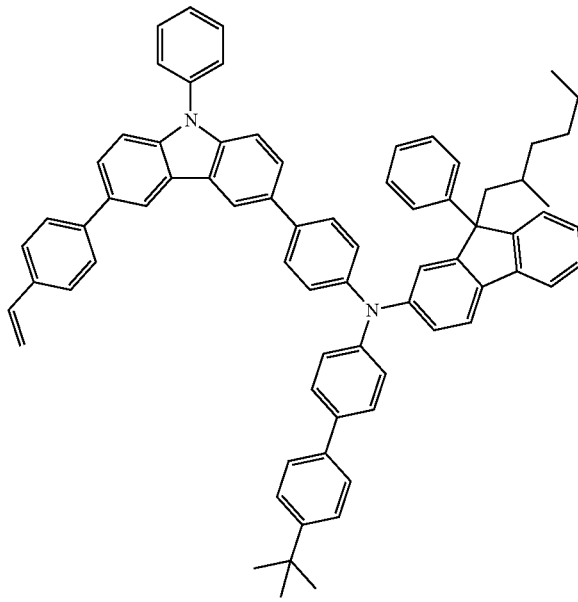
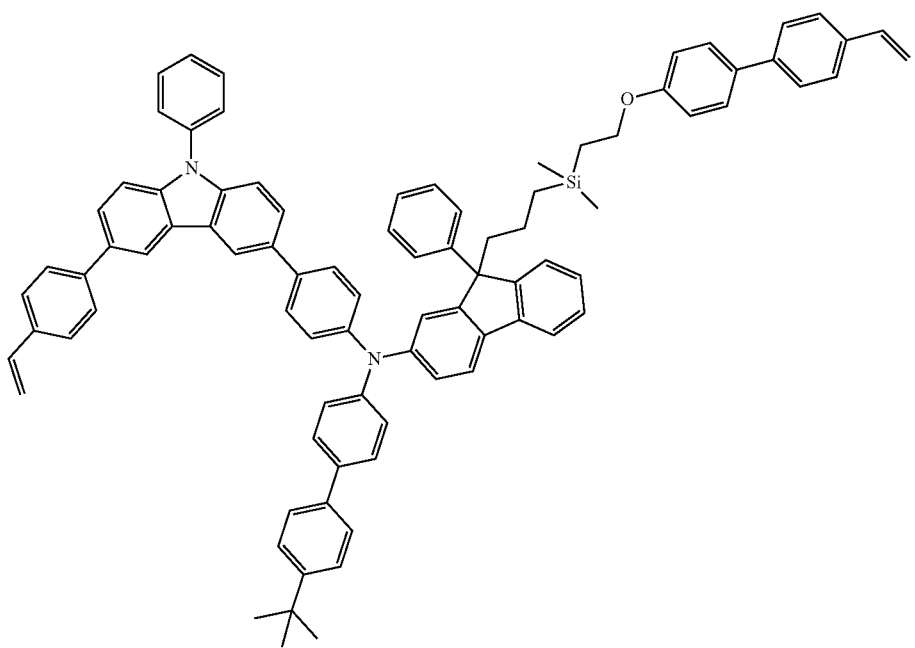

253
254
-continued
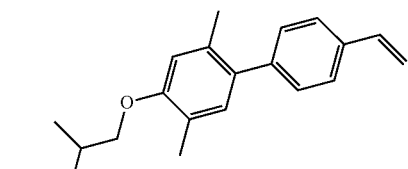
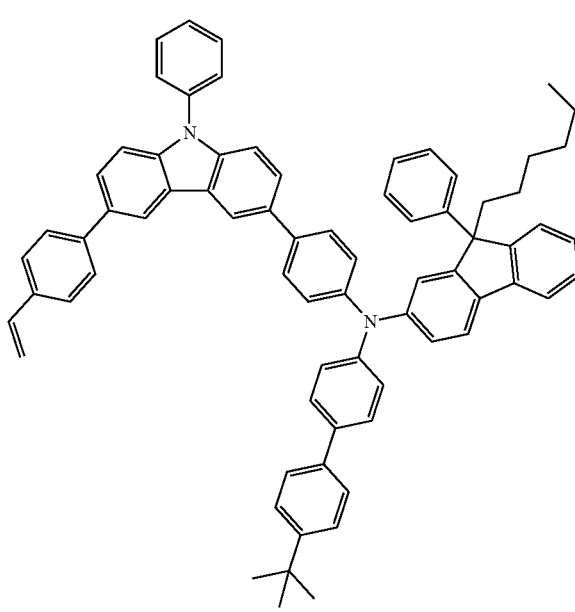
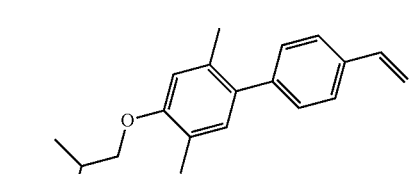
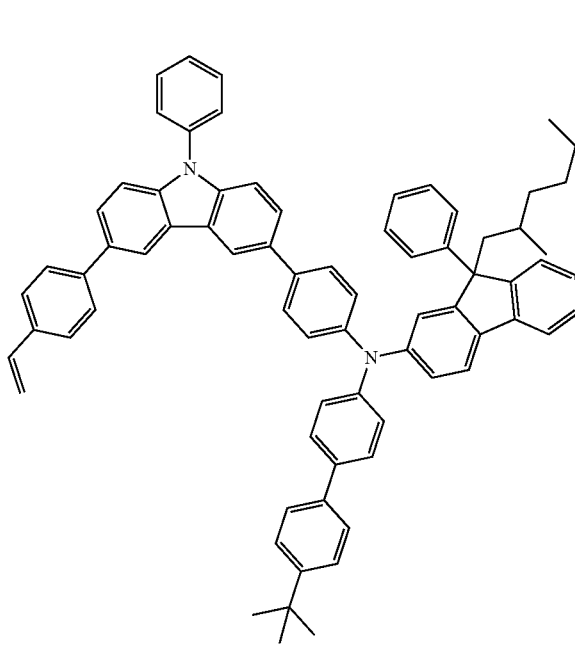

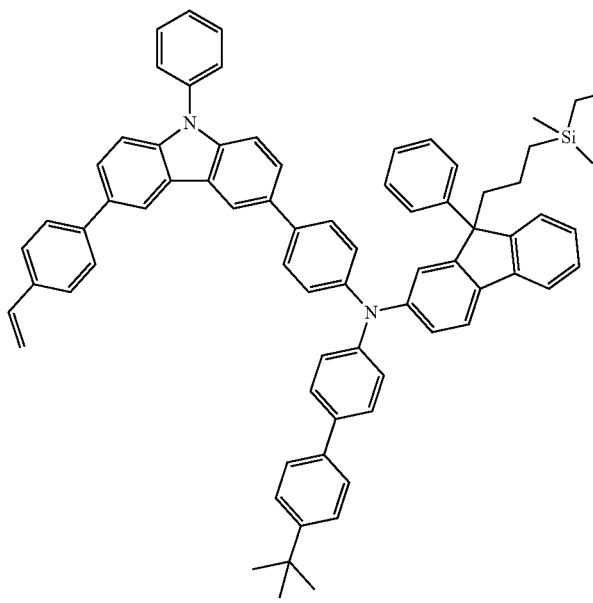
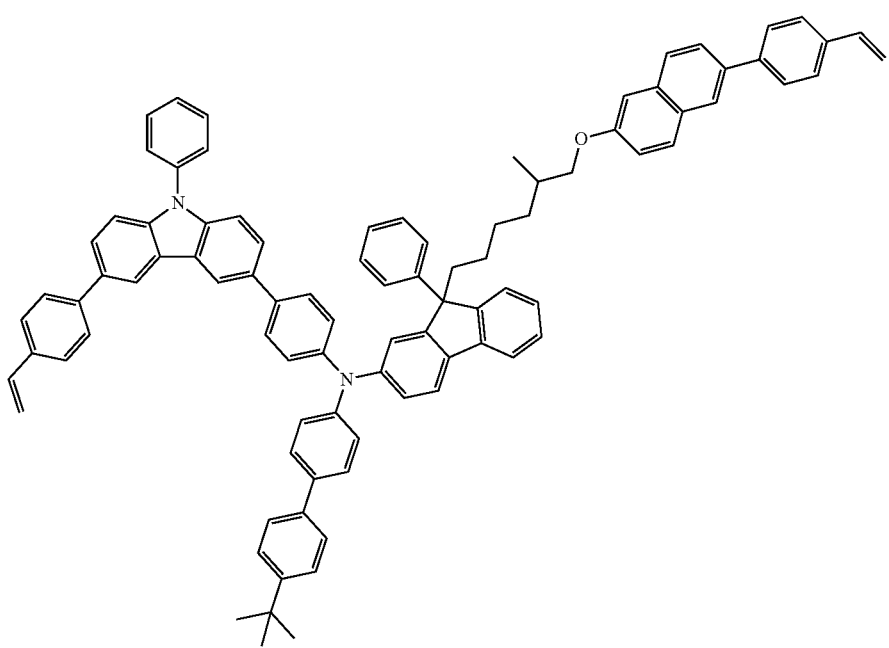

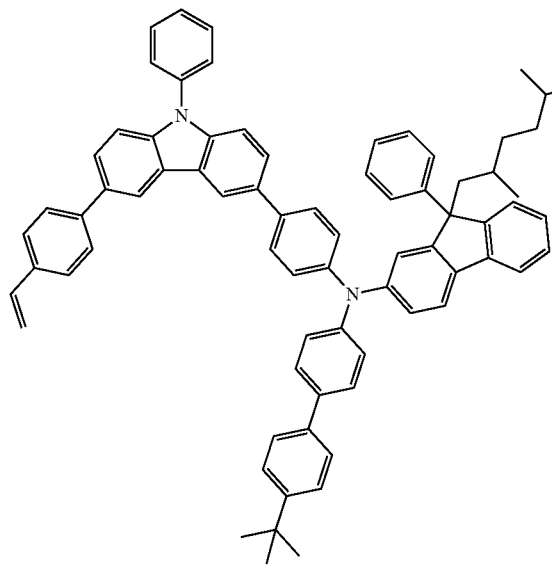
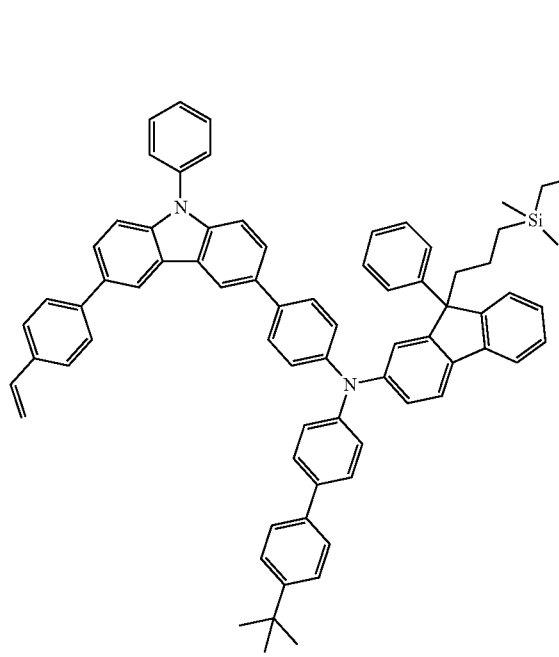

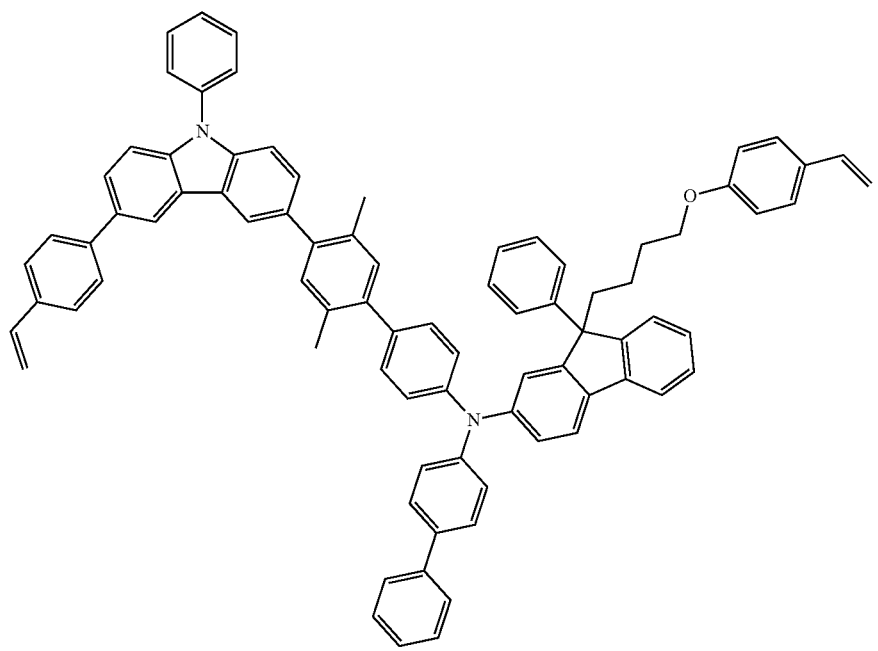
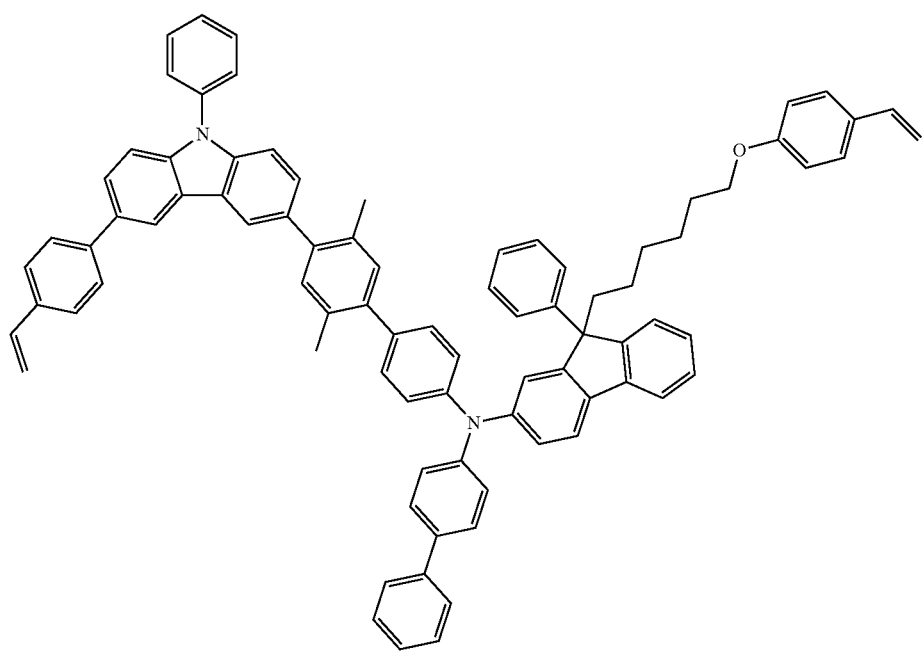

261
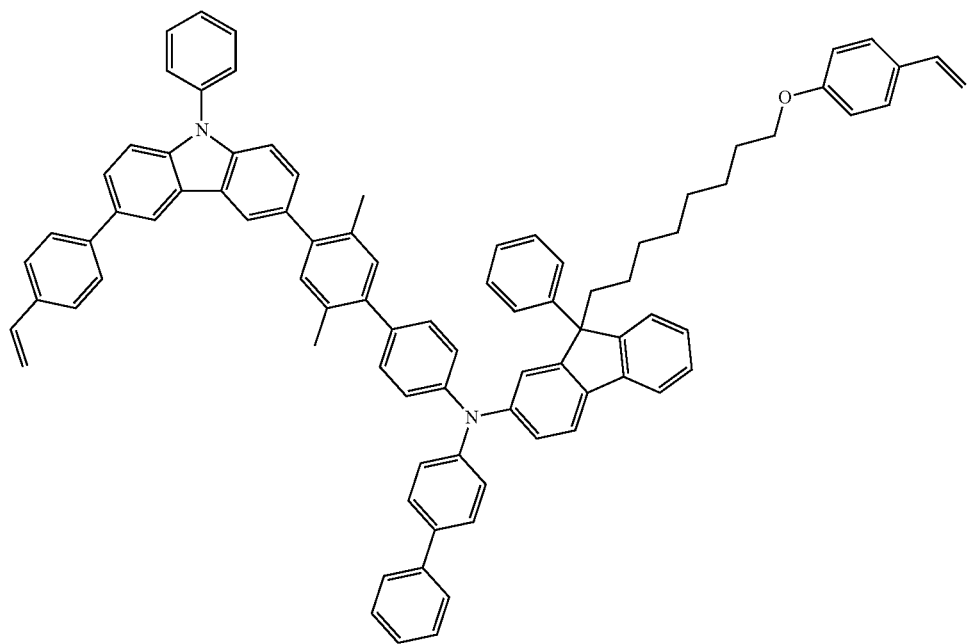
262
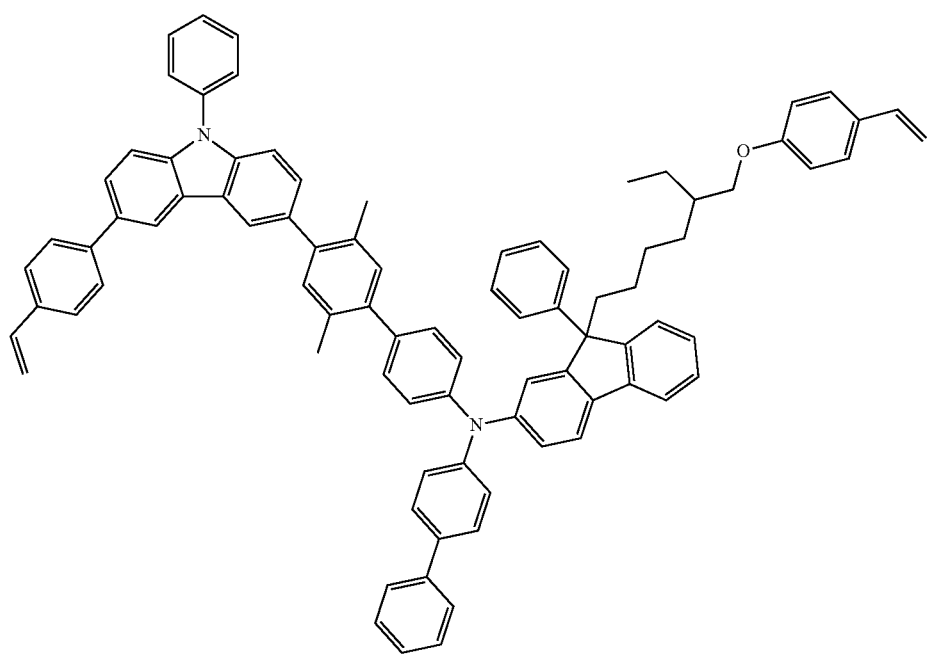

263
-continued
264
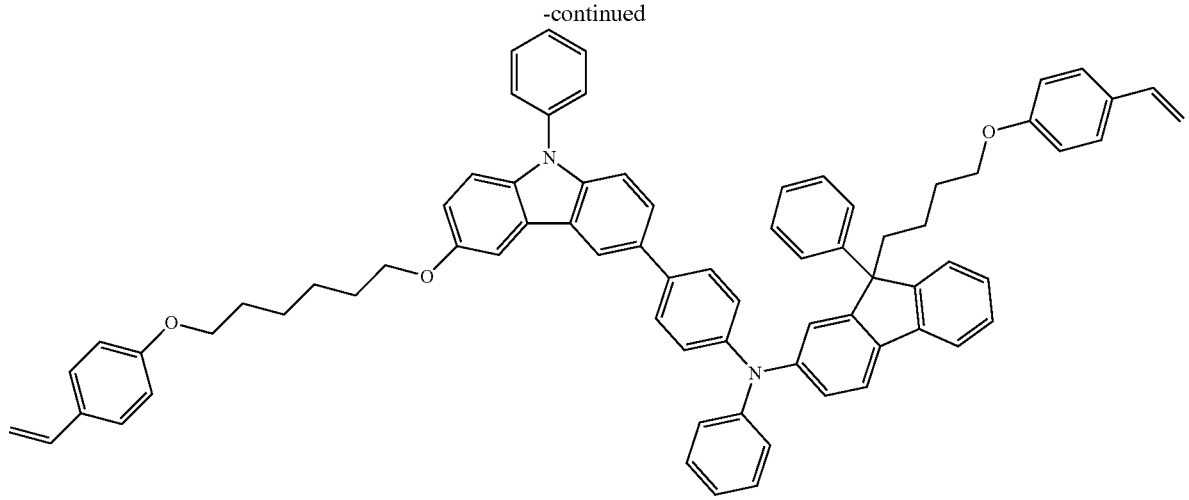
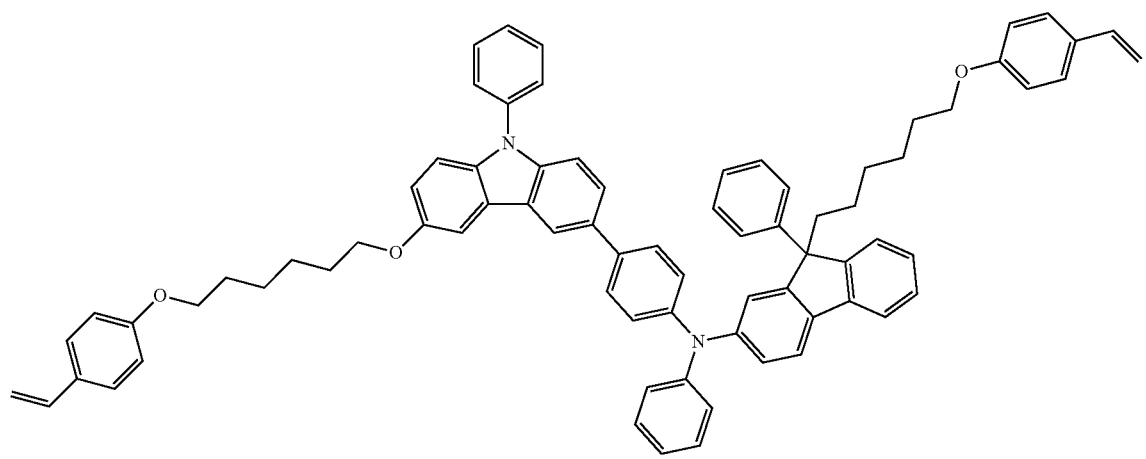
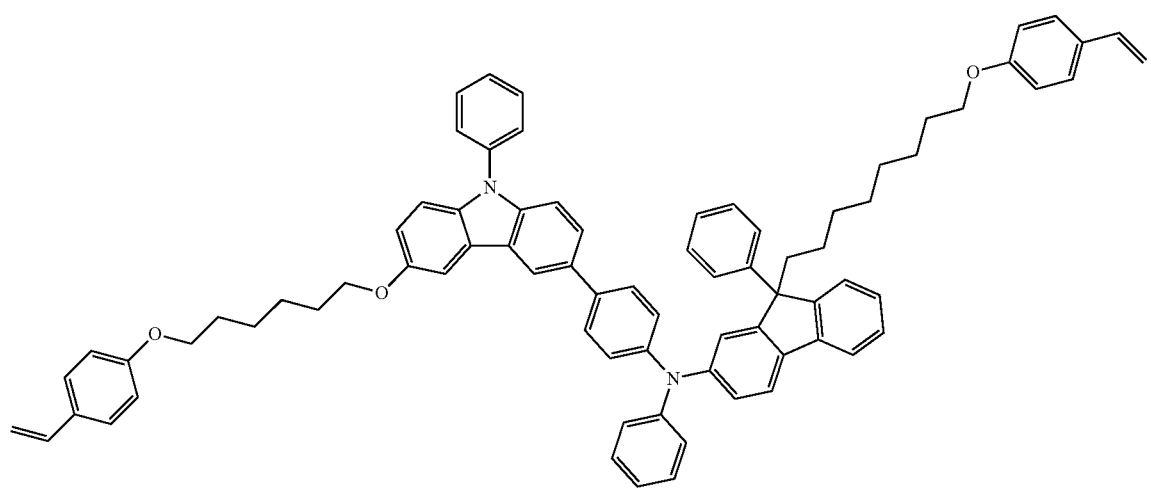

-continued
265
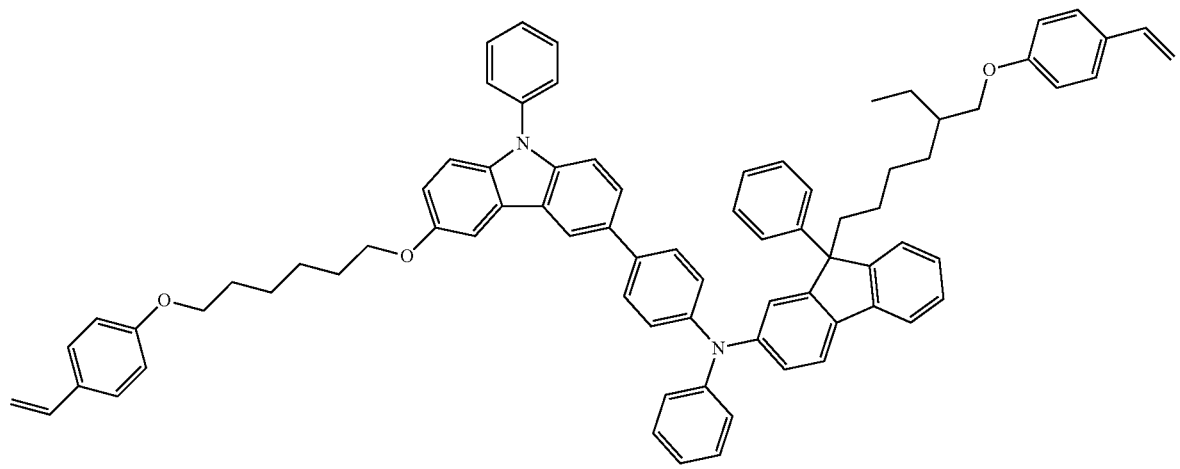 [SMILES: C=Cc1ccc(OCCCCCCOc2ccc3c(c2)c2cc(-c4ccc(N(c5ccccc5)c5ccc6c(c5)C(CCCCC(CC)COc5ccc(C=C)cc5)(c5ccccc5)c5ccccc5-6)cc4)ccc2n3-c2ccccc2)cc1]
266
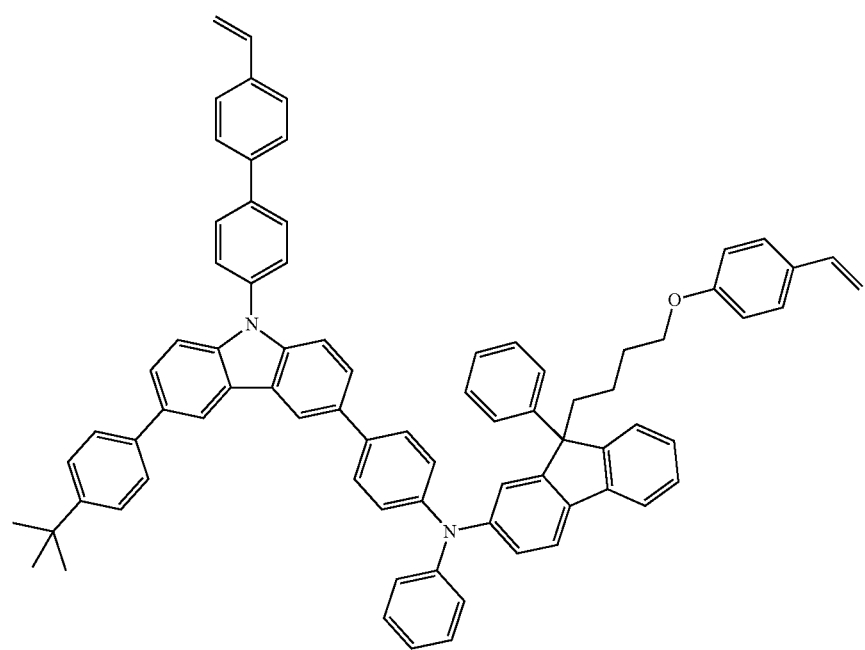

267
268
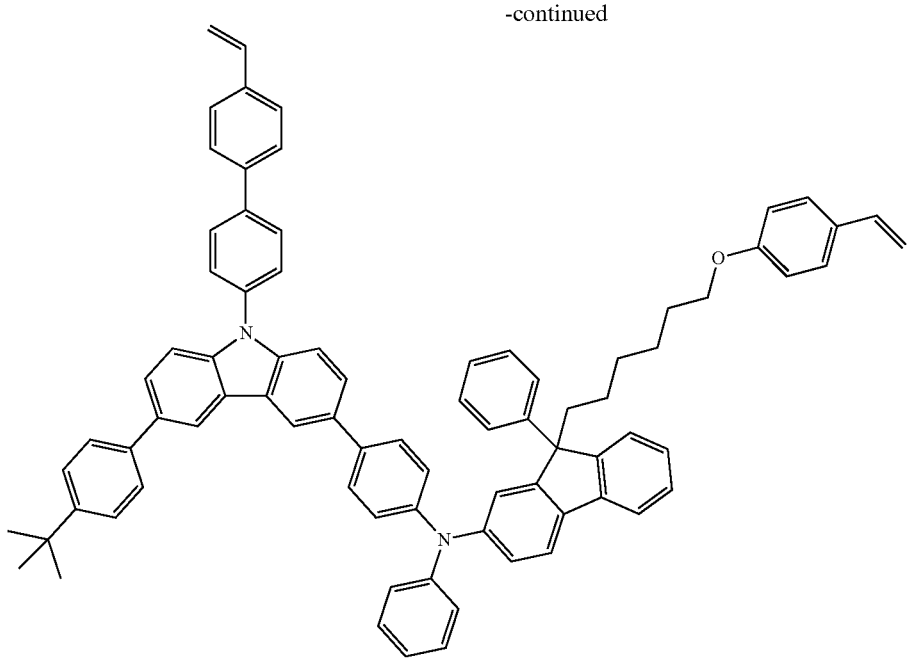
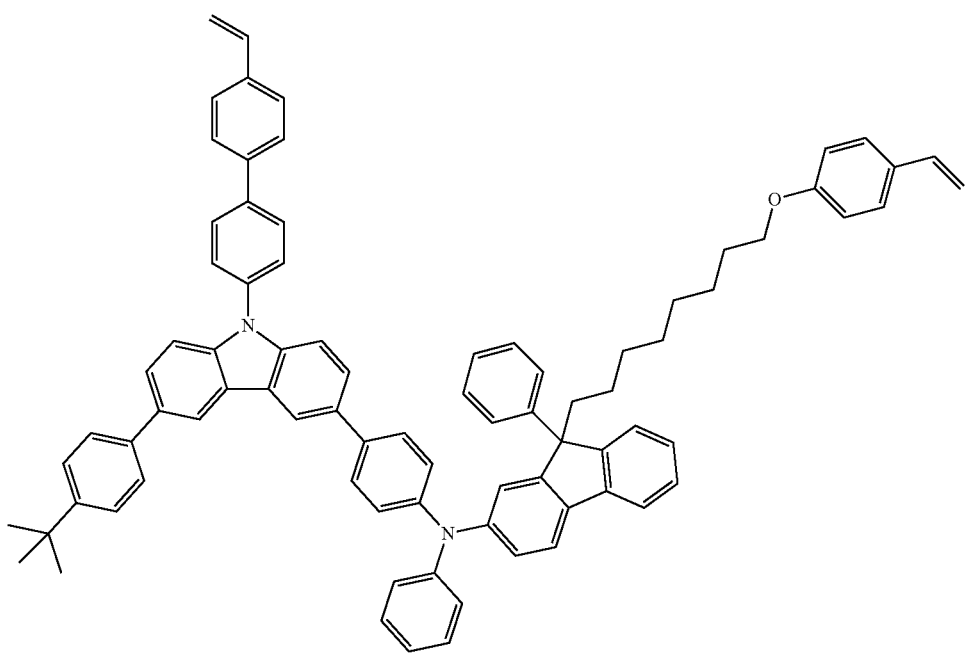

269
-continued
270
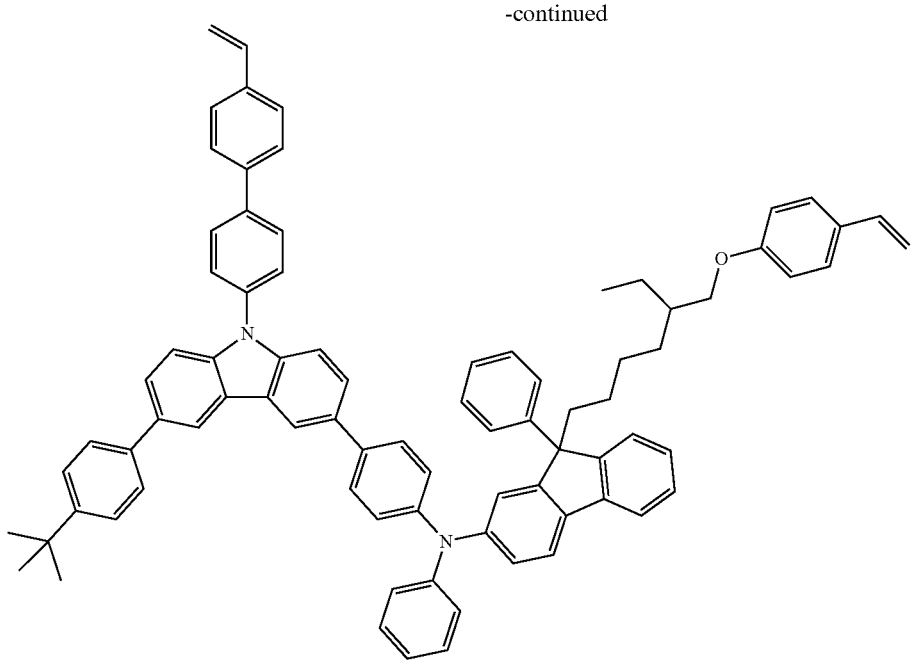
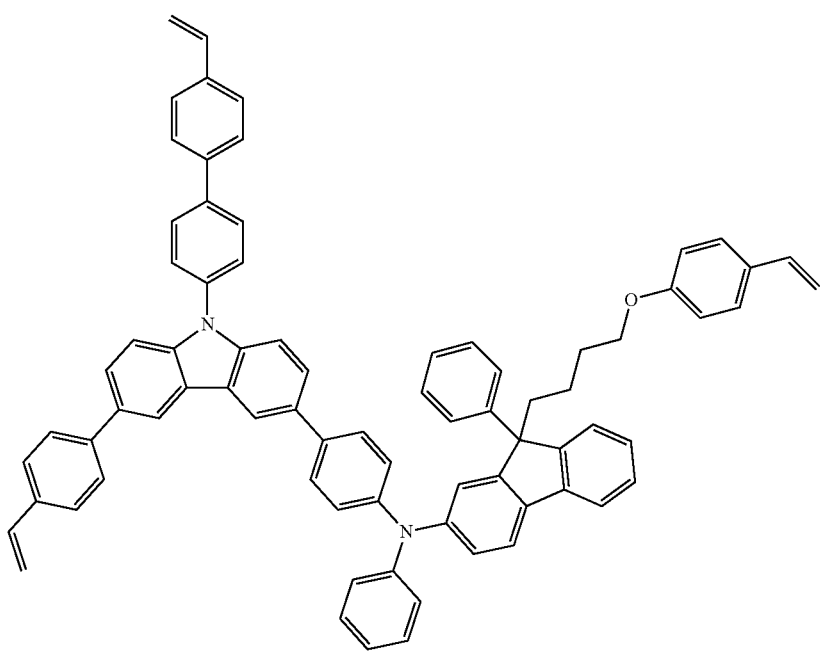

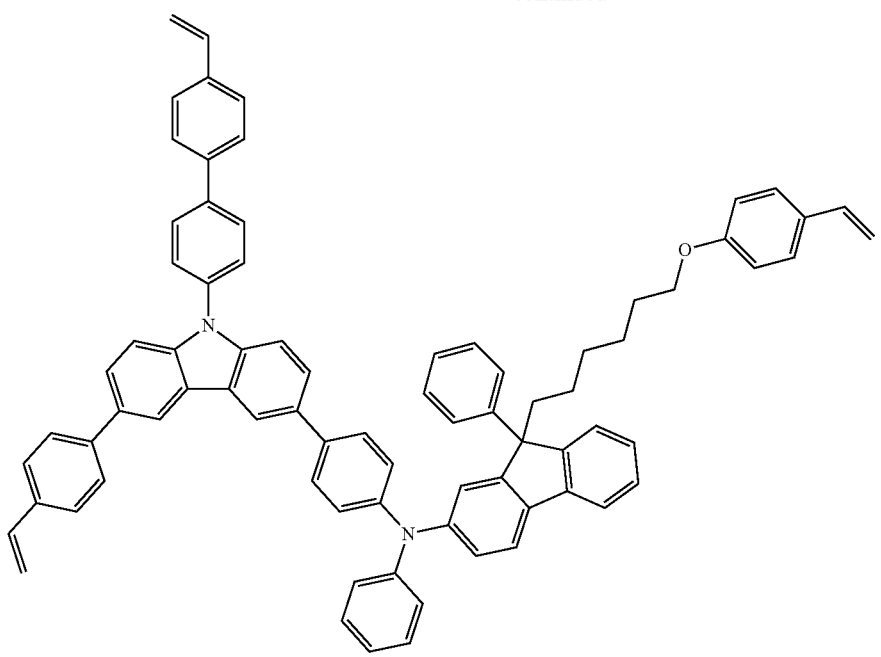
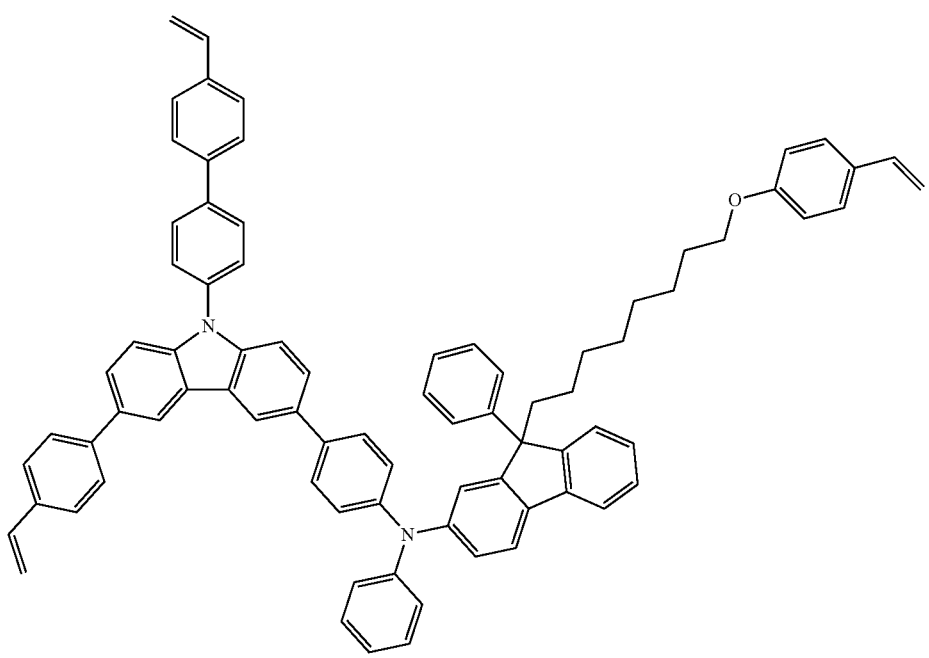

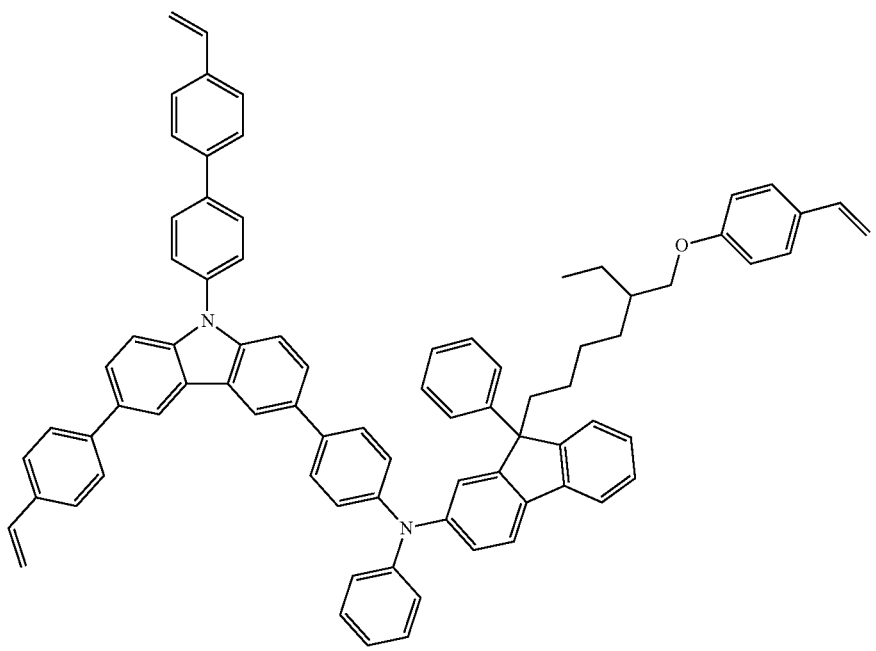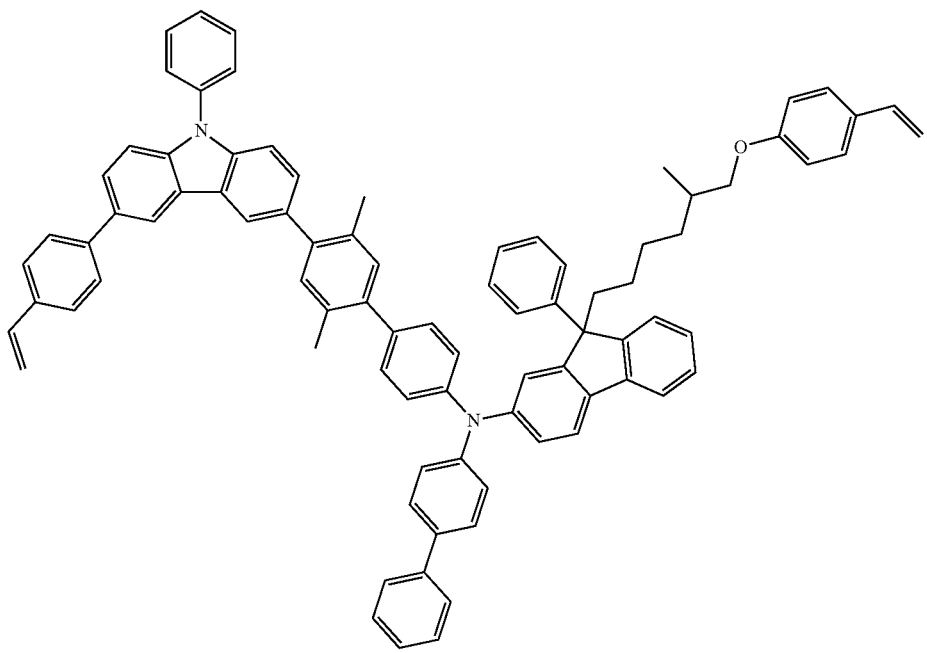

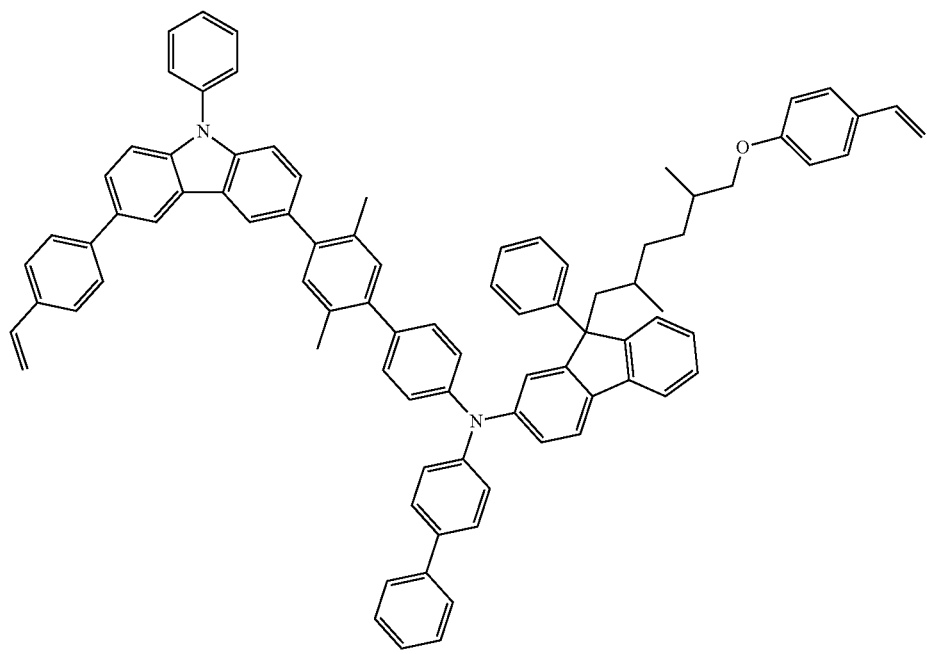
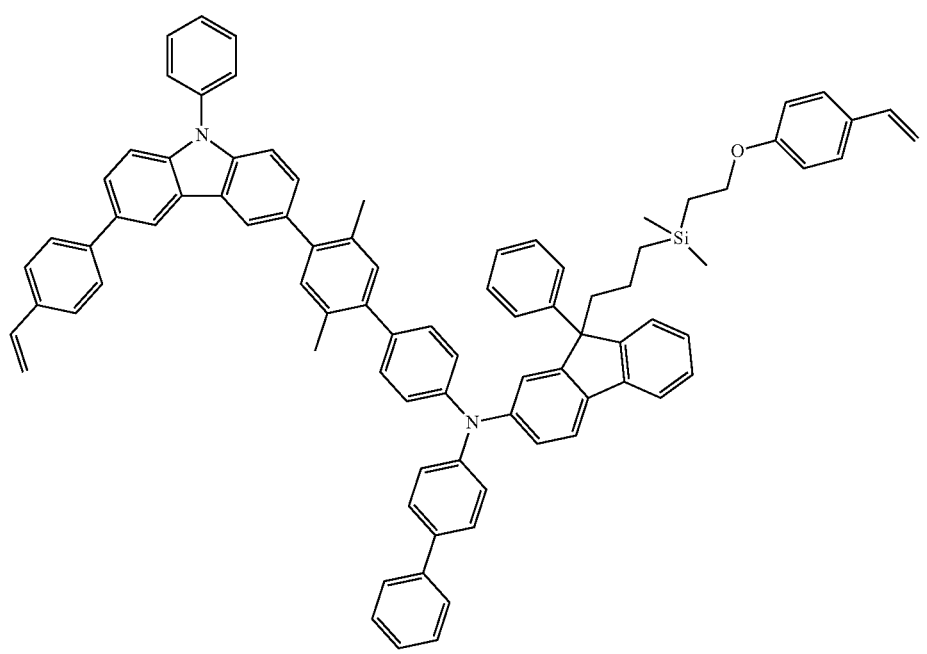 [SMILES: C=Cc1ccc(OCC[Si](C)(C)CCCC2(c3ccccc3)c3ccccc3-c3ccc(N(c4ccc(-c5ccccc5)cc4)c4ccc(-c5cc(C)c(-c6ccc7c(c6)c6cc(-c8ccc(C=C)cc8)ccc6n7-c6ccccc6)cc5C)cc4)cc32)cc1]

277 278
-continued
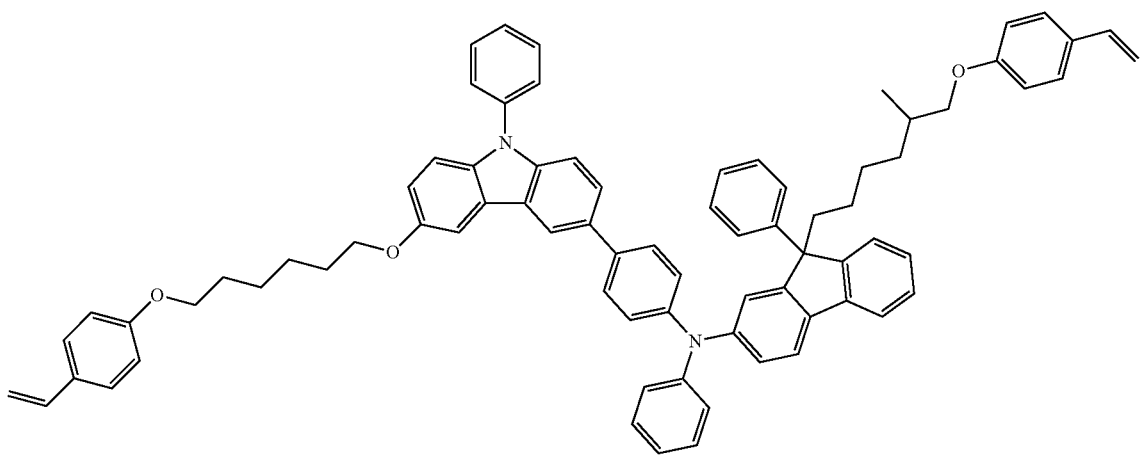
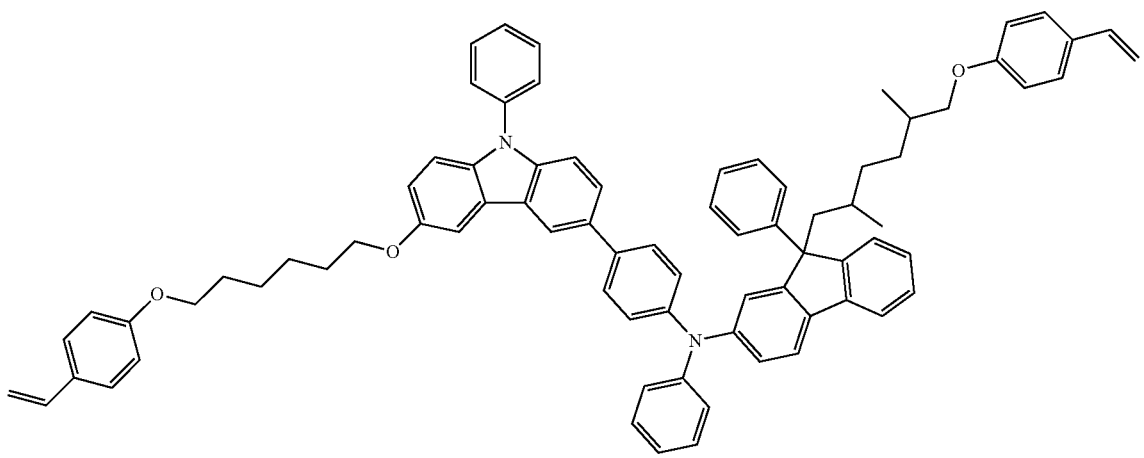
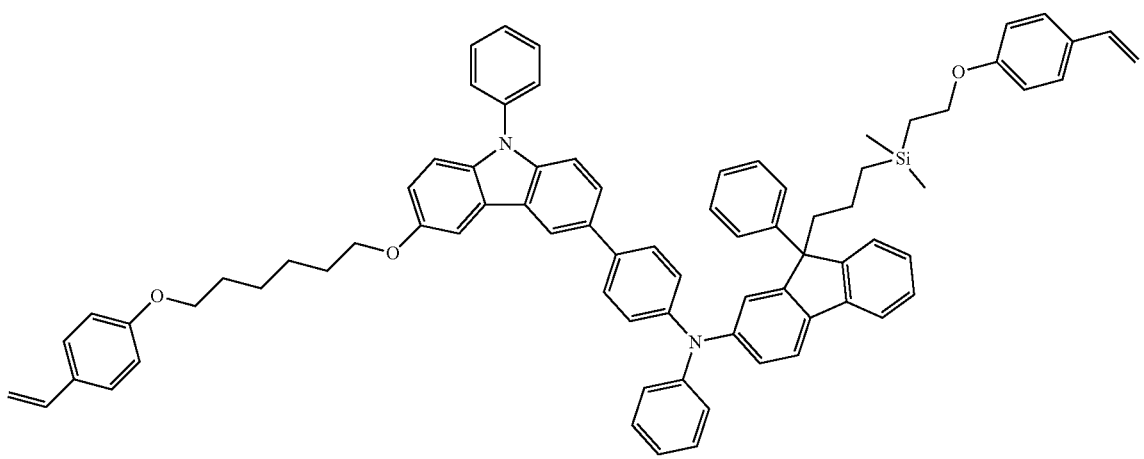

-continued
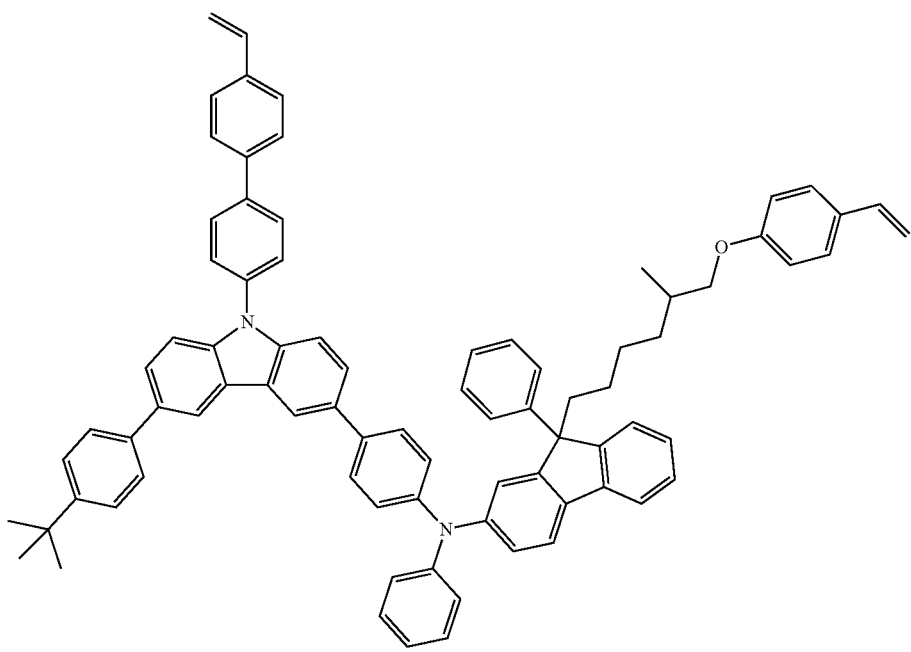
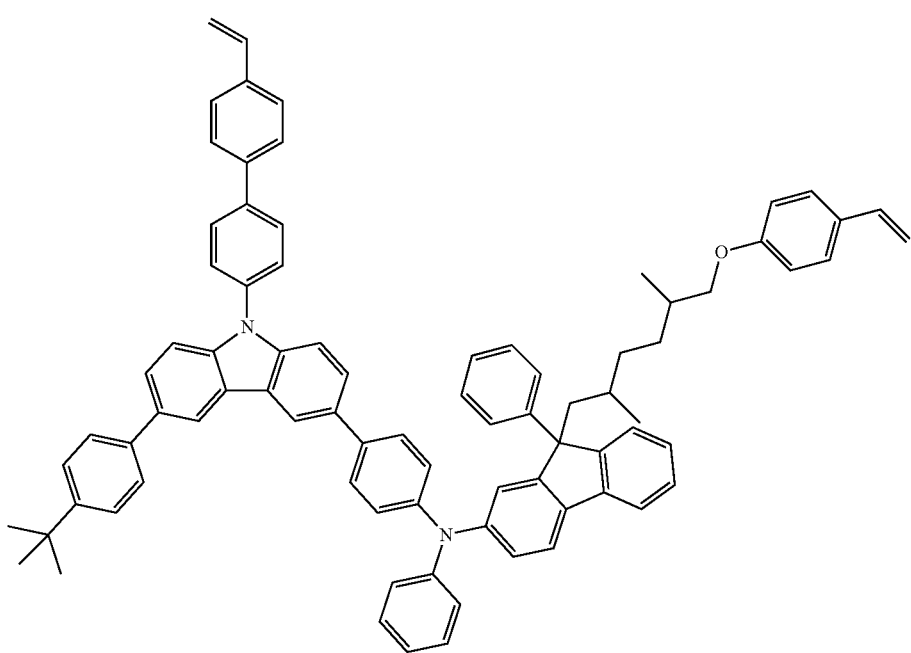

281
282
-continued
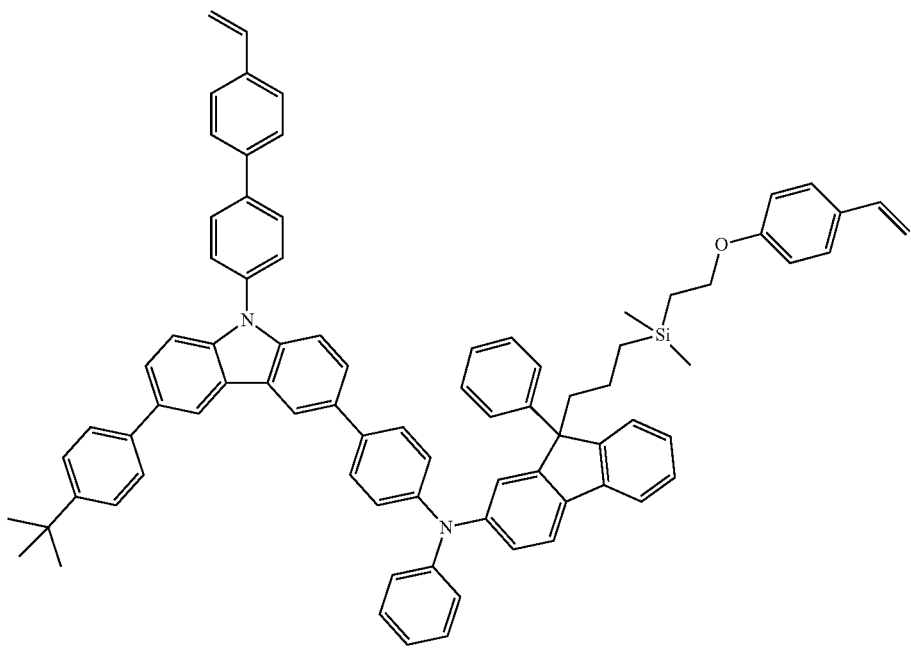 [SMILES: C=Cc1ccc(OCC[Si](C)(C)CCCC2(c3ccccc3)c3ccccc3-c3ccc(N(c4ccccc4)c4ccc(-c5ccc6c(c5)c5cc(-c7ccc(C(C)(C)C)cc7)ccc5n6-c5ccc(-c6ccc(C=C)cc6)cc5)cc4)cc32)cc1]
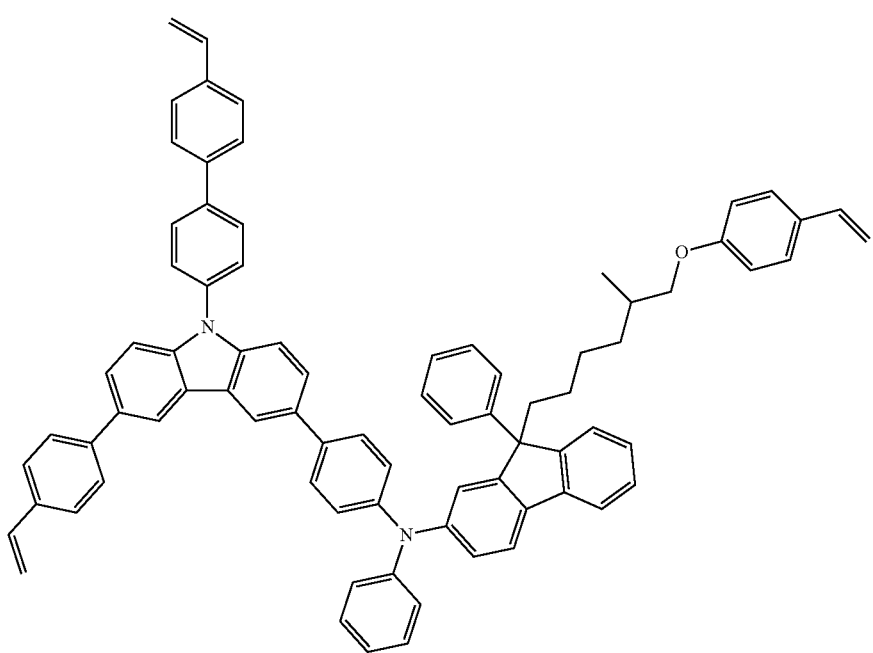

-continued
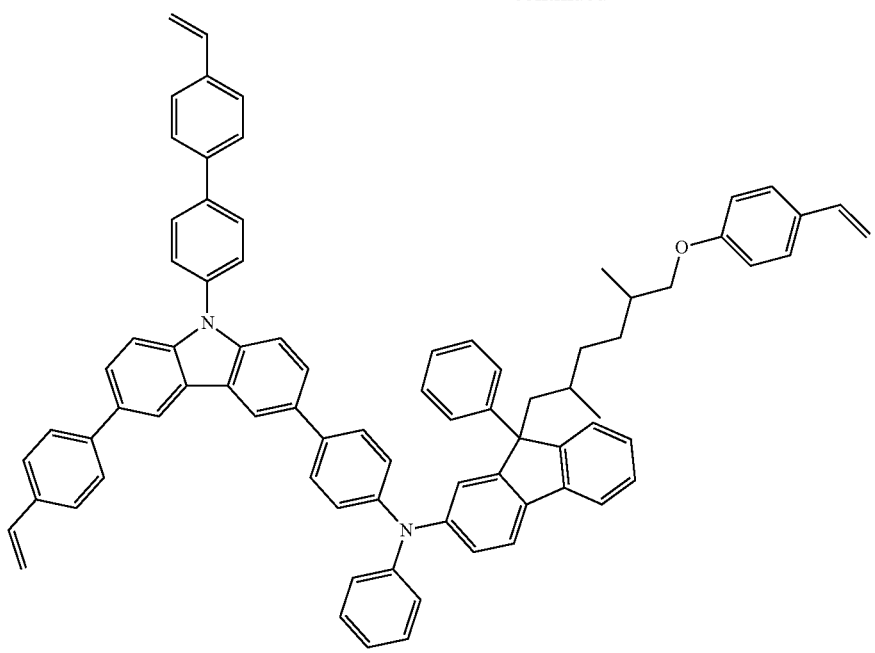
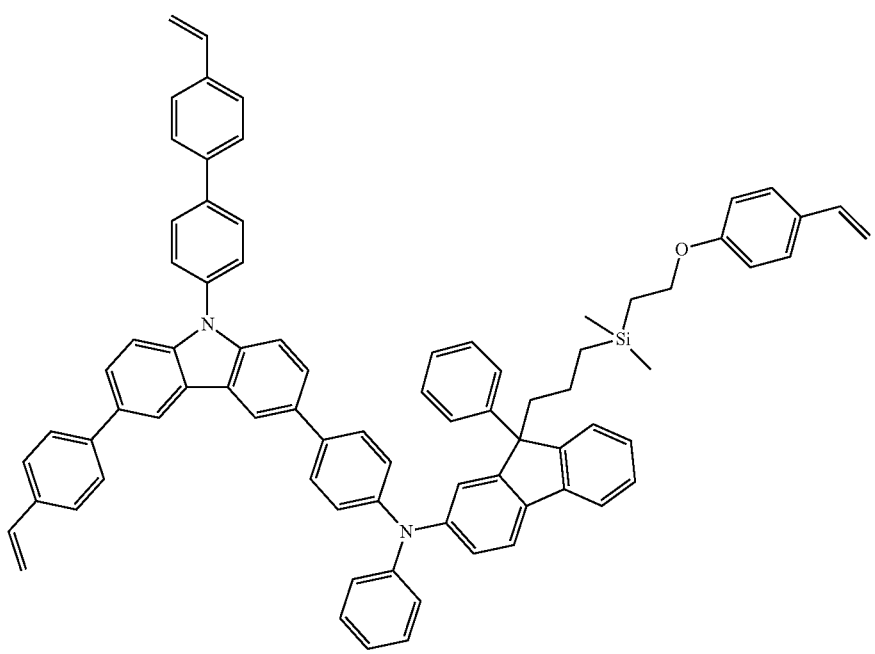 [SMILES: C=Cc1ccc(OCC[Si](C)(C)CCCC2(c3ccccc3)c3ccccc3-c3ccc(N(c4ccccc4)c4ccc(-c5ccc6c(c5)c5cc(-c7ccc(C=C)cc7)ccc5n6-c5ccc(-c6ccc(C=C)cc6)cc5)cc4)cc32)cc1]

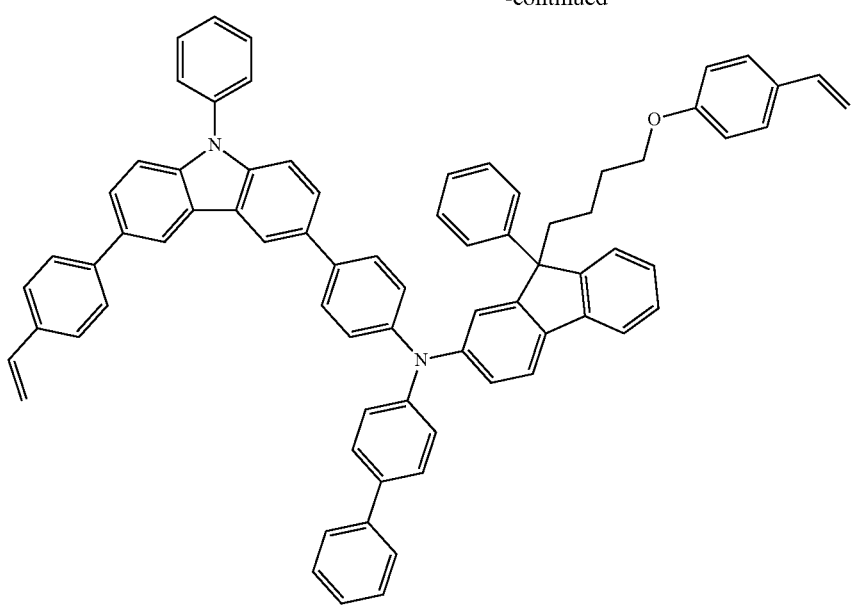
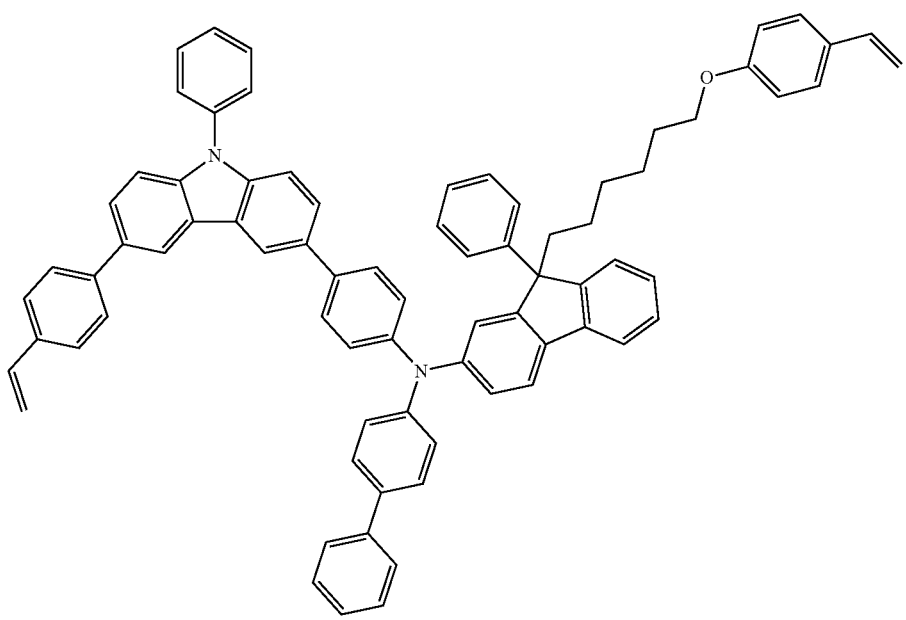

287
288
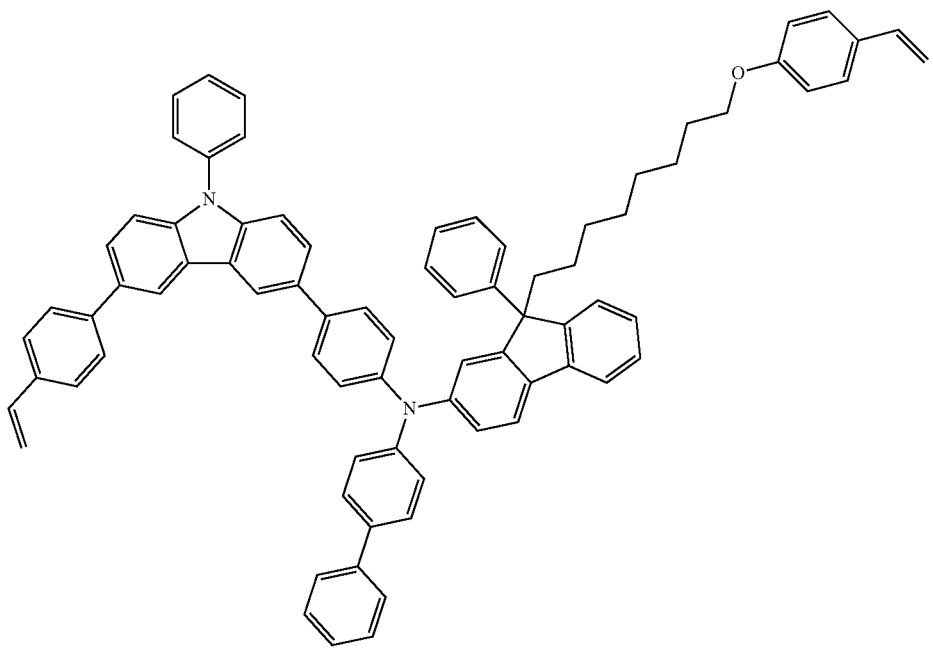
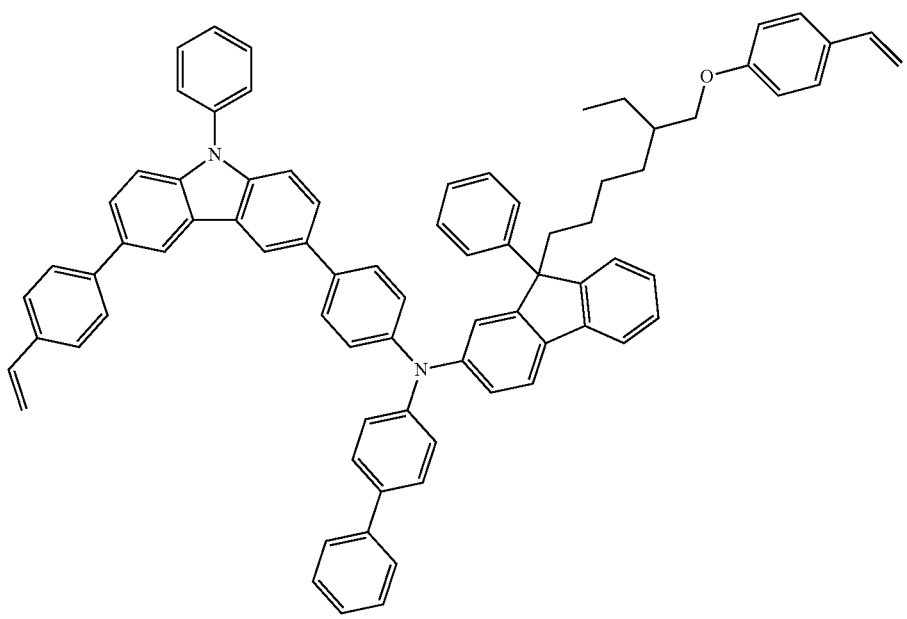

289
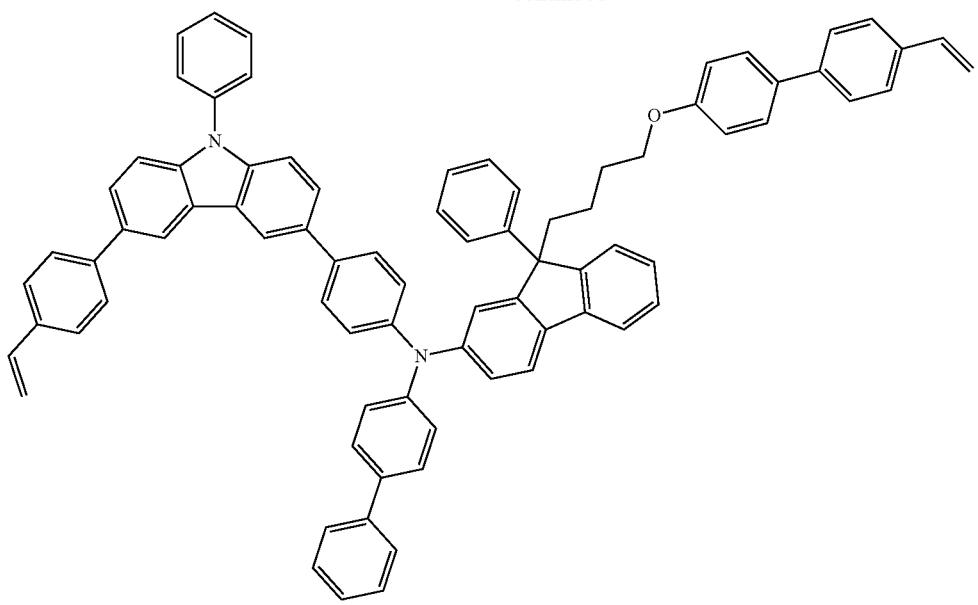
290
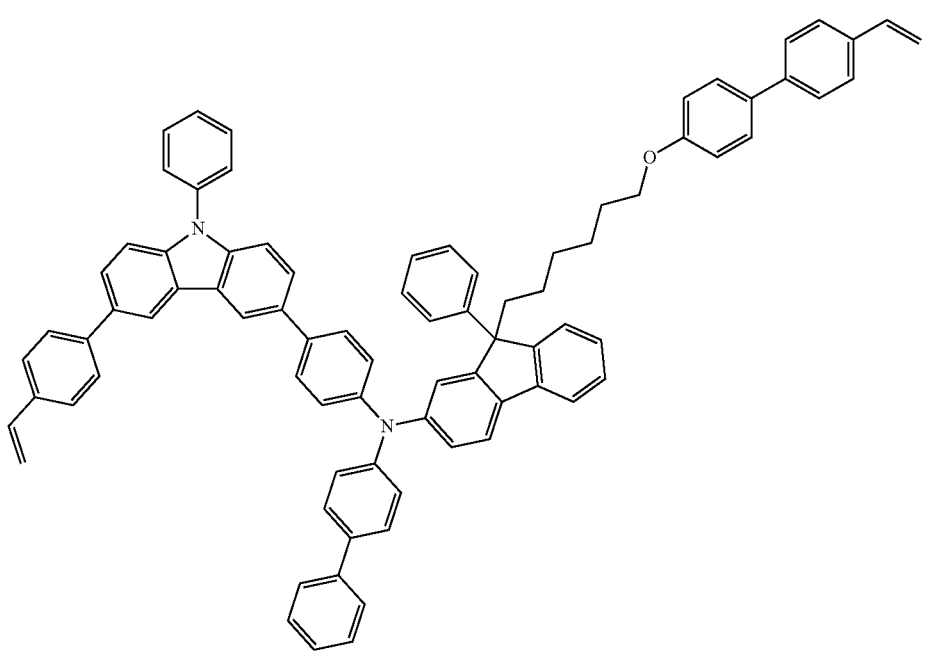

291 292
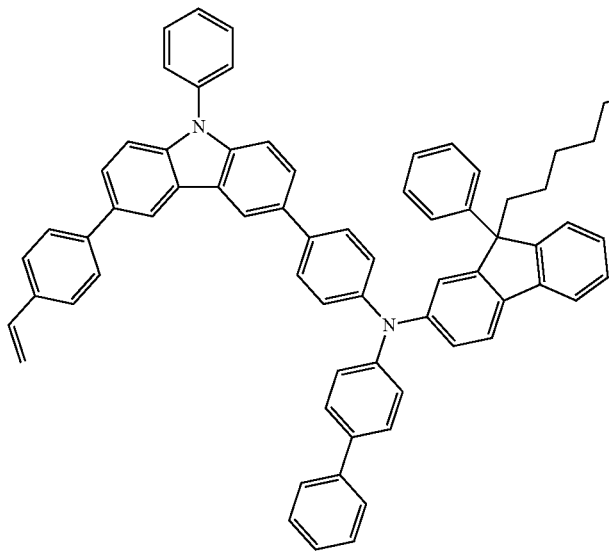
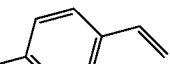
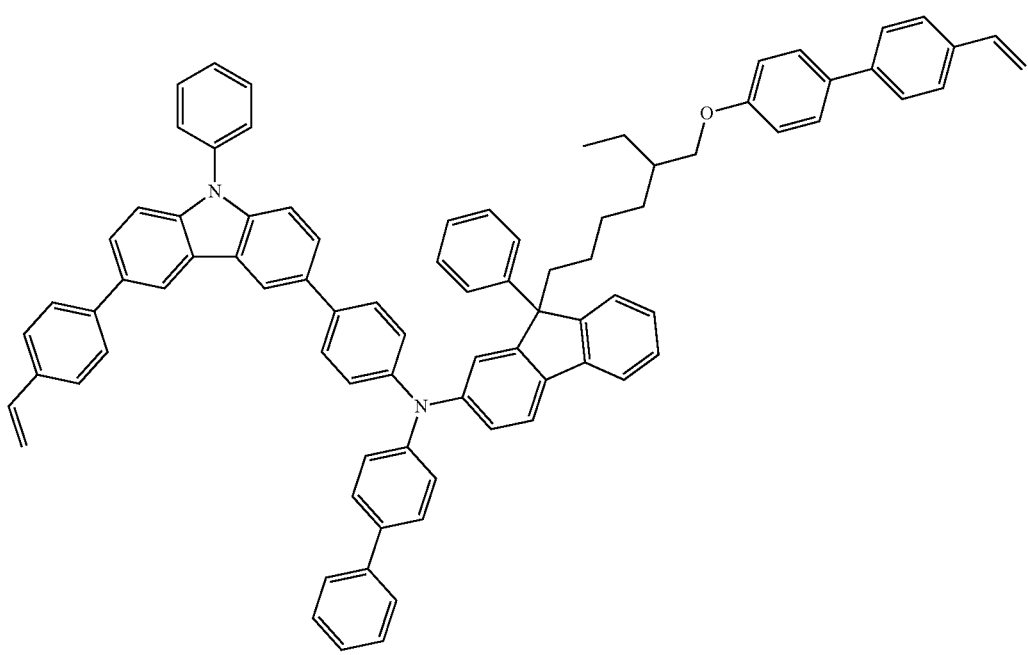

293
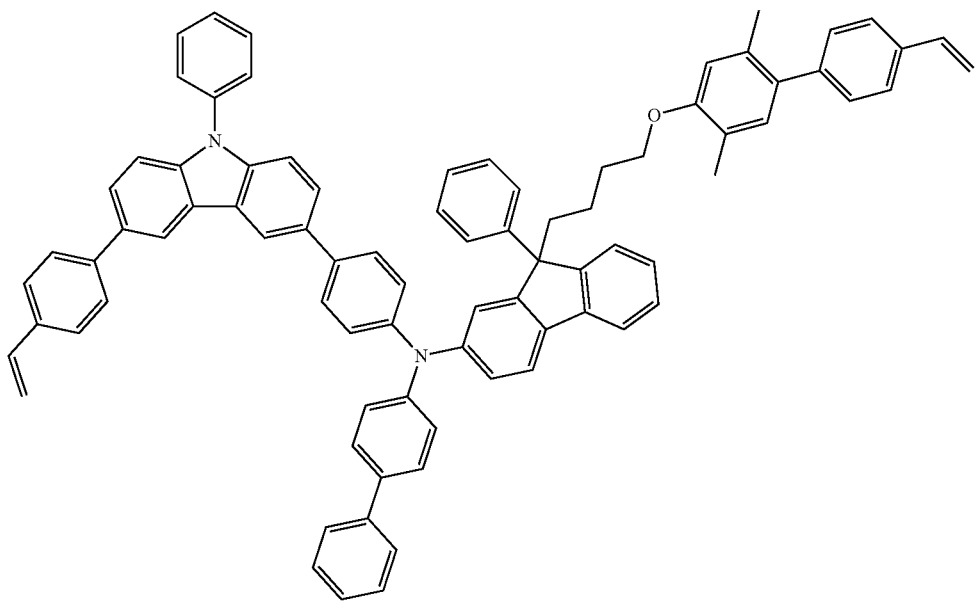
294
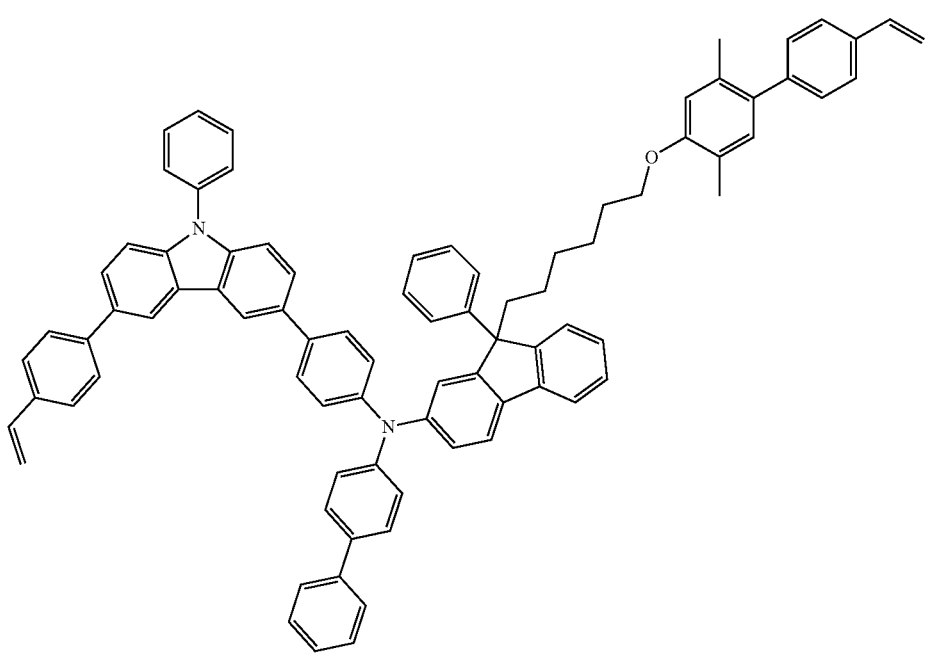

295
296
-continued
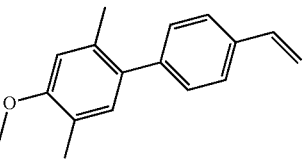
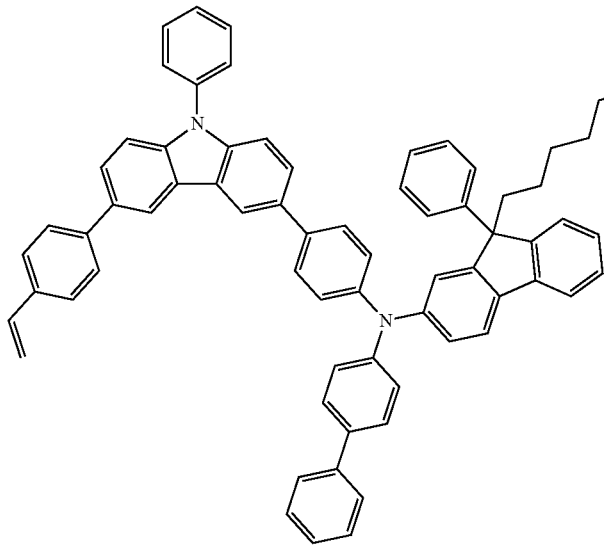
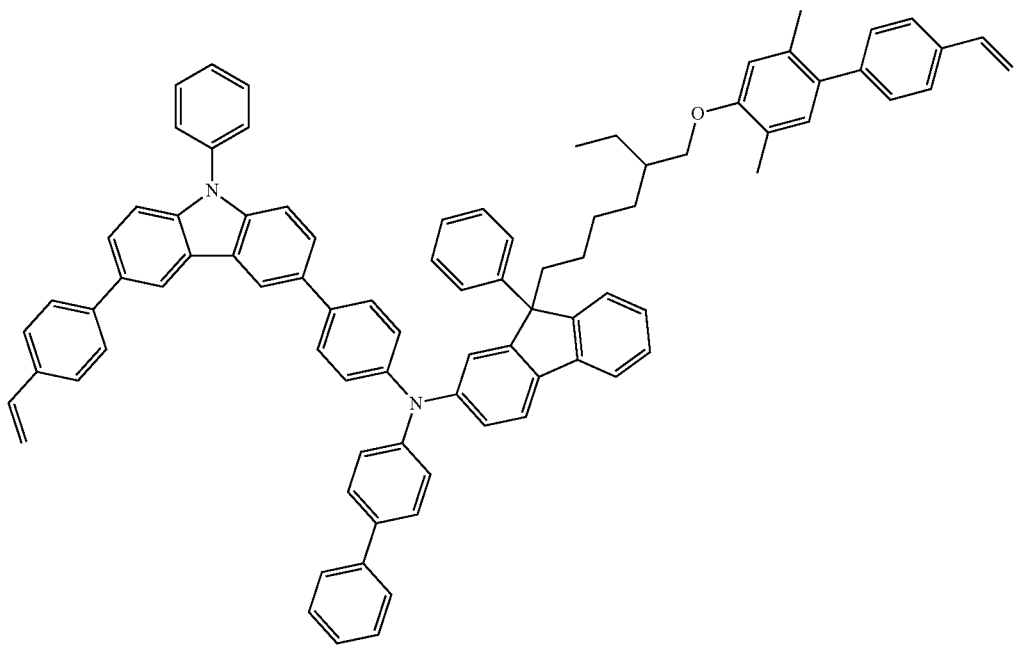

297
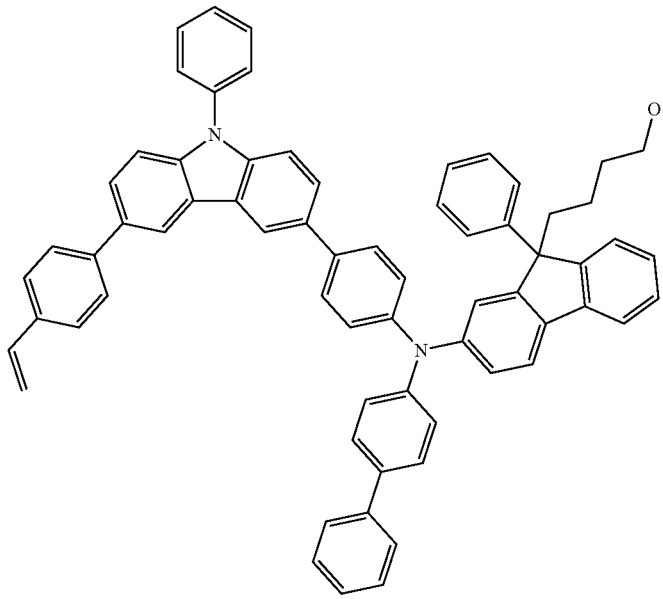
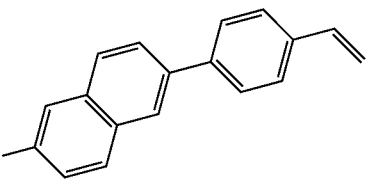
298
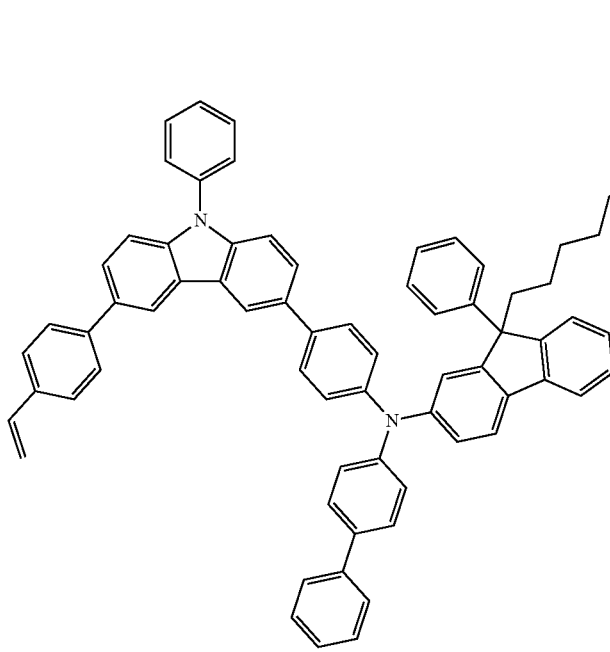
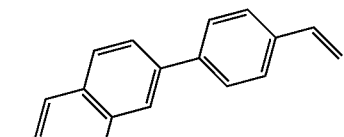

299 300
-continued
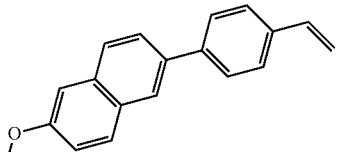
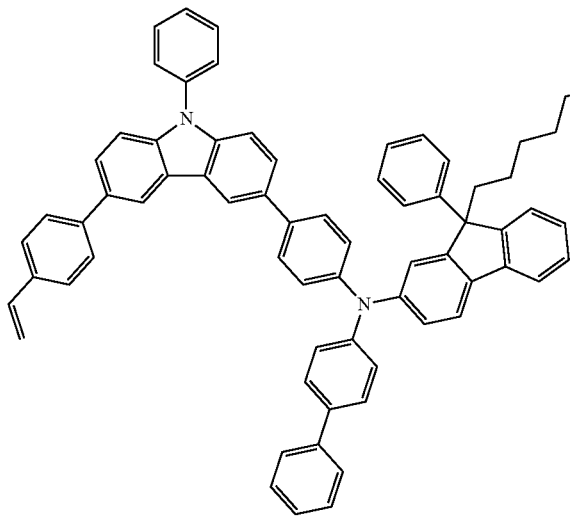
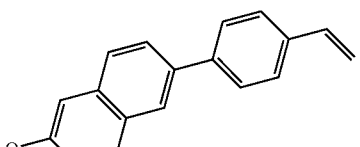
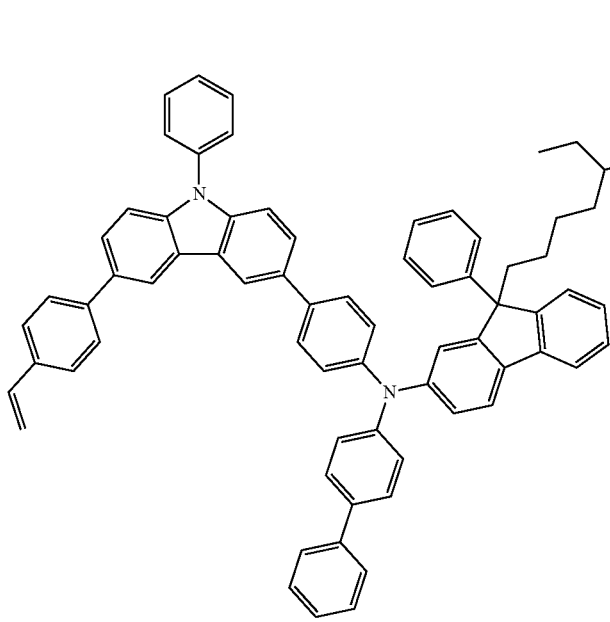

301
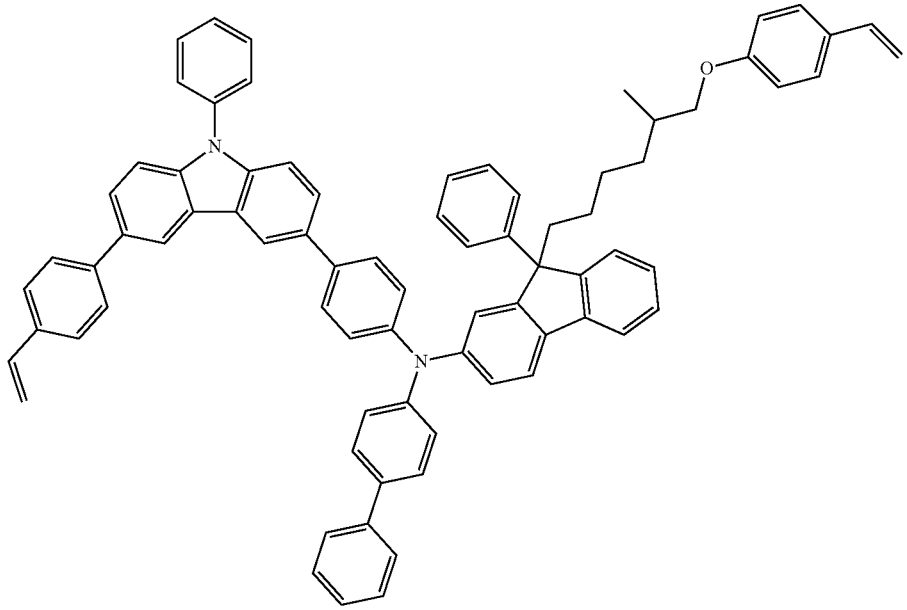
302
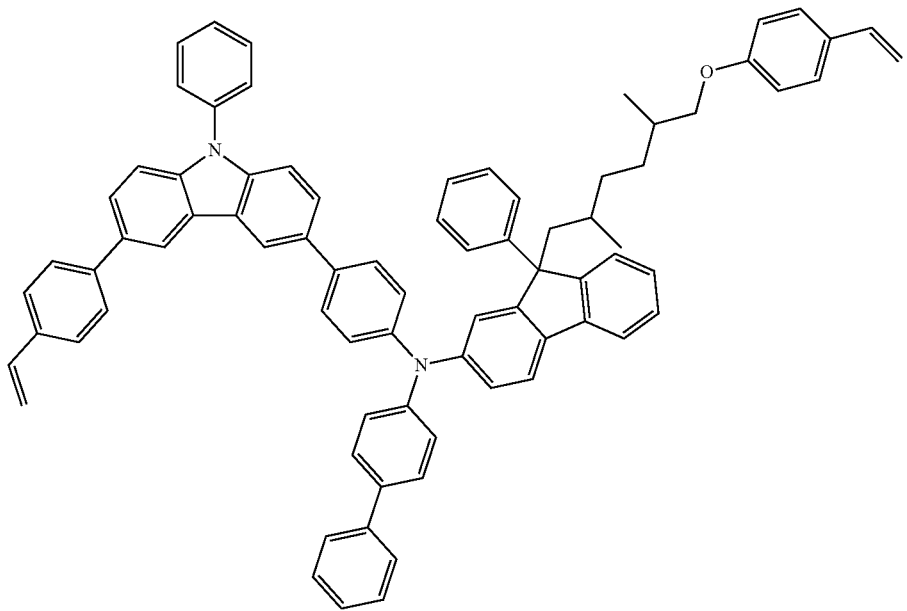

303
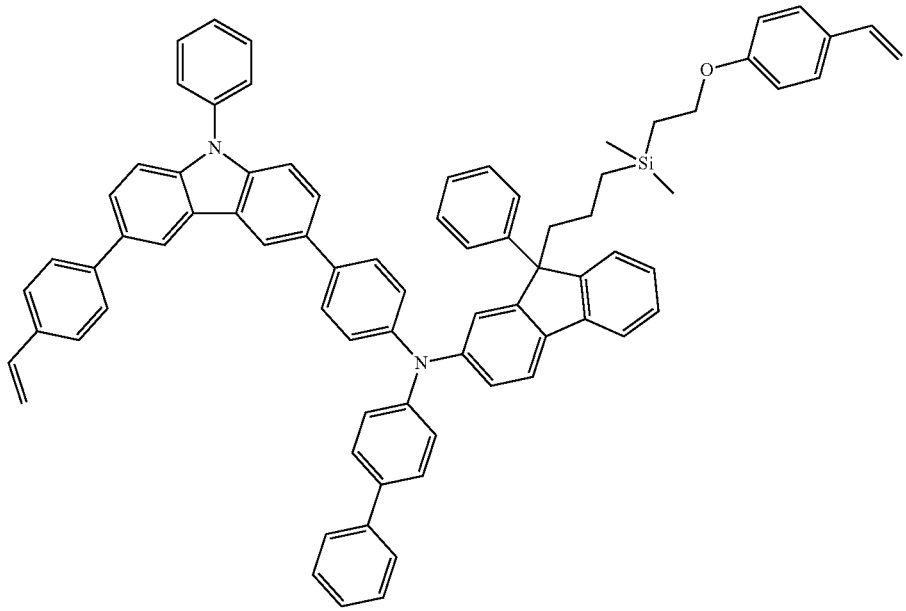
304
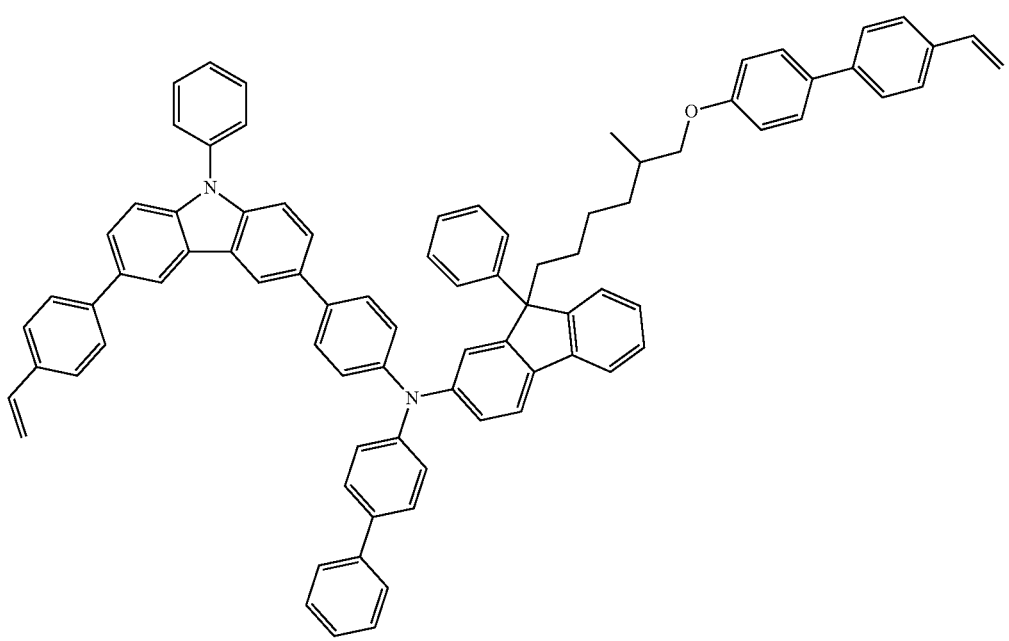

305
306
-continued
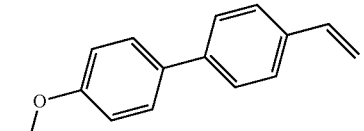
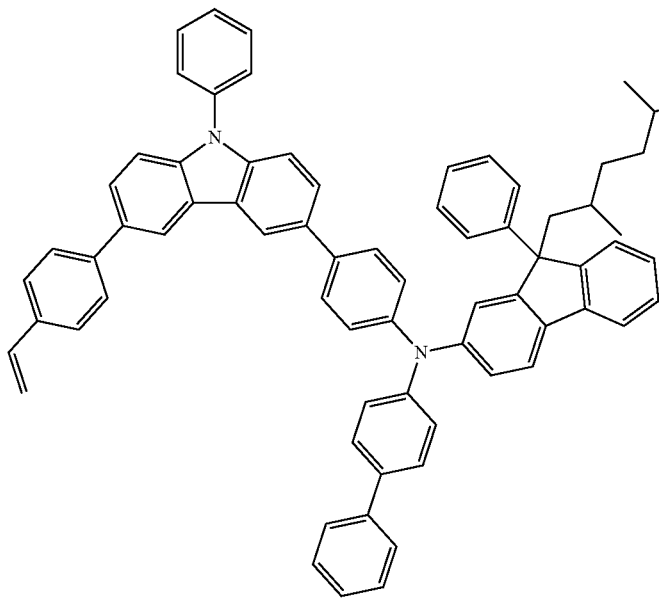
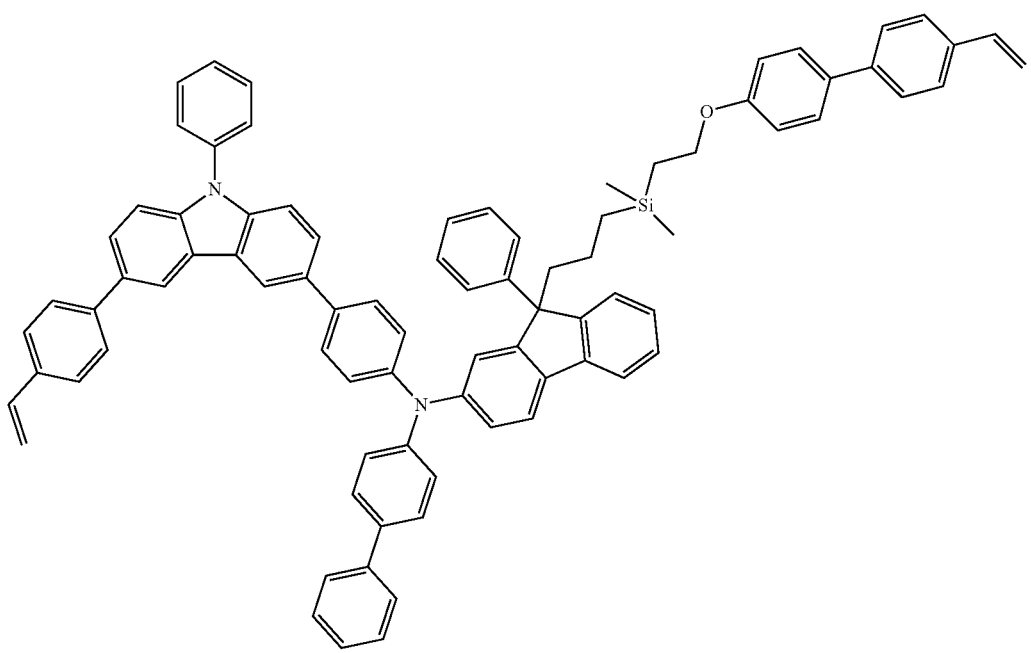

307
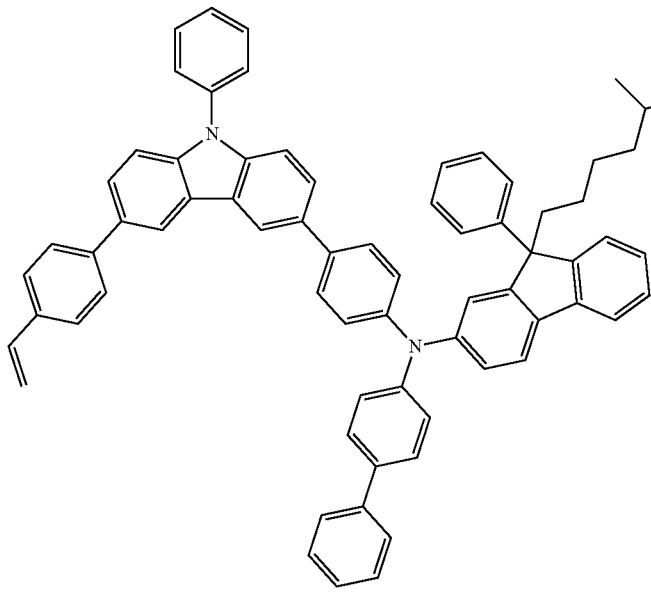
308
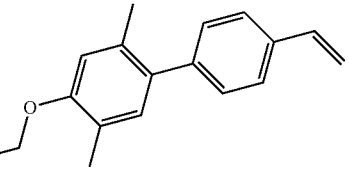
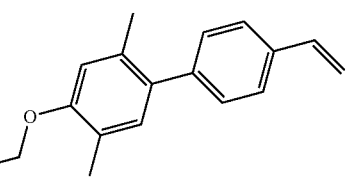
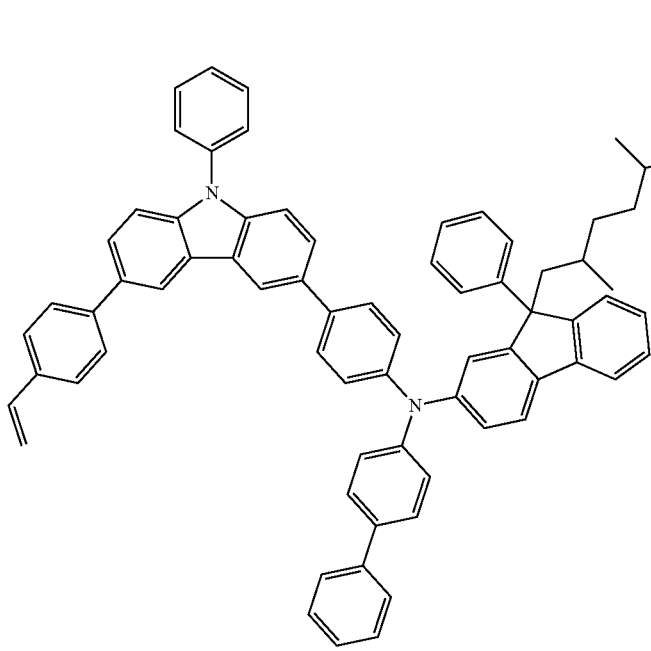

309 310
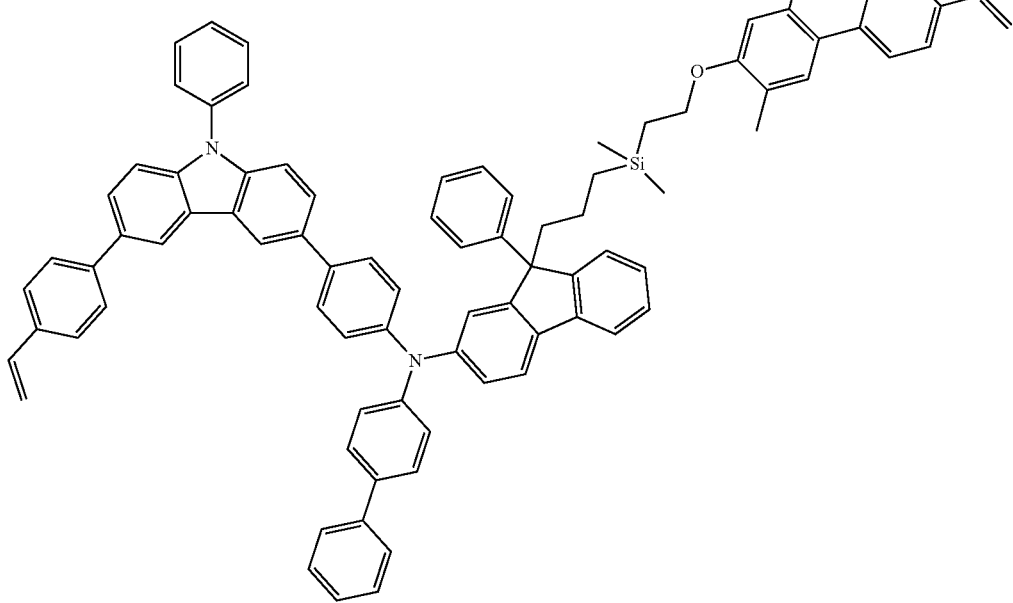
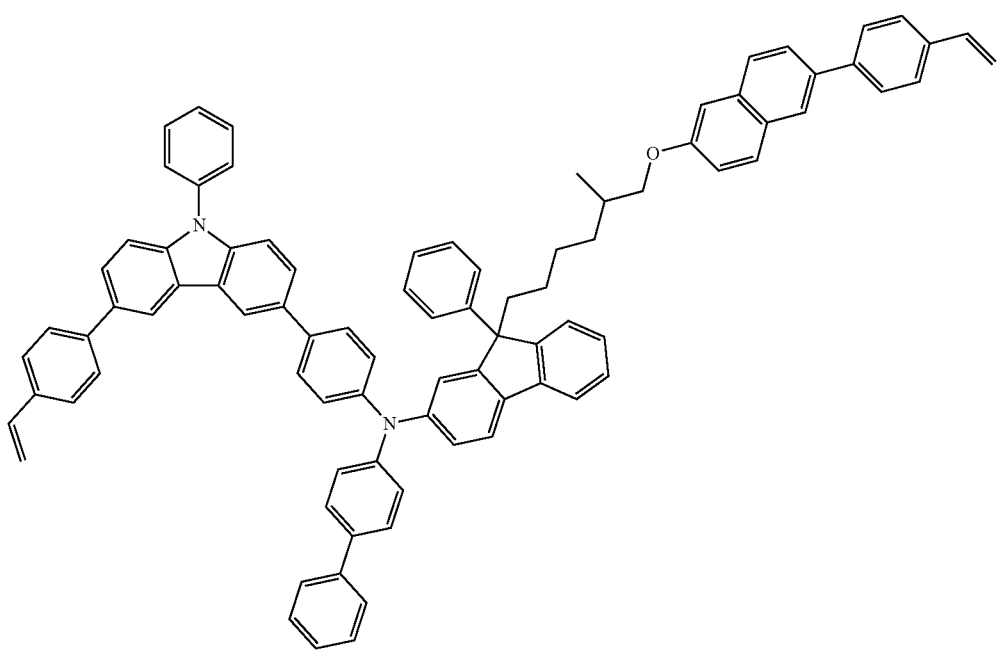

311
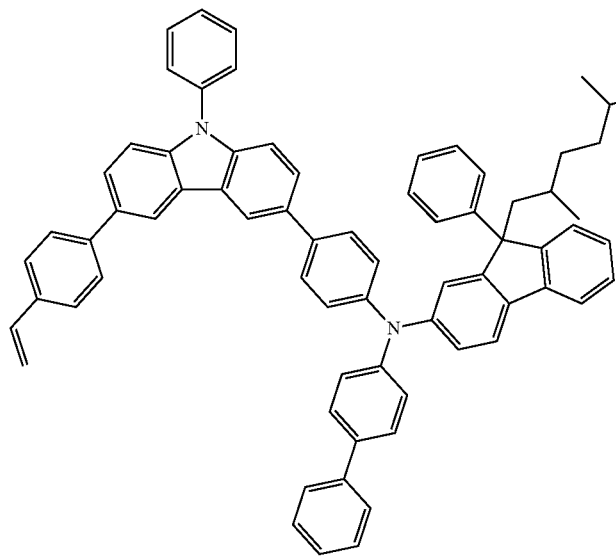
312
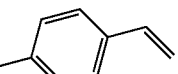
-continued
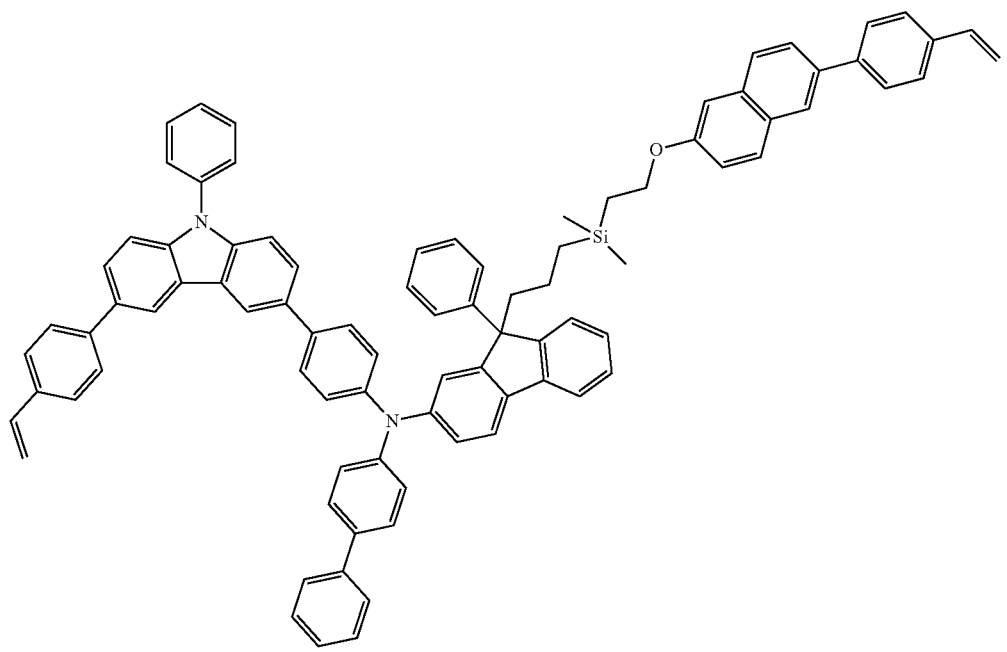

313
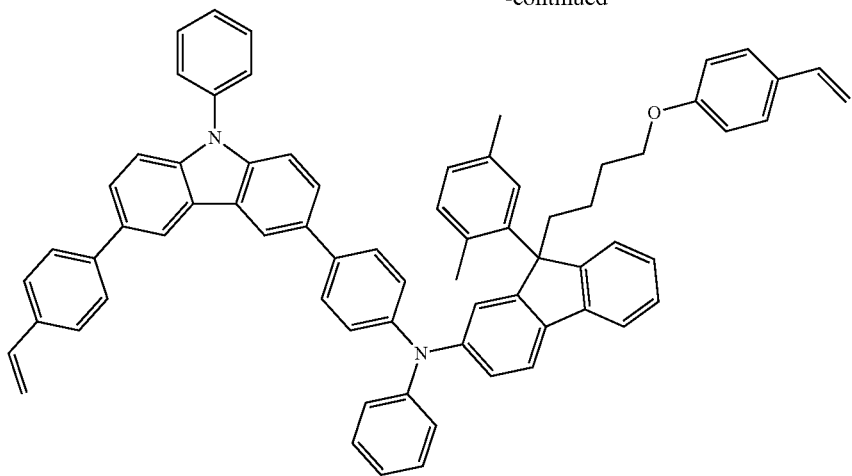
314
-continued
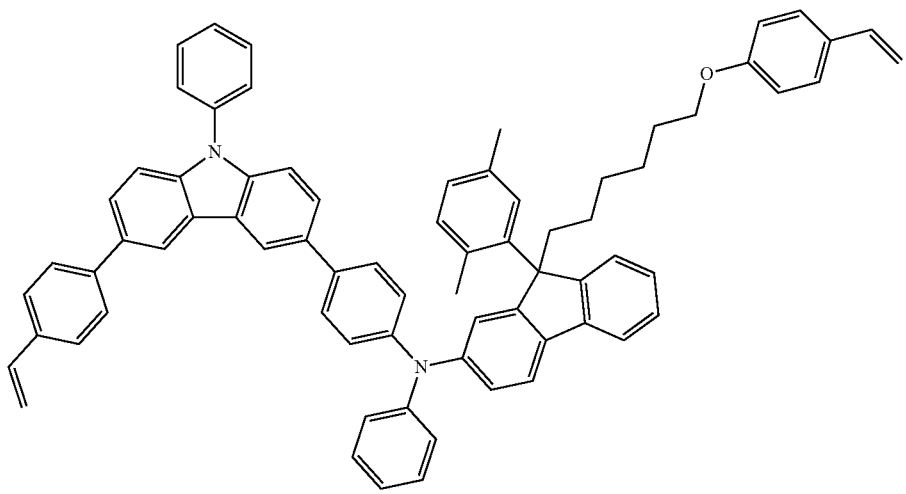
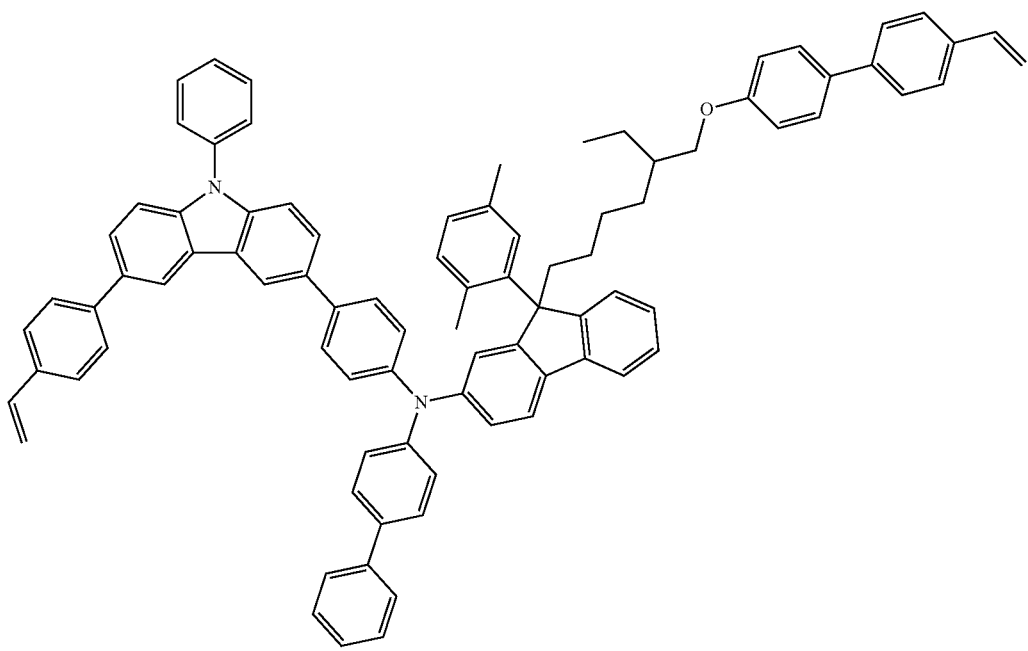

315
316
-continued
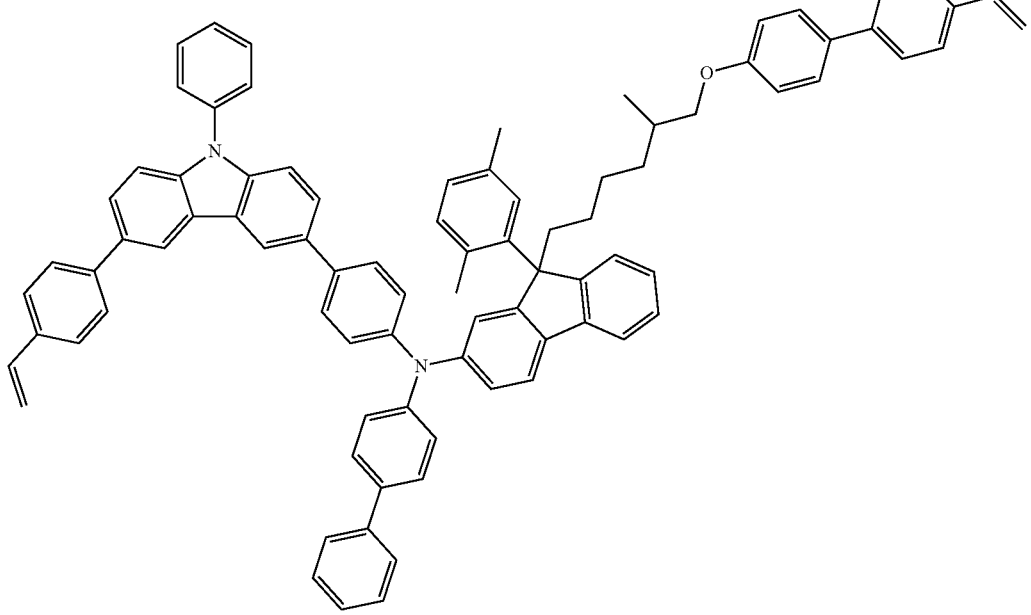
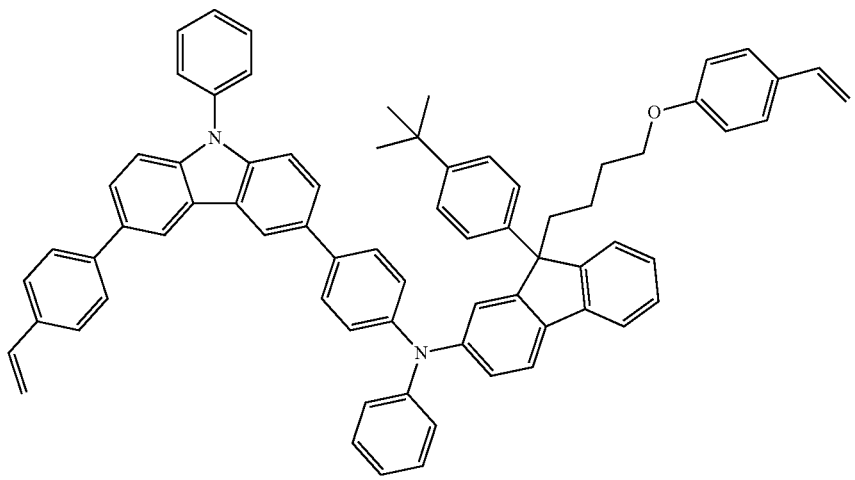
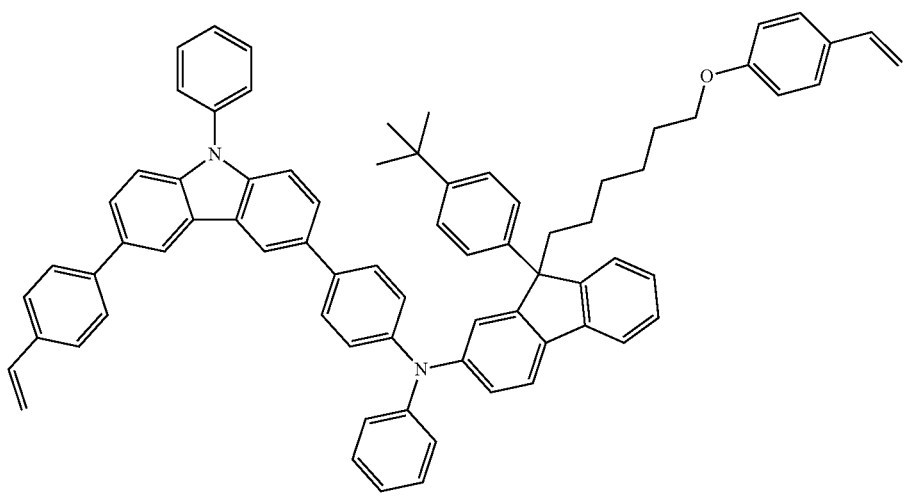

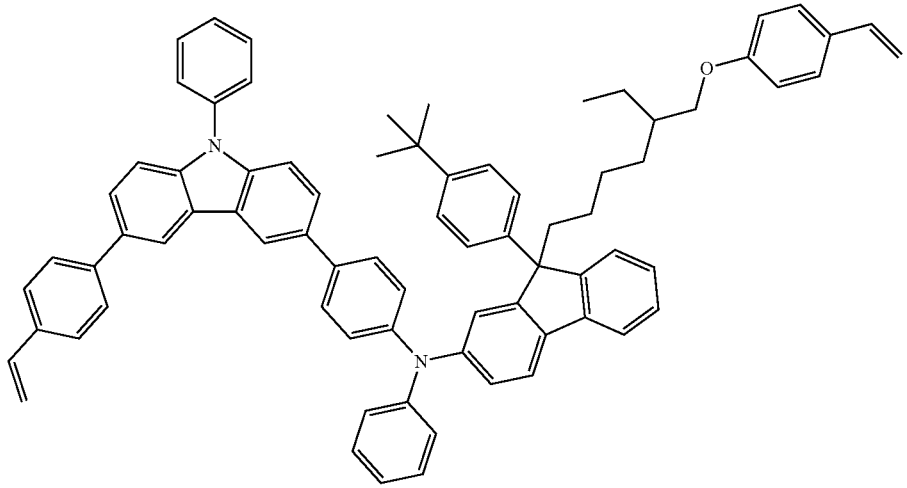
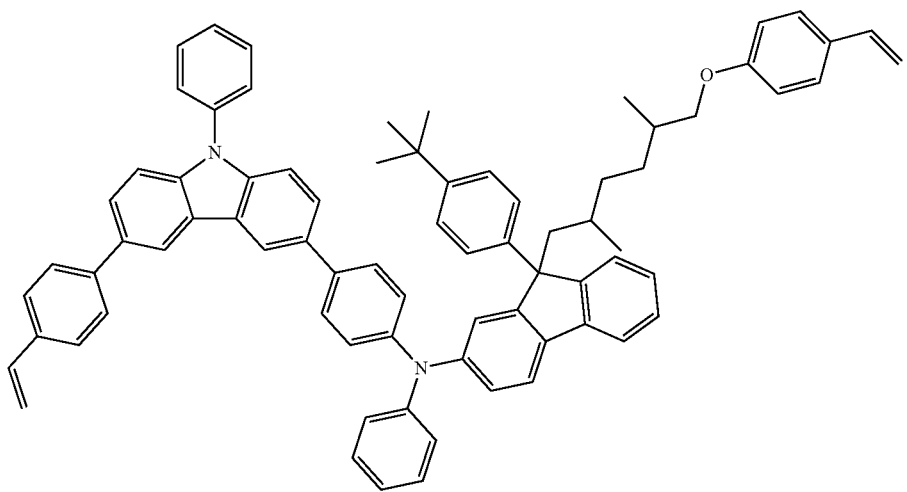
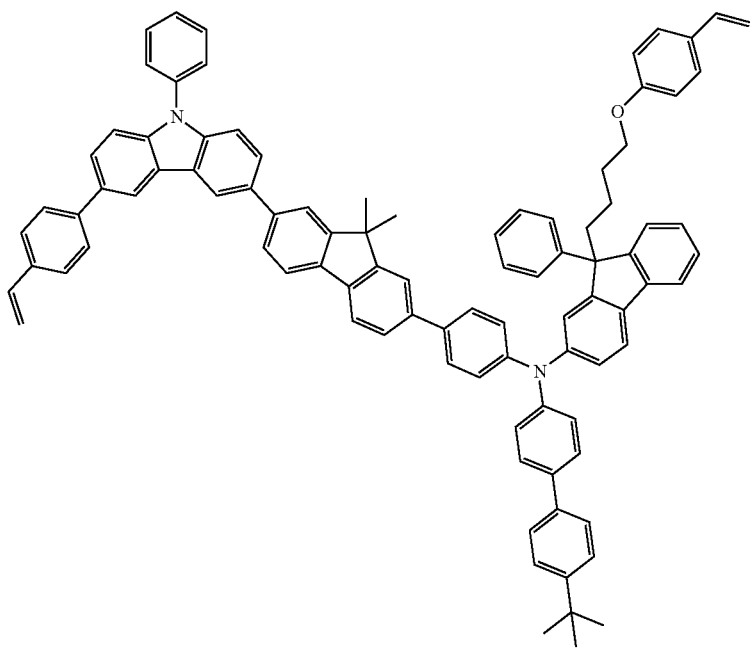

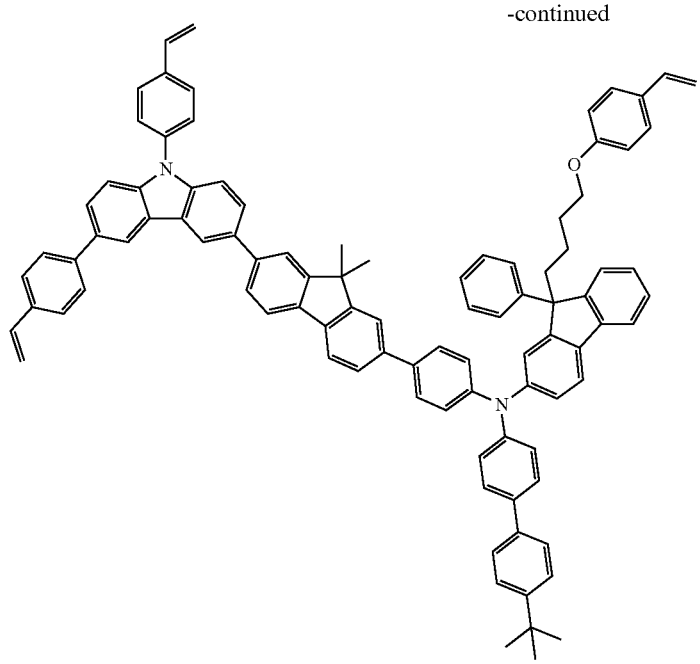
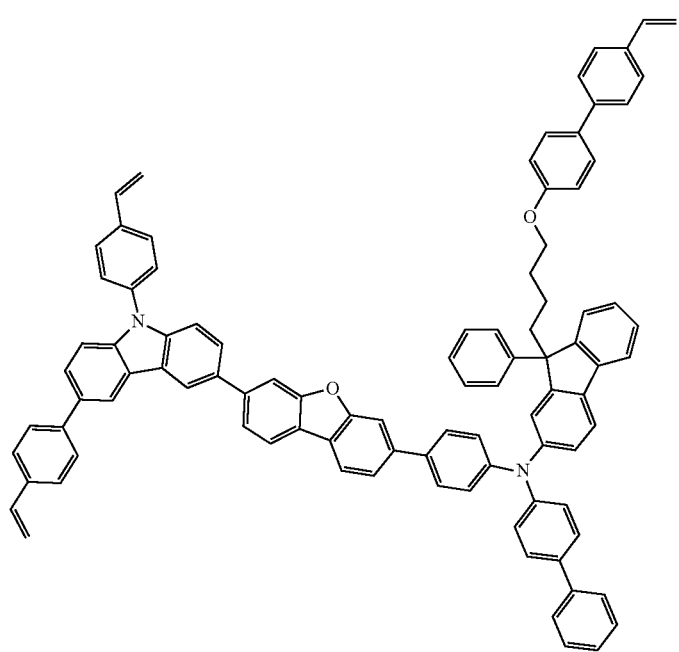 [SMILES: C=Cc1ccc(-c2ccc(OCCCCC3(c4ccccc4)c4ccccc4-c4ccc(N(c5ccc(-c6ccccc6)cc5)c5ccc(-c6ccc7c(c6)oc6cc(-c8ccc9c(c8)c8cc(-c%10ccc(C=C)cc%10)ccc8n9-c8ccc(C=C)cc8)ccc67)cc5)cc43)cc2)cc1]

321
-continued
322
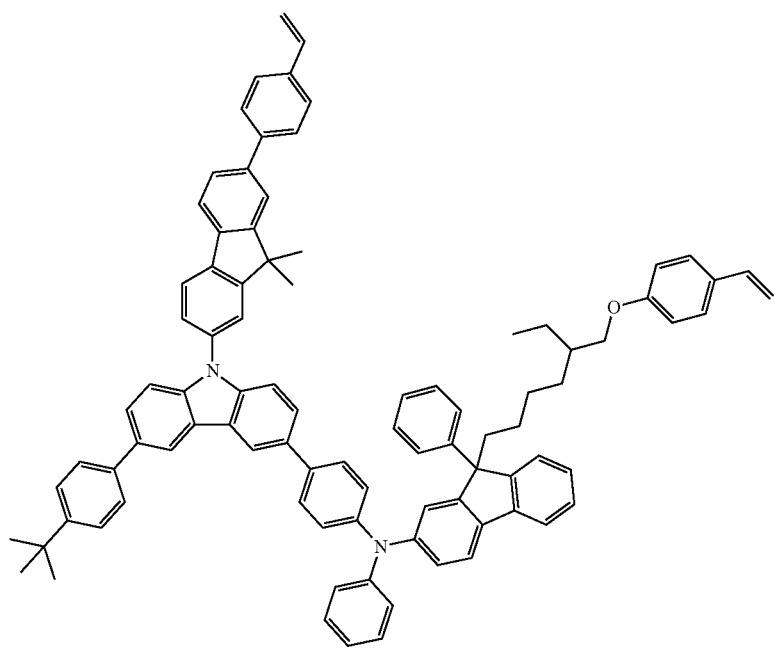
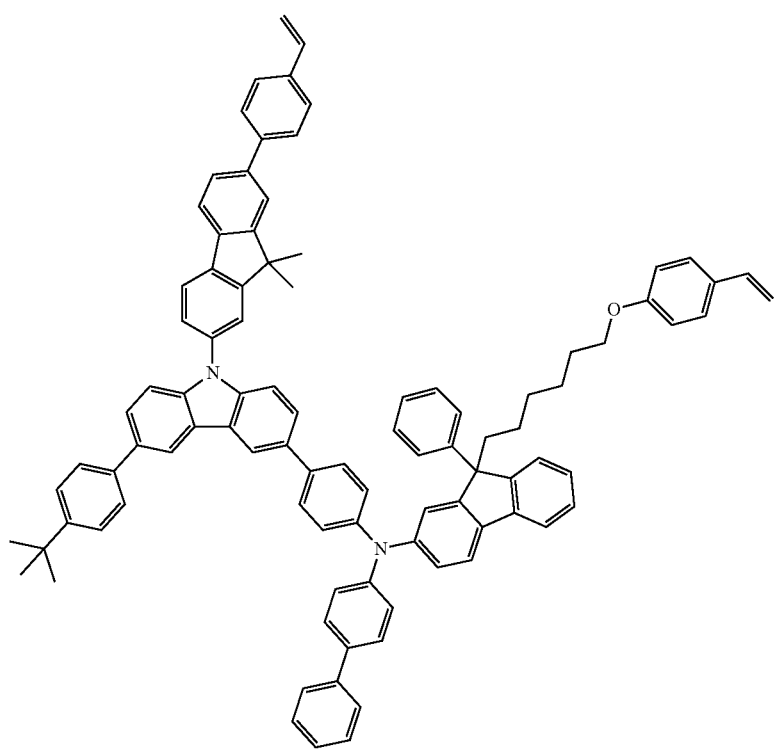

323
324
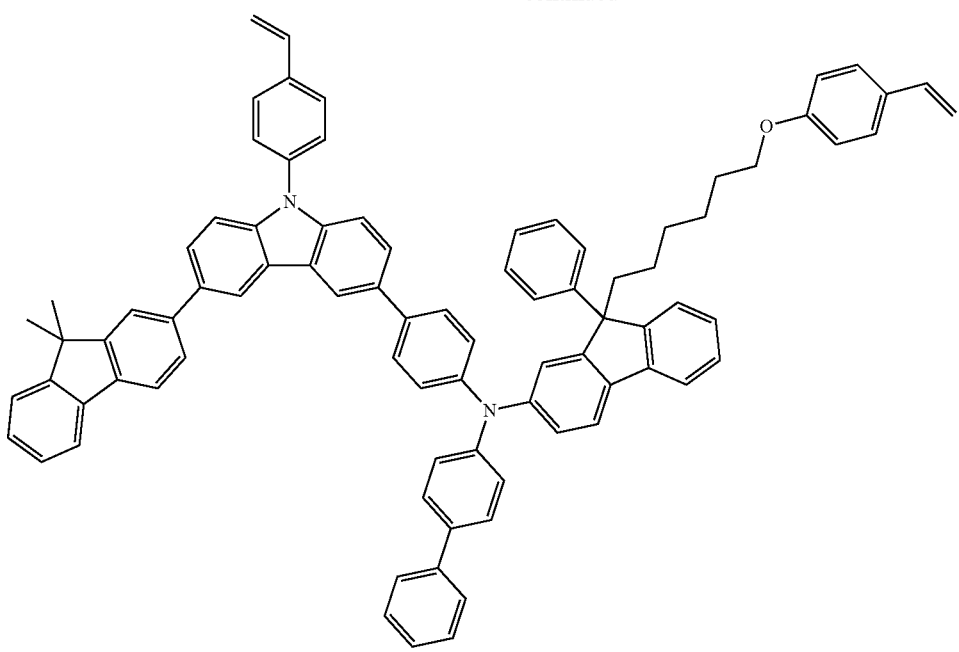
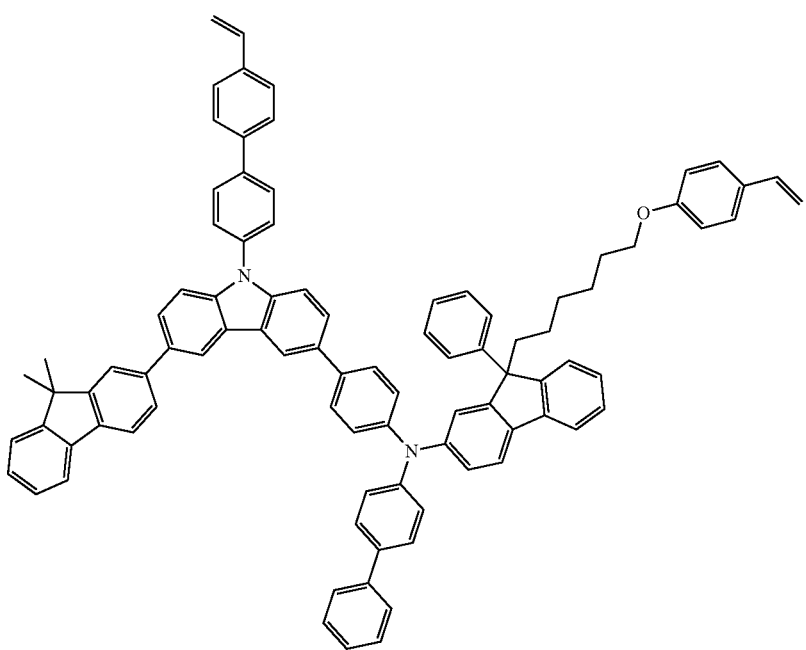

325 326
-continued
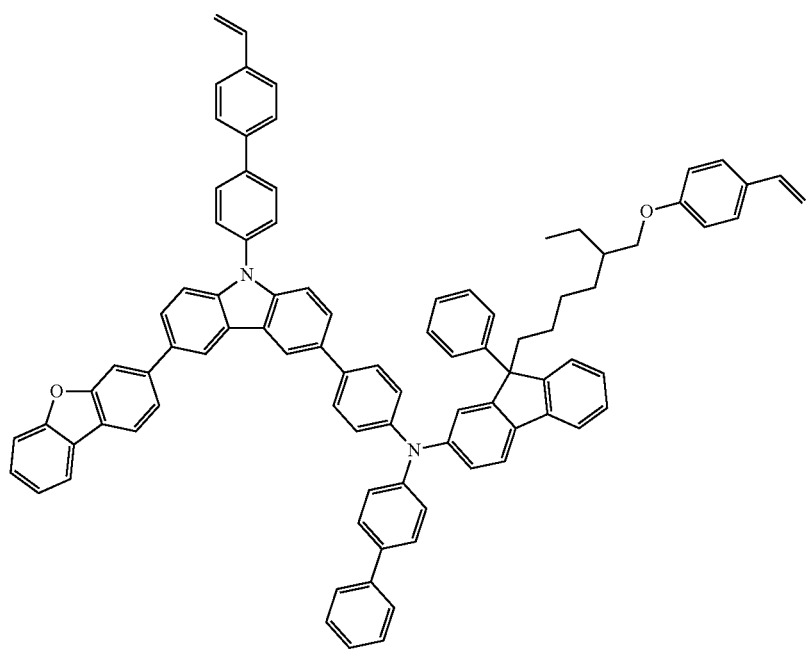
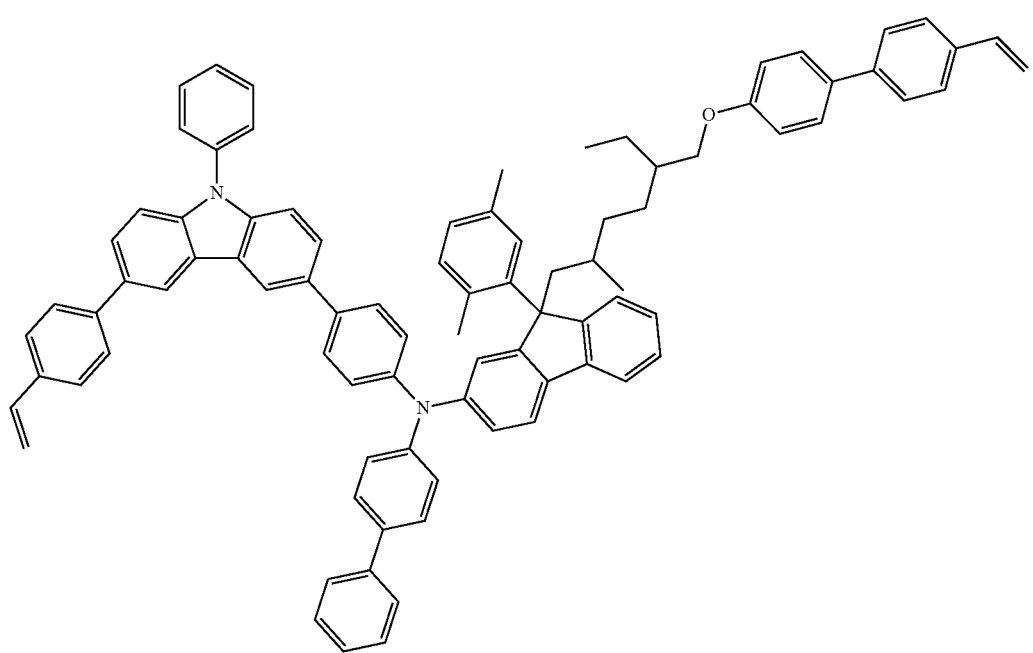

327
328
-continued
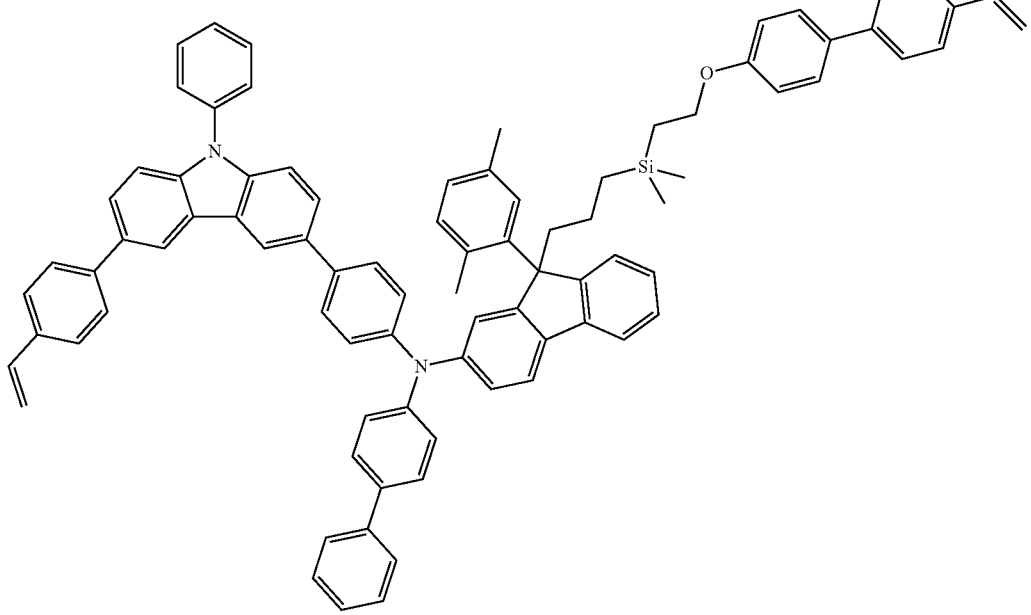
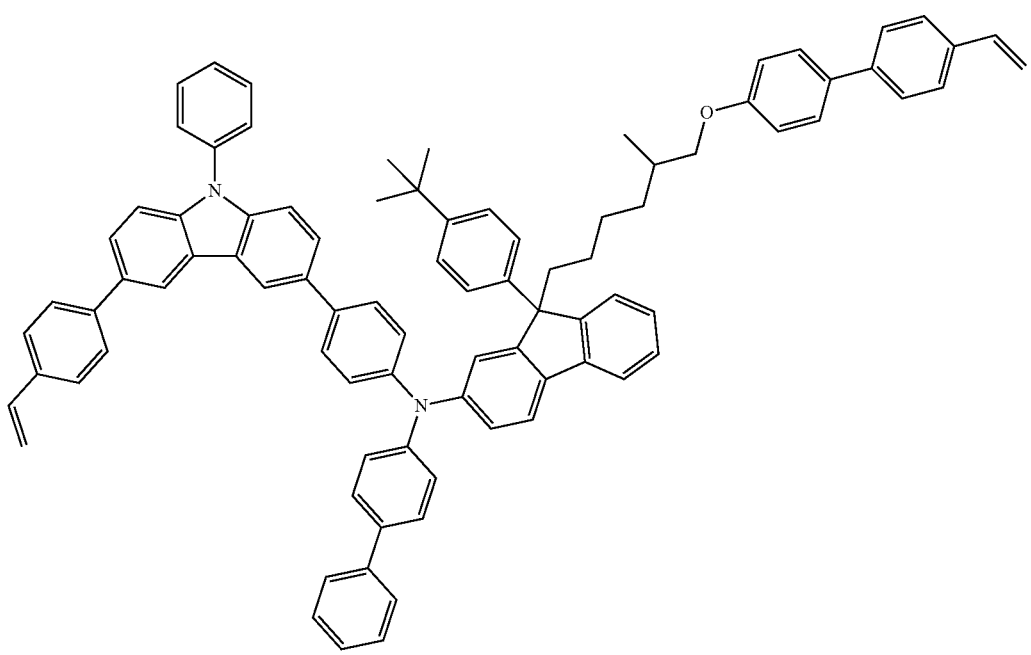

329
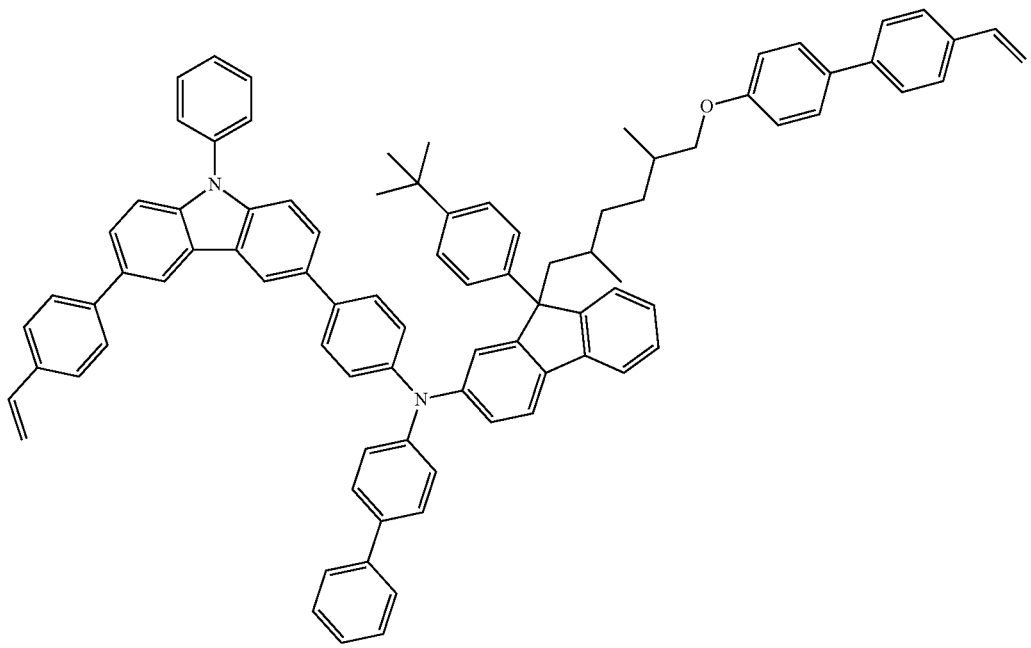
-continued
330
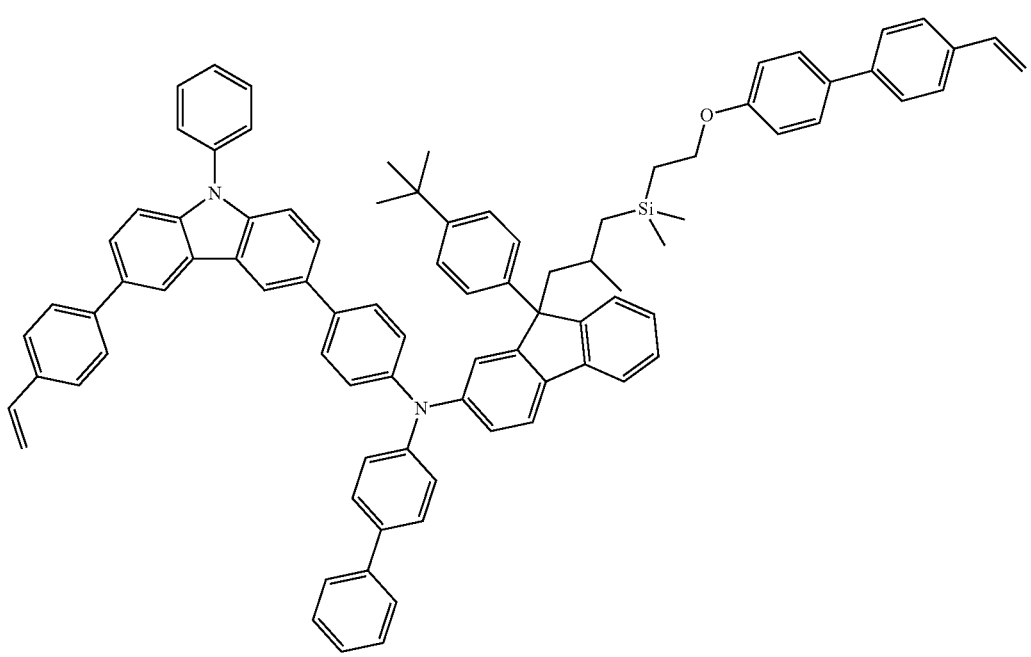

331
332
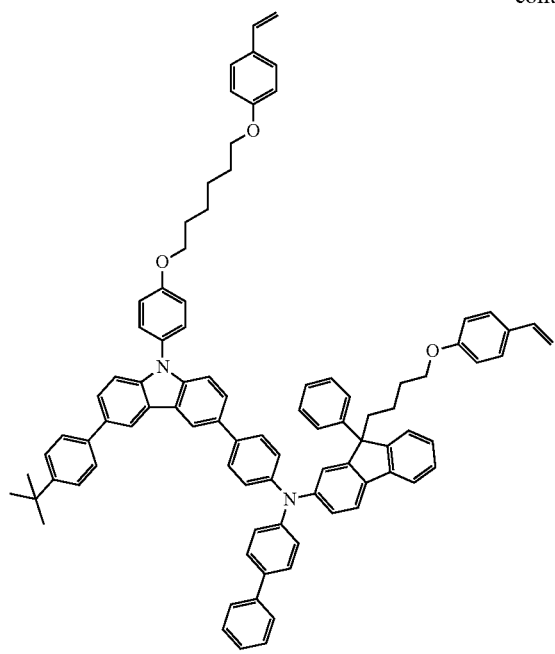
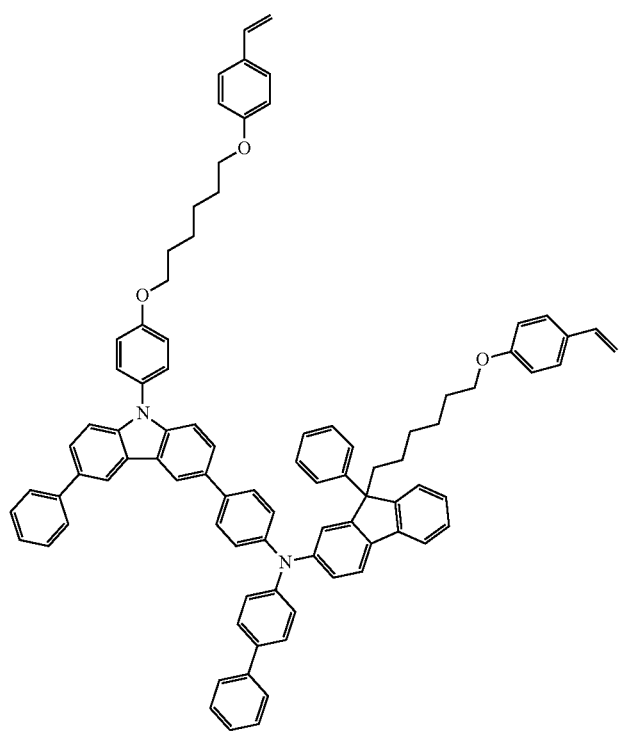

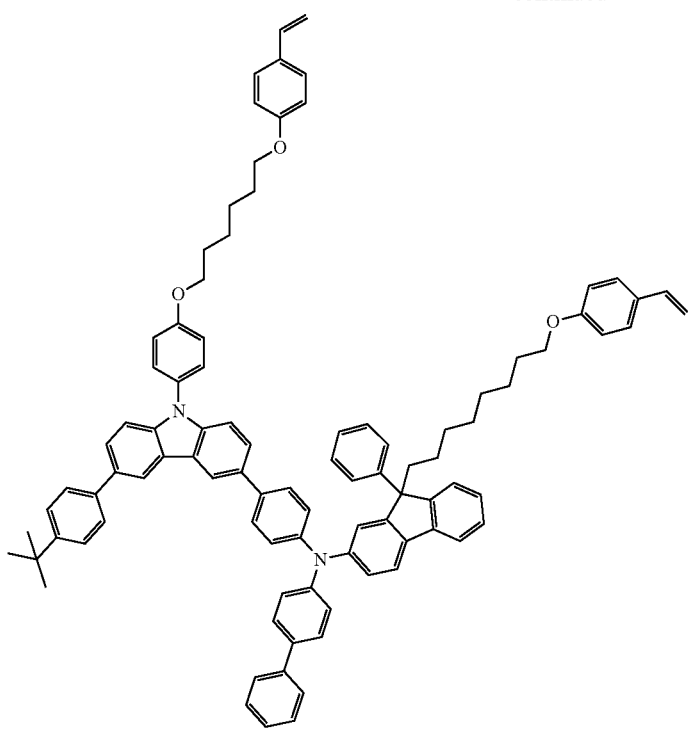 [SMILES: C=Cc1ccc(OCCCCCCCCC2(c3ccccc3)c3ccccc3-c3ccc(N(c4ccc(-c5ccccc5)cc4)c4ccc(-c5ccc6c(c5)c5cc(-c7ccc(C(C)(C)C)cc7)ccc5n6-c5ccc(OCCCCCCOc6ccc(C=C)cc6)cc5)cc4)cc32)cc1]
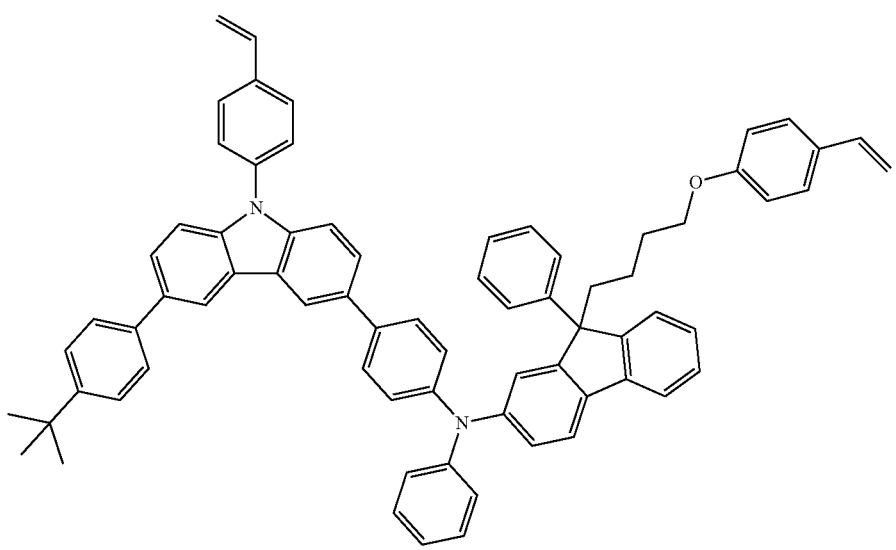

-continued
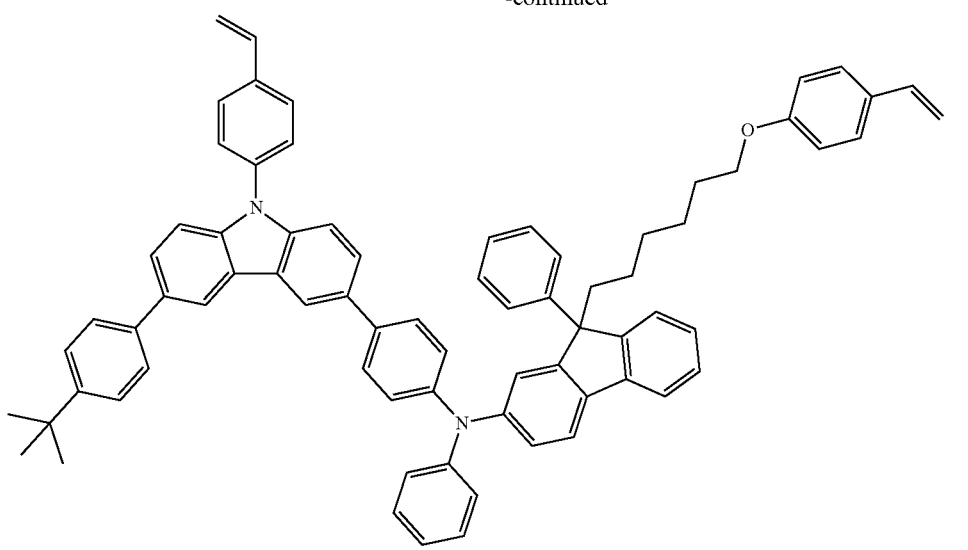
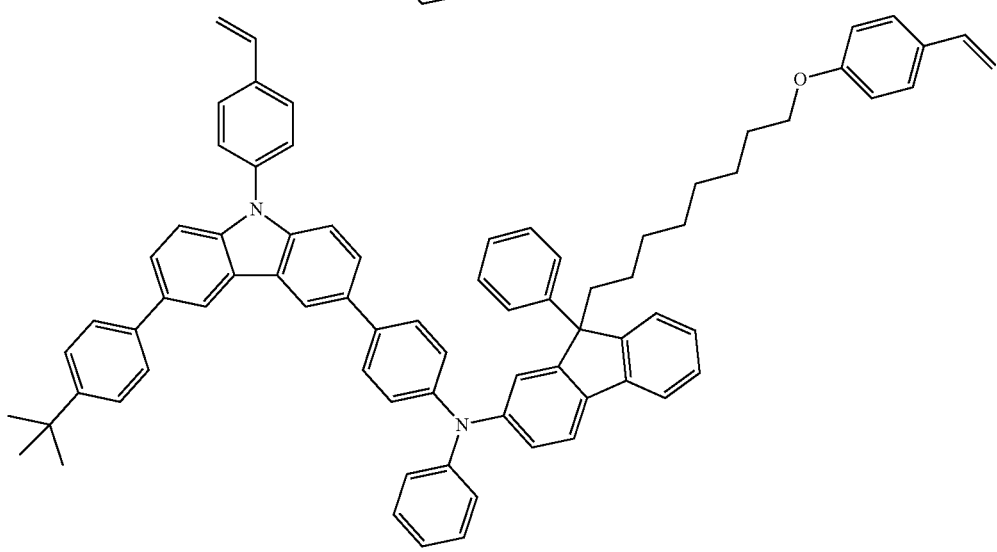
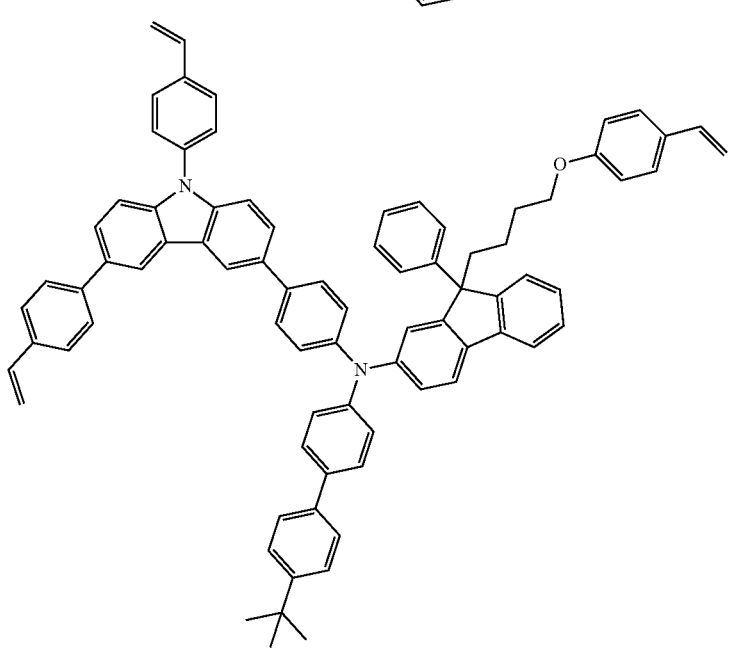

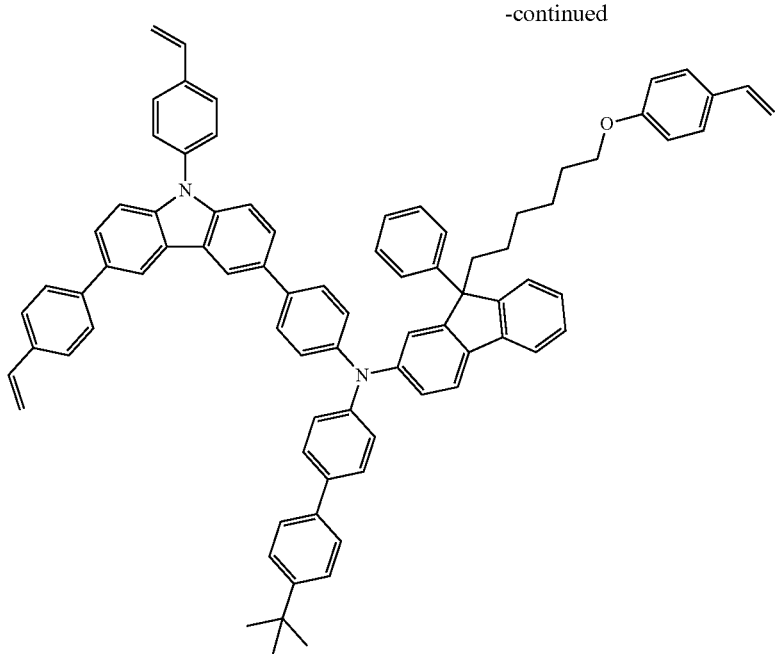
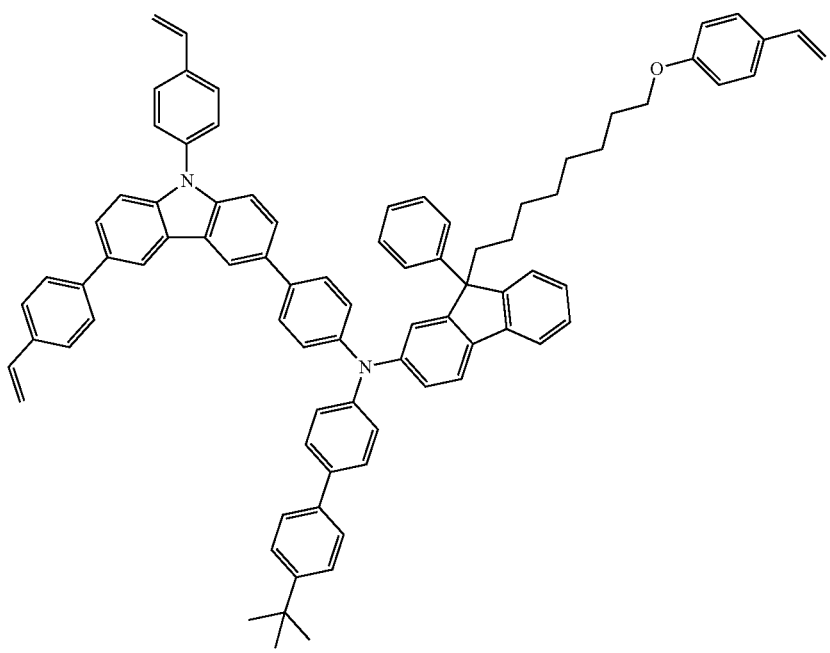 [SMILES: C=Cc1ccc(OCCCCCCCCC2(c3ccccc3)c3ccccc3-c3ccc(N(c4ccc(-c5ccc(C(C)(C)C)cc5)cc4)c4ccc(-c5ccc6c(c5)c5cc(-c7ccc(C=C)cc7)ccc5n6-c5ccc(C=C)cc5)cc4)cc32)cc1]

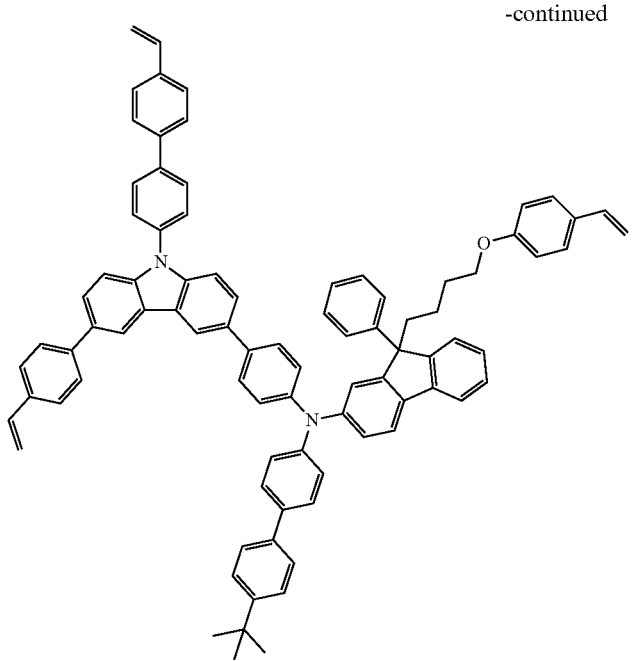
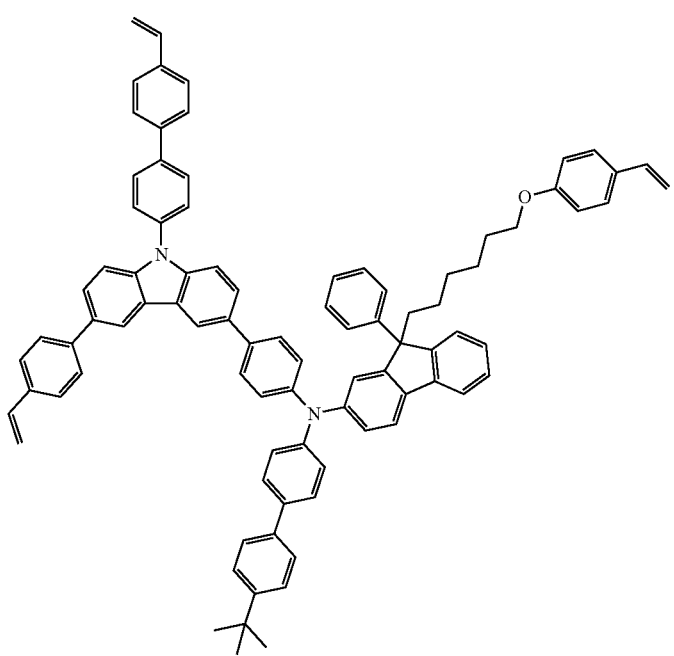

341
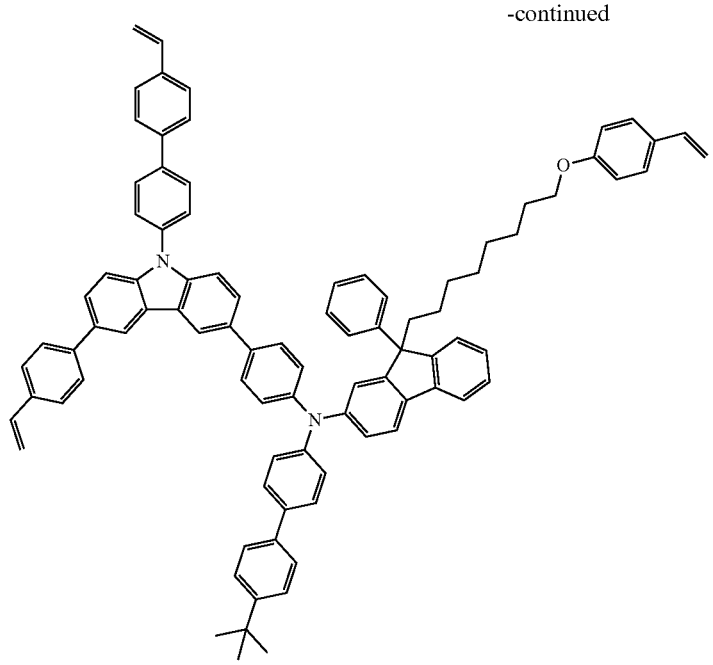
342
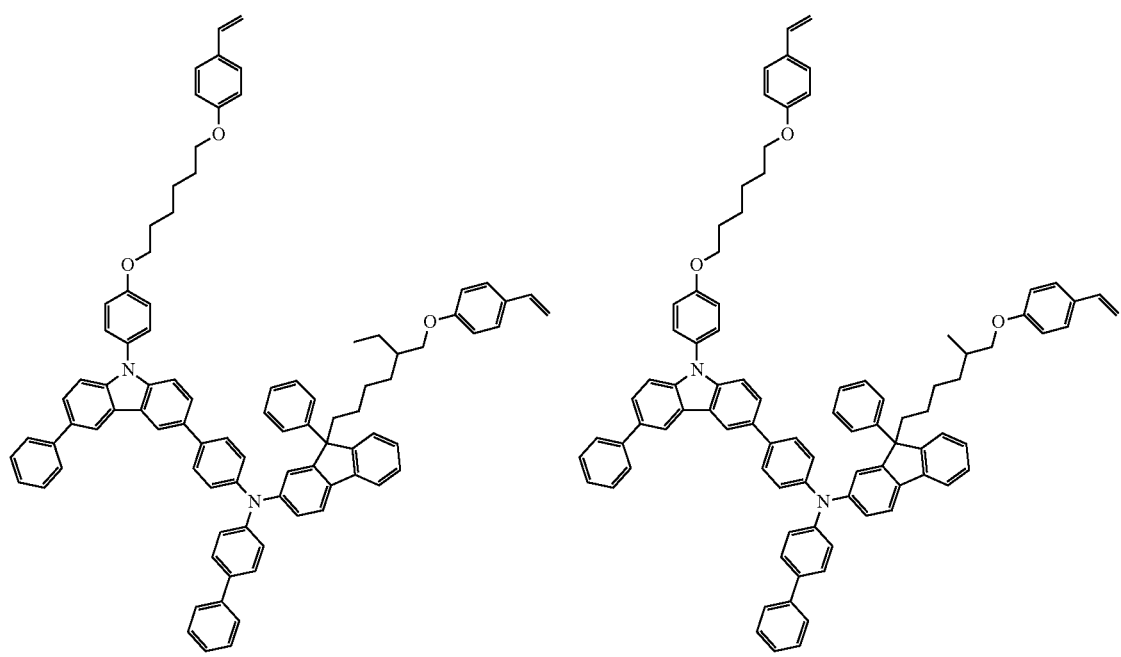

343 344
-continued
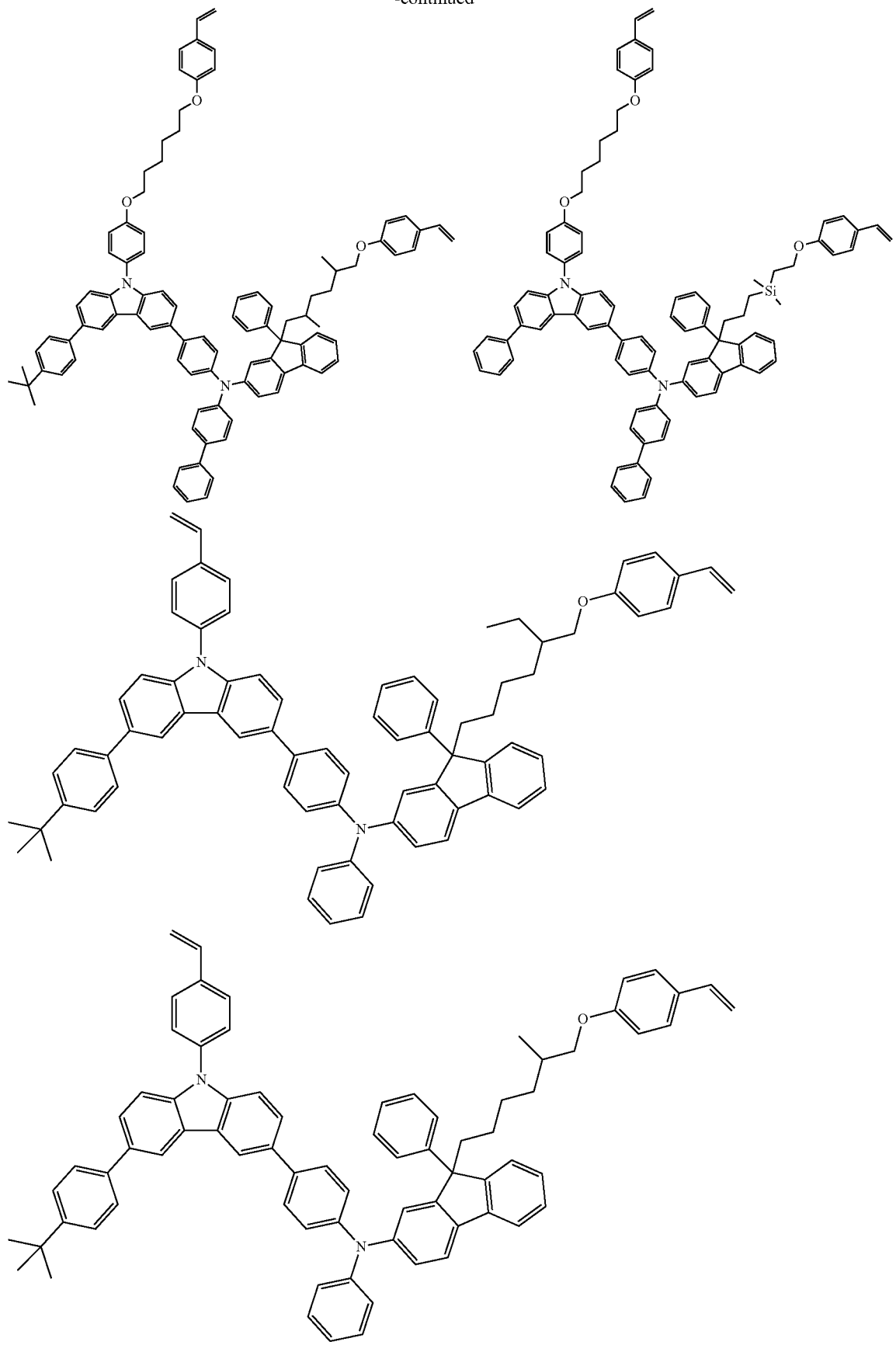

345 346
-continued
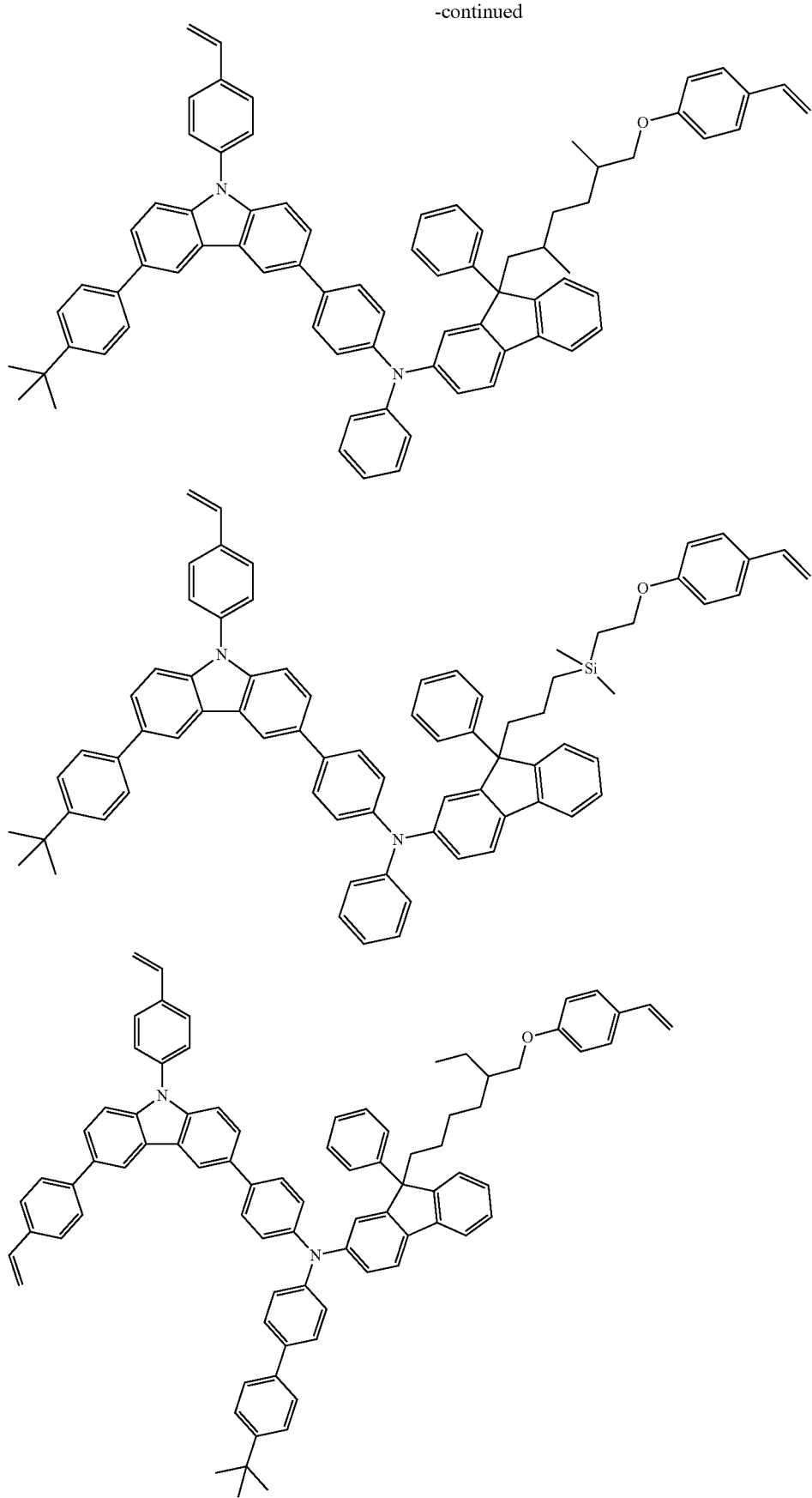

-continued
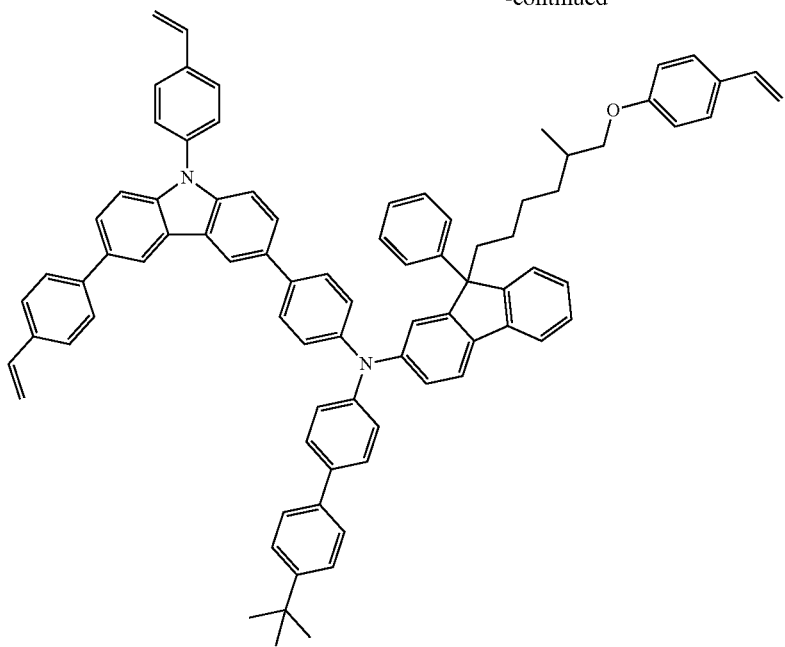
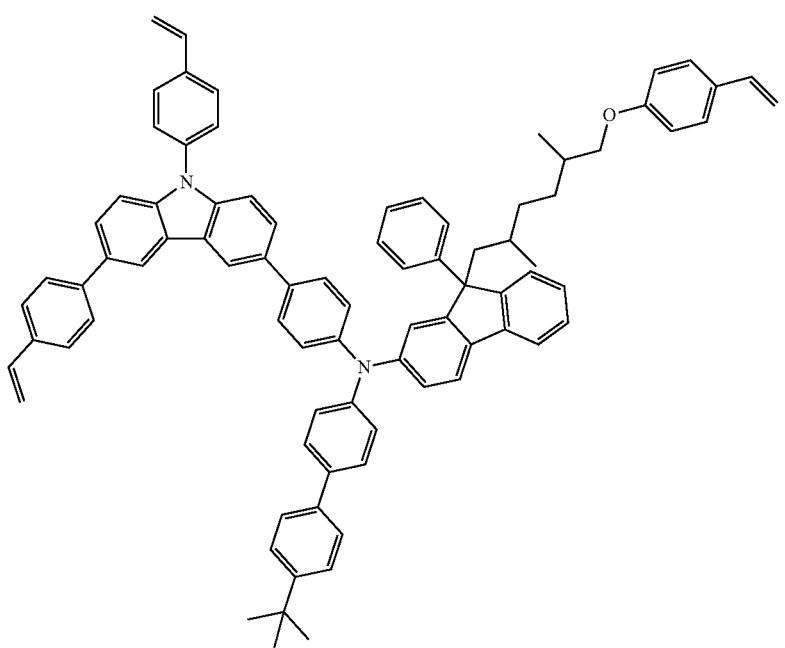 [SMILES: C=Cc1ccc(OCC[Si](C)(C)CCCC2(c3ccccc3)c3ccccc3-c3ccc(N(c4ccc(-c5ccc(C(C)(C)C)cc5)cc4)c4ccc(-c5ccc6c(c5)c5cc(-c7ccc(C=C)cc7)ccc5n6-c5ccc(C=C)cc5)cc4)cc32)cc1]

-continued
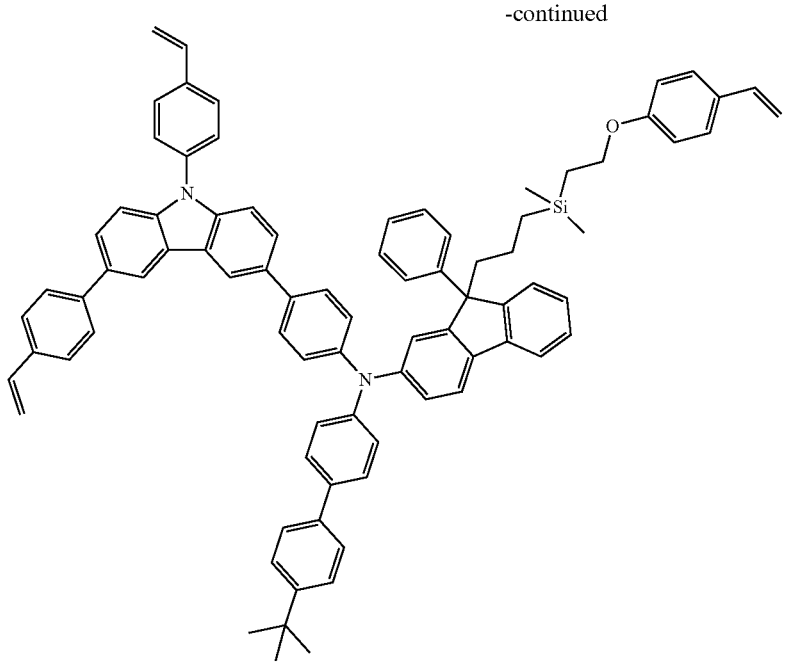
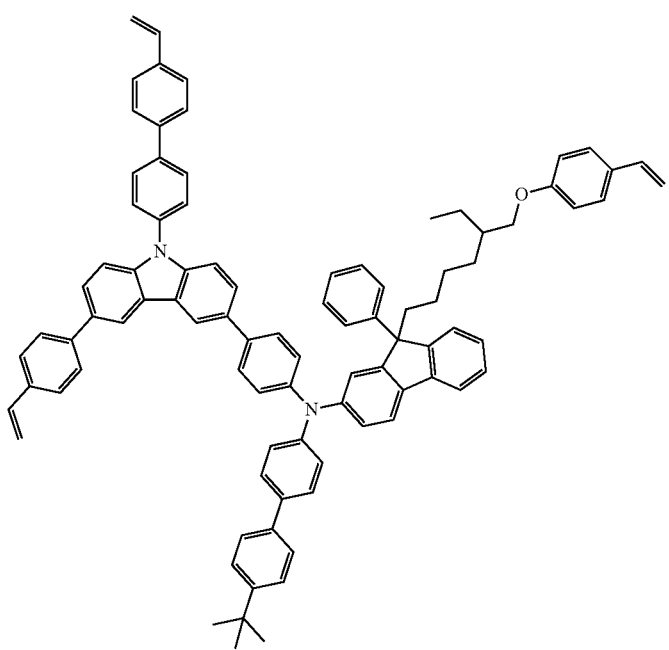

351
-continued
352
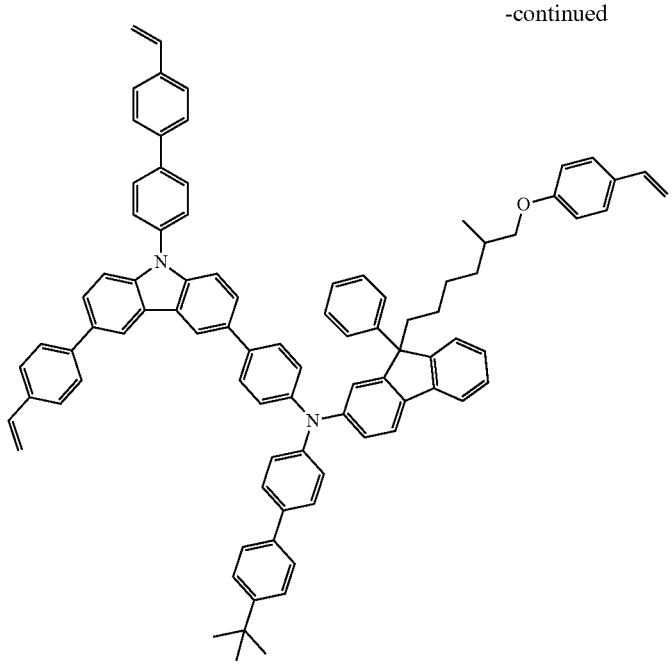
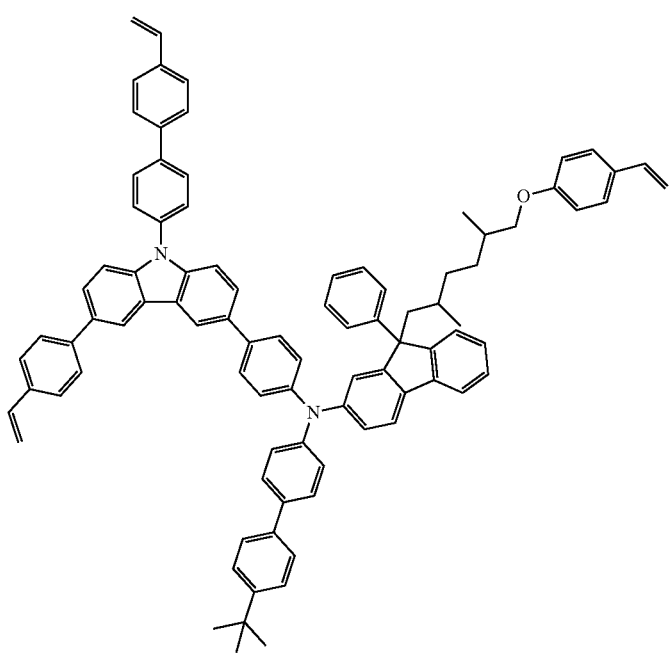

-continued

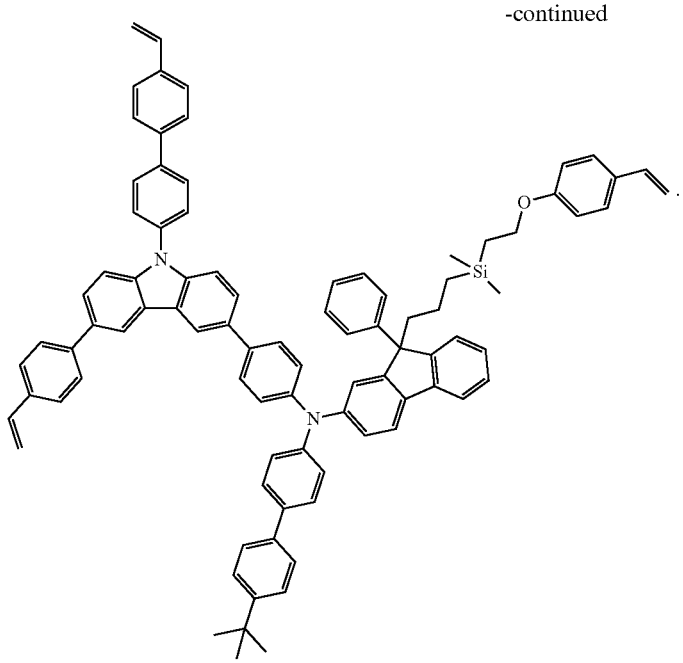

6. A coating composition comprising the compound of claim 1.

7. An organic light emitting device comprising:
a first electrode;
a second electrode provided opposite to the first electrode; and
at least one organic material layers provided between the first electrode and the second electrode,
wherein the at least one organic material layer includes the coating composition of claim 6 or a cured material thereof.

8. The organic light emitting device of claim 7, wherein the cured material of the coating composition is in a cured state by heat treating or light treating the coating composition.

9. The organic light emitting device of claim 7, wherein the at least one organic material layer including the coating composition or a cured material thereof is a hole transfer layer, a hole injection layer, or a layer carrying out hole transfer and hole injection at the same time.

10. The organic light emitting device of claim 7, wherein the at least one organic material layer including the coating composition or a cured material thereof is a light emitting layer.

11. The organic light emitting device of claim 7, wherein coating composition further includes an ionic compound including an anion group represented by the following Chemical Formula 11; and a cation group represented by the following Chemical Formula 12:

[Chemical Formula 11]

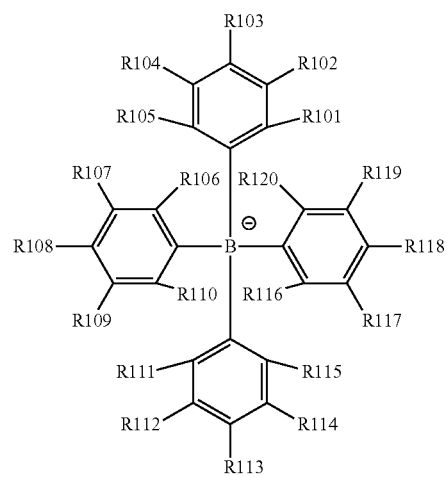

in Chemical Formula 11, at least one of R101 to R120 is F; a cyano group; or a substituted or unsubstituted fluoroalkyl group;

at least one of the remaining R101 to R120 is a curing group; and the remaining R101 to R120 if present are the same as or different from each other, and each independently hydrogen; deuterium; a nitro group; a substituted or unsubstituted alkyl group; a substituted or unsubstituted alkenyl group; a substituted or unsubstituted amine group; a substituted or unsubstituted aryl group; or a substituted or unsubstituted heterocyclic group,

[Chemical Formula 12]

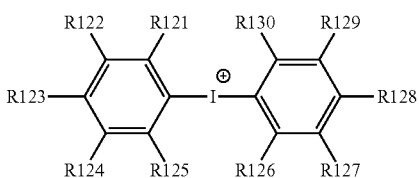

in Chemical Formula 12,

R121 to R130 are the same as or different from each other, and each independently hydrogen; deuterium; a nitro group; a halogen group; a substituted or unsubstituted alkyl group; a substituted or unsubstituted cycloalkyl group; a substituted or unsubstituted alkenyl group; a substituted or unsubstituted aryl group; or a substituted or unsubstituted heterocyclic group, or a curing group.

12. The organic light emitting device of claim 11, wherein at least one of R103, R108, R113 and R118 is a curing group.

13. The organic light emitting device of claim 11, wherein the curing group is any one selected from among the following structures:

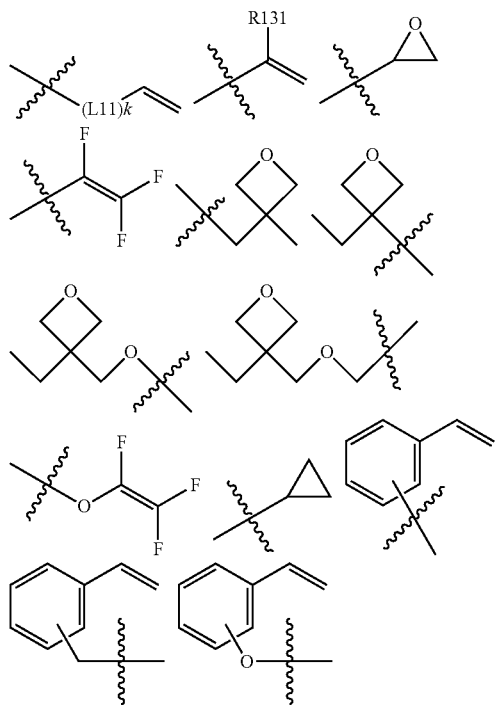

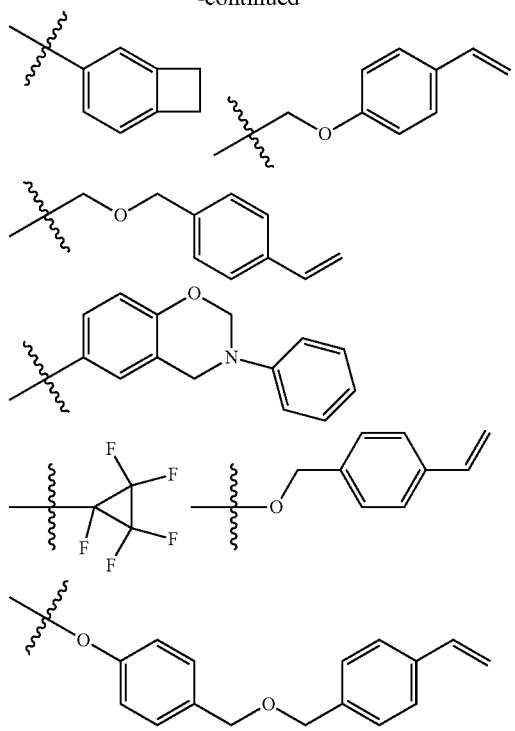

in the structures,

L11 is a direct bond; —O—; —S—; a substituted or unsubstituted alkylene group; a substituted or unsubstituted arylene group; or a substituted or unsubstituted heteroarylene group;

k is 1 or 2;

when k is 2, L1 is are the same as or different from each other;

R131 is a substituted or unsubstituted alkyl group; and each

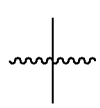

means a linking site.

14. The organic light emitting device of claim 11, wherein the anion group represented by Chemical Formula 11 is any one selected from among the following structures:

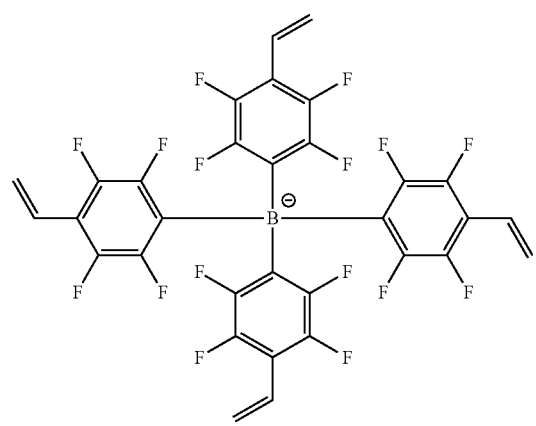

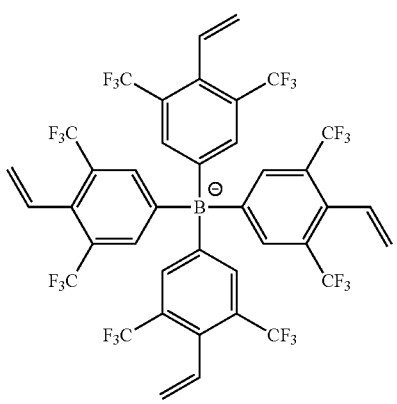

357 358
-continued
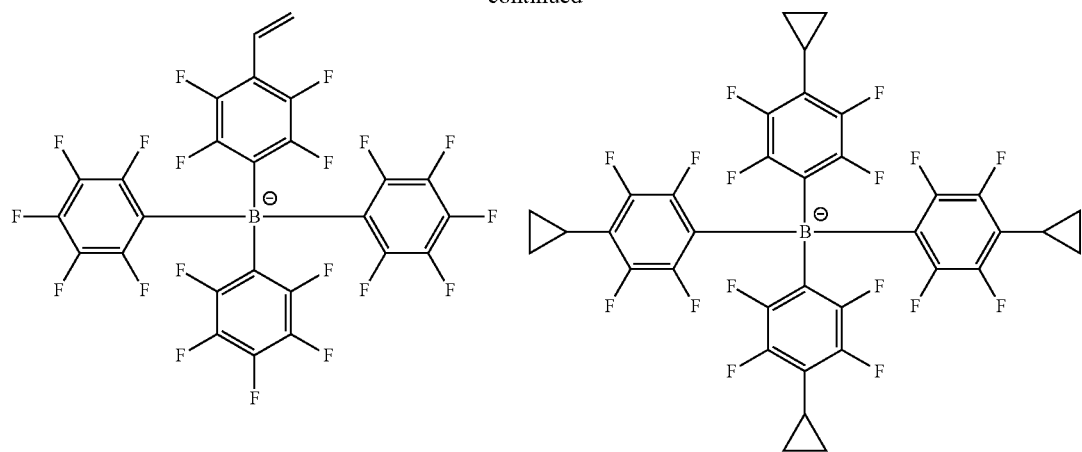
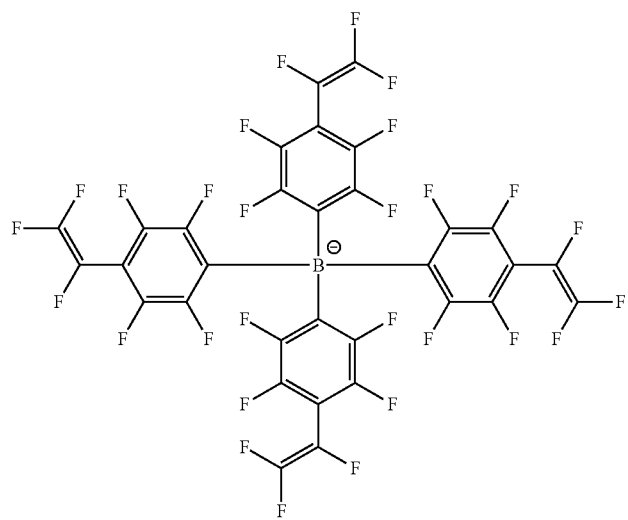
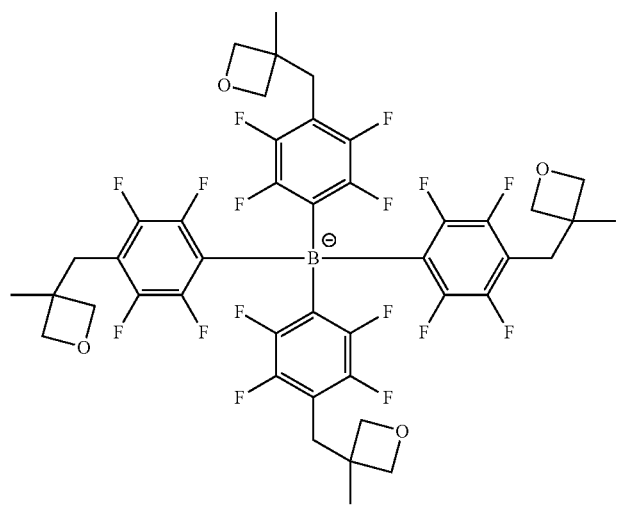

-continued
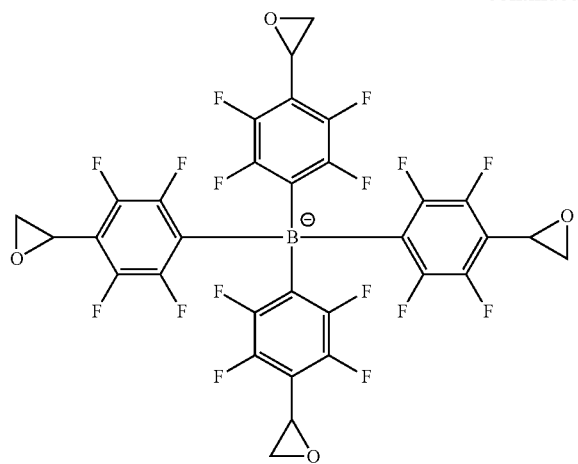
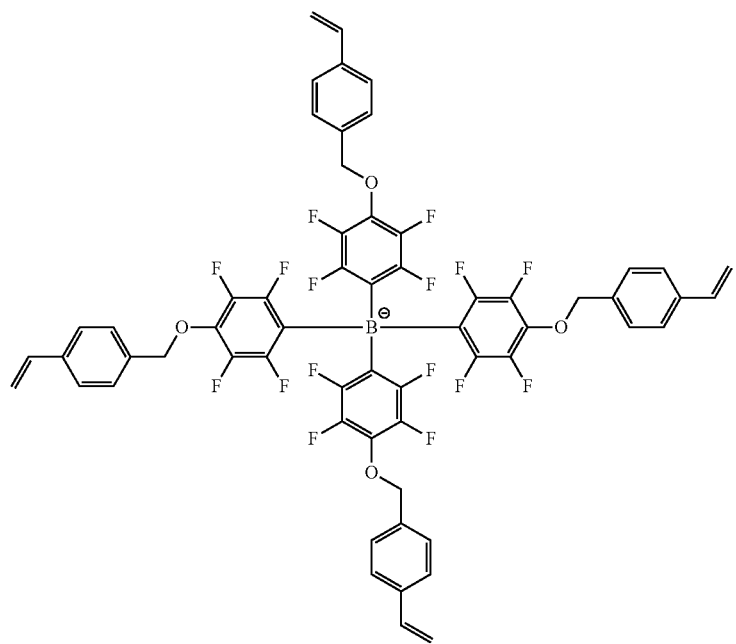
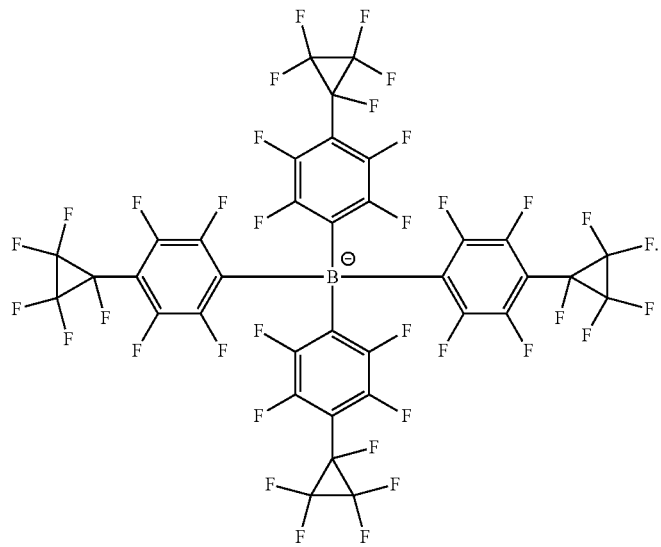

15. The organic light emitting device of claim 11, wherein the cation group represented by Chemical Formula 12 is any one selected from among the following structures:

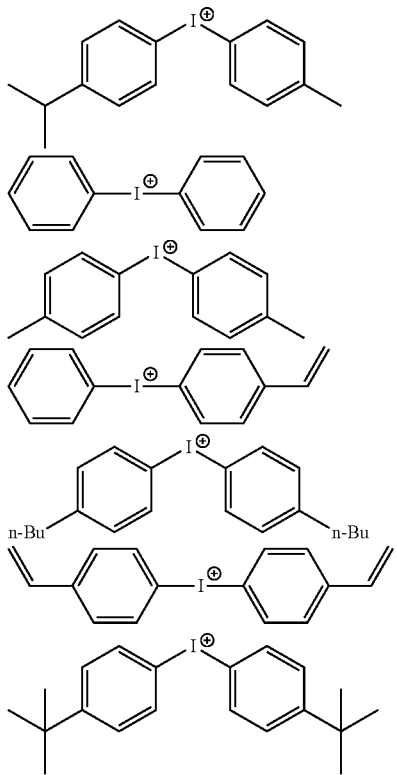

-continued

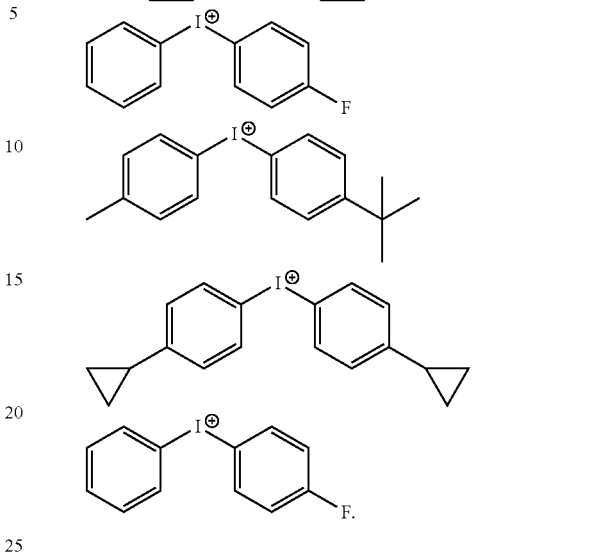

16. The compound of claim 1, wherein R1 to R4 are the same as or different from each other, and each independently hydrogen; or a phenyl group unsubstituted or substituted with an alkyl group.

17. The organic light emitting device of claim 11, wherein the curing group of Chemical Formula 11 is a vinyl group.

18. The organic light emitting device of claim 11, wherein R103, R108, R113 and R118 are the same as or different from each other, and each independently a vinyl group or F.

* * * * *